(12) United States Patent
Adorante et al.

(10) Patent No.: US 7,754,440 B2
(45) Date of Patent: *Jul. 13, 2010

(54) HIGH-THROUGHPUT SCREEN FOR IDENTIFYING SELECTIVE PERSISTENT SODIUM CHANNELS CHANNEL BLOCKERS

(75) Inventors: Joseph S. Adorante, Irvine, CA (US); George R. Ehring, Huntington Beach, CA (US)

(73) Assignee: Allergan, Inc., Irvine, CA (US)

( * ) Notice: Subject to any disclaimer, the term of this patent is extended or adjusted under 35 U.S.C. 154(b) by 65 days.

This patent is subject to a terminal disclaimer.

(21) Appl. No.: 12/041,739

(22) Filed: Mar. 4, 2008

(65) Prior Publication Data

US 2008/0182288 A1      Jul. 31, 2008

Related U.S. Application Data

(60) Division of application No. 11/313,450, filed on Dec. 19, 2005, now Pat. No. 7,361,478, which is a continuation-in-part of application No. 09/989,797, filed on Nov. 20, 2001, now Pat. No. 6,991,910.

(51) Int. Cl.
  *G01N 33/566* (2006.01)
  *G01N 27/04* (2006.01)
  *C12N 13/00* (2006.01)
  *G01R 27/08* (2006.01)
  *C12M 1/34* (2006.01)

(52) U.S. Cl. .................. 435/7.2; 435/173.1; 435/173.4; 435/288.7; 324/447; 324/692

(58) Field of Classification Search .................. None
  See application file for complete search history.

(56) References Cited

U.S. PATENT DOCUMENTS

| | | | |
|---|---|---|---|
| 5,527,814 A | 6/1996 | Louvel | |
| 5,610,184 A | 3/1997 | Shahinian, Jr. | |
| 5,922,746 A | 7/1999 | Adorante | |
| 5,981,268 A | 11/1999 | Kovacs et al. | |
| 6,686,193 B2 | 2/2004 | Maher et al. | |
| 6,869,772 B2 | 3/2005 | Lichtman et al. | |
| 6,991,910 B2 | 1/2006 | Adorante et al. | |

FOREIGN PATENT DOCUMENTS

| | | |
|---|---|---|
| EP | 0608604 | 10/1993 |
| EP | 0659430 | 12/1994 |
| FR | 2714828 | 1/1994 |
| WO | WO9641166 | 12/1996 |

OTHER PUBLICATIONS

Eglen et al, Ions in the Fire: Recent Ion-Channel Research and Approaches to Pain Therapy, TIPS, vol. 20, pp. 337-342 1999.
Gonzalez et al, Cell-Based Assays and Instrumentation for Screening Ion-Channel Targets, DDT, 1999, vol. 4, No. 9, pp. 431-439.
Stys et al, Ionic Mechanisms of Anoxic Injury in Mammalian Role of Na+ Channels and Na+Ca2+ Exchange, Journal of Neuroscience, 1992, vol. 12, pp. 430-439.
Neher et al, The Extracellular Patch Clamp: A Method for Resolving Currents Through Individual Open Channels in Biological Membranes, 1978.
Hamill et al, Improved Patch-Clamp Techniques for High-Resolution Current Recording From Cells and Cell-Free Membrane Patch, 1981.
Stys et al, Role of Extracellular Calcium in Anoxic Injury of Mammalian Central White Matter, 1990.
Fraser, Arachidonic Acid Inhibits Sodium Currents and Synaptic Transmission in Cultured Straital Neurons, 1993.
Stys, Protective Effects of Antiarrhythmic Agents Against Anoxic Injury in CNS White Matter, 1994.
Choi, Calcium: Still Center-Stage in Hypoxic-Ischemic Neuronal Death, 1995, pp. 58-60.
Ono, Interaction Between External Na+ and Mexilentine on Na+ Channel in Guinea-Pig Ventricular Myoctes, 1995, pp. 101-109.
Textbook of Ocular Pharmacology, 1997, pp. 330-334.
Stys, Noninactivating Tetrodtoxin-Sensitive Na+ Conductance in Rat Optic Nerve Axons, 1993, 6976-6980.
Gleitz, J. et al, (+/−)-Kavain inhibits veratridine-activated voltage-dependent Na(+)-channels in synaptosomes prepared from rat cerebral cortex. Neuropharmacology. Sep. 1995:34(9): pp. 1133-1138.
Ransom et al, Anoxic Injury of Central Myelinated Axons: 1993, pp. 121-151.
Waxman et al, Role of Na+ Conductance and the Na+Ca++ Exchanger in Anoxic Injury of CNS White Matter, 1992, pp. 13-31.
Taylor, Na+ Currents That Fail to Inactivate, 1993, vol. 16, No. 11, pp. 455-460.
Gonzalez et al, Voltage Sensing by Fluorescence Resonance Energy Transfer in Single Cells, Biophysical Journal, 1995, vol. 69, pp. 1272-1280.
Doggrel et al, Effects of Potassium Channel Blockers on the Action Potentials and Contractility of the Rat Right Ventricle, Gen. Pharmac., 1996, vol. 27. No. 2, pp. 379-385.
Nguyen et al, Capillary Electrophoresis of Cardiovascular Drugs, Journal of Chromatography, 1996, vol. 735, pp. 123-150.
U.S. Appl. No. 11/313,450, filed Dec. 19, 2005, Adorante et al.

*Primary Examiner*—Robert Landsman
*Assistant Examiner*—Ian Dang
(74) *Attorney, Agent, or Firm*—Dean G. Stathakis; Joel B. German; Allergan, Inc.

(57) ABSTRACT

A method for identifying a selective persistent $Na^+$ channel blocker by measuring the ability of the blocker to reduce or inhibit a persistent $Na^+$ current to a greater degree than a transient $Na^+$ current. Aspects of the present method provide $Na^+$ depletion/repletion methods for identifying a selective blocker of a persistent $Na^+$ channel, hyperpolarization methods for identifying a blocker of a persistent $Na^+$ channel, and Na/K ATPase pump inhibitor methods for identifying a selective blocker of a persistent $Na^+$ channel.

12 Claims, 24 Drawing Sheets

Providing sample

Depolarizing cell

Generating current
Detecting fluorescence emitted

Generating current
Detecting fluorescence emitted

Providing sample

Adding Potential Blocker
Detecting fluorescence emitted

Adding Potential Blocker
Detecting fluorescence emitted

Providing sample

Depolarizing cell
Detecting fluorescence emitted

Depolarizing cell
Detecting fluorescence emitted

Providing sample

Depolarizing cell
Detecting fluorescence emitted

Depolarizing cell
Detecting fluorescence emitted

FIG. 15A.

|   | 1 | 2 | 3 | 4 | 5 | 6 | 7 | 8 | 9 | 10 | 11 | 12 |
|---|---|---|---|---|---|---|---|---|---|----|----|----|
| A |   |   |   |   |   |   |   |   |   |    |    |    |
| B |   |   |   |   |   |   |   |   |   |    |    |    |
| C |   |   | Control |  |  | 1 uM TTX | | Control | | | | |
| D |   |   |   |   |   |   |   |   |   |    |    |    |
| E |   |   |   |   |   |   |   |   |   |    |    |    |
| F |   |   |   |   |   |   |   |   |   |    |    |    |
| G |   |   |   |   |   |   |   |   |   |    |    |    |
| H |   |   |   |   |   |   |   |   |   |    |    |    |

FIG. 15B.

|   | 1 | 2 | 3 | 4 | 5 | 6 | 7 | 8 | 9 | 10 | 11 | 12 |
|---|---|---|---|---|---|---|---|---|---|----|----|----|
| A | Control | | 0.5 | 1.4 | 4 | 12 | 37 | 111 | 333 | 1000 | Control | |
| B | | | | | | | | | | | | |
| C | | | | | | | | | | | | |
| D | | | | | | | | | | | | |
| E | | | | | | | | | | | | |
| F | | | | | | | | | | | | |
| G | | | | | | | | | | | | |
| H | | | | | | | | | | | | |

HIGH-THROUGHPUT SCREEN FOR IDENTIFYING SELECTIVE PERSISTENT SODIUM CHANNELS CHANNEL BLOCKERS

This application is a divisional that claims priority pursuant 35 U.S.C. §120 to U.S. patent application Ser. No. 11/313,450, filed Dec. 19, 2005, now U.S. Pat. No. 7,361,478, a continuation-in-part application that claims priority pursuant to 35 U.S.C. §120 to U.S. patent application Ser. No. 09/989,797, now U.S. Pat. No. 6,991,910, filed Nov. 20, 2001, each of which is hereby incorporated by reference in its entirety.

All of the patents and publications cited in this application are hereby incorporated by reference in their entirety.

The lipid bilayer membrane of all cells forms a barrier that is largely impermeable to the flux of ions and water. Residing within the membrane is a superfamily of proteins called ion channels, which provide selective pathways for ion flux. Precisely regulated conductances produced by ion channels are required for intercellular signaling and neuronal excitability. In particular, a group of ion channels that open upon depolarization of excitable cells are classified as voltage-gated and are responsible for electrical activity in nerve, muscle and cardiac tissue. In neurons, ion currents flowing through voltage-gated sodium ion ($Na^+$) channels are responsible for rapid spike-like action potentials. During action potentials the majority of $Na^+$ channels open very briefly. These brief openings result in transient $Na^+$ currents. However, a subset of voltage-gated $Na^+$ channels does not close rapidly, but remain open for relatively long intervals. These channels therefore generate sustained or persistent $Na^+$ currents. The balance between transient and persistent $Na^+$ current is crucial for maintaining normal physiological function and electrical signaling throughout the entire nervous system.

Over the past 50 years, an increasing number of diseases of the nervous system and other excitable tissues have been shown to result from the dysregulation of ion channels. This class of disease has been termed channelopathies. Aberrant persistent sodium current can contribute to the development or progression of many channelopathic conditions because normal function is disrupted when neurons discharge signals inappropriately. For example, abnormal persistent sodium current is thought to induce deleterious phenomena, including, e.g., neuropathies, neurodegenerative diseases, movement disorders, cardiac arrhythmia, epileptic seizure, neuronal cell death, behavioral disorders and dementia, see, e.g., Robert S. Kass, *The Channelopathies: Novel Insights into Molecular and Genetic Mechanisms of Human Disease,* 115(8) J. Clin. Invest. 1986-1989 (2005); Alfred L. George, *Inherited Disorders of Voltage-gated Sodium Channels,* 115(8) J. Clin. Invest. 1990-1999 (2005); Karin Jurkat-Rott and Frank Lehmann-Horn, Muscle Channelopathies and Critical Points in Functional and Genetic Studies, 115(8) J. Clin. Invest. 2000-2009 (2005); Miriam H. Meisler and Jennifer A. Kearney, *Sodium Channel Mutations in Epilepsy and Other Neurological Disorders,* 115(8) J. Clin. Invest. 2010-2017 (2005); Arthur J. Moss and Robert S. Kass, *Long QT Syndrome: from Channels to Cardiac Arrhythmias,* 115(8) J. Clin. Invest. 2018-2024 (2005); Christoph Lossin et al., *Molecular Basis of an Inherited Epilepsy* 34(6) NEURON 877-84 (2002); Peter K. Stys et al., *Ionic Mechanisms of Anoxic Injury in Mammalian CNS White Matter: Role of $Na^+$ Channels and $Na^{(+)}$-$Ca^{2+}$ Exchanger,* 12(2) J. NEUROSCI. 430-439 (1992); Peter K. Stys et al., *Noninactivating, Tetrodotoxin-Sensitive $Na^+$ Conductance in Rat Optic Nerve Axons,* 90(15) PROC. NATL. ACAD. SCI. USA, 6976-6980 (1993); and Giti Garthwaite et al., *Mechanisms of Ischaemic Damage to Central White Matter Axons: A Quantitative Histological Analysis Using Rat Optic Nerve,* 94(4) NEUROSCIENCE 1219-1230 (1999). For example, in the case of the neuropathies embraced by epilepsy, there can be a brief electrical "storm" arising from neurons that are inherently unstable because of a genetic defect as in various types of inherited epilepsy, or from neurons made unstable by metabolic abnormalities such as low blood glucose, or alcohol. In other cases, the abnormal discharge can come from a localized area of the brain, such as in patients with epilepsy caused by head injury or brain tumor. In the case of ischemic injuries, such as, e.g., cerebral ischemia and myocardial ischemia, there can be prolonged electrical activity arising from neurons in which persistent sodium channel expression or activity is increased. Such aberrant electrical activity can cause or contribute to neuronal death, which can lead to debilitating injury or death of an individual. Aberrant electrical activity also can contribute to neurodegenerative disorders such as, without limitation, Parkinson's disease, Alzheimer's disease, Huntington's disease, amyotrophic lateral sclerosis and multiple sclerosis. Thus, aberrant persistent sodium current can contribute to development or progression of pathological conditions by collapsing the normal cell transmembrane gradient for sodium, leading to reverse operation of the sodium-calcium exchanger, and resulting in an influx of intracellular calcium, which injures the axon, see, e.g., Stys et al., supra, (1992). Therefore, selective reduction in the expression or activity of sodium channels capable of mediating persistent current relative to any reduction in normal voltage-gated (transient) sodium current can be useful for treating channelopathic conditions associated with increased persistent sodium current.

Recent evidence has revealed that increased activity from persistent $Na^+$ channels may be responsible for the underlying basis of chronic pain, see e.g., Fernando Cervero & Jennifer M. A. Laird, *Role of Ion Channels in Mechanisms Controlling Gastrointestinal Pain Pathways,* 3(6) CURR. OPIN. PHARMACOL. 608-612 (2003); Joel A. Black et al., *Changes in the Expression of Tetrodotoxin-Sensitive Sodium Channels Within Dorsal Root Ganglia Neurons in Inflammatory Pain,* 108(3) PAIN 237-247 (2004) and Li Yunru et al., *Role of Persistent Sodium and Calcium Currents in Motoneuron Firing and Spasticity in Chronic Spinal Rats,* 91(2) J. NEUROPHYSIOL. 767-783 (2004). Alterations in persistent sodium channel expression and/or function has a profound effect on the firing pattern of neurons in both the peripheral and central nervous systems. For example, injury to sensory primary afferent neurons often results in rapid redistribution of persistent sodium channels along the axon and dendrites and in abnormal, repetitive discharges or exaggerated responses to subsequent sensory stimuli. Such an exaggerated response is considered to be crucial for the incidence of spontaneous pain in the absence of external stimuli that is characteristic of chronic pain. In addition, inflammatory pain is associated with lowered thresholds of activation of nociceptive neurons in the periphery and altered persistent sodium channel function is thought to underlie aspects of this phenomenon. Likewise, neuropathic pain states resulting from peripheral nerve damage is associated with altered persistent sodium channel activity and ectopic action potential propagation. Therefore, selective reduction in the expression or activity of sodium channels capable of mediating persistent current relative to any reduction in normal voltage-gated (transient) sodium current can be useful for treating chronic pain conditions associated with increased persistent sodium current.

Besides their importance under physiological conditions, $Na^+$ channels are also important under pathophysiological situations. For example they appear play a role in epileptic seizures, cardiac arrhythmias, and ischemia/hypoxia-induced cardiac and neuronal cell death (Taylor et al, 1997; Ragsdale et al, 1998). Importantly, the persistent $Na^+$ current appears to play a major role in generating the above mentioned cellular abnormalities (Stys, 1998; Taylor et al, 1997). For example persistent $Na^+$ current is unregulated in both cardiac and neuronal cells during hypoxia (Saint et al, 1996; Hammarstrom, 1998) and may ultimately lead to overload of cell $Na^+$ and calcium, conditions leading to cell death (Stys, 1998). Blockers of voltage-gated $Na^+$ channels have been shown to be effective in ameliorating cellular dysfunctions and death resulting from errant operation of voltage-gated sodium channels (Stys, 1998). However, in many cases these blockers inhibit both the normal inactivating (transient) and non-inactivating (persistent) $Na^+$ channels to the same extent. Significant block of normal transient $Na^+$ channels could seriously compromise cellular and organ function or may even cause death. Thus assuming that the persistent $Na^+$ current is the therapeutic target, it is important to develop drugs that will block this component of $Na^+$ current but not the normal transient. However, in order to discern whether a compound selectively blocks the persistent over the transient $Na^+$ current conventional electrophysiological methods such as whole cell patch clamping or voltage clamping in oocyte preparations must be performed (Marty and Neher, 1995; Shih et al, 1998).

Thus, there exists a need for new screening methods that can be used to identify persistent $Na^+$ channel blockers useful for treating channelopathies and chronic pain. The present invention satisfies this need and provides related advantages as well, such as, e.g., high-throughput screens for identifying voltage-gated $Na^+$ channel blockers that selectively reduce or prevent persistent $Na^+$ currents.

BRIEF DESCRIPTION OF THE DRAWINGS

FIGS. 11A-C show histograms representing data obtained from three different assay plates. The screening window for a run was considered adequate $1.0 \geq Z \geq 0.5$.

FIG. 14A shows raw fluorescence signals are shown during application of the Na⁺ depletion/repletion protocol. Base line measurements in the presence of a Na⁺-free buffer are shown for the first 4 seconds of the record. After establishing of the base line fluorescence, a depolarizing buffer containing Na⁺ is applied to the well resulting a an initial rapid increase in fluorescence followed by a longer sustained increase (Control). In the presence of a saturating concentration of TTX (1 μM TTX) to block all the Na⁺ channel mediated signal, the initial response is lost and only the sustained non-channel mediated response remains. FIG. 14B shows a plot of the response after subtraction of the TTX resistant response from the control response. This analysis reveals the persistent Na⁺ current mediated signal.

FIG. 15A-B shows typical compound plate layouts for the persistent current assay on the FLIPR-tetra. FIG. 15A shows a 96-well plate layout for the screening window format. In this screening window format, a 96-well compound plate is organized such that columns 1-5 & 8-12 contain the normal Na⁺ repletion solution while columns 6-7 contain the Na⁺ repletion solution plus 1 μM TTX. FIG. 15B shows a 96-well plate layout for the dose-response format. For this drug screening dose-response protocol, columns 1-2 & 11-12 were used for positive and negative controls. The remaining columns contained different concentrations of the test compound with the highest concentration in column 10 and serial three-fold dilutions from column 9 through 3.

FIG. 16A shows a screenshot of the fluorescence responses from the FLIPR-Tetra. Plate was loaded as described in FIG. 15 A. Data are presented following the subtraction of the non-specific (TTX-resistant) response. FIG. 16B shows a bar graph of a screening window analysis of the data in FIG. 16A. Measurement of the peak response in the presence and absence of 1 μM TTX. Data are displayed as mean±SD. Z' factor of 0.70 was calculated as described in example 2 demonstrates an acceptable screening window for this assay.

FIG. 17A shows a screenshot of the fluorescence responses from the FLIPR-Tetra. This screenshot illustrates the persistent Na⁺ current mediated signal in wells loaded as described in FIG. 15 B. Columns 1 and 11 illustrate a negative control with no persistent current blocker and columns 2 and 12 show positive controls in the presence of 1 μM TTX. The remaining columns show a dose-response for TTX with increasing concentrations left to right. FIG. 17B shows the averaged responses from each column are plotted vs. the time for the TTX dose response. FIG. 17C shows the averaged data for TTX, Lidocaine, and Tetracaine are plotted as a semi-log dose response as mean±SD. The data is fitted by logistic function (lines) and the estimated IC$_{50}$ values are shown (mean±SD).

DETAILED DESCRIPTION

In the normal functioning of the nervous system, neurons are capable of receiving a stimulus, and in response, propagating an electrical signal away from their neuron cell bodies (soma) along processes (axons). From the axon, the signal is delivered to the synaptic terminal, where it is transferred to an adjacent neuron or other cell. It is the action potential that is responsible for electrical transmission in the nervous system, and contractility in the heart and skeletal muscle, see, e.g., Bertil Hille, *Ion Channels of Excitable Membranes* 3rd ed. Sinauer Associates, Inc. (Sunderland, Mass.) 2001. Generally, under resting conditions, sodium channels are closed until a threshold stimulus depolarizes the cell membrane. During membrane depolarization, sodium channels activate by opening the channel pore briefly (one millisecond) to rapidly generate the upstroke of the action potential and then inactivate by closing the channel pore until the excitable cell returns to its resting potential and the sodium channels re-enter the resting state.

Without wishing to be bound by the following, this behavior of voltage-gated sodium channels can be understood as follows. Sodium channels can reside in three major conformations or states. The resting or closed state predominates at membrane potentials more negative than approximately −60 mV. Upon depolarization, the channels open rapidly to allow current flow and, thereby, enter the active state. The transition from resting to active states occurs within a millisecond after depolarization to positive membrane potentials. Finally during sustained depolarizations of greater than 1-2 ms, the channels enter a second closed or inactivated state. Subsequent re-openings of the channels require a recycling of the channels from the inactive to the resting state, which occurs when the membrane potential returns to negative values. This means that membrane depolarization not only opens sodium channels but also causes them to close even during sustained depolarizations (Hodgkin and Huxley, 1952). Thus normal $Na^+$ channels open briefly during depolarization and are closed at rest.

Figure 1:
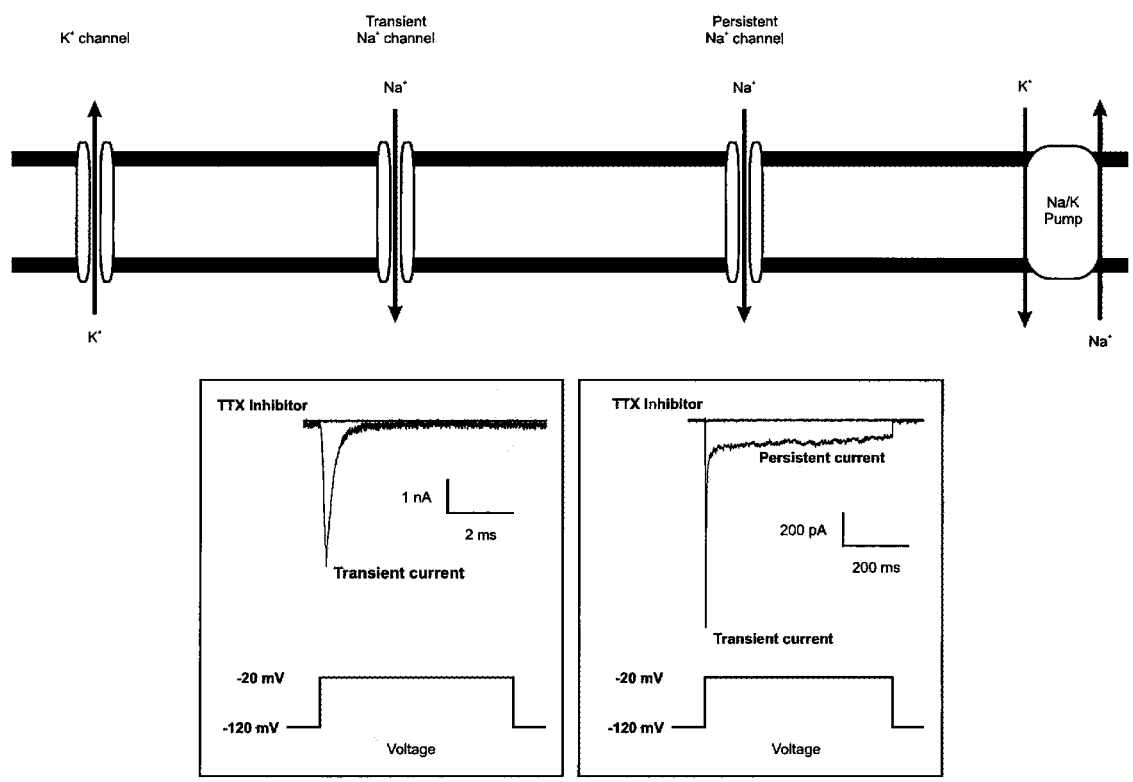
FIG. 1 a schematic of a basic ion channel mechanism. The top illustration shows a $K^+$ channel and $K^+$ ion flow, a transient $Na^+$ channel and ion flow, a persistent $Na^+$ channel and ion flow and a Na/K ATPase pump and $K^+$ and $Na^+$ ion flow. While drawn as separate channels here, the same $Na^+$ channel can have both transient and persistent current properties. The bottom panels show a current recording from a cell containing a transient $Na^+$ current (left panel) and a recording from a cell containing both transient and persistent $Na^+$ currents (right panel). Current vs. time is plotted for a voltage-gated $Na^+$ current. In the left panel, the initial transient current is shown during a 2 msec depolarization. In the right panel, the initial transient current and a smaller sustained persistent current are shown during a 200 msec depolarization.

However, some $Na^+$ channels may be open under resting conditions at relatively negative membrane potentials and even during sustained depolarization (Stys, 1998; Taylor, 1993). These non-inactivating $Na^+$ channels generate what is known as a persistent $Na^+$ current, see FIG. 1. Persistent $Na^+$ channels have these properties because they activate (open) at more negative membrane potentials than normal $Na^+$ channels and inactivate at more positive potentials (Alonso et al, 1999). This means that these persistent $Na^+$ channels may be open at membrane potentials as negative as −80 mV (Stys, 1998) and stay open at potentials as positive as 0 mV (Alonso, et al, 1999). These persistent $Na^+$ channels are thought to be involved in synaptic amplification and modification of spiking behavior and also in the generation of conditions leading to cellular dysfunction (Ragsdale et al, 1998; and Taylor, 1993). This unique property of persistent $Na^+$ channels is exploited in the assays in accordance with the present invention.

Aspects of the present invention provide $Na^+$ depletion/repletion methods for identifying a selective blocker of a persistent $Na^+$ channel, such method comprising the steps of a) providing a test sample 1 comprising a $Na^+$-free physiological solution, a voltage-sensitive fluorescence dye, a cell having a $K^+$ channel, a transient $Na^+$ channel and a persistent $Na^+$ channel; and a potential $Na^+$ channel blocker; b) depolarizing the membrane of the cell in the test sample 1; c) generating a current through the persistent $Na^+$ channel by adding $Na^+$ to test sample 1 at least 10 msec after step (b); d) detecting fluorescence emitted by the voltage-sensitive dye in test sample 1; e) providing a control sample 1 comprising a $Na^+$-free physiological solution, a voltage-sensitive fluorescence dye, and a cell having a $K^+$ channel, a transient $Na^+$ channel and a persistent $Na^+$ channel; f) depolarizing the membrane of the cell in the control sample 1; g) generating a current through the persistent $Na^+$ channel by adding $Na^+$ ions to the control sample 1 at least 10 msec after step (f); h) detecting fluorescence emitted by the voltage-sensitive dye in the control sample 1; i) comparing the emitted fluorescence from step (d) to the emitted fluorescence from step (h).

Other aspects of the present invention $Na^+$ depletion/repletion provide a method for identifying a selective blocker of a persistent $Na^+$ channel, such method comprising the steps of a) providing a test sample 1 comprising a $Na^+$-free physiological solution, a voltage-sensitive fluorescence dye, a cell having a $K^+$ channel, a transient $Na^+$ channel and a persistent $Na^+$ channel, and a potential $Na^+$ channel blocker; b) depolarizing the membrane of the cell in the test sample 1; c) generating a current through the persistent $Na^+$ channel by adding $Na^+$ to test sample 1 at least 10 msec after step (b); d) detecting fluorescence emitted by the voltage-sensitive dye in test sample 1; e) providing a control sample 1 comprising a $Na^+$-free physiological solution, a voltage-sensitive fluorescence dye, and a cell having a $K^+$ channel, a transient $Na^+$ channel and a persistent $Na^+$ channel; f) depolarizing the membrane of the cell in the control sample 1; g) generating a current through the persistent $Na^+$ channel by adding $Na^+$ ions to the control sample 1 at least 10 msec after step (f); h) detecting fluorescence emitted by the voltage-sensitive dye in the control sample 1; i) determining the relative emitted fluorescence 1 by comparing the emitted fluorescence from step (d) to the emitted fluorescence from step (h); j) providing a test sample 2 comprising a physiological solution, a voltage-sensitive fluorescence dye, a cell having a $K^+$ channel and a transient $Na^+$ channel, and a potential $Na^+$ channel blocker; k) depolarizing membrane of the cell in test sample 2; l) detecting the fluorescence emitted by the voltage-sensitive dye in test sample 2; m) providing a control sample 2 comprising a physiological solution, a voltage-sensitive fluorescence dye, and a cell having a $K^+$ channel and a transient $Na^+$ channel; n) depolarizing membrane of the cell in control sample 2; o) detecting the fluorescence emitted by the voltage-sensitive dye in control sample 2; p) determining a relative emitted fluorescence 2 by comparing the emitted fluorescence from step (l) to the emitted fluorescence from step (o); and q) comparing the relative emitted fluorescence 1 in step (i) with the relative emitted fluorescence 2 in step (p).

Other aspects of the present invention provide a hyperpolarization method for identifying a blocker of a persistent $Na^+$ channel, such method comprising the steps of a) providing a test sample 1 comprising a physiological solution, a voltage-sensitive fluorescence dye, and a cell having a $K^+$ channel and a persistent $Na^+$ channel wherein a resting membrane potential of the cell is approximately halfway between an equilibrium potential of $Na^+$ and an equilibrium potential of $K^+$; b) detecting fluorescence emitted by the voltage-sensitive dye in test sample 1; c) adding a potential $Na^+$ channel blocker to test sample 1; d) detecting fluorescence emitted by the voltage-sensitive dye in the test sample 1; e) comparing the emitted fluorescence from step (b) with the emitted fluorescence from step (d).

Other aspects of the present invention provide a hyperpolarization method for identifying a blocker of a persistent Na$^+$ channel, such method comprising the steps of a) providing a test sample 1 comprising a physiological solution, a voltage-sensitive fluorescence dye, and a cell having a K$^+$ channel and a persistent Na$^+$ channel wherein a resting membrane potential of the cell is approximately halfway between an equilibrium potential of Na$^+$ and an equilibrium potential of K$^+$; b) detecting fluorescence emitted by the voltage-sensitive dye in test sample 1; c) adding a potential Na$^+$ channel blocker to test sample 1; d) detecting fluorescence emitted by the voltage-sensitive dye in the test sample 1; e) determining a relative emitted fluorescence 1 by comparing the emitted fluorescence from step (b) with the emitted fluorescence from step (d); f) providing a test sample 2 comprising a physiological solution, a voltage-sensitive fluorescence dye, a cell having a K$^+$ channel and a transient Na$^+$ channel, and a potential Na$^+$ channel blocker; g) depolarizing the membrane of the cell in test sample 2; h) detecting the fluorescence emitted by the voltage-sensitive dye in test sample 2; i) providing a control sample 2 comprising a physiological solution, a voltage-sensitive fluorescence dye, and a cell having a K$^+$ channel and a transient Na$^+$ channel; j) depolarizing the membrane of the cell in control sample 2; k) detecting the fluorescence emitted by the voltage-sensitive dye in control sample 2; l) determining a relative emitted fluorescence 2 by comparing the emitted fluorescence from step (h) relative to an emitted fluorescence from step (k); and m) comparing the relative emitted fluorescence in step (e) with the relative emitted fluorescence in step (l).

Other aspects of the present invention provide a Na/K ATPase pump inhibitor method for identifying a blocker of a persistent Na$^+$ channel, such method comprising the steps of a) providing a test sample 1 comprising a Cl$^-$-free physiological solution, a voltage-sensitive fluorescence dye, a cell having a K$^+$ channel and a persistent Na$^+$ channel wherein a K$^+$ conductance of the K$^+$ channel is at least 20-fold higher than a Na$^+$ conductance from the persistent Na$^+$ channel, and a potential Na$^+$ channel blocker; b) depolarizing the membrane of the cell with a Na/K pump inhibitor to the test sample 1; c) detecting fluorescence emitted by the voltage-sensitive dye in test sample 1; d) providing a control sample 1 comprising a Cl$^-$-free physiological solution, a voltage-sensitive fluorescence dye, and a cell having a K$^+$ channel and a persistent Na$^+$ channel wherein a K$^+$ conductance of the K$^+$ channel is at least 20-fold higher than a Na$^+$ conductance from the persistent Na$^+$ channel; e) depolarizing the membrane of the cell with a Na/K pump inhibitor to the control sample 1; f) detecting fluorescence emitted by the voltage-sensitive dye in the control sample 1; g) comparing the emitted fluorescence from step (c) to the emitted fluorescence from step (f).

Other aspects of the present invention provide a Na/K ATPase pump inhibitor method for identifying a selective blocker of a persistent Na$^+$ channel, such method comprising the steps of a) providing a test sample 1 comprising a Cl$^-$-free physiological solution, a voltage-sensitive fluorescence dye, a cell having a K$^+$ channel and a persistent Na$^+$ channel wherein a K$^+$ conductance of the K$^+$ channel is at least 20-fold higher than a Na$^+$ conductance from the persistent Na$^+$ channel, and a potential Na$^+$ channel blocker; b) depolarizing the membrane of the cell with a Na/K pump blocker to the test sample 1; c) detecting fluorescence emitted by the voltage-sensitive dye in test sample 1; d) providing a control sample 1 comprising a Cl$^-$-free physiological solution, a voltage-sensitive fluorescence dye, and a cell having a K$^+$ channel and a persistent Na$^+$ channel wherein a K$^+$ conductance of the K$^+$ channel is at least 20-fold higher than a Na$^+$ conductance from the persistent Na$^+$ channel; e) depolarizing the membrane of the cell with a Na/K pump blocker to the control sample 1; f) detecting fluorescence emitted by the voltage-sensitive dye in the control sample 1; g) comparing the emitted fluorescence from step (c) to the emitted fluorescence from step (f); h) providing a test sample 2 comprising a physiological solution, a voltage-sensitive fluorescence dye, a cell having a K$^+$ channel and a transient Na$^+$ channel, and a potential Na$^+$ channel blocker; i) depolarizing the membrane of the cell in test sample 2; j) detecting the fluorescence emitted by the voltage-sensitive dye in test sample 2; k) providing a control sample 2 comprising a physiological solution, a voltage-sensitive fluorescence dye, and a cell having a K$^+$ channel and a transient Na$^+$ channel; l) depolarizing the membrane of the cell in control sample 2; m) detecting the fluorescence emitted by the voltage-sensitive dye in control sample 2; n) comparing the emitted fluorescence from step (j) relative to an emitted fluorescence from step (m); and o) comparing the difference in step (g) with the difference in step (n).

Aspects of the present invention provide, in part, a selective persistent Na$^+$ current blocker. As used herein, the term "persistent Na$^+$ current blocker" means any molecule that for at least one particular dose can reduce or prevent a persistent Na$^+$ current. As used herein, the term "selective persistent Na$^+$ current blocker" means any molecule that for at least one particular dose can selectively reduce or prevent a persistent Na$^+$ current as compared to a transient Na$^+$ current. As used herein, the term "selective" means to have a unique effect or influence or reacting in only one way or with only one thing. It is envisioned that a selective persistent Na$^+$ channel blocker can modulate a persistent Na$^+$ current derived from at least one persistent Na$^+$ channel in an antagonistic manner by reducing or preventing a persistent Na$^+$ current. It is further envisioned that a selective persistent Na$^+$ channel blocker acting in an antagonistic manner can do so in a competitive or non-competitive way. Non-limiting examples of a selective persistent Na$^+$ channel blocker acting in an antagonistic manner include, e.g., a persistent Na$^+$ channel pan-antagonist that reduces or prevents persistent Na$^+$ current generated from all persistent Na$^+$ channel subunits, a persistent Na$^+$ channel-selective antagonist that reduces or prevents persistent Na$^+$ current generated from a subgroup of persistent Na$^+$ channel subunits, and a persistent Na$^+$ channel-specific antagonist that reduces or prevents persistent Na$^+$ current generated from only one persistent Na$^+$ channel subunit.

In an aspect of this embodiment, a selective persistent Na$^+$ current blocker prevents persistent Na$^+$ current but does not affect a transient Na$^+$ current. In aspects of this embodiment, a selective persistent Na$^+$ current blocker prevents persistent Na$^+$ current and affects, e.g., at most 5% of a transient Na$^+$ current, at most 10% of a transient Na$^+$ current, at most 15% of a transient Na$^+$ current, at most 20% of a transient Na$^+$ current or at most 25% of a transient Na$^+$ current. In other aspects of this embodiment, a selective persistent Na$^+$ current blocker reduces a persistent Na$^+$ current by, e.g., at least 50%, at least 60%, at least 70%, at least 80%, at least 90% or at least 95%, and affects, e.g., at most 5% of a transient Na$^+$ current, at most 10% of a transient Na$^+$ current, at most 15% of a transient Na$^+$ current, at most 20% of a transient Na$^+$ current or at most 25% of a transient Na$^+$ current.

In aspects of this embodiment, a selective persistent Na$^+$ current blocker can reduce a persistent Na$^+$ current by, e.g., at least 20-fold more than transient sodium current is reduced, at least 30-fold more than transient sodium current is reduced, at least 40-fold more than transient sodium current is reduced, at least 50-fold more than transient sodium current is reduced, at least 60-fold more than transient sodium current is reduced, at least 70-fold more than transient sodium current is reduced, at least 80-fold more than transient sodium current is reduced, at least 90-fold more than transient sodium current is reduced or at least 100-fold more than transient sodium current is reduced. In yet other aspects of this embodiment, a selective persistent $Na^+$ current blocker can reduce a persistent $Na^+$ current by, e.g., at least 100-fold more than transient sodium current is reduced, at least 200-fold more than transient sodium current is reduced, at least 300-fold more than transient sodium current is reduced, at least 400-fold more than transient sodium current is reduced, at least 500-fold more than transient sodium current is reduced, at least 600-fold more than transient sodium current is reduced, at least 700-fold more than transient sodium current is reduced, at least 800-fold more than transient sodium current is reduced, at least 900-fold more than transient sodium current is reduced or at least 1000-fold more than transient sodium current is reduced.

In an embodiment, selective persistent $Na^+$ current blocker can be a persistent $Na^+$ channel pan-antagonist. In an aspect of this embodiment, a persistent $Na^+$ channel pan-antagonist prevents persistent $Na^+$ current generated from all persistent $Na^+$ channel subunits but does not affect a transient $Na^+$ current. In aspects of this embodiment, a persistent $Na^+$ channel pan-antagonist prevents persistent $Na^+$ current generated from all persistent $Na^+$ channel subunits and affects, e.g., at most 5% of a transient $Na^+$ current, at most 10% of a transient $Na^+$ current, at most 15% of a transient $Na^+$ current, at most 20% of a transient $Na^+$ current or at most 25% of a transient $Na^+$ current. In other aspects of this embodiment, a persistent $Na^+$ channel pan-antagonist reduces persistent $Na^+$ current generated from all persistent $Na^+$ channel subunits by, e.g., at least 50%, at least 60%, at least 70%, at least 80%, at least 90% or at least 95%, and affects, e.g., at most 5% of a transient $Na^+$ current, at most 10% of a transient $Na^+$ current, at most 15% of a transient $Na^+$ current, at most 20% of a transient $Na^+$ current or at most 25% of a transient $Na^+$ current.

In aspects of this embodiment, a persistent $Na^+$ channel pan-antagonist can reduce persistent $Na^+$ current generated from all persistent $Na^+$ channel subunits by, e.g., at least 20-fold more than transient sodium current is reduced, at least 30-fold more than transient sodium current is reduced, at least 40-fold more than transient sodium current is reduced, at least 50-fold more than transient sodium current is reduced, at least 60-fold more than transient sodium current is reduced, at least 70-fold more than transient sodium current is reduced, at least 80-fold more than transient sodium current is reduced, at least 90-fold more than transient sodium current is reduced or at least 100-fold more than transient sodium current is reduced. In yet other aspects of this embodiment, a persistent $Na^+$ channel pan-antagonist can reduce a persistent $Na^+$ current generated from all persistent $Na^+$ channel subunits by, e.g., at least 100-fold more than transient sodium current is reduced, at least 200-fold more than transient sodium current is reduced, at least 300-fold more than transient sodium current is reduced, at least 400-fold more than transient sodium current is reduced, at least 500-fold more than transient sodium current is reduced, at least 600-fold more than transient sodium current is reduced, at least 700-fold more than transient sodium current is reduced, at least 800-fold more than transient sodium current is reduced, at least 900-fold more than transient sodium current is reduced or at least 1000-fold more than transient sodium current is reduced.

In an embodiment, selective persistent $Na^+$ current blocker can be a persistent $Na^+$ channel-selective antagonist. In an aspect of this embodiment, a persistent $Na^+$ channel-selective antagonist prevents persistent $Na^+$ current generated from a subgroup of persistent $Na^+$ channel subunits but does not affect a transient $Na^+$ current. In aspects of this embodiment, a persistent $Na^+$ channel-selective antagonist prevents persistent $Na^+$ current generated from a subgroup of persistent $Na^+$ channel subunits and affects, e.g., at most 5% of a transient $Na^+$ current, at most 10% of a transient $Na^+$ current, at most 15% of a transient $Na^+$ current, at most 20% of a transient $Na^+$ current or at most 25% of a transient $Na^+$ current. In other aspects of this embodiment, a persistent $Na^+$ channel-selective antagonist reduces persistent $Na^+$ current generated from a subgroup of persistent $Na^+$ channel subunits by, e.g., at least 50%, at least 60%, at least 70%, at least 80%, at least 90% or at least 95%, and affects, e.g., at most 5% of a transient $Na^+$ current, at most 10% of a transient $Na^+$ current, at most 15% of a transient $Na^+$ current, at most 20% of a transient $Na^+$ current or at most 25% of a transient $Na^+$ current.

In aspects of this embodiment, a persistent $Na^+$ channel-selective antagonist can reduce persistent $Na^+$ current generated from a subgroup of persistent $Na^+$ channel subunits by, e.g., at least 20-fold more than transient sodium current is reduced, at least 30-fold more than transient sodium current is reduced, at least 40-fold more than transient sodium current is reduced, at least 50-fold more than transient sodium current is reduced, at least 60-fold more than transient sodium current is reduced, at least 70-fold more than transient sodium current is reduced, at least 80-fold more than transient sodium current is reduced, at least 90-fold more than transient sodium current is reduced or at least 100-fold more than transient sodium current is reduced. In yet other aspects of this embodiment, a persistent $Na^+$ channel-selective antagonist can reduce a persistent $Na^+$ current generated from a subgroup of persistent $Na^+$ channel subunits by, e.g., at least 100-fold more than transient sodium current is reduced, at least 200-fold more than transient sodium current is reduced, at least 300-fold more than transient sodium current is reduced, at least 400-fold more than transient sodium current is reduced, at least 500-fold more than transient sodium current is reduced, at least 600-fold more than transient sodium current is reduced, at least 700-fold more than transient sodium current is reduced, at least 800-fold more than transient sodium current is reduced, at least 900-fold more than transient sodium current is reduced or at least 1000-fold more than transient sodium current is reduced.

In an embodiment, selective persistent $Na^+$ current blocker can be a persistent $Na^+$ channel-specific antagonist. In an aspect of this embodiment, a persistent $Na^+$ channel-specific antagonist prevents persistent $Na^+$ current generated from only one persistent $Na^+$ channel subunit but does not affect a transient $Na^+$ current. In aspects of this embodiment, a persistent $Na^+$ channel-specific antagonist prevents persistent $Na^+$ current generated from only one persistent $Na^+$ channel subunits and affects, e.g., at most 5% of a transient $Na^+$ current, at most 10% of a transient $Na^+$ current, at most 15% of a transient $Na^+$ current, at most 20% of a transient $Na^+$ current or at most 25% of a transient $Na^+$ current. In other aspects of this embodiment, a persistent $Na^+$ channel-specific antagonist reduces persistent $Na^+$ current generated from only one persistent $Na^+$ channel subunits by, e.g., at least 50%, at least 60%, at least 70%, at least 80%, at least 90% or at least 95%, and affects, e.g., at most 5% of a transient $Na^+$ current, at most 10% of a transient $Na^+$ current, at most 15% of a transient $Na^+$ current, at most 20% of a transient $Na^+$ current or at most 25% of a transient $Na^+$ current.

In aspects of this embodiment, a persistent $Na^+$ channel-specific antagonist can reduce persistent $Na^+$ current generated from only one persistent Na$^+$ channel subunits by, e.g., at least 20-fold more than transient sodium current is reduced, at least 30-fold more than transient sodium current is reduced, at least 40-fold more than transient sodium current is reduced, at least 50-fold more than transient sodium current is reduced, at least 60-fold more than transient sodium current is reduced, at least 70-fold more than transient sodium current is reduced, at least 80-fold more than transient sodium current is reduced, at least 90-fold more than transient sodium current is reduced or at least 100-fold more than transient sodium current is reduced. In yet other aspects of this embodiment, a persistent Na$^+$ channel-specific antagonist can reduce a persistent Na$^+$ current generated from only one persistent Na$^+$ channel subunits by, e.g., at least 100-fold more than transient sodium current is reduced, at least 200-fold more than transient sodium current is reduced, at least 300-fold more than transient sodium current is reduced, at least 400-fold more than transient sodium current is reduced, at least 500-fold more than transient sodium current is reduced, at least 600-fold more than transient sodium current is reduced, at least 700-fold more than transient sodium current is reduced, at least 800-fold more than transient sodium current is reduced, at least 900-fold more than transient sodium current is reduced or at least 1000-fold more than transient sodium current is reduced.

Aspects of the present invention provide, in part, a test sample and a control sample. As used herein, the term "test sample" means a sample comprising a potential persistent Na$^+$ channel blocker. As used herein, the term "potential persistent Na$^+$ channel blocker" means any molecule that is to be tested for its ability to reduce or prevent a persistent Na$^+$ current derived from at least one persistent Na$^+$ channel. A potential persistent Na$^+$ channel blocker can be an inorganic molecule or an organic molecule. As used herein, the term "control sample" means a sample of the same or similar type as the test sample under the same conditions but which does not contain a potential persistent Na$^+$ channel blocker. In addition, a control sample may comprise a defined molecule known not to be a persistent Na$^+$ channel blocker (a negative control molecule) or a defined molecule known to be a persistent Na$^+$ channel blocker (a positive control molecule). One skilled in the art understands that a variety of control samples are useful in the methods of the invention and that a control sample can be a positive control sample or a negative control sample.

Aspects of the present invention provide, in part, a physiological solution. As used herein, the term "physiological solution" means a solutioned solution comprising physiological concentrations of sodium, potassium, magnesium, calcium and chloride. It is also envisioned that any and all physiological solutions that allow an electrical current to be measured from the solution can be used in methods disclosed in the present specification. Optionally, a physiological solution can contain inhibitors for other ion conductances, such as, e.g., a concentration of cadmium that prevents or reduces calcium current. A physiological solution can be varied as appropriate by one skilled in the art and generally depend, in part, on the assay protocol, the cell or the detection method employed. Ion concentration can be varied as appropriate by one skilled in the art and generally depend, in part, on the buffering capacity of a particular buffer being used and the detection means employed.

Aspects of the present invention provide, in part, a Na$^+$-free physiological solution. As used herein, the term "Na$^+$-free physiological solution" means a buffered solution comprising physiological concentrations of a non-permeant sodium substitute, potassium, magnesium, calcium and chloride. It is also envisioned that any and all Na$^+$-free physiological solutions that allow an electrical current to be measured from the solution can be used in methods disclosed in the present specification. A non-permeant sodium substitute substitutes Na$^+$ with an analog cation molecule, such as, e.g., TEA or NMDG$^+$. It is also envisioned that any and all Na$^+$-free physiological solutions that allow an electrical current to be measured from the solution can be used in methods disclosed in the present specification. Optionally, a Na$^+$-free solution can contain inhibitors for other ion conductances, such as, e.g., a concentration of cadmium that prevents or reduces calcium current. A Na$^+$-free physiological solution can be varied as appropriate by one skilled in the art and generally depend, in part, on the assay protocol, the cell or the detection method employed. Ion concentration can be varied as appropriate by one skilled in the art and generally depend, in part, on the buffering capacity of a particular buffer being used and the detection means employed.

Aspects of the present invention provide, in part, a Cl$^-$-free physiological solution. As used herein, the term "Cl$^-$-free physiological solution" means a buffered solution comprising physiological concentrations of a non-permeate chloride substitute, potassium, magnesium, calcium and sodium. It is also envisioned that any and all Cl$^-$-free physiological solutions that allow an electrical current to be measured from the solution can be used in methods disclosed in the present specification. A non-permeant chloride substitute substitutes Cl$^-$ with an analog molecule, such as, e.g., gluconate, aspartate, glutamate, cyclamate and methanesulfonate. It is also envisioned that any and all Cl$^-$-free physiological solutions that allow an electrical current to be measured from the solution can be used in methods disclosed in the present specification. Optionally, a Cl$^-$-free solution can contain inhibitors for other ion conductances, such as, e.g., a concentration of cadmium that prevents or reduces calcium current. A Cl$^-$-free physiological solution can be varied as appropriate by one skilled in the art and generally depend, in part, on the assay protocol, the cell or the detection method employed. Ion concentration can be varied as appropriate by one skilled in the art and generally depend, in part, on the buffering capacity of a particular buffer being used and the detection means employed.

A physiological solution, Na$^+$-free physiological solution or Cl$^-$-free physiological solution can be buffered, e.g., 2-amino-2-hydroxymethyl-1,3-propanediol (Tris) buffers; Phosphate buffers, such as, e.g., potassium phosphate buffers and sodium phosphate buffers; Good buffers, such as, e.g., piperazine-N,N'-bis(2-ethanesulfonic acid) (PIPES), N,N'-bis(2-hydroxyethyl)-2-aminoethanesulfonic acid (BES), 3-(N-morpholino) propanesulfonic acid (MOPS), N-(2-hydroxyethyl) piperazine-N'-(2-ethanesulfonic acid) (HEPES), piperazine-N,N'-bis(2-hydroxypropanesulfonic acid) (POPSO), N-tris(hydroxymethyl) methylglycine (Tricine), N-tris(hydroxymethyl)methyl-3-aminopropanesulfonic acid (TAPS), 3-[(1,1-dimethyl-2-hydroxyethyl)amino]-2-hydroxypropanesulfonic acid (AMPSO, 3-(cyclohexylamino)-2-hydroxy-1-propanesulfonic acid (CAPSO), and 3-(cyclohexylamino)-1-propanesulfonic acid (CAPS); saline buffers, such as, e.g., Phosphate-buffered saline (PBS), HEPES-buffered saline, Tris-buffered saline (TBS) and Ringer's. Thus, aspects of this embodiment may include a buffer concentration of, e.g., at least 1 mM, at least 5 mM, at least 10 mM, at least 20 mM, at least 30 mM, at least 40 mM, at least 50 mM, at least 60 mM, at least 70 mM, at least 80 mM, at least 90 mM, or at least 100 mM. Non-limiting examples of how to make and use specific buffers are described in, e.g., MOLECULAR CLONING, A LABORATORY MANUAL, supra, (2001).

Aspects of the present invention provide, in part, a voltage-sensitive fluorescent dye. The plasma membrane of a cell typically has a transmembrane potential of approximately −70 mV (negative inside) as a consequence of $K^+$, $Na^+$ and $Cl^−$ concentration gradients maintained by active transport processes. Voltage-sensitive fluorescent dyes can directly measure changes in membrane potential resulting from the translocation of these ions. It is envisioned that any voltage-sensitive florescent dye capable of detecting a change in cell membrane potential can be used, including, without limitation, coumarin dyes, such as, e.g., N-(6-chloro-7-hydroxy-coumarin-3-carbonyl)-dimyristoylphosphatidyl-ethanolamine (CC2-DMPE); anionic and hybrid oxonol dyes, such as, e.g., bis-oxonol, oxonol V (bis-(3-phenyl-5-oxoisoxazol-4-yl) pentamethine oxonol), oxonol VI (bis-(3-propyl-5-oxoisoxazol-4-yl) pentamethine oxonol), bis-(1,3-diethylthiobarbituric acid)trimethine oxonol ($DiSBAC_2(3)$), bis-(1,3-dibutylbarbituric acid)trimethine oxonol ($DiBAC_4(3)$), bis-(1,3-dibutylbarbituric acid)pentamethine oxonol ($DiBAC_4(5)$), RH-155 (NK3041), RH-479 (JPW1131), RH-482 (JPW1132, NK3630), RH-1691, RH-1692, RH-1838 R-1114 (WW781), JPW1177 and JPW1245; hemicyanine dyes, such as, e.g., dibutylamino-naphtalene-butylsulfonato-isoquinolinium (BNBIQ); merocyanine dyes, such as, e.g., merocyanine 540, NK2495 (WW375) and JPW1124; cationic or zwitterionic styryl dyes, such as, e.g., di-4-butyl-amino-naphthyl-ethylene-pyridinium-propyl-sulfonate (di-4-ANEPPS), di-8-butyl-amino-naphthyl-ethylene-pyridinium-propyl-sulfonate (di-8-ANEPPS), di-12-ANEPPS, di-18:2-ANEPPS, di-2-ANEPEQ (JPW1114), di-12-ANEPEQ, di-8-ANEPPQ, di-12-ANEPPQ, di-1-ANEPIA, D-6923 (JPW3028), N-(4-sulfobutyl)-4-(6-(4-(dibutylamino)phenyl)hexatrienyl) pyridinium (RH-237), N-(3-triethylammoniumpropyl)-4-(4-(4-(diethylamino)phenyl)butadienyl) pyridinium dibromide (RH-414), N-(4-sulfobutyl)-4-(4-(4-(dipentylamino)phenyl)butadienyl) pyridinium (RH-421) and RH-437, RH-461, RH-795, JPW1063 and FM1-43; and cationic carbocyanines and rhodamines, such as, e.g., 3,3'-diethyloxacarbocyanine iodide ($DiOC_2(3)$), 3,3'-dihexyloxacarbocyanine iodide ($DiOC_6(3)$), 3,3'-dimethyl-naphthoxacarbocyanine iodide (JC-9; $DiNOC1(3)$), 3,3'-dipentyloxacarbocyanine iodide ($DiOC_5(3)$), 3,3'-dipropylthiadicarbocyanine iodide ($DiSC_3(5)$), 1,1',3,3,3',3'-hexamethylindodicarbocyanine iodide ($DiIC_1(5)$), rhodamine, rhodamine 123, 5,5',6,6'-tetrachloro-1,1',3,3'-tetraethylbenzimidazolylcarbocyanine iodide ($CBIC_2(3)$), tetramethylrhodamine, ethyl ester, perchlorate (TMRE) and tetramethylrhodamine, methyl ester, perchlorate (TMRM). The class of dye determines factors such as accumulation in cells, response mechanism and toxicity.

Voltage-sensitive fluorescent dyes can also be divided into two general categories of based on whether there is a relatively fast intramolecular redistribution of electrons or a relatively slow transmembrane movement of entire dye (Table 1). Fast-response dyes undergo electric field-driven changes of intramolecular charge distribution in response to a change in the surrounding electric field. This change in electronic structure produce corresponding changes in the spectral properties or intensity of their fluorescence. The optical response of these dyes is sufficiently fast to detect transient (millisecond) potential changes in excitable cells, including single neurons, cardiac cells and intact brains. However, the magnitude of their potential-dependent fluorescence change is often small; fast-response probes typically show a 2-10% fluorescence change per 100 mV. Non-limiting examples of Fast-response dyes include, e.g., di-2-ANEPEQ (JPW1114), di-1-ANEPIA, di-8-ANEPPQ, di-12-ANEPPQ, di-4-ANEPPS, di-8-ANEPPS, di-18:2-ANEPPS, RGA-30, RH-155, RH-795, RH-237, RH-421, RH-414 and WW 781.

Slow-response dyes are lipophilic anions or cations that are exhibit potential-dependent changes in their transmembrane distribution by an electrophoretic mechanism. Fluorescence changes associated with transmembrane redistribution result from sensitivity of the dye to intracellular and extracellular environments. The magnitude of their optical responses is much larger than that of fast-response probes (typically a 1% fluorescence change per mV). Slow-response probes, which include cationic carbocyanines and rhodamines and anionic oxonols, are suitable for detecting changes in average membrane potentials of non-excitable cells caused by respiratory activity, ion-channel permeability, drug binding and other factors. Non-limiting examples of Slow-response dyes include, e.g., $DiSBAC_4(3)$, $DiBAC_4(5)$, $DiBAC_4(3)$, $DiOC_5(3)$, $DiOC_6(3)$, $DiSC_3(5)$, $DiOC_2(3)$, $DiNOC_1(3)$, $DiIC_1(5)$, merocyanine 540, Oxonol V, Oxonol VI, rhodamine 123, TMRM, TMRE and $CBIC_2(3)$.

TABLE 1

Voltage-sensitive fluorescent dyes

| Dye | Response | Absorbance | Emission |
|---|---|---|---|
| di-2-ANEPEQ (JPW1114) | Fast | 517 | 721 |
| di-1-ANEPIA | Fast | — | — |
| di-8-ANEPPQ | Fast | 516 (467) | 721 (631) |
| di-12-ANEPPQ | Fast | 519 | 719 |
| di-1-ANEPMI | Fast | — | — |
| di-4-ANEPPS | Fast | 497 (475) | 705 (617) |
| di-8-ANEPPS | Fast | 498 | 713 |
| di-18:2-ANEPPS | Fast | 501 | 705 |
| RGA-30 | Fast | 629 | 659 |
| RH-155 | Fast | 650 | none |
| RH-795 | Fast | 530 | 712 |
| RH-237 | Fast | 528 (506) | 782 (687) |
| RH-421 | Fast | 515 (493) | 704 (638) |
| RH-414 | Fast | 532 | 716 |
| WW781 | Fast | 605 | 639 |
| $DiSBAC_4(3)$ | Slow | 535 | 560 |
| $DiBAC_4(5)$ | Slow | 590 | 616 |
| $DiBAC_4(3)$ | Slow | 493 | 516 |
| $DiOC_5(3)$ | Slow | 484 | 500 |
| $DiOC_6(3)$ | Slow | 484 | 501 |
| $DiSC_3(5)$ | Slow | 651 | 675 |
| $DiOC_2(3)$ | Slow | 482 | 497 |
| $DiNOC_1(3)$ | Slow | 522 | 535 |
| $DiIC_1(5)$ | Slow | 638 | 658 |
| merocyanine 540 | Slow | 555 | 578 |
| Oxonol V | Slow | 610 | 639 |
| Oxonol VI | Slow | 599 | 634 |
| rhodamine 123 | Slow | 507 | 529 |
| TMRM | Slow | 549 | 573 |
| TMRE | Slow | 549 | 574 |
| $CBIC_2(3)$ | Slow | 514 | 529 |

Spectra values are in methanol with values in parenthesis in a membrane environment. Absorbance and emission spectra of styryl dyes are at shorter wavelengths in membrane environments than in reference solvents such as methanol. The difference is typically 20 nm for absorption and 80 nm for emission, but varies considerably from one dye to another. Styryl dyes are generally nonfluorescent in water.

Voltage-sensitive fluorescent dyes have been widely used to monitor membrane potential within neuronal and other cell types, see, e.g., Amiram Grinvald et al., Optical imaging of neuronal activity, 68(4) Physiol. Rev. 1285-1366 (1988); C. R. Lowe and M J. Goldfinch, Solid-phase optoelectronic biosensors, 137 Methods Enzymol. 338-348 (1988); and Haralambos E. Katerinopoulos, The coumarin moiety as chromophore of fluorescent ion indicators in biological systems, 10(30) Curr. Pharm. Des. 3835-3852 (2004). Voltage-sensitive fluorescent dye with high sensitivity and rapidly response to a change in membrane potential and methods for measuring membrane potential using such dyes are well known to those skilled in the art, and are described in, e.g., Iain D. Johnson, *Fluorescent Probes for Living Cells* 30(3) HISTOCHEM. J. 123-140 (1998); and IMAGING NEURONS: A LABORATORY MANUAL (Rafael Yuste, et al., eds., Cold Spring Harbor Laboratory Press, 2000). In addition, the methods disclosed in the present specification can take advantage of the high temporal and spatial resolution utilized by fluorescence resonance energy transfer (FRET) in the measurement of membrane potential by voltage-sensitive dyes as described, see, e.g., Jesus E. Gonzalez & Roger Y. Tsien, *Improved Indicators of Cell Membrane Potential That Use Fluorescence Resonance Energy Transfer* 4(4) CHEM. BIOL. 269-277 (1997); Roger Y. Tsien & Jesus E. Gonzalez, *Voltage Sensing by Fluorescence Resonance Energy Transfer*, U.S. Pat. No. 5,661,035 (Aug. 26, 1997); Roger Y. Tsien & Jesus E. Gonzalez, *Detection of Transmembrane Potentials by Optical Methods*, U.S. Pat. No. 6,107,066 (Aug. 22, 2000).

It is also envisioned that assays involving Fluorescence Resonance Energy Transfer (FRET) can be used to detect a change in cell membrane potential. FRET is a distance dependent interaction between the electronic excited states of two molecules in which excitation is transferred from a donor fluorophore to an acceptor without emission of a photon. The process of energy transfer results in a reduction (quenching) of fluorescence intensity and excited state lifetime of the donor fluorophore and, where the acceptor is a fluorophore, can produce an increase in the emission intensity of the acceptor. Upon induction of a persistent $Na^+$ current, the membrane is depolarized, resulting in a separation of the donor/acceptor pair and thus the resonance energy transfer is reduced and can be detected, for example, by increased donor fluorescence emission, decreased acceptor fluorescence emission, or by a shift in the emission maxima from near the acceptor emission maxima to near the donor emission maxima. In the presence of a persistent current blocker, membrane depolarization and thus changes in FRET are reduced or prevented. If desired, the amount of persistent $Na^+$ current reduction or prevention, modulated by a persistent $Na^+$ channel, can be calculated as a function of the difference in the degree of FRET using the appropriate standards.

As a non-limiting example, a FRET pair comprises a voltage-sensitive mobile acceptor $DiSBAC^2(3)$ and a fluorescent, membrane-bound donor CC2-DMPE. When the cell interior has a relatively negative potential, the $DiSBAC^2(3)$ will bind to the exterior of the cell membrane, resulting in efficient FRET. When the cell interior has a relatively positive potential, however, the $DiSBAC^2(3)$ will bind to the interior of the cell membrane, thus separating the FRET pair and disrupting FRET. Other non-limiting examples of fluorophores useful as acceptors for the CC2-DMPE donor are listed in Table 2.

TABLE 2

| Donor Fluorophores and Acceptors | |
|---|---|
| Donor | Acceptor |
| CC2-DMPE | $DiSBAC^2(3)$ |
| CC2-DMPE | $DiSBAC^4(3)$ |
| CC2-DMPE | RH-155 (NK3041) |
| CC2-DMPE | RH-479 (JPW1131) |
| CC2-DMPE | RH-482 (JPW1132, NK3630) |
| CC2-DMPE | RH-1691 |
| CC2-DMPE | RH-1692 |
| CC2-DMPE | RH-1838 |
| CC2-DMPE | R-1114(WW781) |
| CC2-DMPE | JPW1177 |
| CC2-DMPE | JPW1245 |

Aspects of the present invention provide, in part, a cell. As used herein, the term "cell," means any cell that natively expresses the molecules necessary to practice a method disclosed in the present specification, such as, e.g., a persistent $Na^+$ channel, a transient $Na^+$ channel a $K^+$ channel or a Na/K ATPase pump, or can be genetically engineered to express the molecules necessary to practice a method disclosed in the present specification, such as, e.g., a persistent $Na^+$ channel, a transient $Na^+$ channel a $K^+$ channel or a Na/K ATPase pump. As a non-limiting example, a cell useful for practicing a method using a $Na^+$ depletion/repletion protocol would be a cell that natively express a $K^+$ channel, a transient $Na^+$ channel and a persistent $Na^+$ channel, or a cell genetically engineered to express a $K^+$ channel, a transient $Na^+$ channel and a persistent $Na^+$ channel. As another non-limiting example, a cell useful for practicing a method using a hyperpolarization protocol would be a cell that natively express a $K^+$ channel and a persistent $Na^+$ channel, or a cell genetically engineered to express a $K^+$ channel and a persistent $Na^+$ channel. As yet another non-limiting example, a cell useful for practicing a method using a Na/K ATPase pump inhibitor protocol would be a cell that natively express a persistent $Na^+$ channel and Na/K ATPase pump, or a cell genetically engineered to express a persistent $Na^+$ channel and Na/K ATPase pump.

A cell can be obtained from a variety of organisms, such as, e.g., murine, rat, porcine, bovine, equine, primate and human cells; from a variety of cell types such as, e.g., neural and non-neural; and can be isolated from or part of a heterogeneous cell population, tissue or organism. It is understood that cells useful in aspects of the invention can include, without limitation, primary cells; cultured cells; established cells; normal cells; transformed cells; tumor cells; infected cells; proliferating and terminally differentiated cells; and stably or transiently transfected cells. It is further understood that cells useful in aspects of the invention can be in any state such as proliferating or quiescent; intact or permeabilized such as through chemical-mediated transfection such as, e.g., calcium phosphate-mediated, diethylaminoethyl (DEAE) dextran-mediated, lipid-mediated, polyethyleneimine (PEI)-mediated, polybrene-mediated, and protein delivery agents; physical-mediated transfection, such as, e.g., biolistic particle delivery, microinjection and electroporation; and viral-mediated transfection, such as, e.g., retroviral-mediated transfection. It is further understood that cells useful in aspects of the invention may include those which express a $Na^+$ channel under control of a constitutive, tissue-specific, cell-specific or inducible promoter element, enhancer element or both.

Naturally occurring cells having persistent sodium current include, without limitation, neuronal cells, such as, e.g., squid axon, cerebellar Purkinje cells, neocortical pyramidal cells, thalamic neurons, CA1 hipppocampal pyramidal cells, striatal neurons and mammalian CNS axons. Other naturally occurring cells having persistent sodium current can be identified by those skilled in the art using methods disclosed herein below and other well known methods. Genetically engineered cells expressing a persistent $Na^+$ current can include, without limitation, isolated mammalian primary cells; established mammalian cell lines, such as, e,g, COS, CHO, HeLa, NIH3T3, HEK 293-T and PC12; amphibian cells, such as, e,g, *Xenopus* embryos and oocytes; insect cells such as, e,g, *D. melanogaster*, yeast cells such as, e,g, *S. cerevisiae, S. pombe*, or *Pichia pastoris* and prokaryotic cells, such as, e,g, *E. coli*.

Cells can be genetically engineered to express a polynucleotide molecule encoding a molecule necessary to practice a method disclosed in the present specification, such as, e.g., a persistent Na$^+$ channel, a transient Na$^+$ channel a K$^+$ channel or a Na/K ATPase pump. The sequences of polynucleotide molecules encoding a molecule necessary to practice a method disclosed in the present specification, such as, e.g., a persistent Na$^+$ channel, a transient Na$^+$ channel a K$^+$ channel or a Na/K ATPase pump are well-known and publicly available to one skilled in the art. For example, both polynucleotide and protein sequences of all currently described persistent Na$^+$ channels, transient Na$^+$ channels, K$^+$ channels and Na/K ATPase pumps are publicly available from the GenBank database (National Institutes of Health, National Library of Medicine. In addition, polynucleotide and protein sequences are described, see, e.g, Alan L. Goldin, *Diversity of Mammalian Voltage-gated Sodium Channels*, 868 ANN. N.Y. ACAD. SCI. 38-50 (1999), William A. Catterall, *From Ionic Currents to Molecular Mechanisms: The Structure and Function of Voltage-gated Sodium Channels*, 26(1) NEURON 13-25 (2000); John N. Wood & Mark D. Baker, *Voltage-gated Sodium Channels*, 1(1) CURR. OPIN. PHARMACOL. 17-21 (2001); and Frank H. Yu & William A. Catterall, *Overview of the Voltage-Gated Sodium Channel Family*, 4(3) GENOME BIOL. 207 (2003).

Voltage-gated Na$^+$ channels are members of a large mammalian gene family encoding at least nine alpha- (Na$_v$1.1-Na$_v$1.9) and four beta-subunits. While all members of this family conduct Na$^+$ ions through the cell membrane, they differ in tissue localization, regulation and, at least in part, in kinetics of activation and inactivation, see, e.g., Catterall, supra, (2000); and Sanja D. Novakovic et al., *Regulation of Na$^+$ Channel Distribution in the Nervous System*, 24(8) TRENDS NEUROSCI. 473-478 (2001). Four sodium channels, Na$_v$1.3, Na$_v$1.5, Na$_v$1.6 and Na$_v$1.9, have historically been known to generate a persistent current. Recent evidence, however, suggests that all voltage-gated sodium channels are capable of producing a persistent current, see, e.g., Abraha Taddese & Bruce P. Bean, *Subthreshold Sodium Current from Rapidly Inactivating Sodium Channels Drives Spontaneous Firing of Tubermammillary Neurons*, 33(4) NEURON 587-600 (2002); Michael Tri H. Do & Bruce P. Bean, *Subthreshold Sodium Currents and Pacemaking of Subthalamic Neurons: Modulation by Slow Inactivation*, 39(1) NEURON 109-120 (2003). As of Nov. 21, 2005, accession numbers for representative human voltage-gated Na$^+$ channel family members include gi29893559, gi10337597, gi25014054, gi40255316, gi37622907, gi7657544, gi4506813, gi56748895 and gi7657542, which are hereby incorporated by reference in their entirety.

Voltage-gated K$^+$ channels are members of a large mammalian gene family encoding at least 5 six transmembrane subunits: K$_v$1.x, K$_v$2.x, K$_v$3.x, K$_v$4.x and K$_v$CNQ, see, e.g., Gary Yellen, The voltage-gated potassium channels and their relatives, 419(6902) Nature 35-42 (2002). These ion channels help maintain and regulate the K$^+$-based component of the membrane potential and are thus central to many critical physiological processes. Each subunit family is composed of several genes. Thus, the K$_v$1.x family in mammals is comprised of five distinct genes: K$_v$1.1, K$_v$1.2, K$_v$1.3, K$_v$1.4 and K$_v$1.5. The K$_v$2.x family in mammals is comprised of two distinct genes: K$_v$2.1 and K$_v$2.2. The K$_v$3.x family in mammals is comprised of four distinct genes: K$_v$3.1, K$_v$3.2a, K$_v$3.2b, K$_v$3.2c, K$_v$3.3, K$_v$3.4a and K$_v$3.4b. The K$_v$4.x family in mammals is comprised of three distinct genes: K$_v$4.1, K$_v$4.2, K$_v$4.3-1 and K$_v$4.3-2. As of Nov. 21, 2005, accession numbers for representative human voltage-gated K$^+$ channel family members include K$_v$1.x channels gi4557685, gi4826782, gi25952082, gi4504817 and gi25952087; K$_v$2.x channels gi4826784 and gi27436974; K$_v$3.x channels gi76825377, gi21217561, gi21217563, gi24497458, gi24497460, gi24497462 and gi24497464; and K$_v$4.x channels gi27436981, gi9789987 and gi27436984, gi27436986, which are hereby incorporated by reference in their entirety.

The Na/K ATPase pump family is a member of the P-type ATPase superfamily. Two subunits α and β comprise the Na/K pump. In mammals, four a isoforms have been identified (α1, α2, α3, α4). A housekeeping function is assigned to α1. This isoform is expressed throughout the body. The α2 isoform is expressed mainly in brain, heart and skeletal muscle and appears to be involved in regulation cell Ca2+. The α4 isoform is believed to help maintain sperm motility. The Na/K ATPase pump family in mammals is comprises Na/K α1a, Na/K α1b, Na/K α2, Na/K α3 and Na/K α4. As of Nov. 21, 2005, accession numbers for representative human Na/K ATPase pump family members include gi21361181, gi48762682, gi1703467, gi29839750 and gi37577153, which are hereby incorporated by reference in their entirety.

Another aspect of the present invention provides, in part, an expression construct that allow for expression of a polynucleotide molecule encoding a molecule necessary to practice a method disclosed in the present specification, such as, e.g., a persistent Na$^+$ channel, a transient Na$^+$ channel, a K$^+$ channel or a Na/K ATPase pump. These expression constructs comprise an open reading frame encoding a molecule necessary to practice a method disclosed in the present specification, such as, e.g., a persistent Na$^+$ channel, a transient Na$^+$ channel, a K$^+$ channel or a Na/K ATPase pump, operably-linked to control sequences from an expression vector useful for expressing a the necessary molecule in a cell. The term "operably linked" as used herein, refers to any of a variety of cloning methods that can ligate a polynucleotide molecule disclosed in the present specification into an expression vector such that a polypeptide encoded by the composition is expressed when introduced into a cell. Well-established molecular biology techniques that may be necessary to make an expression construct disclosed in the present specification including, but not limited to, procedures involving polymerase chain reaction (PCR) amplification restriction enzyme reactions, agarose gel electrophoresis, nucleic acid ligation, bacterial transformation, nucleic acid purification, nucleic acid sequencing are routine procedures well within the scope of one skilled in the art and from the teaching herein. Non-limiting examples of specific protocols necessary to make an expression construct are described in e.g., MOLECULAR CLONING A LABORATORY MANUAL, supra, (2001); and CURRENT PROTOCOLS IN MOLECULAR BIOLOGY (Frederick M. Ausubel et al., eds. John Wiley & Sons, 2004). These protocols are routine procedures well within the scope of one skilled in the art and from the teaching herein.

A wide variety of expression vectors can be employed for expressing an open reading frame encoding a molecule necessary to practice a method disclosed in the present specification, such as, e.g., a persistent Na$^+$ channel, a transient Na$^+$ channel, a K$^+$ channel or a Na/K ATPase pump, and include without limitation, viral expression vectors, prokaryotic expression vectors and eukaryotic expression vectors including yeast, insect and mammalian expression vectors. Non-limiting examples of expression vectors, along with well-established reagents and conditions for making and using an expression construct from such expression vectors are readily available from commercial vendors that include, without limitation, BD Biosciences-Clontech, Palo Alto, Calif.; BD Biosciences Pharmingen, San Diego, Calif.; Invitrogen, Inc, Carlsbad, Calif.; EMD Biosciences-Novagen, Madison, Wis.; QIAGEN, Inc., Valencia, Calif.; and Stratagene, La Jolla, Calif. The selection, making and use of an appropriate expression vector are routine procedures well within the scope of one skilled in the art and from the teachings herein.

It is envisioned that any of a variety of expression systems may be useful for expressing a construct disclosed in the present specification. An expression system encompasses both cell-based systems and cell-free expression systems. Cell-based systems include, without limited, viral expression systems, prokaryotic expression systems, yeast expression systems, baculoviral expression systems, insect expression systems and mammalian expression systems. Cell-free systems include, without limitation, wheat germ extracts, rabbit reticulocyte extracts and E. coli extracts. Expression using an expression system can include any of a variety of characteristics including, without limitation, inducible expression, non-inducible expression, constitutive expression, viral-mediated expression, stably-integrated expression, and transient expression. Expression systems that include well-characterized vectors, reagents, conditions and cells are well-established and are readily available from commercial vendors that include, without limitation, Ambion, Inc. Austin, Tex.; BD Biosciences-Clontech, Palo Alto, Calif.; BD Biosciences Pharmingen, San Diego, Calif.; Invitrogen, Inc, Carlsbad, Calif.; QIAGEN, Inc., Valencia, Calif.; Roche Applied Science, Indianapolis, Ind.; and Stratagene, La Jolla, Calif. Non-limiting examples on the selection and use of appropriate heterologous expression systems are described in e.g., PROTEIN EXPRESSION. A PRACTICAL APPROACH (S. J. Higgins and B. David Hames eds., Oxford University Press, 1999); Joseph M. Fernandez & James P. Hoeffler, GENE EXPRESSION SYSTEMS. USING NATURE FOR THE ART OF EXPRESSION (Academic Press, 1999); and Meena Rai & Harish Padh, *Expression Systems for Production of Heterologous Proteins,* 80(9) CURRENT SCIENCE 1121-1128, (2001). These protocols are routine procedures well within the scope of one skilled in the art and from the teaching herein.

An expression construct comprising a polynucleotide molecule encoding a molecule necessary to practice a method disclosed in the present specification, such as, e.g., a persistent $Na^+$ channel, a transient $Na^+$ channel, a $K^+$ channel or a Na/K ATPase pump, can be operationally-linked to a variety of regulatory elements that can positively or negatively modulate, either directly or indirectly, the expression of a polynucleotide molecule, such as, e.g., constitutive, tissue-specific, inducible or synthetic promoters and enhancers. Using such systems, one skilled in the art can express the desired levels of a molecule necessary to practice a method disclosed in the present specification, such as, e.g., a persistent $Na^+$ channel, a transient $Na^+$ channel, a $K^+$ channel or a Na/K ATPase pump, using routine laboratory methods as described, see, e.g., Molecular Cloning A Laboratory Manual (Joseph Sambrook & David W. Russell eds., Cold Spring Harbor Laboratory Press, 3 ed. 2001); and CURRENT PROTOCOLS IN MOLECULAR BIOLOGY (Frederick M. Ausubel et al., eds., John Wiley & Sons, 2004). Non-limiting examples of constitutive regulatory elements include, e.g., the cytomegalovirus (CMV), herpes simplex virus thymidine kinase (HSV TK), simian virus 40 (SV40) early, 5' long terminal repeat (LTR), elongation factor-1α (EF-1α) and polybiquitin (UbC) regulatory elements. Non-limiting examples of inducible regulatory elements useful in aspects of the present invention include, e.g., chemical-inducible regulatory elements such as, without limitation, alcohol-regulated, tetracycline-regulated, steroid-regulated, metal-regulated and pathogenesis-related; and physical-inducible regulatory elements such as, without limitation, temperature-regulated and light-regulated. Such inducible regulatory elements can be prepared and used by standard methods and are commercially available, including, without limitation, tetracycline-inducible and tetracycline-repressible elements such as, e.g., Tet-On™ and Tet-Off™ (BD Biosciences-Clontech, Palo Alto, Calif.) and the T-REx™ (Tetracycline-Regulated Expression) and Flp-In™ T-REx™ systems (Invitrogen, Inc., Carlsbad, Calif.); ecdysone-inducible regulatory elements such as, e.g., the Complete Control® Inducible Mammalian Expression System (Stratagene, Inc., La Jolla, Calif.); isopropyl β-D-galactopyranoside (IPTG)-inducible regulatory elements such as, e.g., the LacSwitch® $^{II}$ Inducible Mammalian Expression System (Stratagene, Inc., La Jolla, Calif.); and steroid-inducible regulatory elements such as, e.g., the chimeric progesterone receptor inducible system, GeneSwitch® (Invitrogen, Inc., Carlsbad, Calif.). The skilled person understands that these and a variety of other constitutive and inducible regulatory systems are commercially available or well known in the art and can be useful in the invention for controlling expression of a polynucleotide which encodes a molecule necessary to practice a method disclosed in the present specification, such as, e.g., a persistent $Na^+$ channel, a transient $Na^+$ channel, a $K^+$ channel or a Na/K ATPase pump.

Aspects of the present invention provide, in part, cells comprising a certain gK/gNa ratio, or relative gK/gNa conductance. The relative gK/gNa conductance of genetically engineered cells can be measured simply by increasing the extracellular $K^+$ concentration and monitoring the change in membrane potential. Contributions of other ions, such as, e.g., $Cl^-$, to the overall membrane potential can be controlled by substituting non-permeate analogs or pharmacological blockers to prevent their contribution to the equilibrium potential. The relative gK/gNa conductance can be calculated using the modified form of the Chord Conductance equation below:

$$\Delta E_m = \lambda (E_{K2} - E_{K1})/(\lambda+1)$$

Where:
$\lambda$=GK/GNa; $EK_2$=the equilibrium potential for $K^+$ following a 10-fold increase in extracellular $K^+$; $EK_1$=the equilibrium potential for $K^+$ prior to increasing $K^+$ 10-fold.
For any ion the equilibrium potential is defined as $$E_i = (RT/ZF)\log [I_{out}/I_{in}]$$

Where:
at physiological temperature, with monovalent ions, RT/ZF=60 mV; and $I_{out}$ and $I_{in}$ are the concentrations of the relevant ion in the extracellular and intracellular compartments respectively.

As a non-limiting example, to determine the relative gK/gNa conductance for a particular cell line, a 10-fold increase in extracellular $K^+$ concentration is added to the physiological solution. This added $K^+$ induces a depolarization by shifting the equilibrium potential by approximately 60 mV in the positive direction. The values obtained from the experiment can then be used in the modified form of the Chord Conductance equation above to calculate the relative gK/gNa conductance. For a Na/K ATPase pump inhibitor protocol, a relative gK/gNa conductance ≧20-fold is indicative of a depolarization near the theoretical equilibrium potential 60 mV, and thus suitable for this protocol.

Aspects of the present invention provide, in part, detecting fluorescence emitted by the voltage-sensitive dye. The fluorescence emitted from a sample is typically determined using a fluorimeter. In fluorescence detection relying on a single fluorophore, an excitation radiation from an excitation source passes through excitation optics and excites the voltage-sensitive dye. In response, voltage-sensitive dye emits radiation which has an emission wavelength that is different from the excitation wavelength, which is collected by collection optics. In fluorescence detection relying on FRET, an excitation radiation from an excitation source having a first wavelength passes through excitation optics. The excitation optics cause the excitation radiation to excite the voltage-sensitive dye. In response, voltage-sensitive dye emits radiation which has an emission wavelength that is different from the excitation wavelength, which is collected by collection optics. If desired, the device includes a temperature controller to maintain the cell at a specific temperature while being scanned. If desired, a multi axis translation stage moves a microtiter plate containing a plurality of samples in order to position different wells to be exposed. It is understood that the multi-axis translation stage, temperature controller, auto-focusing feature, and electronics associated with imaging and data collection can be managed by the appropriate digital computer.

It is further understood that the methods of the invention can be automated and can be configured in a high throughput or ultra high-throughput format using, without limitation, 96 well, 384-well or 1536 well plates. Instrumentation useful for measuring membrane potential for high-throughput screening procedures include, without limitation, Fluorometric Imaging Plate Reader (FLIPR®; Molecular Devices, Sunnyvale, Calif.) and Voltage/Ion Probe Reader (VIPR; Aurora Biosciences, San Diego, Calif.), see, e.g., Roger Y. Tsien & Jesus E. Gonzalez, *Detection of Transmembrane Potentials by Optical Methods*, U.S. Pat. No. 6,342,379 (Jan. 29, 2002); Jesus E. Gonzalez & Michael P. Maher, *Cellular Fluorescent Indicators and Voltage/Ion Probe Reader (VIPR) Tools for Ion Channel and Receptor Drug Discovery*, 8(5-6) RECEPTORS CHANNELS 283-295, (2002); and Michael P. Maher & Jesus E. Gonzalez, *High Throughput Method and System for Screening Candidate Compounds for Activity Against Target Ion Channels*, U.S. Pat. No. 6,686,193 (Feb. 3, 2004). As a non-limiting example, fluorescence emission can be detected using the FLIPR® instrumentation system, which is designed for 96-well plate assays. FLIPR® utilizes a water-cooled 488 nm argon ion laser (5 watt) or a xenon arc lamp and a semi-confocal optical system with a charge coupled device (CCD) camera to illuminate and image the entire plate. The FPM-2 96-well plate reader (Folley Consulting and Research; Round Lake, Ill.) also can be useful in detecting fluorescence emission in the methods of the invention. One skilled in the art understands that these and other automated systems with the appropriate spectroscopic compatibility can be useful in high-throughput screening methods disclosed in the present specification.

Aspects of the present invention provide, in part, determining a relative emitted fluorescence. A relative emitted fluorescence is determined by comparing the fluorescence emitted from a test sample to the corresponding control sample for that test sample. A decrease in emitted fluorescence from a test sample relative to a control sample is indicative of a reduction or prevention of a persistent $Na^+$ current, i.e., the presence of a persistent $Na^+$ channel blocker in the test sample. As a non-limiting example, a decrease in emitted fluorescence from a test sample relative to a control sample using a $Na^+$ depletion/repletion protocol is indicative of a reduction or prevention of a persistent $Na^+$ current, i.e., the presence of a persistent $Na^+$ channel blocker in the test sample. As another non-limiting example, a decrease in emitted fluorescence from a test sample relative to a control sample using a hyperpolarization protocol is indicative of a reduction or prevention of a persistent $Na^+$ current, i.e., the presence of a persistent $Na^+$ channel blocker in the test sample. As yet another non-limiting example, a decrease in emitted fluorescence from a test sample relative to a control sample using a Na/K ATPase pump inhibitor protocol is indicative of a reduction or prevention of a persistent $Na^+$ current, i.e., the presence of a persistent $Na^+$ channel blocker in the test sample.

In an embodiment, a decrease in emitted fluorescence from a test sample relative to a control sample is indicative of a reduction or prevention of a persistent $Na^+$ current, i.e., the presence of a persistent $Na^+$ channel blocker. In aspects of this embodiment, a decreased relative emitted fluorescence from a test sample can be, e.g., at least two-fold, at least three-fold, at least four-fold, at least five-fold, at least ten-fold, at least twenty-fold or more as compared to the relative emitted fluorescence from a control sample. In other aspects of this embodiment, a decreased relative emitted fluorescence from a test sample can be, e.g., at most two-fold, at most three-fold, at most four-fold, at most five-fold, at most ten-fold, at most twenty-fold as compared to the relative emitted fluorescence from a control sample.

In another embodiment, an increase is emitted fluorescence from a control sample relative to a test sample is indicative of a reduction or prevention of a persistent $Na^+$ current, i.e., the presence of a persistent $Na^+$ channel blocker. In aspects of this embodiment, an increased relative emitted fluorescence from a control sample can be, e.g., at least two-fold, at least three-fold, at least four-fold, at least five-fold, at least ten-fold, at least twenty-fold or more as compared to the relative emitted fluorescence from a test sample. In other aspects of this embodiment, an increased relative emitted fluorescence from a control sample can be, e.g., at most two-fold, at most three-fold, at most four-fold, at most five-fold, at most ten-fold, at most twenty-fold as compared to the relative emitted fluorescence from a test sample.

Figure 2:
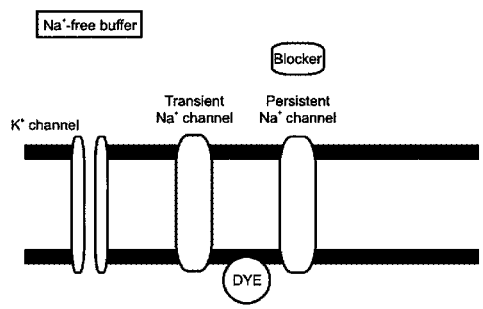
FIG. 2 shows a schematic of a $Na^+$ depletion/repletion protocol. Four steps integral to the assay are illustrated. 1) Providing Sample: A cell containing the principal components of the assay—a $K^+$ channel and channel(s) capable of producing transient and persistent $Na^+$ currents are incubated in $Na^+$-free solution containing a voltage-sensitive dye (Dye) and a test compound (Blocker). 2) Depolarizing the cell: A small aliquot of solution containing concentrated $K^+$ is added to the solution to initiate a depolarization of the membrane sufficient to activate the $Na^+$ channels. In the absence of external $Na^+$ to act as charge carrier through the $Na^+$ channels only small background $K^+$-induced depolarization and fluorescence change is produced (see also FIG. 3). 3) Generating current and detecting fluorescence emitted in the absence of an effective persistent $Na^+$ channel blocker: Following and interval sufficient to allow the closure of transient $Na^+$ channels, an aliquot of solution containing concentrated $Na^+$ sufficient to raise the external $Na^+$ concentration to physiological levels is added. In the absence of an effective persistent $Na^+$ channel blocker, $Na^+$ ions acting as a charge carrier through persistent $Na^+$ channels produce a depolarization of the cell membrane and a subsequent change in fluorescence of the voltage-sensitive dye. 4) Generating current and detecting fluorescence emitted in the presence of an effective persistent $Na^+$ channel blocker: With solution additions as in (3) above, except that the solution now contains an effective blocker of persistent $Na^+$ channels, $Na^+$ ions are prevented from entering the cell, no depolarization occurs and no change in fluorescence is observed.
Figure 2:
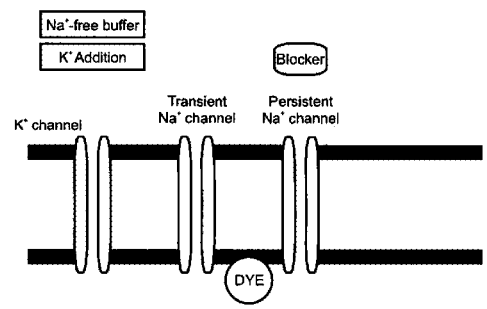
Figure 2:
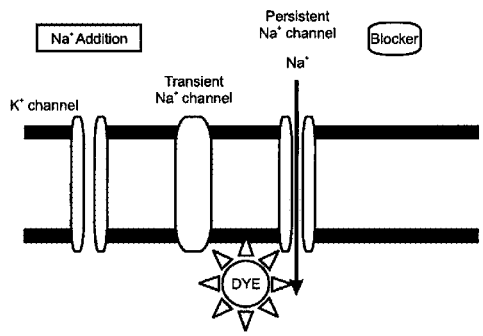
Figure 2:
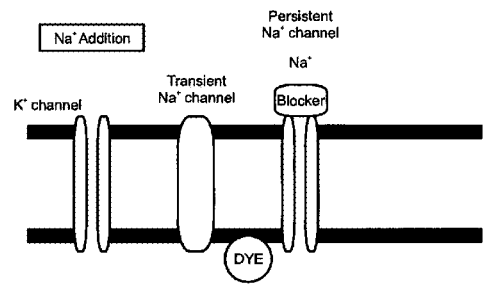
Figure 3:
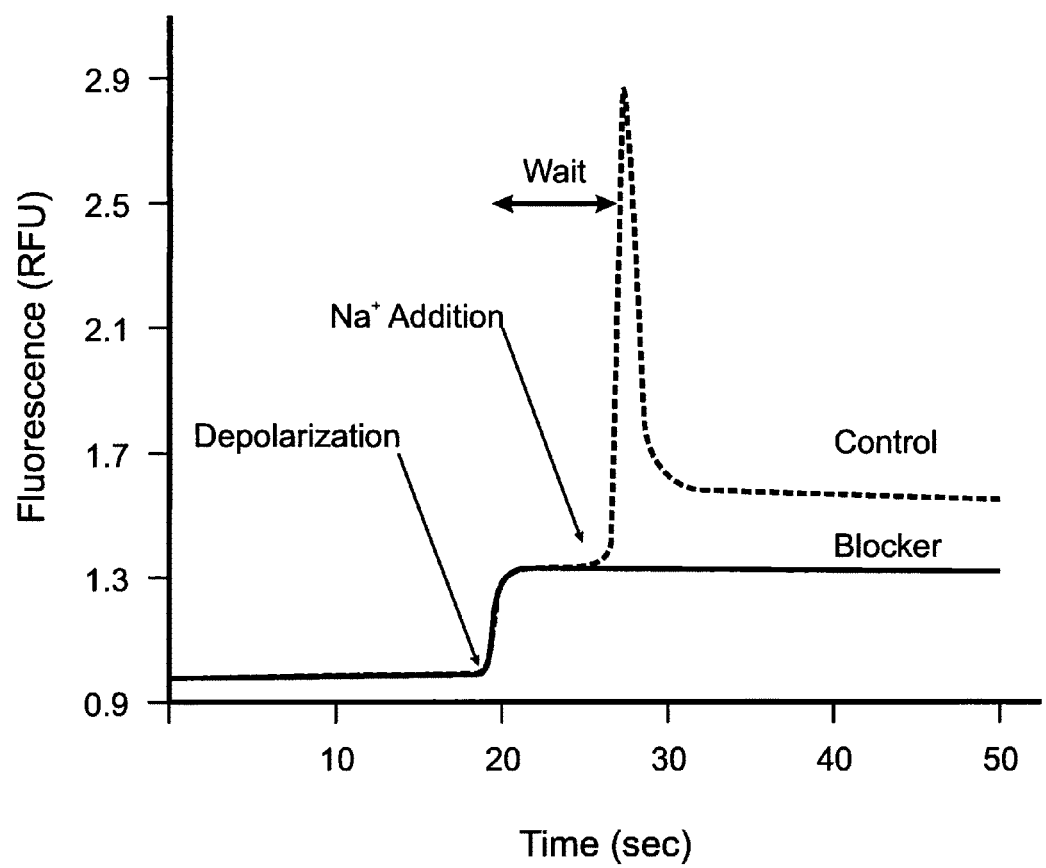
FIG. 3 shows a graphic depiction of an emitted fluorescence readout using a $Na^+$ depletion/repletion protocol. Fluorescence in relative fluorescence units vs. time is plotted for a voltage-gated $Na^+$ current. The recording of a molecule exhibiting a blocking activity of a persistent $Na^+$ current is indicated by a black line. A control sample which lacks blocking activity of a persistent $Na^+$ current is indicated by a dashed line.

Aspects of the present invention provide a method for identifying a selective blocker of a persistent $Na^+$ channel using a $Na^+$ depletion/repletion protocol (FIG. 2). This protocol relies on the essential requirement of $Na^+$ to generate a persistent current. Generally, cells having a $K^+$ channel, a transient $Na^+$ channel and a persistent $Na^+$ channel are incubated in a $Na^+$-free physiological solution. A small depolarization of the membrane of the cells is induced to activate both transient and persistent $Na^+$ channels. However, no additional depolarization will be observed in the absence of extracellular $Na^+$. Thus, within a few milliseconds following depolarization the transient $Na^+$ channels will close, but the channels capable of generating a persistent $Na^+$ current will remain open. The addition of $Na^+$ to the $Na^+$-free physiological solution will cause these opened persistent $Na^+$ channels to generate a persistent current causing the membrane to depolarize. The presence of a persistent $Na^+$ channel blocker will either eliminate or reduce the magnitude of this depolarization event (FIG. 3). Therefore, screens based on the $Na^+$ depletion/ repletion protocol can identify a potential persistent $Na^+$ channel blocker by absent or reduction of membrane depolarization. Conversely, molecules that lack this blocking capability, whether a potential test molecule or a control sample, will not affect the magnitude of this depolarization event. The $Na^+$ depletion/repletion protocol therefore allows the discovery of molecules that block the persistent Na$^+$ current and as such is a screen for persistent Na$^+$ channels blockers.

In one embodiment, a Na$^+$ depletion/repletion protocol test sample comprises a cell comprising a K$^+$ channel, a transient Na$^+$ channel and a persistent Na$^+$ channel.

Aspects of the present invention provide, in part, depolarizing a membrane of the cell. A cell membrane may be depolarized by adding K$^+$ to the medium to shift the K$^+$ equilibrium potential in the positive direction. As an non-limiting example, in a cell in which the K$^+$ conductance dominates at the resting potential and the intracellular and extracellular K$^+$ concentrations are 120 mM and 4.5 mM respectively the equilibrium potential for potassium would be approximately −84 mV. Addition of K$^+$ to bring the extracellular K$^+$ to 13 mM would result in a equilibrium potential for potassium of approximately −57 mV. Depending on the relative contribution of the other ionic conductances of the cell membrane this increase in K$^+$ could result in depolarization of up to 27 mV. One skilled in the art will recognize that there are many other methods for depolarizing a cell membrane. As additional non-limiting examples it would be possible to depolarize the cell membrane by adding K$^+$ channel blockers such as the ions, e.g., Cs$^+$, Ba$^{2+}$, TEA$^+$, or small organic molecules, e.g., 4-aminopyridine, quinidine or phencyclidine, or peptide toxins e.g. charybdotoxin, margatoxin, iberiotoxin, noxiustoxin, kaliotoxin to the extracellular medium. One skilled in the art would recognize that inhibition of the electrogenic Na$^+$/K$^+$ pump with cardiac glycosides such as ouabain, or and dihydro-ouabain; isothiouronium or derivative thereof, such as, e.g., 1-bromo-2,4,6-tris(methylisothiouronium) benzene (Br-TITU) and 1,3-dibromo-2,4,6-tris (methylisothiouronium) benzene (Br2-TITU); digitoxigenin or derivative thereof, such as, e.g., digitalis, 22-benzoyloxy-digitoxigenin, 22-acetoxy-digitoxigenin, 22-allyl-digitoxigenin, 22-hydroxy-digitoxigenin and 14β, 17β-cycloketoester-3β-OH androstane (INCICH-D7); coumestan or derivative thereof, such as, e.g., 2-methoxy-3,8,9-trihydroxy coumestan (PCALC36); vanadate or derivative thereof; cardenolide or derivative thereof; and natural cardiac glycosides would depolarize the cell membrane. Additionally, one skilled in the art would recognize that the use of electric field stimulation (EFS) to deliver electrical stimuli to the cell would result in a depolarization of the cell membrane. Each of the above non-limiting examples could be used in combination with each other or other methods to deliver depolarizing stimuli to the cell membrane.

In one embodiment, depolarizing a membrane of the cell can be with the addition of K$^+$. It is envisioned that any K$^+$ concentration can be useful with the proviso that this K$^+$ addition induces a membrane depolarization of at least 5 mV and such addition does not prevent the additional depolarization due to Na$^+$ repletion. For example, a K$^+$-induced depolarization of range of about 5 to about 50 mV. In aspects of this embodiment, the K$^+$-induced depolarization can be, e.g., about 5 mV, about 10 mV, about 20 mV, about 30 mV, about 40 mV or about 50 mV.

Aspects of the present invention provide, in part, generating a current through the persistent Na$^+$ channel by adding a Na$^+$ containing solution into a well containing cells depolarized in the absence Na$^+$. The magnitude of the depolarization will depend on the concentration of Na$^+$ added and the relative conductance of the Na$^+$ channels generating the persistent current. As a non-limiting example addition of Na$^+$ to the extracellular solution that results in a final Na$^+$ concentration of 70-100 mM will result in a robust depolarization of the cell membrane in the presence of persistent sodium channels. In addition, one skilled in the art will recognize that to obtain a reliable measurement of persistent Na$^+$ current a wide range timings for the applications of the Na$^+$ solution would be possible as long as the transient sodium channels were allowed to inactivate.

Figure 4:
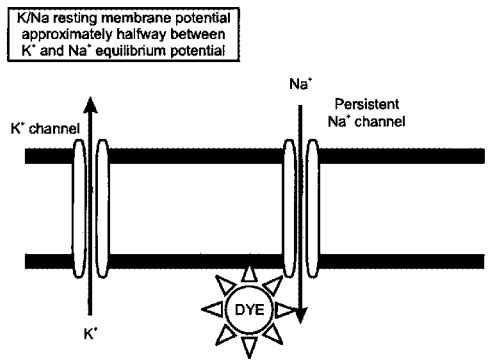
FIG. 4 shows a schematic of a hyperpolarization protocol. The hyperpolarization protocol illustrated here is similar to the depletion/repletion protocol shown in FIG. 2, except that test cell is engineered to have approximately equal $K^+$ and $Na^+$ conductances and a resting potential midway between the equilibrium potentials for $K^+$ and $Na^+$. This resting potential would also be engineered to result in the inactivation of transient $Na^+$ channels. Three steps integral to the assay are illustrated. 1) Providing Sample: A cell containing the principal components of the assay—a $K^+$ channel and channel capable of producing persistent $Na^+$ currents are incubated in $Na^+$-containing solution which also contains a voltage-sensitive dye (Dye). In this case $Na^+$ ions acting as charge carriers through the open persistent $Na^+$ channels will result in a steady-state depolarization of the cell membrane and significant fluorescent emission from the voltage-sensitive dye. 2) Adding a potential blocker (ineffective compound) and detecting fluorescence emitted: If the compound is ineffective in blocking the persistent $Na^+$ current, no change in $Na^+$ influx, depolarization or emitted fluorescence will occur. 3) Adding a potential blocker (effective compound) and detecting fluorescence emitted: If the compound is effective in blocking the persistent $Na^+$ current, a decrease in $Na^+$ influx, depolarization and emitted fluorescence will occur.
Figure 4:
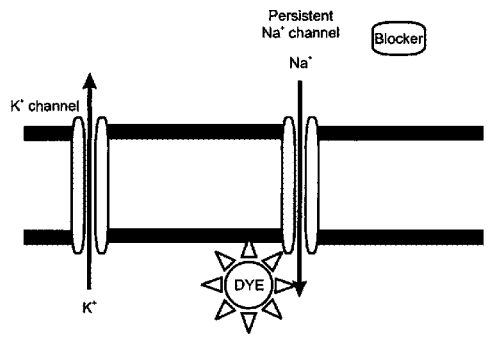
Figure 4:
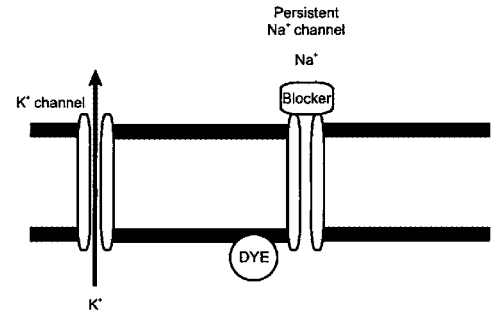
Figure 5:
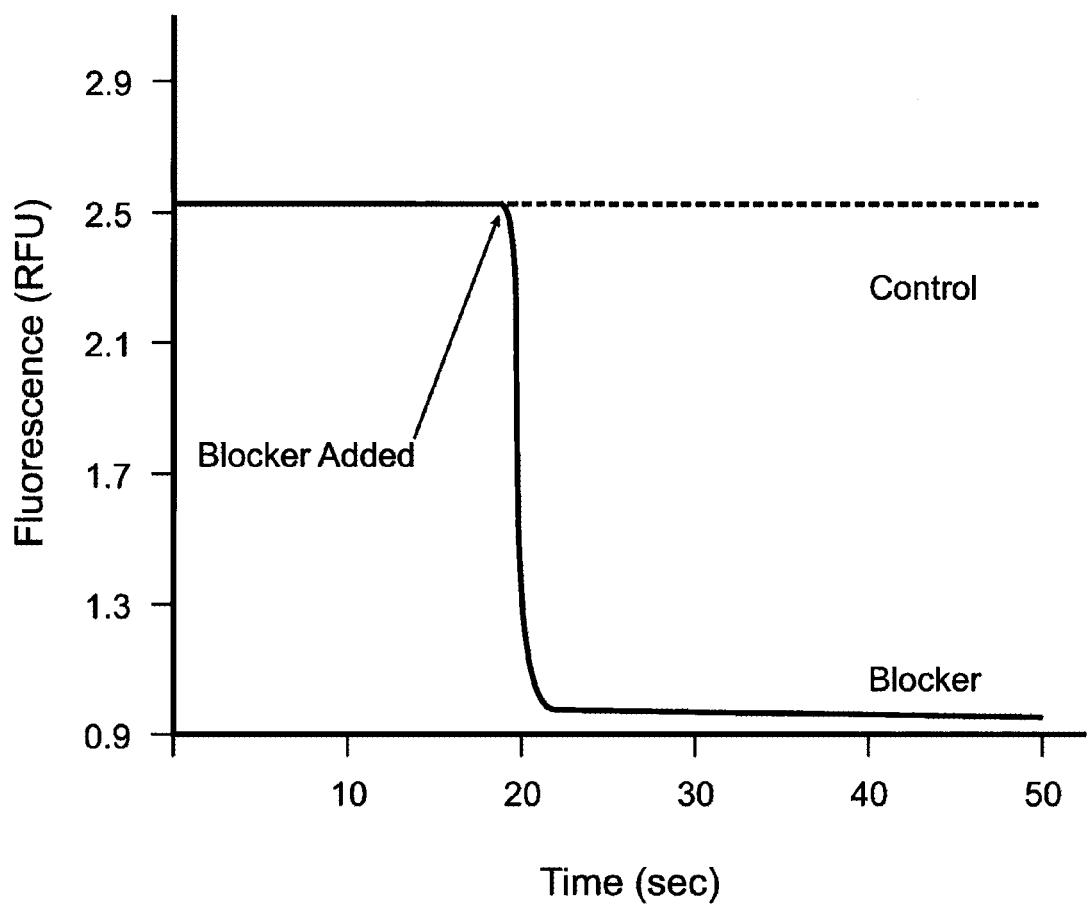
FIG. 5 shows a graphic depiction of an emitted fluorescence readout using a hyperpolarization protocol. Fluorescence in relative fluorescence units vs. time is plotted for a voltage-gated $Na^+$ current. The recording of a molecule exhibiting a blocking activity of a persistent $Na^+$ current is indicated by a black line. A control sample which lacks blocking activity of a persistent $Na^+$ current is indicated by a dashed line.

Aspects of the present invention provide a method for identifying a selective blocker of a persistent Na$^+$ channel using a hyperpolarization protocol (FIG. 4). In this protocol, the proportion of K$^+$ and persistent Na$^+$ channels present in cells is such that their conductances are essentially equal. Assuming all other ion conductances are minimal the resting membrane potential will lie approximately halfway between the equilibrium potential for Na$^+$ and the equilibrium potential of K$^+$. Under these conditions adding a K channel blocker will depolarize the cells toward the equilibrium potential of Na$^+$ (ENa>50 mV). On the other hand, adding a persistent Na$^+$ channel blocker will hyperpolarize the cells driving the membrane potential towards the equilibrium potential for K$^+$ (EK<−85 mV). These predictions can be understood via the chord conductance equation when a cell is solely permeable to Na$^+$ and K$^+$ (the media is Cl$^−$-free and appropriate inhibitors are present as in the Na$^+$ depletion/repletion protocol. Thus, the presence of a persistent Na$^+$ channel blocker generates a hyperpolarization event (FIG. 5). The more potent the persistent Na$^+$ channel blocker the greater the hyperpolarization with complete block bringing the membrane potential to EK. Therefore, screens based on the hyperpolarization protocol can identify a potential persistent Na$^+$ channel blocker by the induction of membrane hyperpolarization. Conversely, molecules that lack this blocking capability, whether a potential test molecule or a control sample, will not induce this hyperpolarization event. The hyperpolarization protocol therefore allows the discovery of molecules that block the persistent Na$^+$ current and as such is a screen for persistent Na$^+$ channels blockers.

In an embodiment, a hyperpolarization protocol test sample comprises a cell comprising a K$^+$ channel and a persistent Na$^+$ channel wherein a resting membrane potential of the cell is approximately halfway between the equilibrium potential of K$^+$ and the equilibrium potential of Na$^+$. In aspects of this embodiment, the resting membrane potential can comprise an approximate range of, e.g., −50 mV to 15 mV, −45 mV to 10 mV, −40 mV to 5 mV, −35 mV to 0 mV, −30 mV to −5 mV, −25 mV to −10 mV or −20 mV to −15 mV. In other aspects of this embodiment, the resting membrane potential can comprise an approximate range of, e.g., −50 mV to −20 mV, −40 mV to −10 mV, −30 mV to 0 mV, −20 mV to 10 mV or −10 mV to 20 mV.

In another embodiment, a hyperpolarization protocol test sample comprises a cell comprising a K$^+$ channel and a persistent Na$^+$ channel wherein a resting membrane potential of the cell is approximately halfway between the equilibrium potential of K$^+$ and the equilibrium potential of Na$^+$ can detect a hyperpolarization of a membrane. In aspects of this embodiment, membrane potential can hyperpolarize by at least 20 mV, at least 30 mV, at least 40 mV, at least 50 mV or at least 60 mV. In other aspects of this embodiment, membrane potential can hyperpolarize by at most 20 mV, at most 30 mV, at most 40 mV, at most 50 mV or at most 60 mV.

Figure 6:
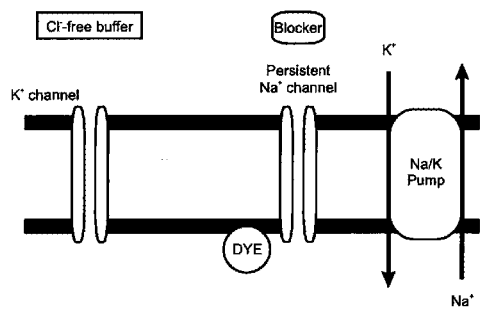
FIG. 6 shows a schematic of a Na/K pump inhibitor protocol. Two steps integral to the assay are illustrated. 1) Adding Ouabain: In a Cl-free physiological solution ouabain (100 uM) is added to engineered cells where $G_K$ is at least 20 fold>than $G_{Na+}$ persistent. 2) Detecting fluorescence emitted: Inhibition of the Na/K pump causes the cells to exchange extracellular $Na^+$ (via influx through persistent $Na^+$ channels) for intracellular K. The loss of K changes $E_K$ favoring cell depolarization, reflected as an increase in fluorescence intensity for the case of an anionic dye. In the presence of a persistent $Na^+$ channel blocker the K-dependent depolarization will be inhibited.
Figure 6:
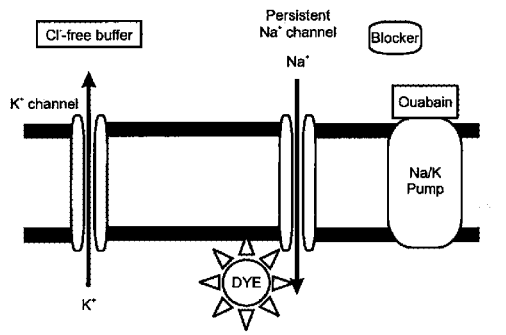
Figure 6:
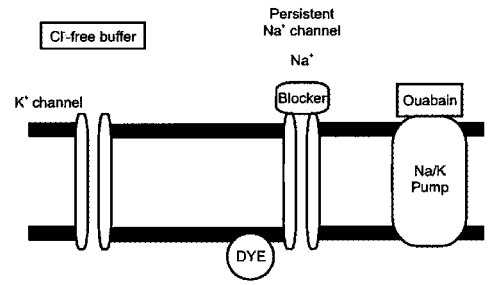
Figure 7:
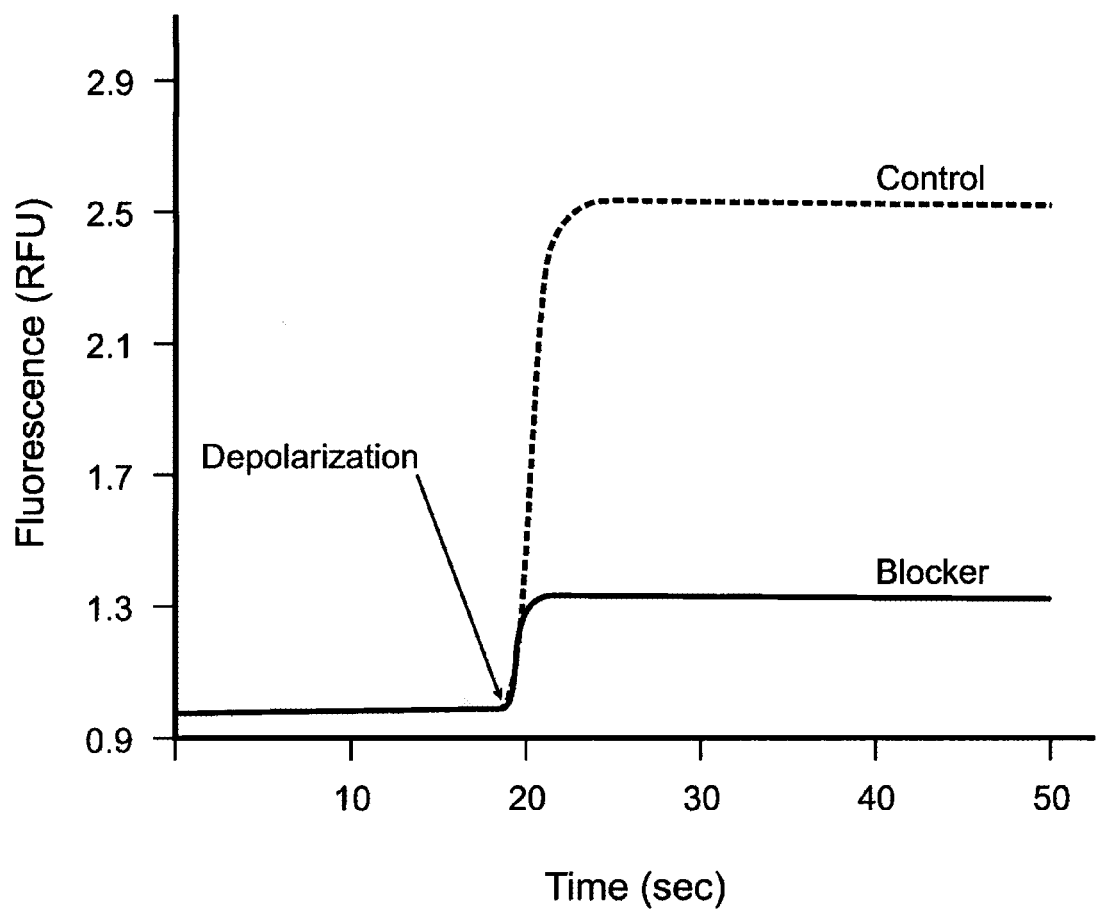
FIG. 7 shows a graphic depiction of an emitted fluorescence readout using a Na/K pump inhibitor protocol. Fluorescence in relative fluorescence units vs. time is plotted for a voltage-gated $Na^+$ current. The recording of a molecule exhibiting a blocking activity of a persistent Na⁺ current is indicated by a black line. A control sample which lacks blocking activity of a persistent Na⁺ current is indicated by a dashed line.

Aspects of the present invention provide a method for identifying a selective blocker of a persistent Na$^+$ channel using a Na/K ATPase pump inhibitor protocol, see FIG. 6. This assay relies on the fact that inhibition of the Na/K ATPase will allow net cellular Na$^+$ entry and K loss. In this protocol cells containing persistent Na$^+$ channels, K$^+$ channels, and Na/K ATPase, assayed in a Cl$^−$-free medium physiological solution, are treated with a pump inhibitor. This inhibition will lead to an initial small membrane depolarization due to blockage of the Na/K ATPase pump and a subsequent large secondary depolarization. This secondary depolarization is the key to the assay and relies on the fact that the equilibrium potential for $K^+$ will become more positive as the cells lose $K^+$. The rationale is as follows. For this assay to work GK must be $>>GNa_{persistent}$. Following addition of a Na/K ATPase pump inhibitor, the cells will gain $Na^+$ via persistent $Na^+$ channels that are open at near resting membrane potential. In the absence of a $Cl^-$ conductance the $Na^+$ gained by the cells will be electrically compensated for by an equimolar loss of $K^+$. Since $GK>>GNa$, the membrane potential will be dominated by K and therefore a decrease in cell $K^+$ will result in a positive change in the potassium equilibrium potential. As a result, a depolarization of the membrane will occur because of millimolar $K^+$ loss. It should be understood that although the cell gains $Na^+$ this gain is of little effect on the membrane potential since $GK>>GNa$. Instead it is the compensatory movement of $K^+$ ions drives the membrane potential in this assay. Thus, the extent of the depolarization will depend on the amount $K^+$ lost by the cell following the addition of a Na/K ATPase pump inhibitor. The presence of a persistent $Na^+$ channel blocker will either eliminate or reduce the magnitude of this secondary depolarization event (FIG. 7). Therefore, screens based on the Na/K ATPase pump inhibitor protocol can identify a potential persistent $Na^+$ channel blocker by absent or reduction of the secondary depolarization of the membrane. Conversely, molecules that lack this blocking capability, whether a potential test molecule or a control sample, will not affect the magnitude of this depolarization event. The Na/K ATPase pump inhibitor protocol therefore allows the discovery of molecules that block the persistent $Na^+$ current and as such is a screen for persistent $Na^+$ channels blockers.

In an embodiment, a Na/K ATPase pump inhibitor protocol test sample comprises a cell comprising a $K^+$ channel and a persistent $Na^+$ channel wherein a $K^+$ conductance of the $K^+$ channel is greater than the $Na^+$ conductance from the persistent $Na^+$ channel. In aspect of this embodiment, the $K^+$ conductance of the $K^+$ channel is greater than the $Na^+$ conductance by, e.g., at least 10-fold higher, at least 20-fold higher, at least 30-fold higher, at least 40-fold higher, at least 50-fold In other aspect of this embodiment, the $K^+$ conductance of the $K^+$ channel is greater than the $Na^+$ conductance by, e.g., at most 10-fold higher, at most 20-fold higher, at most 30-fold higher, at most 40-fold higher, at most 50-fold higher or at most 60-fold higher.

Aspects of the present invention provide, in part, a Na/K ATPase pump inhibitor. It is envisioned that any molecule capable of inhibiting the activity of a Na/K ATPase pump can be useful. Non-limiting examples of a Na/K ATPase pump inhibitor include oubain or derivative thereof, such as, e.g., ouabain and dihydro-ouabain; isothiouronium or derivative thereof, such as, e.g., 1-bromo-2,4,6-tris (methylisothiouronium) benzene (Br-TITU) and 1,3-dibromo-2,4,6-tris(methylisothiouronium) benzene (Br2-TITU); digitoxigenin or derivative thereof, such as, e.g., digitalis, 22-benzoyloxy-digitoxigenin, 22-acetoxy-digitoxigenin, 22-allyl-digitoxigenin, 22-hydroxy-digitoxigenin and 14β, 17β-cyclo ketoester-3β-OH androstane (INCICH-D7); coumestan or derivative thereof, such as, e.g., 2-methoxy-3,8,9-trihydroxy coumestan (PCALC36); vanadate or derivative thereof; cardenolide or derivative thereof; and natural cardiac glycosides. The magnitude of the depolarization will depend on the concentration of inhibitor added and the absolute conductance of the $Na^+$ channels generating the persistent current.

In another embodiment, depolarizing a membrane of the cell can be with a Na/K ATPase pump inhibitor. In an embodiment, a Na/K ATPase pump inhibitor depolarizes the cell membrane by inhibiting Na/K ATPase pump activity. In aspects of this embodiment, a Na/K ATPase pump inhibitor used can be, e.g., oubain or derivative thereof, an isothiouronium or derivative thereof, digitoxigenin or derivative thereof, a coumestan or derivative thereof, vanadate or derivative thereof, a cardenolide or derivative thereof or a natural cardiac glycoside.

Figure 8:
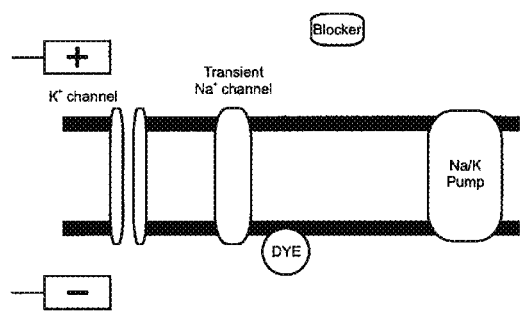
FIG. 8 shows a schematic of a transient blocker protocol. 1) Field stimulation of cells in wells: The engineered cells are placed in wells containing an appropriate physiological solution and a pair of stimulating electrodes capable of passing sufficient current to reach threshold for action potential initiation. 2) Detection of emitted fluorescence following stimulation to threshold: Depolarization of the cell following the upstroke to the action potential is detected by an increase in emitted fluorescence. 3) Adding a potential blocker and detecting emitted fluorescence. If a compound is a persistent Na⁺ channel blocker an increase in emitted fluorescence will not be detected.
Figure 8:
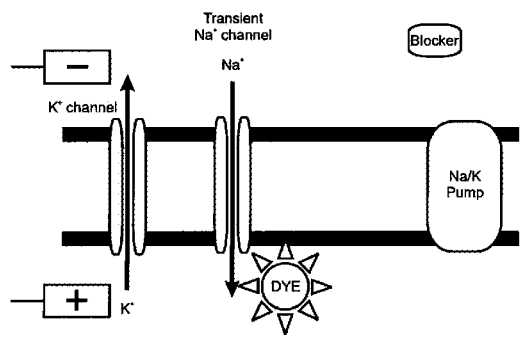
Figure 8:
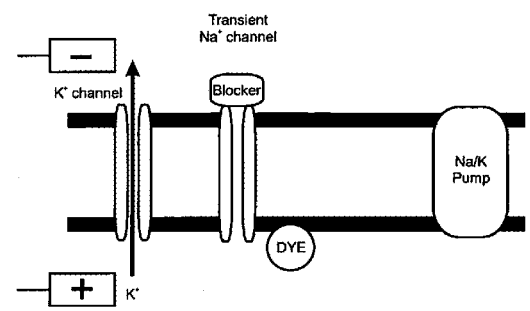
Figure 9:
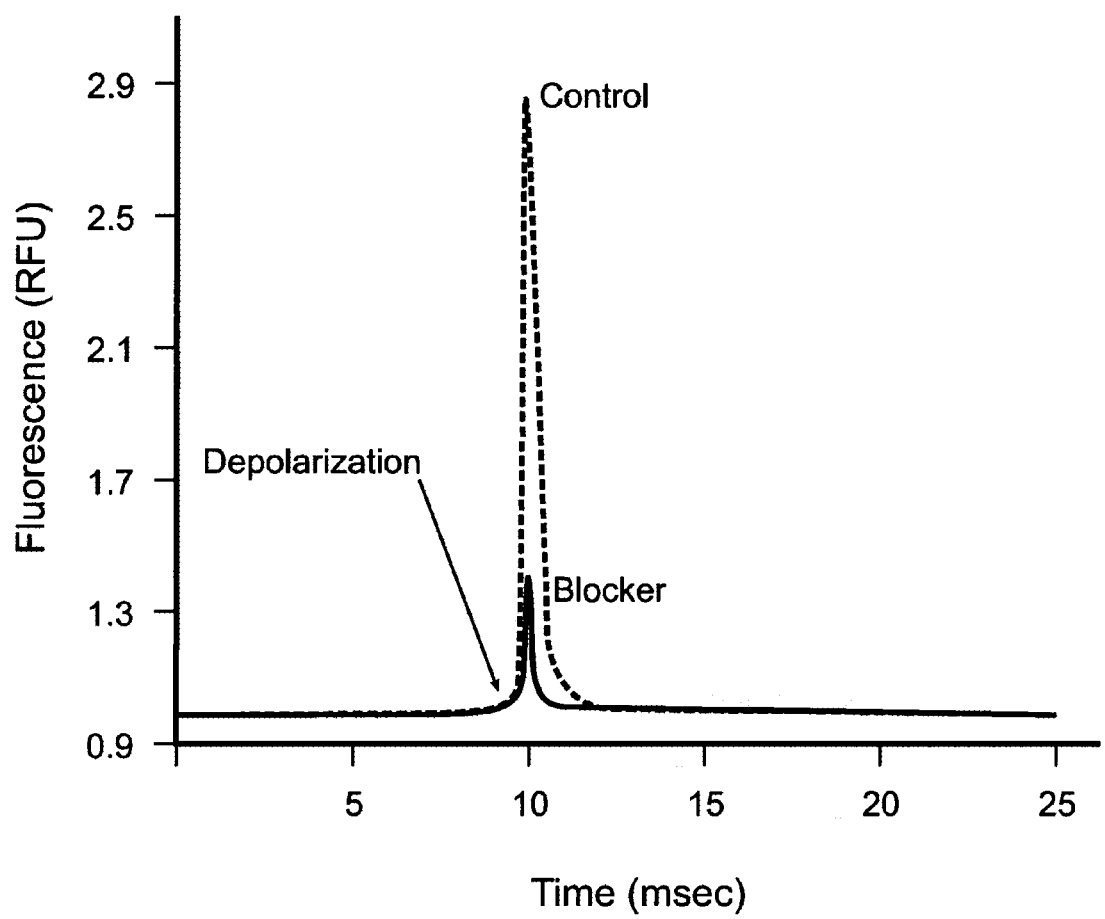
FIG. 9 shows a graphic depiction of an emitted fluorescence readout using a transient blocker protocol. Fluorescence in relative fluorescence units vs. time is plotted for a voltage-gated Na⁺ current. The recording of a molecule exhibiting a blocking activity of a transient Na⁺ current is indicated by a black line. A control sample which lacks blocking activity of a transient Na⁺ current is indicated by a dashed line. A selective persistent Na⁺ channel blocker would lack significant blocking activity of a transient Na⁺ current and thus behave more like a control sample.

Aspects of the present invention provide a method for identifying a selective blocker of a persistent $Na^+$ channel using transient $Na^+$ current protocol, see FIG. 8. Protocols such as, e.g., a $Na^+$ depletion/repletion protocol, a hyperpolarization protocol and a Na/K ATPase pump inhibitor protocol, can allow for the identification of a molecule that reduces or prevents a persistent $Na^+$ current. However, these protocols do not address whether the persistent $Na^+$ channel blockers found selectively block persistent $Na^+$ channels, or also block $Na^+$ channels generating the transient current. Thus another part of the screen in accordance with aspects of the present invention addresses how molecules that selectively block persistent $Na^+$ current but not transient $Na^+$ current can be distinguished, i.e., identification of a selective persistent $Na^+$ channel blocker (FIG. 9). In general, a persistent $Na^+$ channel blocker, as determined from a persistent $Na^+$ channel assay, such as, e.g., a $Na^+$ depletion/repletion protocol, a hyperpolarization protocol and a Na/K ATPase pump inhibitor protocol, is retested for its ability to block a transient current. A persistent $Na^+$ channel blocker that is selective for a persistent $Na^+$ channel will not greatly affect transient $Na^+$ current. On the other hand, a persistent $Na^+$ channel blocker that reduces or prevents transient $Na^+$ current as well would not be considered a selective persistent $Na^+$ channel blocker.

It is envisioned that any and all protocols useful for determining a transient $Na^+$ current can be used, including, without limitation, field stimulation. In a field stimulation protocol, electrodes are placed in the well and generate a stimulating current through the cell sufficient to generate an action potential before and after the addition of the persistent $Na^+$ channel blocker. The use of EFS to activate ion channels is a standard procedure well known to one skilled in the art, see, e.g., J. Malmivuo and R. Plonsey, Bioelectromagnetism: Principles and Applications of Bioelectric and Biomagnetic Fields, (Oxford University Press, New York. 1-472 pp. 1995); and J. P. Reilly, Electrical Stimulation and Electropathology (Cambridge University Press, Cambridge. 1-522 pp, 1992). Furthermore, methods to implement these protocols in HTS format have been described, see, e.g., Michael P. Maher & Jesus E. Gonzalez, *Multi-well Plate and Electrode Assemblies for Ion Channel Assays*, U.S. Pat. No. 6,969,449 (Nov. 29, 2005); and Paul Burnett et al., *Fluorescence Imaging of Electrically Stimulated Cells*, 8(6) J. Biomol. Screen. 660-667 (2003).

In an embodiment, a field stimulation protocol can depolarize a membrane of the cell.

Aspects of the present invention provide, in part, comparing the emitted fluorescence. Comparisons of emitted fluorescence is achieved by comparing the emitted fluorescence from a persistent $Na^+$ current assay relative to an emitted fluorescence from a transient $Na^+$ current assay for the same potential persistent $Na^+$ channel blocker. With respect to the $Na^+$ depletion/repletion, hyperpolarization and Na/K ATPase pump inhibitor protocols, a decrease is emitted fluorescence from a persistent $Na^+$ current assay relative to a transient $Na^+$ current assay is indicative of a selective reduction or prevention of a persistent Na$^+$ current relative to a transient Na$^+$ current, i.e., the presence of a selective persistent Na$^+$ channel blocker in the test sample.

Although there has been hereinabove described a method and screen for identifying a Na$^+$ channel blocker, in accordance with the present invention, for the purposes of illustrating the manner in which the invention may be used to advantage, it will be appreciated that the invention is not limited thereto. Accordingly, any and all modification, variations or equivalent arrangements which may occur to those skilled in the art should be considered to be within the scope of the invention as defined in the appended claims.

EXAMPLES

Example 1

Screening Assay for Identifying Persistent Sodium Current Blockers Using Fret Technology To establish an assay plate, HEK-293 cells grown in Minimum Essential Medium (Invitrogen, Inc., Carlsbad, Calif.) supplemented with 10% Fetal Bovine Serum (Invitrogen, Inc., Carlsbad, Calif.), 1% Penicillin-Streptomycin (Invitrogen, Inc., Carlsbad, Calif.) were either transiently or stably transfected with a polynucleotide molecule expressing a Na$_v$1.3 sodium channel capable of mediating persistent sodium current. Stably transfected cells were grown in the presence of 500 mg/mL G418 Geneticin (Invitrogen, Inc., Carlsbad, Calif.) and 2 µM TTX (Calbiochem, Inc., San Diego, Calif.) to maintain selective pressure. Cells were grown in vented cap flasks, in 90% humidity and 10% CO$_2$, to about 80% confluence, harvested by trypsinization and cell density was determined. Approximately 16 to 24 hours before the assay, each well of a clear-bottom, black-wall 96-well plate (Becton-Dickinson, San Diego, Calif.) coated with Matrigel (Becton-Dickinson, San Diego, Calif.) was seeded with approximately 75,000 HEK-Na$_v$1.3 cells in 150 µL of supplemented MEM. Cells were sometimes incubated in 96-well plates at somewhat lower densities (20,000 per well), and incubated for up to 40-48 hours.

To examine the ability of test molecules to alter persistent sodium current, the medium was aspirated, HEK cells were washed 3 times with 150 uL of TEA-MeSO$_3$ solution using CellWash (Thermo LabSystems, Franklin, Mass.) and 150 uL of a Na$^+$-free media and physiologic concentrations of K$^+$ (4.5 mM) was added. Extracellular Cl$^-$ was replaced with MeSO$_3$ during preincubation and throughout the assay. This eliminates a complicating Cl$^-$ current during the assay and results in an amplified and more stable voltage-change induced by the persistent Na$^+$ current. The HEK cells were preincubated for 30-60 minutes with the ion-sensitive FRET dye CC2-DMPE (final concentration 10 µM). CC2-DMPE is a stationary coumarin-tagged phospholipid resonance energy donor that has an optimal excitation wavelength at approximately 405 nm wavelength light and an optimal emission wavelength at approximately at 460 nm. While the HEK cells were being stained with coumarin, a 10 µM DiSBAC$_2$(3) solution in TEA-MeSO$_3$ solution was prepared. DiSBAC$_2$(3) is a mobile resonance energy acceptor that partition across the membrane as a function of the electric field. The optimal excitation spectra for these dyes overlap the emission spectra of the coumarin donor and, thus, they act as FRET acceptors. DiSBAC$_2$(3) has an emission spectrum in the range of 570 nm. In addition to DiSBAC$_2$(3), this solution contained any test molecule being tested or a DMSO control, at 4 times the desired final concentration (e.g., 20 µM for 5 µM final), 1.0 mM ESS-AY17 to reduce background fluorescence, and 400 µM CdCl$_2$, which stabilizes the membrane potential of the cells at negative resting potential, resulting in the maximum number of Na$^+$ channels being available for activation. After 30-60 minutes of CC2-DMPE staining, the cells were washed 3 times with 150 µL of TEA-MeSO$_3$ solution. Upon removing the solution, the cells were loaded with 80 µL of the DiSBAC$_2$(3) solution and incubated for 20-30 minutes as before. Typically, wells in one column on each plate were free of test drug(s) and served as positive and negative controls.

Figure 10:
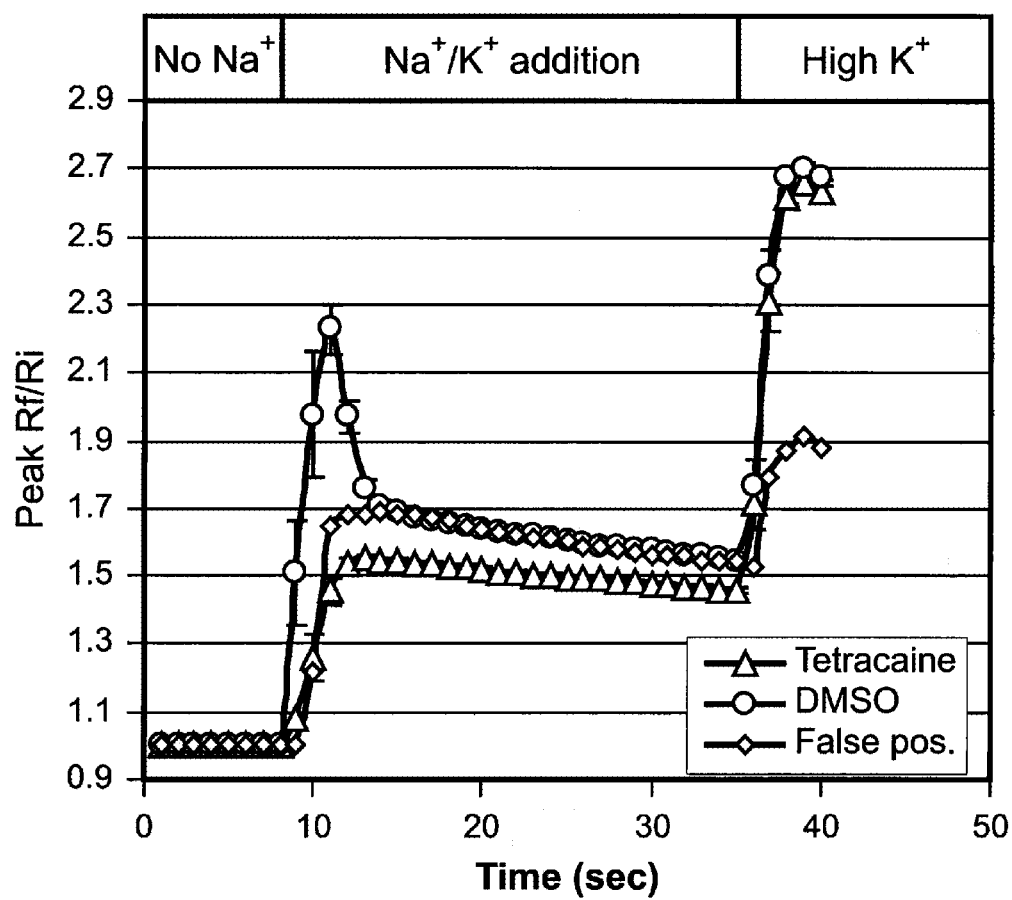
FIG. 10 shows inhibition of persistent current-dependent depolarization by Na⁺ channel blockers. In this assay, cells are resting in wells containing a 80 μL solution of 140 mM TEA-MeSO₃ (Na⁺-free box) to which is added 240 μL solution of 140 mM NaMeSO₃ and 13 mM KMeSO₃ for a final K⁺ concentration of 10 mM and a final Na⁺ concentration of 110 mM (Na⁺/K⁺-addition). This elicits a robust depolarizing response. Following the resolution of the sodium-dependent depolarization, a second aliquot of KMeSO₃ is added to the well bringing the final K⁺ concentration to 80 mM (high potassium-addition). This addition results in a second depolarizing response. Compounds that reduce the sodium-dependent, but not the potassium-dependent depolarizations are selected as persistent sodium channel blockers. Circles indicate the control response with 0.1% DMSO added, triangles show the effects of the sodium channel inhibitor tetracaine (10 μM) and the diamonds show the response during the application of a non-specific channel blocker.

The assay plates were then transferred to a voltage/ion probe reader (VIPR) (Aurora Biosciences, San Diego, Calif.) and the VIPR was adjusted so that the fluorescent emission ratio from the donor ands acceptor FRET dyes equaled 1.0. To elicit persistent sodium current, a double addition protocol was performed by first adding 240 µL of NaMeSO$_3$ solution to adjust the concentration of sodium and potassium ions in the well to 110 mM and 10 mM, respectively, and measuring the resulting sodium-dependent depolarization and second by adding K$^+$ to a final concentration of 80 mM, and measuring potassium-dependent depolarization. 240 µL of TEA-MeSO$_3$ solution or 1 µM TTX was used as a positive control. Test compounds that block the Na$^+$-dependent signal, but not the K$^+$-dependent signal were selected for further analysis. The Na$^+$-dependent depolarization resulting from the persistent Na$^+$ was measured as shown in FIG. 10. The labeled boxes indicate the application of Na$^+$ or K$^+$. Circles indicate the control response with 0.1% DMSO added, triangles show the effects of the Na$^+$ channel inhibitor tetracaine (10 µM), and the diamonds show the response during the application of a non-specific channel blocker.

In this high-throughput assay, non-specific blockers that inhibit membrane depolarization induced by any effector must be distinguished from selective persistent Na$^+$ current blockers, which block only persistent Na$^+$-dependent depolarizations. Therefore, a counter-screen to determine the ability of compounds to alter K$^+$-dependent depolarization was performed. As shown in FIG. 10, following pre-incubation with vehicle alone (DMSO) both Na$^+$ and K$^+$ additions produced a robust depolarization as indicated by the increase in Rf/Ri. Tetracaine, a Na$^+$ channel blocker, inhibited the Na$^+$-dependent, but not the K$^+$-dependent change in Rf/Ri. In contrast, a non-specific inhibitor of Na$^+$ and K$^+$-dependent depolarization blocked the change in Rf/Ri following either addition. This data demonstrates that selective blockers of the persistent sodium current can be identified using the described method.

To eliminate compounds that non-specifically inhibited the Na$^+$-dependent depolarization, data obtained using the above procedure were analyzed with respect to a counter-screen that used K$^+$-dependent depolarization as a readout. To select hits from the primary screen, the data were plotted as histograms. Inhibition of the Na$^+$-dependent depolarization was plotted against inhibition of the K$^+$-dependent depolarization. Based on these data, the criteria for selection as a hit, was a greater or equal to 90% inhibition of the Na$^+$-dependent depolarization and a less than or equal to 20% inhibition of the K$^+$-dependent depolarization. This protocol provided a distinction between compounds that were inert or non-specific in their effects and compounds that specifically block the persistent sodium current.

Optical experiments in microtiter plates were performed on the Voltage/Ion Probe Reader (VIPR) using two 400 nm excitation filters and filter sticks with 460 nm and 570 nm filters on the emission side for the blue and red sensitive PMTs, respectively. The instrument was run in column acquisition mode with 2 or 5 Hz sampling and 30 seconds of recording per column. Starting volumes in each well were 80 mL; usually 240 mL was added to each well during the course of the experiment. The lamp was allowed to warm up for about 20 minutes and power to the PMTs was turned on for about 10 minutes prior to each experiment.

Ratiometric measurements of changes in fluorescent emissions at 460- and 570 nm on the VIPR platform (Aurora Bioscience, San Diego, Calif.) demonstrated that this assay format produces a robust and reproducible fluorescent signal upon depolarization of HEK-Na$_v$ 1.3 cells with a Na$^+$/K$^+$ addition. From a normalized ratio of 1.0 in Na$^+$-free media, Na$^+$-dependent depolarization resulted in an increase in the 460/570 ratio to over 2.2 (FIG. 10). Inter-well analysis of the ratios indicated that the amplitude of signal was large enough and consistent enough to be used in high-throughput screening.

Data were analyzed and reported as normalized ratios of intensities measured in the 460 nm and 580 nm channels. The VIPR sampling rate varied between 2 and 5 Hz in different experiments, with 5 Hz used for higher resolution of the peak sodium responses. The process of calculating these ratios was performed as follows. On all plates, column 12 contained TEA-MeSO$_3$ solution with the same DiSBAC2(3) and ESS-AY17 concentrations as used in the cell plates; however no cells were included in column 12. Intensity values at each wavelength were averaged for the duration of the scan. These average values were subtracted from intensity values in all assay wells. The initial ratio obtained from samples 5-10 (Ri) was defined as:

$$Ri = \frac{Intensity_{460\ nm, samples\ 5\text{-}10} - background_{460\ nm}}{Intensity_{580\ nm, samples\ 5\text{-}10} - background_{580\ nm}}$$

and the ratio obtained from sample f (Rf) was defined as:

$$Rf = \frac{Intensity_{460\ nm, sample f} - background_{460\ nm}}{Intensity_{580\ nm, sample f} - background_{580\ nm}}$$

Final data were normalized to the starting ratio of each well and reported as Rf/Ri. The fluorescent response in the Na$_v$1.3 persistent current assay reached a peak approximately 10 seconds following the start of the run, therefore, the maximum ratio was selected as the readout for the assay (FIG. 10).

Figure 11A:
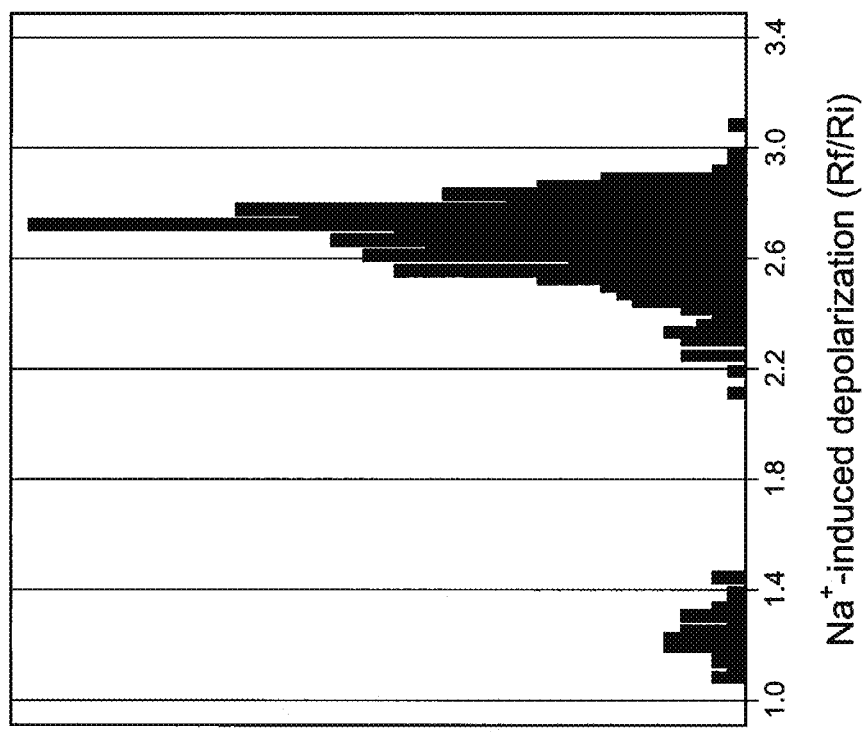
FIG. 11A-C shows data from assays in which the screening window for the persistent current assay is determined. To evaluate the size of the "screening window," data was examined from assays in which responses to sodium-dependent depolarization were measured in the presence of 10 μM Tetracaine to completely block the sodium-dependent depolarization or in the presence of a 0.1% DMSO control to obtain a maximum depolarization. Data were binned into histograms and a screening window (Z) was calculated from the mean and standard deviation for the maximal and minimum values according to the equation: $Z=1-(3\times STD_{Max}+3\times STD_{Min})/(Mean_{Max}-Mean_{Min})$.
Figure 11B:
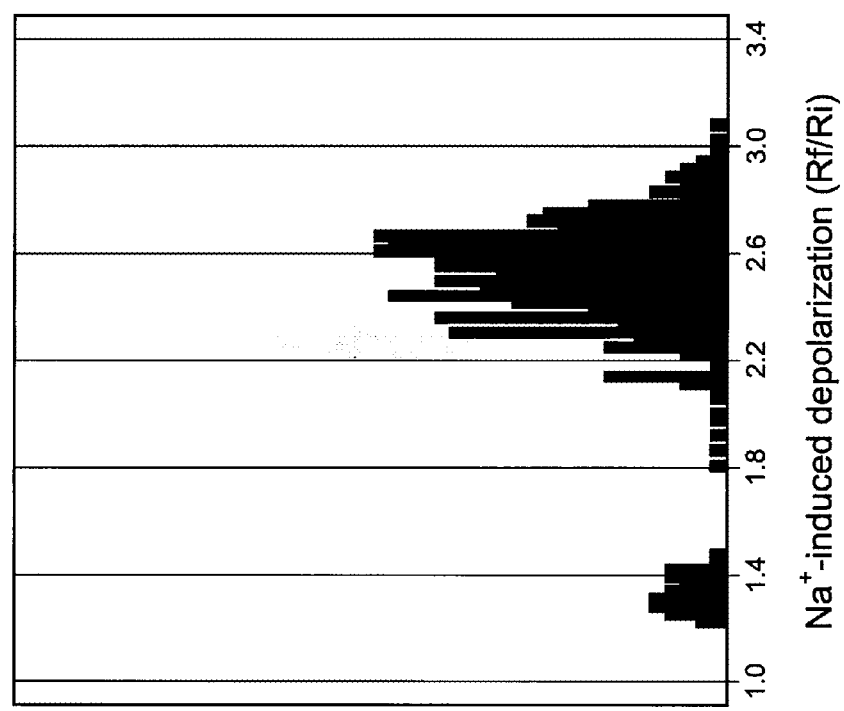
Figure 11C:
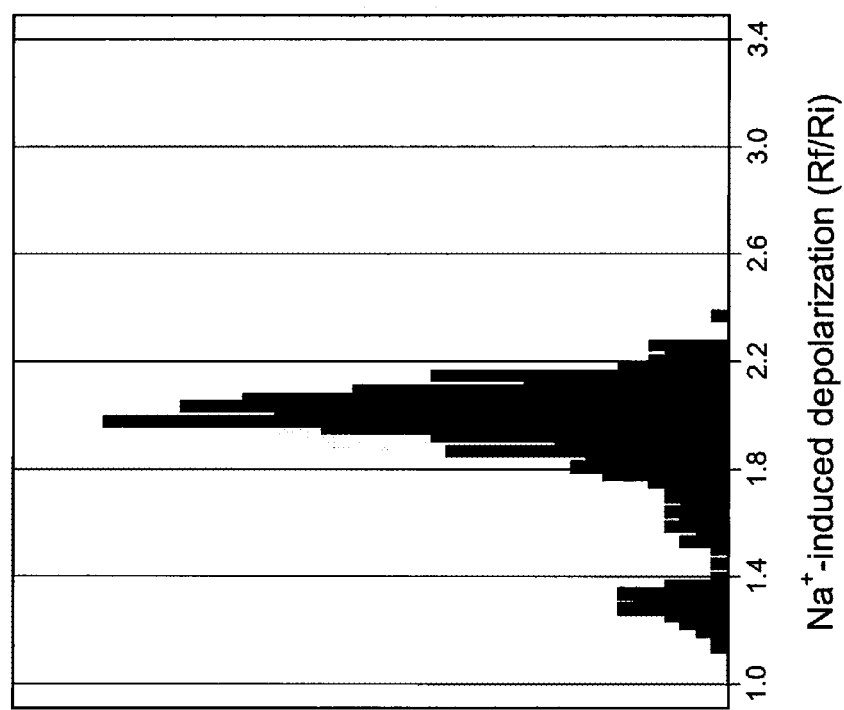

The assay format described above allows for quality assurance by measuring both negative (DMSO 0.1%) and positive (tetracaine 10 μM) controls. Every 10th plate in an assay run was a control plate. The data from these plates were used to verify that the assay conditions were optimal and to normalize the data from the test compounds. FIG. 11 shows results from control plates from multiple assays.

In FIG. 11, control plates having wells containing either 0.1% DMSO or 10 μM tetracaine were run after every ninth assay plate. The response to Na$^+$-dependent depolarization was measured and the data were binned into histograms as shown. The mean maximum response (Max) obtained in the presence of (0.1% DMSO) and the mean minimum response (Min) obtained in the presence of 10 μM tetracaine were determined. For quality control, data variance was calculated using a Z' factor method that compares the difference between the maximum and minimum signals in order to discriminate hit compounds from the background variation, see, e.g., Ji-Hu Zhang et al, *A Simple Statistical Parameter for Use in Evaluation and Validation of High Throughput Screening Assays*, 4(2) J. Biomol. Screen. 67-73 (1999). This was accomplished by calculating a screening window (z) for each control plate. Data for the run was accepted if $1.0 \geq Z \geq 0.5$. The Z' factor is calculated by comparing the difference of the means of a positive and negative control with their respective standard deviations as in equation:

$$Z = 1 - \frac{3 \times STD_{max} + 3 \times STD_{min}}{Mean_{max} - Mean_{min}}$$

Example 2

Screening Assay for Identifying Persistent Sodium Current Blockers Using Single Wavelength Voltage-Sensitive Dyes To establish an assay plate HEK-293 cells stably transfected with a cDNA for the Na$_v$1.3 sodium channel capable of mediating a persistent sodium current (HEK-Na$_v$ 1.3 cells) were grown in Minimum Essential Medium (Invitrogen, Inc., Carlsbad, Calif.) supplemented with 10% Fetal Bovine Serum (Invitrogen, Inc., Carlsbad, Calif.), 1% Penicillin-Streptomycin (Invitrogen, Inc., Carlsbad, Calif.), 500 mg/mL G418 Geneticin (Invitrogen, Inc., Carlsbad, Calif.) and 2 μM TTX (Calbiochem, Inc., San Diego, Calif.) for maintaining selective pressure. Cells were grown in vented cap flasks, in 90% humidity and 10% CO$_2$, to about 80% confluence, harvested by trypsinization and cell density was determined. Approximately 16 to 24 hours before the assay, cells were seeded at 75,000 cells per well in 150 μL of MEM media in clear bottom, black-wall, poly-d-lysine coated 96-well plates (BD Biosciences) and stored in a 5% CO$_2$, 37° C. incubator overnight. This plating procedure resulted in an optimal cell confluence (80%-90%) at the time of the assay.

To examine the ability of test molecules to alter persistent sodium current, the medium was aspirated from the wells and replaced with 40 mL of TEA-MeSO$_3$ (Na$^+$ depletion) solution containing the following: TEA-MeSO$_3$ (140 mM), HEPES-MeSO$_3$ (10 mM), KMeSO$_3$ (4.5 mM), Glucose (10 mM) MgCl$_2$ (1 mM), CaCl$_2$ (1 mM), CdCl$_2$ (0.2 mM) with a pH of 7.4 and an osmolarity of 300-310 mOsm. The Na$^+$ depletion solution also contained 4× of the final test concentration of Molecular Devices membrane potential dye (Molecular Devices Corp., Sunnyvale, Calif.) made up according to manufacturers instructions. The Molecular Devices membrane potential dye is a lipophilic, anionic, bis-oxonol dye that can partition across the cytoplasmic membrane of live cells, dependent on the membrane potential across the plasma membrane. Its fluorescence intensity increases when the dye is bound to cytosolic proteins. When the cells are depolarized, more dye enters the cells, and the increased intracellular concentration of the dye binding to intracellular lipids and proteins causes an increase in fluorescence signal. When the cells are hyperpolarized, dye exits the cells, and the decreased intracellular concentration of dye binding to lipids and proteins results in a decreased of fluorescence signal. The dye was excited at the 488 nm wavelength. At this time either positive or negative control compounds or test molecules were added to the wells of the plate at 1× their final test concentration. The plate was allowed to incubate with the dye and compounds were allowed to incubate for about 25-30 minutes at room temperature in dark.

The assay plates were then transferred to a Fluorometric Imaging Plate Reader (FLIPR-Tetra, Molecular Devices Corp., Sunnyvale, Calif.) for measurement of depolarization induced by addition of the Na$^+$ repletion buffer. The Na$^+$ repletion buffer solution comprised the following: NaMeSO$_3$ (140 mM), HEPES-MeSO$_3$ (10 mM), KMeSO$_3$ (13 mM), Glucose (10 mM) MgCl$_2$ (1 mM), CaCl$_2$ (1 mM), CdCl$_2$ (0.2 mM) with a pH of 7.4 and an osmolarity of 300-310 mOsm. The Na$^+$ depletion solution also contained 1× of the final test concentration of either positive or negative control compounds or test molecules.

The parameters for the FLIPR-Tetra data acquisition were set as follows: the excitation wavelength was set to a bandpass of 510-545 nm; the emission wavelength was set to a bandpass of 565-625 nm; the gain of camera was set between 60-100 with an exposure time of 0.1 s and with an acquisition rate of 5 Hz.

Figure 14A:
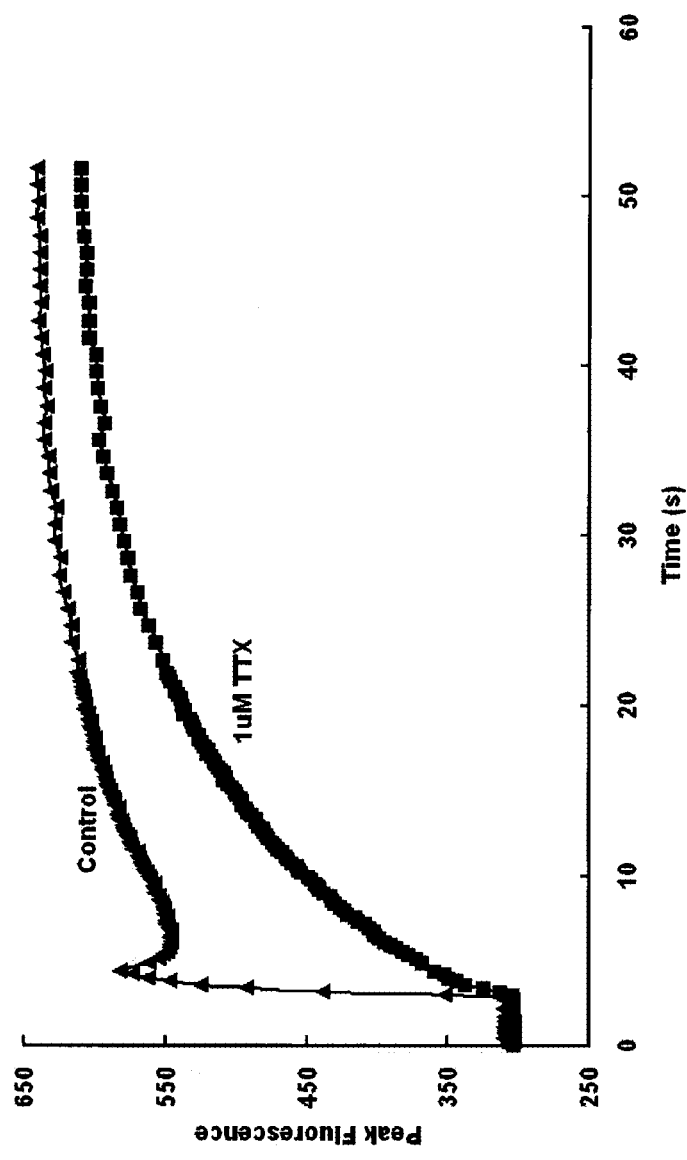
FIG. 14A-B shows the use of a single-wavelength dye to measure persistent Na⁺ channel activity to measure fluorescence on the FLIPR-Tetra.
Figure 14B:
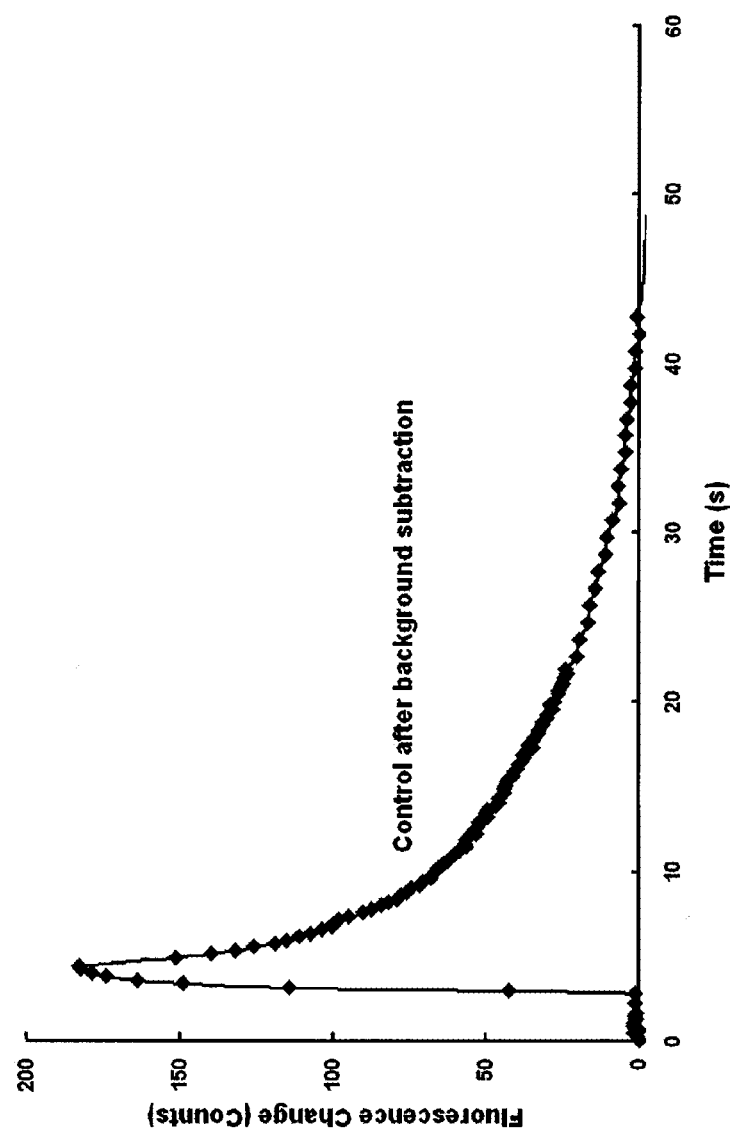

The assay protocol was as follows: after transferring the plates to the FLIPR-Tetra baseline fluorescence was measured for 5 sec at which time 120 μL of the Na$^+$ repletion buffer was added to initiate a depolarizing response (FIG. 14A, Control). This response contained both a specific depolarization a result of Na$^+$ flux across voltage-gated sodium channels (VGSC) and a non-specific depolarization resulting from other Na$^+$-dependent mechanisms in the HEK cells. The background response was revealed in wells that contained an excess of TTX (1 μM) to block all VGSC. Specific responses were measured by subtracting the average response of wells containing 1 μM TTX from the test wells (FIG. 14B).

For data analysis the peak fluorescence amplitude measures from each well of the test plates in the FLIPR were calculated automatically by Screenworks (Molecular Devices Corp, Sunnyvale, Calif.) which determined the maximum peak as the difference from the most positive peak relative to baseline. Peak amplitude measures were then imported to an excel template file which is used to calculate mean and SD. Mean amplitude measures from each drug-treated group were normalized with respect to the mean of control group. Normalized mean amplitude measures from control and drug treated wells were imported into Origin for plotting concentration-response curves of and determination IC$_{50}$ values of persistent sodium channel blockers.

To test the accuracy and reproducibility of the Na$^+$ depletion/repletion assay on the FLIPR system, two assay formats were used: a screening window format to measure the ability to obtain reproducible data in the single-concentration or HTS mode of screening (FIG. 15A) and a dose-response format to measure the ability to accurately predict IC$_{50}$ of known reference compounds (FIG. 15B)

Figure 16A:
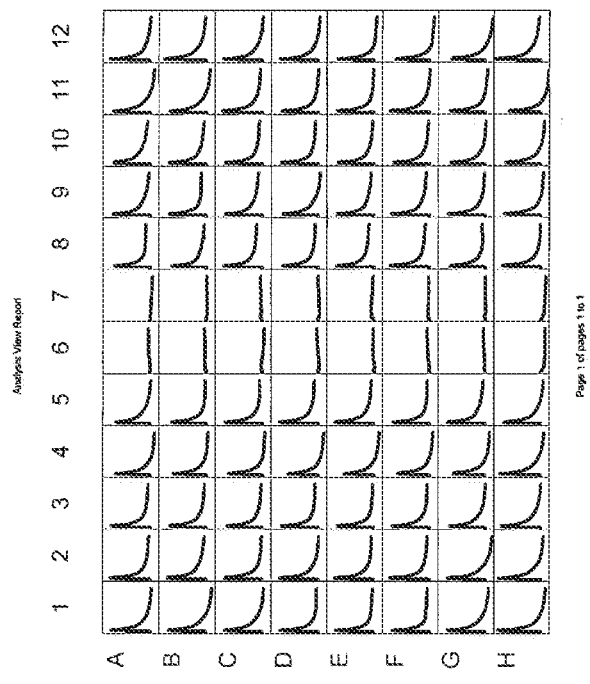
FIG. 16A-B shows the results of the screening window experiment.

Results from 96-well plate setup in the screening window format demonstrated the overall reproducibility of the response (FIG. 16). In this plate Na$^+$ was added to wells A1-H6 to induce depolarization while 1 μM TTX were incubated for 30 minutes in wells A7-H12 prior to Na$^+$ addition. The Na$^+$ channel dependent component of the fluorescence response in wells A7-H12 was blocked by TTX.

Within HTS assays a standard method to evaluate the ability to discriminate hit compounds from the background variation in the signal-to-noise ratio of the assay was calculated using a metric called Z' factor, see, e.g., Ji-Hu Zhang et al, *A Simple Statistical Parameter for Use in Evaluation and Validation of High Throughput Screening Assays,* 4(2) J. Biomol. Screen. 67-73 (1999). The Z' factor was calculated by comparing the difference of the means of a positive and negative control with their respective standard deviations as in equation:

$$Z = 1 - \frac{3 \times STD_{max} + 3 \times STD_{min}}{Mean_{max} - Mean_{min}}$$

Figure 16B:
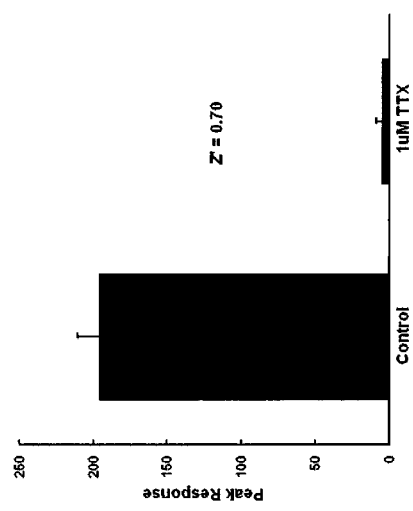

Mean Fluorescence peak amplitude and standard deviation from control and drug treated wells was used to calculate the screening window factor (Z'). Peak fluorescence amplitude measures from each well was calculated automatically by Screenworks which determined the maximum peak as the difference from the most positive peak relative to baseline. Peak amplitude measures were then imported to an excel template file which was used to calculate mean and SD. Mean and SD from control and drug treated groups were input to equation 1 for determination of screening window factor (Z'). For the data illustrated in FIG. 15 the Z' factor was 0.52 (FIG. 16B). Assays were generally considered acceptable when z' varies between 0.5 and 1.0.

Figure 17A:
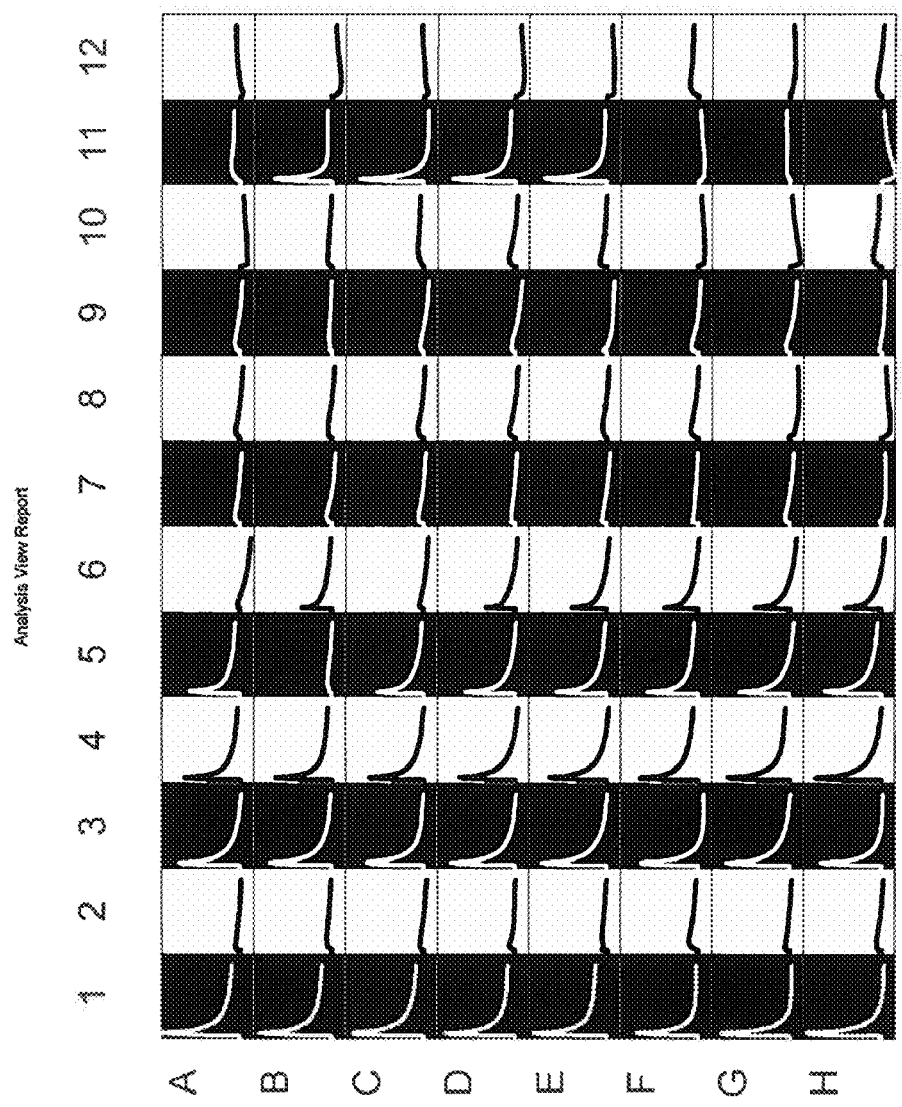
FIG. 17A-C shows a dose response analysis using the FLIPR-tetra based persistent current assay.
Figure 17B:
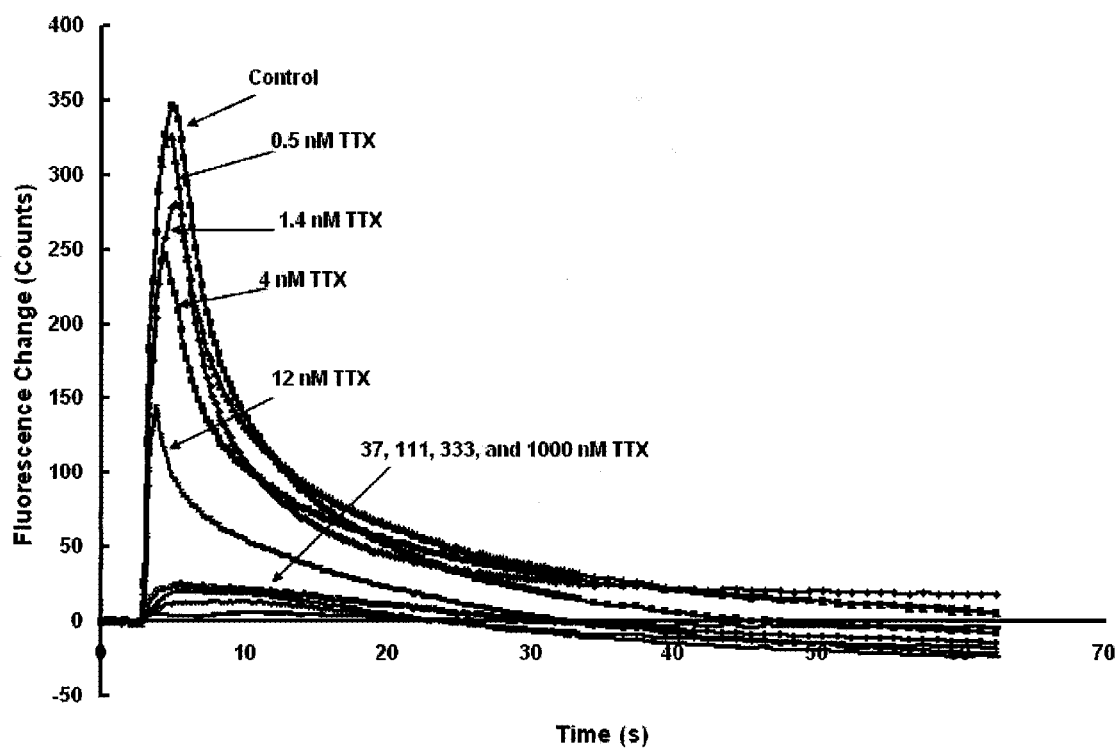

To examine the relative potency of test molecules against persistent sodium currents their IC$_{50}$ was determined from dose response data as shown in FIG. 17. In this assay plate in FIG. 17A, wells A1-H2, and A11-H12 received Na$^+$ addition while other wells from column 3-10 were treated with TTX ranging from 0.5 nM to 1000 nM (see plate layout in FIG. 15B). The average fluorescence waveforms from control and TTX treated groups were plotted to illustrate the dose dependent blockade of Na$^+$-induced fluorescence response by TTX (FIG. 17B). Peak amplitude measures from the reduced data were exported to an Excel analysis template file which calculated mean fluorescence amplitude and SD. Mean amplitude measures from test-molecule treated groups were normalized with respect to the mean of control group. Normalized mean amplitude measures from control and TTX treated wells were imported into Origin for determination of IC$_{50}$. Normalized mean amplitudes were plotted as a function of dose response of TTX in log scale. IC$_{50}$ was determined by curve fitting using the logistic dose response equation:

$$Y = \frac{A_1 - A_2 + A_2}{1 + (x/x_0)^p}$$

where $x_0$=center $p$=power $A_1$=Initial Y value $A_2$=Final Y value

Figure 17C:
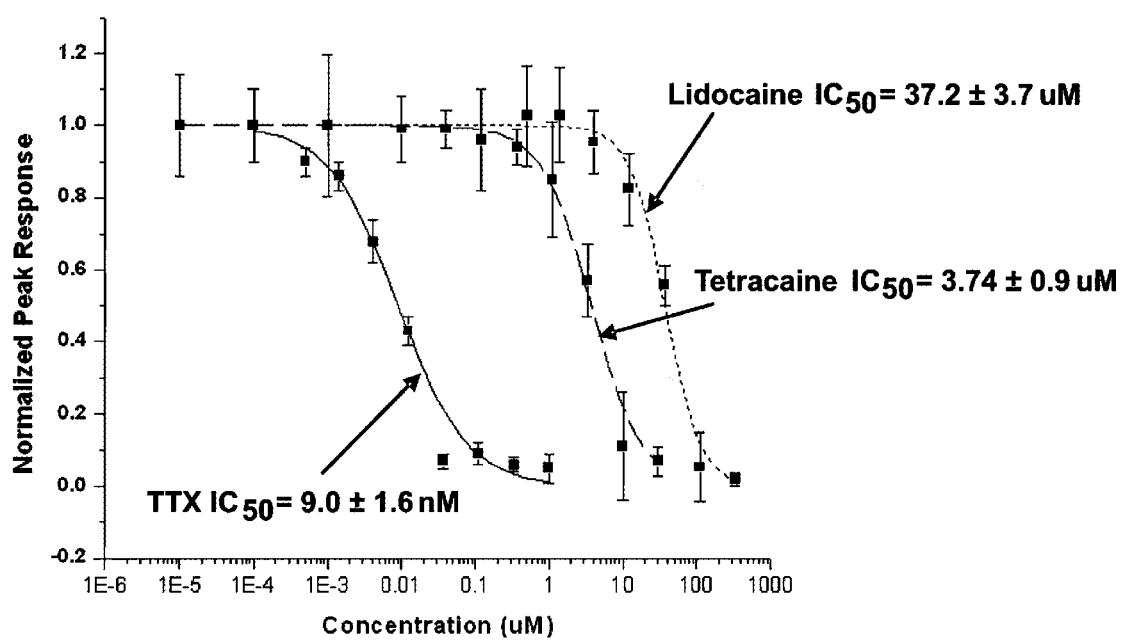

The Y value at $x_0$ is half way between the two limiting values $A_1$ and $A_2$ $Y(x_0)=(A_1+A_2)/2$ Concentration-response curves obtained from three test compounds are shown in FIG. 17C. The IC$_{50}$ values for TTX, Tetracaine and Lidocaine of 5 nM, 1.8 μM and 32 μM obtained in this assay correspond well with the values obtained using patch-clamp (5 nM, 1 μM and 90 μM respectively).

Example 3

Screening Assay for Identifying Transient Sodium Current Blockers Using Electric Field Stimulation (EFS)

Methods for applying external electric fields to stimulate excitable cells and tissues are well known and have been extensively reviewed, see, e.g., Peter J. Basser and Bradley J. Roth, *New Currents in Electrical Stimulation of Excitable Tissues*, 2 Annu. Rev. Biomed. Eng. 377-397 (2000); Jaakko Malmivuo and Robert Plonsey, Bioelectromagnetism: Principles and Applications of Bioelectric and Biomagnetic Fields, (Oxford University Press, New York. 472 pp. 1995); and J. Patrick Reilly, Electrical Stimulation and Electropathology, (Cambridge University Press, Cambridge. 1-522 pp. 1992).

To establish an assay to measure the potency of compounds for blocking transient sodium currents in order to compare their potency against blocking persistent sodium currents, HEK-293-$Na_v$ 1.3 cells will be grown in Minimum the presence of 500 mg/mL G418 Geneticin (Invitrogen, Inc., Carlsbad, Calif.) and 2 µM TTX (Calbiochem, Inc., San Diego, Calif.) to maintain selective pressure.

To measure transient currents cells will be transferred to a recording chamber suitably instrumented with electrodes to produce EFS as described in, e.g., Michael P. Maher & Jesus E. Gonzalez, *Multi-well Plate and Electrode Assemblies for Ion Channel Assays*, U.S. Pat. No. 6,969,449 (Nov. 29, 2005); Michael P. Maher & Jesus E. Gonzalez, *High Throughput Method and System for Screening Candidate Compounds for Activity Against Target Ion Channels*, U.S. Pat. No. 6,686,193 (Feb. 3, 2004). and Paul Burnett et al., *Electrophysiology Assay Methods*, U.S. Patent Publication No. 2004/0115614 (Jun. 17, 2004).

Cells will be loaded with either an appropriate FRET donor/acceptor voltage-sensitive dye pair as described in Example 1 or a single wavelength voltage-sensitive dye as described in Example 2. The cells will be transferred to appropriate device to record membrane potential induced changes in fluorescence, e.g., a VIPR (Aurora Bioscience, San Diego, Calif.) or FLIPR-tetra (Molecular Devices, Sunnyvale, Calif.).

Optical measurement of fluorescent changes in response of EFS will be measured of a series of stimuli. The transient Na+ current produces rapid change in fluorescence due to the rapid depolarization. For quantification of the block of transient current, the amplitude of peak response will be averaged form a series of stimuli. The average response will be converted to activity by normalizing against the difference between the responses in Ringer's solution with DMSO and Ringer's solution containing 10 µM tetracaine or 100 nM TTX. Normalized activity against the transient current will be plotted as a concentration dose response curve and $IC_{50}$ for block against transient currents can be calculated by a fitting a logistic function to the data.

Example 4

Screening Assay for Identifying Transient Sodium Current Blockers Using Automated Patch-Clamp Technology HEK-293 cells stably transfected with a cDNA for the $Na_v$ 1.3 sodium channel capable of mediating a persistent sodium current (HEK-$Na_v$ 1.3 cells) were grown in Minimum Essential Medium (Invitrogen, Inc., Carlsbad, Calif.) supplemented with 10% Fetal Bovine Serum (Invitrogen, Inc., Carlsbad, Calif.), 1% Penicillin-Streptomycin (Invitrogen, Inc., Carlsbad, Calif.), 500 mg/mL G418 Geneticin (Invitrogen, Inc., Carlsbad, Calif.) and 2 µM TTX (Calbiochem, Inc., San Diego, Calif.) for maintaining selective pressure. Cells were grown in vented cap flasks, in 90% humidity and 10% $CO_2$, to about 80% confluence, harvested by trypsinization and cell density was determined. Cells were resuspended at a density of $2\times10^6$/mL in the extracellular solution described below and transferred to either a IonWorks (Molecular Devices, Sunnyvale, Calif.) or Flyscreen (Flyion, GmbH) automated patch clamp for measurement of peak transient $Na^+$ current.

Solutions used for these experiments were as follows: Internal Solution (in mM): 140 KCl, 2 $MgCl_2$ 5 EGTA, 10 Hepes pH to 7.2 with KOH; External Solution (in mM): 137 NaCl, 4 KCl, 1 $MgCl_2$, 1.8 $CaCl_2$, 10 Hepes, 10 Glucose, pH to 7.4 with NaOH.

Figure 18:
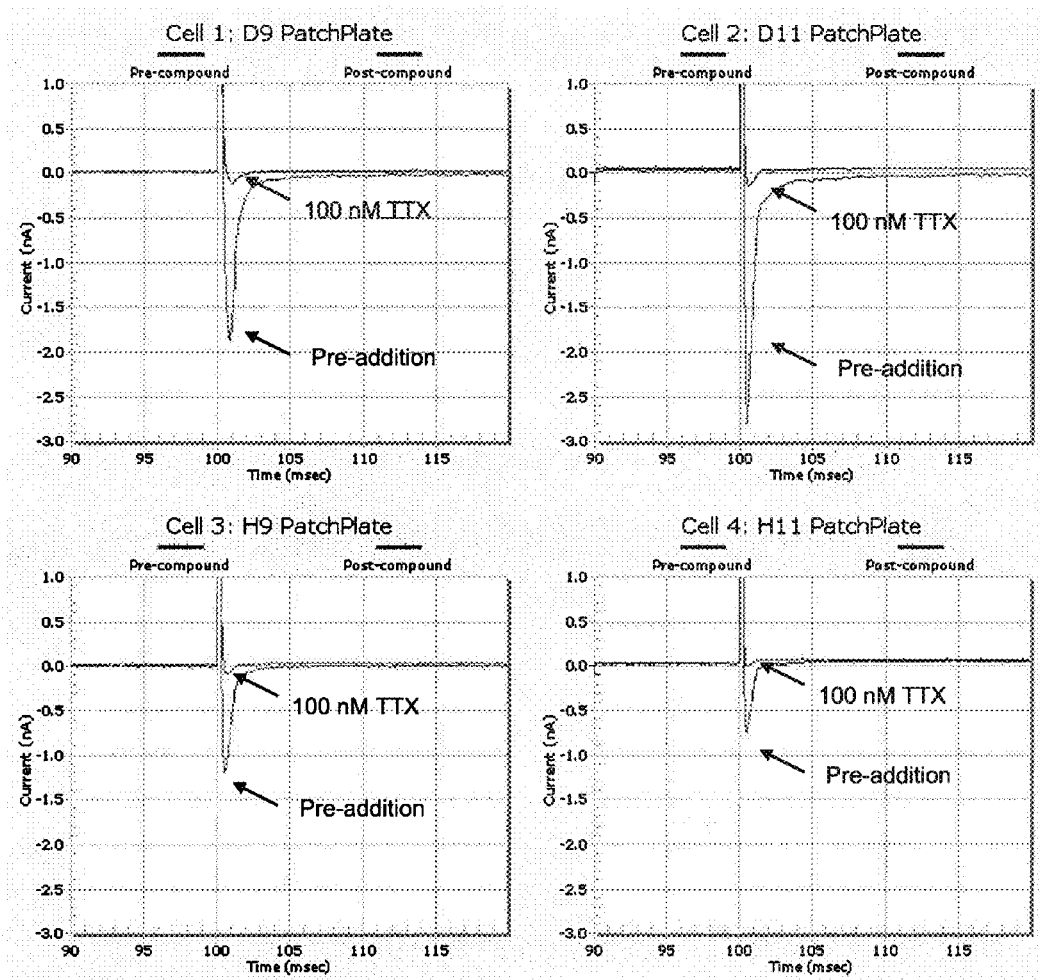
FIG. 18 shows transient Na⁺ currents taken from 4 wells on an IonWorks automated patch clamp device. Control (Pre-addition) and TTX blocked (100 nM TTX) traces are shown for each cell.

$Na^+$ currents were elicited by the following pulse protocol: Cells were held at a −90 mV and stimulated every 5 sec with a voltage step to 0 mV for 25 ms. Peak inward current was measured between 1 and 5 ms after the onset of the voltage pulse. After a pre-addition run to determine baseline currents, compounds were applied by and allowed to incubate for 5 minutes and a second reading was then taken to compare currents in the present of either positive or negative control compounds or test compounds. FIG. 18 shows an example of four such experiments from an IonWorks automated patch clamp. The peak currents from the pre-addition run and after exposure to 100 nM TTX are labeled.

Figure 19:
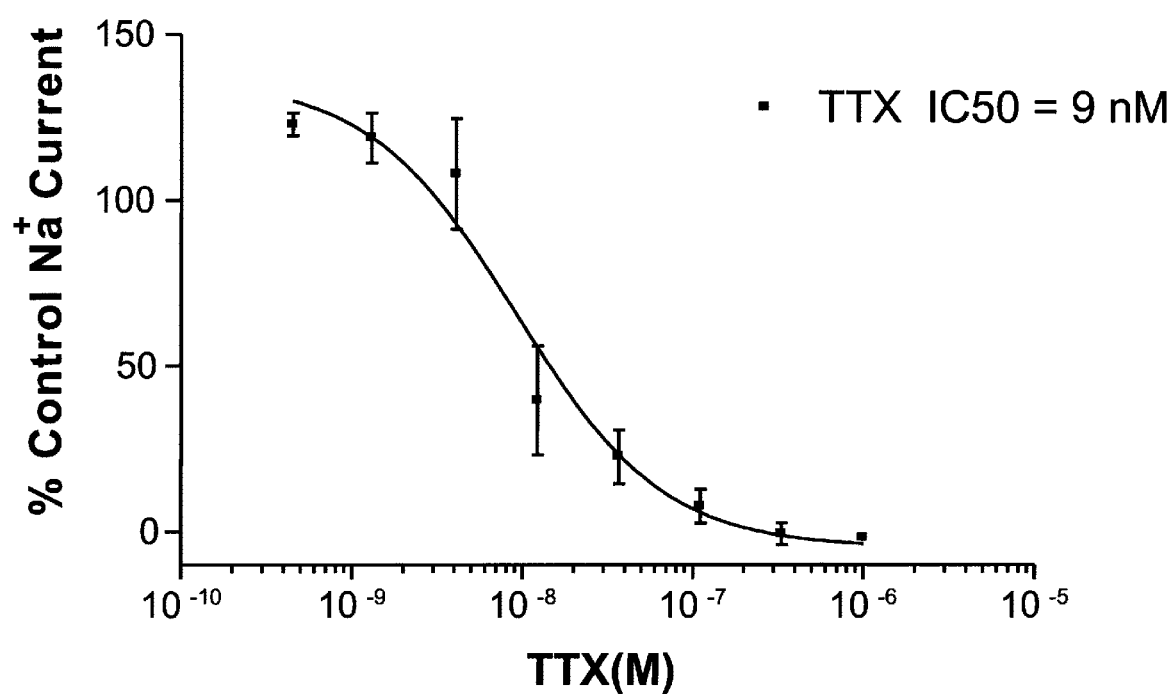
FIG. 19 shows a dose response analysis of the IonWorks transient current assay. Averaged currents are plotted as a semi-log dose response as mean±SD in the presence of increasing concentrations of TTX. The data is fitted by logistic function (line) and the estimated $IC_{50}$ value is shown.

To examine the relative potency of test molecules against transient sodium currents their $IC_{50}$ was determined from dose response data as shown in FIG. 19. Peak current measures from the reduced data shown in FIG. 18 were exported to an Excel analysis template file which calculated mean current amplitude and SD. Mean amplitude measures from test-molecule treated groups were normalized with respect to the mean of control group. Normalized mean amplitude measures from control and TTX treated wells were imported into Origin for determination of $IC_{50}$. Normalized mean amplitudes were plotted as a function of dose response of TTX in log scale. $IC_{50}$ was determined by curve fitting using the logistic dose response equation:

$$Y = \frac{A_1 - A_2}{1 + (x/x_0)^p} + A_2$$

where $x_0$=center $p$=power $A_1$=Initial Y value $A_2$=Final Y value

The Y value at $x_0$ is half way between the two limiting values $A_1$ and $A_2$ $$Y(x_0)=(A_1+A_2)/2$$

$IC_{50}$ values obtained in this assay were then be compared against $IC_{50}$ for blocking persistent currents as measured in examples 1 and 2. This allows the calculation of the relative selectivity of block for persistent vs. transient currents.

Example 5

Electrophysiological Assay for Selectivity of Inhibitors of Persistent Sodium Current To confirm the blocking selectivity of test compounds for persistent sodium current, individual compounds were examined using a whole-cell patch clamp method. HEK cells transfected with $Na_v$ 1.3 sodium channels that express transient and persistent sodium currents were plated onto glass coverslips and cultured in MEM cell culture media with Earle's salts and GlutaMAX (Invitrogen, Inc., Carlsbad, Calif.) supplemented with: 10% Fetal bovine serum, heat inactivated (Invitrogen, Inc., Carlsbad, Calif.), 0.1 mM MEM non-essential amino acids (Invitrogen, Inc., Carlsbad, Calif.), 10 mM HEPES (Invitrogen, Inc., Carlsbad, Calif.), 1% Penicillin/Streptomycin (Invitrogen, Inc., Carlsbad, Calif.).

After an incubation period of from 24 to 48 hours the culture medium was removed and replaced with external recording solution (see below). Whole cell patch clamp experiments were performed using an EPC10 amplifier (HEKA Instruments, Lambrecht, Germany.) linked to an IBM compatible personal computer equipped with PULSE software. Borosilicate glass patch pipettes were pulled to a fine tip on a P90 pipette puller (Sutter Instrument Co., Novato, Calif.) and were polished (Microforge, Narishige, Japan) to a resistance of about 1.5 Mohm when filled with intracellular recording solution (Table 3).

Persistent and transient currents in HEK cells expressing $Na_v$1.3 channels were measured by applying 200-msec depolarizations from a holding potential of −90 mV to 0 mV. Background currents that remained in the presence of 500 nM TTX were subtracted from all traces. Drugs were perfused directly into the vicinity of the cells using a microperfusion system.

TABLE 3

Patch Clamp Solutions

| External Recording Solution | | Internal Recording Solution | |
|---|---|---|---|
| Compound | Concentration | Compound | Concentration |
| NaCl | 127 mM | $CsMeSO_3$ | 125 mM |
| HEPES (free acid) | 10 mM | CsCl | 25 mM |
| KCl | 5 mM | NaHEPES | 10 mM |
| CsCl | 5 mM | Amphotericin | 240 µg/mL |
| Glucose | 10 mM | | |
| $MgCl_2$ | 0.6 mM | | |
| $CaCl_2$ | 1.2 mM | | |
| $CdCl_2$ | 200 µM | | |
| pH to 7.4 with NaOH @ room temp. 290 mOsm. | | pH 7.20 with CsOH 300 mOsm | |

Figure 12:
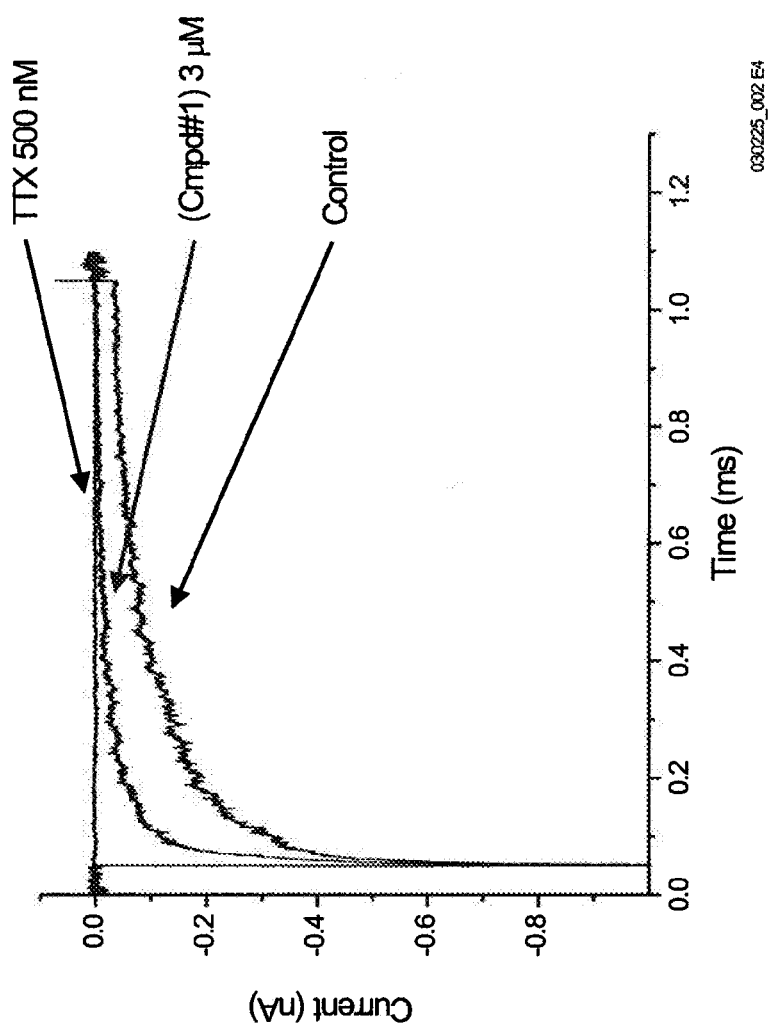
FIG. 12 shows sodium current traces before and after the addition of 3 μM Compound 1 or 500 nM TTX. HEK cells expressing Na$_v$ 1.3 channels were patch clamped in the perforated-patch mode. Currents were elicited by 200 msec test pulses to 0 mV from a holding potential of −90 mV.
Figure 13:
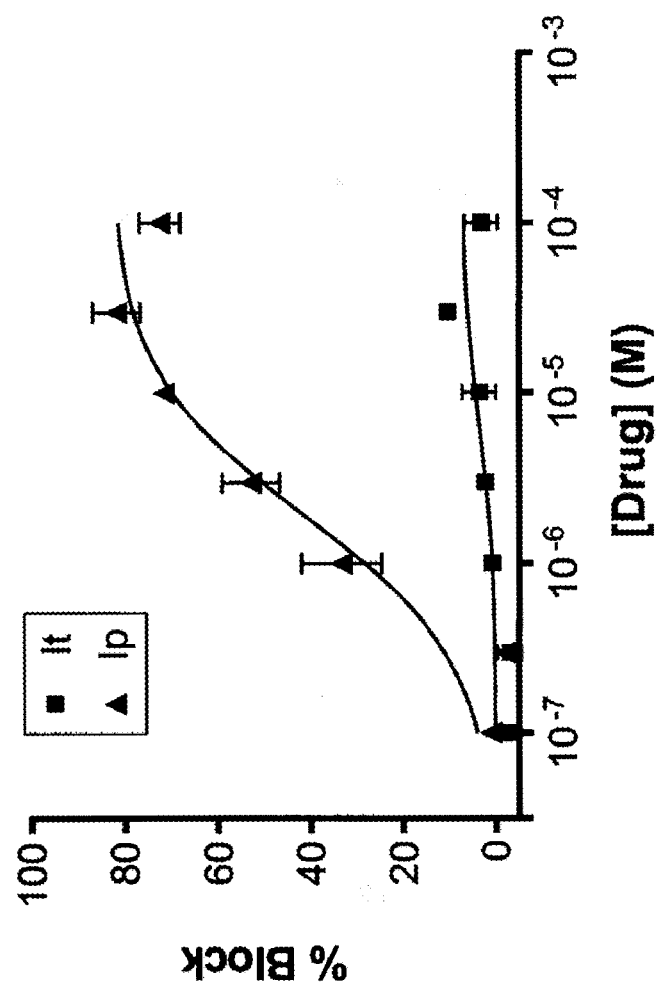
FIG. 13 shows a dose-response curve for Compound 1. The peak amplitudes of transient Na⁺ current ($I_t$) and the steady state amplitude of the persistent current ($I_p$) were measured at various Compound 1 concentrations, normalized to the amplitude of the control currents. The percent block was then plotted against drug concentration. Solid lines represent fits to the data with the Hill equation. The calculated IC$_{50}$ values and Hill coefficients are as follows: Hill slope, $I_t$ is 0.354 and $I_p$ is 0.733; IC$_{50}$, $I_t$ is 0.167 M and $I_p$ is 3.71×10⁻⁶ M.

Under control conditions, depolarizing pulses elicited a large transient inward current that declined to a smaller persistent current, which remained stable during the remainder of the pulse (FIG. 12, control). Addition of 500 nM TTX completely blocked both the transient and persistent currents (FIG. 12, TTX). Application of 3 µM of Compound 1 produced a much different effect. Inspection of FIG. 12 reveals that the Compound 1 blocked 99% of the persistent current while only reducing the transient current by 16%. Dose-response analysis for Compound 1 demonstrates its significant selectivity for blocking the persistent sodium current relative to the transient sodium current over a four order of magnitude range (FIG. 13).

What is claimed:

1. A method for identifying a selective blocker of a persistent Na⁺ channel whereby the method comprises the steps of:
   a) providing a test sample 1 comprising
      i) a physiological solution;
      ii) a voltage-sensitive fluorescence dye; and
      iii) a cell having a K⁺ channel and a persistent Na⁺ channel wherein a resting membrane potential of the cell is between −50 mV to −20 mV;
   b) detecting fluorescence emitted by the voltage-sensitive dye in test sample 1;
   c) adding a potential Na⁺ channel blocker to test sample 1;
   d) detecting fluorescence emitted by the voltage-sensitive dye in test sample 1;
   e) determining a relative emitted fluorescence 1 by comparing the emitted fluorescence from step (b) with the emitted fluorescence from step (d);
   f) providing a test sample 2 comprising
      i) a physiological solution;
      ii) a voltage-sensitive fluorescence dye;
      iii) a cell having a K⁺ channel and a transient Na⁺ channel; and
      iv) a potential Na⁺ channel blocker
   g) depolarizing the membrane of the cell in test sample 2;
   h) detecting the fluorescence emitted by the voltage-sensitive dye in test sample 2;
   i) providing a control sample 2 comprising
      i) a physiological solution;
      ii) a voltage-sensitive fluorescence dye; and
      iii) a cell having a K⁺ channel and a transient Na⁺ channel;
   j) depolarizing the membrane of the cell in control sample 2;
   k) detecting the fluorescence emitted by the voltage-sensitive dye in control sample 2;
   l) determining a relative emitted fluorescence 2 by comparing the emitted fluorescence from step (h) relative to an emitted fluorescence from step (k);
   m) comparing the relative emitted fluorescence in step (e) with the relative emitted fluorescence in step (l); wherein a decrease in emitted fluorescence from step (e) relative to the emitted fluorescence in step (l) is indicative of the presence of a selective persistent Na⁺ channel blocker in the test sample.

2. The method according to claim 1, wherein the resting membrane potential of the cell is between −40 mV and −10 mV.

3. The method according to claim 1, wherein the resting membrane potential of the cell is between −30 mV and 0 mV.

4. The method according to claim 1, wherein the resting membrane potential of the cell is between −20 mV and 10 mV.

5. The method according to claim 1, wherein the resting membrane potential of the cell is between −10 mV and 20 mV.

6. The method according to claim 1, wherein the cell expresses a persistent Na$^+$ channel selected from the group consisting of Na$_v$1.3, Na$_v$1.5, Na$_v$1.6 and Na$_v$1.9.

7. A method for identifying a blocker of a persistent Na$^+$ channel whereby the method comprises the steps of:
  a) providing a test sample 1 comprising
    i) a physiological solution;
    ii) a voltage-sensitive fluorescence dye; and
    iii) a cell having a K$^+$ channel and a persistent Na$^+$ channel wherein a resting membrane potential of the cell is between −50 mV to −20 mV;
  b) detecting fluorescence emitted by the voltage-sensitive dye in test sample 1;
  c) adding a potential Na$^+$ channel blocker to test sample 1;
  d) detecting fluorescence emitted by the voltage-sensitive dye test sample 1;
  e) comparing the emitted fluorescence from step (b) with the emitted fluorescence from step (d); wherein a decrease in emitted fluorescence from step (b) relative to the emitted fluorescence from step (d) is indicative of the presence of a persistent Na$^+$ channel blocker in the test sample.

8. The method according to claim 7, wherein the resting membrane potential of the cell is between −40 mV and −10 mV.

9. The method according to claim 7, wherein the resting membrane potential of the cell is between −30 mV and 0 mV.

10. The method according to claim 7, wherein the resting membrane potential of the cell is between −20 mV and 10 mV.

11. The method according to claim 7, wherein the resting membrane potential of the cell is between −10 mV and 20 mV.

12. The method according to claim 7, wherein the cell expresses a persistent Na$^+$ channel selected from the group consisting of Na$_v$1.3, Na$_v$1.5, Na$_v$1.6 and Na$_v$1.9.

* * * * *

UNITED STATES PATENT AND TRADEMARK OFFICE
CERTIFICATE OF CORRECTION

PATENT NO. : 7,754,440 B2
APPLICATION NO. : 12/041739
DATED : July 13, 2010
INVENTOR(S) : Joseph S. Adorante et al.

It is certified that error appears in the above-identified patent and that said Letters Patent is hereby corrected as shown below:

On the title page, item (56), in column 2, under "Other Publications", line 19, delete "Mexilentine" and insert -- Mexiletine --, therefor.

On the title page, item (56), in column 2, under "Other Publications", line 20, delete "Mycotes," and insert -- Myocytes, --, therefor.

On the title page, item (56), in column 2, under "Other Publications", line 22, delete "Tetrodtoxin" and insert -- Tetrodotoxin --, therefor.

In column 2, line 40, delete "Motoneuron" and insert -- Motorneuron --, therefor.

In column 14, line 23, delete "non-permeate" and insert -- non-permeant --, therefor.

In column 15, line 26, delete "naphtalene" and insert -- naphthalene --, therefor.

In column 15, line 26, delete "butylsulfonato" and insert -- butylsulfonate --, therefor.

In column 17, line 45, delete "DiSBAC$^2$(3)" and insert -- DiSBAC$_2$(3) --, therefor.

In column 17, line 47, delete "DiSBAC$^2$(3)" and insert -- DiSBAC$_2$(3) --, therefor.

In column 17, line 50, delete "DiSBAC$^2$(3)" and insert -- DiSBAC$_2$(3) --, therefor.

In column 17, line 60, delete "DiSBAC$^2$(3)" and insert -- DiSBAC$_2$(3) --, therefor.

In column 17, line 61, delete "DiSBAC$^4$(3)" and insert -- DiSBAC$_4$(3) --, therefor.

In column 18, line 62, delete "hipppocampal" and insert -- hippocampal --, therefor.

In column 19, line 2, delete "e,g," and insert -- e.g., --, therefor.

Signed and Sealed this

Fourteenth Day of September, 2010

David J. Kappos
*Director of the United States Patent and Trademark Office*

CERTIFICATE OF CORRECTION (continued)
U.S. Pat. No. 7,754,440 B2

In column 19, line 4, delete "e,g," and insert -- e.g., --, therefor.

In column 19, line 5, delete "e,g," and insert -- e.g., --, therefor.

In column 19, line 5, delete "e,g," and insert -- e.g., --, therefor.

In column 19, line 7, delete "e,g," and insert -- e.g., --, therefor.

In column 19, line 23, delete "e.g," and insert -- e.g., --, therefor.

In column 19, line 48, delete "tubermammillary" and insert -- tuberomammillary --, therefor.

In column 21, line 62, delete "3 ed." and insert -- $3^{rd}$ ed. --, therefor.

In column 22, line 1, delete "polybiquitin" and insert -- polyubiquitin --, therefor.

In column 22, line 23, delete "GeneSwitch®" and insert -- GeneSwitch™ --, therefor.

In column 22, line 39, delete "non-permeate" and insert -- non-permeant --, therefor.

In column 23, line 6, delete "fluorimeter" and insert -- fluorometer --, therefor.

In column 27, line 54, delete "oubain" and insert -- ouabain --, therefor.

In column 28, line 6, delete "oubain" and insert -- ouabain --, therefor.

In column 253, line 20, in claim 7, delete "dye test" and insert -- dye in test --, therefor.

SEQUENCE LISTING

<160> NUMBER OF SEQ ID NOS: 41

<210> SEQ ID NO 1
<211> LENGTH: 5997
<212> TYPE: DNA
<213> ORGANISM: Homo sapiens

<400> SEQUENCE: 1

```
atggagcaaa cagtgcttgt accaccagga cctgacagct tcaacttctt caccagagaa      60
tctcttgcgg ctattgaaag acgcattgca gaagaaaagg caaagaatcc caaaccagac     120
aaaaaagatg acgacgaaaa tggcccaaag ccaaatagtg acttggaagc tggaaagaac     180
cttccattta tttatggaga cattcctcca gagatggtgt cagagcccct ggaggacctg     240 gaccctact atatcaataa gaaaacttttt atagtattga ataaagggaa ggccatcttc     300
cggttcagtg ccacctctgc cctgtacatt ttaactccct tcaatcctct taggaaaata     360
gctattaaga ttttggtaca ttcattattc agcatgctaa ttatgtgcac tattttgaca     420
aactgtgtgt ttatgacaat gagtaaccct cctgattgga caaagaatgt agartacacc     480
ttcacaggaa tatatacttt tgaatcactt ataaaaatta ttgcaagggg attctgttta     540
gaagatttta ctttccttcg ggatccatgg aactggctcg atttcactgt cattacattt     600
gcgtacgtca cagagtttgt ggacctgggc aatgtctcgg cattgagaac attcagagtt     660
ctccgagcat tgaagacgat ttcagtcatt ccaggcctga aaaccattgt gggagccctg     720
```

```
atccagtctg tgaagaagct ctcagatgta atgatcctga ctgtgttctg tctgagcgta      780
tttgctctaa ttgggctgca gctgttcatg ggcaacctga ggaataaatg tatacaatgg      840
cctcccacca atgcttcctt ggaggaacat agtatagaaa agaatataac tgtgaattat      900
aatggtacac ttataaatga aactgtcttt gagtttgact ggaagtcata tattcaagat      960
tcaagatatc attatttcct ggagggtttt ttggatgcac tactatgtgg aaatagctct     1020
gatgcaggcc aatgtccaga gggatatatg tgtgtgaaag ctggtagaaa tcccaattat     1080
ggctacacaa gctttgatac cttcagttgg gcttttttgt ccttgtttcg actaatgact     1140
caggacttct gggaaaatct ttatcaactg acattacgtg ctgctgggaa aacgtacatg     1200 atatttttg tattggtcat tttcttgggc tcattctacc taataaattt gatcctggct     1260
gtggtggcca tggcctacga ggaacagaat caggccacct ggaagaagc agaacagaaa     1320 gaggccgaat ttcagcagat gattgaacag cttaaaaagc aacaggaggc agctcagcag     1380
gcagcaacgg caactgcctc agaacattcc agagagccca gtgcagcagg caggctctca     1440
gacagctcat ctgaagcctc taagttgagt tccaagagtg ctaaggaaag aagaaatcgg     1500
aggaagaaaa gaaacagaa agagcagtct ggtggggaag agaaagatga ggatgaattc     1560
caaaaatctg aatctgagga cagcatcagg aggaaaggtt ttcgcttctc cattgaaggg     1620
aaccgattga catatgaaaa aggtactcc tccccacacc agtctttgtt gagcatccgt     1680
ggctccctat tttcaccaag gcgaaatagc agaacaagcc ttttcagctt tagagggcga     1740
gcaaaggatg tgggatctga gaacgacttc gcagatgatg agcacagcac ctttgaggat     1800
aacgagagcc gtagagattc cttgtttgtg ccccgacgac acggagagag acgcaacagc     1860
aacctgagtc agaccagtag gtcatcccgg atgctggcag tgtttccagc gaatgggaag     1920
atgcacagca ctgtggattg caatggtgtg gtttccttgg ttggtggacc ttcagttcct     1980
acatcgcctt ttggacagct tctgccagag ggaacaacca ctgaaactga atgagaaag     2040 agaaggtcaa gttctttcca cgtttccatg gactttctag aagatccttc ccaaaggcaa     2100
cgagcaatga gtatagccag cattctaaca aatacagtgg aagaacttga agaatccagg     2160
cagaaatgcc caccctgttg gtataaattt tccaacatat tcttaatctg ggactgttct     2220
ccatattggt taaagtgaa acatgttgtc aacctggtcg tgatggaccc atttgttgac     2280
ctggccatca ccatctgtat tgtcttaaat actcttttca tggccatgga gcactatcca     2340
atgacggacc atttcaataa tgtgcttaca gtaggaaact tggttttcac tgggatctt     2400 acagcagaaa tgtttctgaa aattattgcc atggatcctt actattattt ccaagaaggc     2460
tggaatatct ttgacggttt tattgtgacg cttagcctgg tagaacttgg actcgccaat     2520
gtggaaggat tatctgttct ccgttcattt cgattgctgc gagttttcaa gttggcaaaa     2580
tcttggccaa cgttaaatat gctaataaag atcatcggca attccgtggg ggctctggga     2640
aatttaaccc tcgtcttggc catcatcgtc ttcattttg ccgtggtcgg catgcagctc     2700
tttggtaaaa gctacaaaga ttgtgtctgc aagatcgcca gtgattgtca actcccacgc     2760
tggcacatga atgacttctt ccactccttc ctgattgtgt tccgcgtgct gtgtgggag     2820 tggatagaga ccatgtggga ctgtatggag gttgctggtc aagccatgtg ccttactgtc     2880
ttcatgatgg tcatggtgat tggaaaccta gtggtcctga atctctttct ggccttgctt     2940
ctgagctcat ttagtgcaga caaccttgca gccactgatg atgataatga aatgaataat     3000
ctccaaattg ctgtggatag gatgcacaaa ggagtagctt atgtgaaaag aaaaatatat     3060
```

```
gaatttattc aacagtcctt cattaggaaa caaaagattt tagatgaaat taaaccactt    3120
gatgatctaa acaacaagaa agacagttgt atgtccaatc atacaacaga aattgggaaa    3180
gatcttgact atcttaaaga tgtaaatgga actacaagtg gtataggaac tggcagcagt    3240
gttgaaaaat acattattga tgaaagtgat tacatgtcat tcataaacaa ccccagtctt    3300
actgtgactg taccaattgc tgtaggagaa tctgactttg aaaatttaaa cacggaagac    3360
tttagtagtg aatcggatct ggaagaaagc aaagagaaac tgaatgaaag cagtagctca    3420
tcagaaggta gcactgtgga catcggcgca cctgtagaag aacagcccgt agtggaacct    3480
gaagaaactc ttgaaccaga agcttgtttc actgaaggct gtgtacaaag attcaagtgt    3540
tgtcaaatca atgtggaaga aggcagagga aaacaatggt ggaacctgag aaggacgtgt    3600
ttccgaatag ttgaacataa ctggtttgag accttcattg ttttcatgat tctccttagt    3660
agtggtgctc tggcatttga agatatatat attgatcagc gaaagacgat taagacgatg    3720
ttggaatatg ctgacaaggt tttcacttac attttcattc tggaaatgct tctaaaatgg    3780
gtggcatatg gctatcaaac atatttcacc aatgcctggt gttggctgga cttcttaatt    3840
gttgatgttt cattggtcag tttaacagca aatgccttgg gttactcaga acttggagcc    3900
atcaaatctc tcaggacact aagagctctg agacctctaa gagccttatc tcgatttgaa    3960
gggatgaggg tggttgtgaa tgccctttta ggagcaattc catccatcat gaatgtgctt    4020
ctggtttgtc ttatattctg gctaattttc agcatcatgg gcgtaaattt gtttgctggc    4080
aaattctacc actgtattaa caccacaact ggtgacaggt tgacatcga agacgtgaat    4140 aatcatacag attgcctaaa actaatagaa agaaatgaga ctgctcgatg gaaaaatgtg    4200
aaagtaaact tgataatgt aggatttggg tatctctctt tgcttcaagt tgccacattc    4260
aaaggatgga tggatataat gtatgcagca gttgattcca gaaatgtgga actccagcct    4320
aagtatgaag aaagcctgta catgtatctt tactttgtta ttttcatcat ctttgggtct    4380 ttcttcaccct tgaacctgtt tattggtgtc atcatagata atttcaacca gcagaaaaag    4440
aagtttggag tcaagacat ctttatgaca gaagaacaga agaaatacta taatgcaatg    4500
aaaaaattag gatcgaaaaa accgcaaaag cctataccc gaccaggaaa caaatttcaa    4560
ggaatggtct ttgacttcgt aaccagacaa gttttttgaca taagcatcat gattctcatc    4620
tgtcttaaca tggtcacaat gatggtggaa acagatgacc agagtgaata tgtgactacc    4680
attttgtcac gcatcaatct ggtgttcatt gtgctattta ctggagagtg tgtactgaaa    4740
ctcatctctc tacgccatta ttattttacc attggatgga atatttttga ttttgtggtt    4800
gtcattctct ccattgtagg tatgtttctt gccgagctga tagaaaagta tttcgtgtcc    4860
cctaccctgt tccgagtgat ccgtcttgct aggattggcc gaatcctacg tctgatcaaa    4920
ggagcaaagg ggatccgcac gctgctcttt gctttgatga tgtcccttcc tgcgttgttt    4980
aacatcggcc tcctactctt cctagtcatg ttcatctacg ccatctttgg gatgtccaac    5040
tttgcctatg ttaagaggga agttgggatc gatgacatgt tcaactttga gacctttggc    5100
aacagcatga tctgcctatt ccaaattaca acctctgctg gctgggatgg attgctagca    5160
cccattctca cagtaagcc acccgactgt gaccctaata agttaaccc tggaagctca    5220 gttaagggag actgtgggaa cccatctgtt ggaattttct tttttgtcag ttacatcatc    5280
atatccttcc tggttgtggt gaacatgtac atcgcggtca tcctggagaa cttcagtgtt    5340
gctactgaag aaagtgcaga gcctctgagt gaggatgact tgagatgtt ctatgaggtt    5400 tgggagaagt ttgatcccga tgcaactcag ttcatggaat ttgaaaaatt atctcagttt    5460
```

-continued

```
gcagctgcgc ttgaaccgcc tctcaatctg ccacaaccaa acaaactcca gctcattgcc   5520
atggatttgc ccatggtgag tggtgaccgg atccactgtc ttgatatctt atttgctttt   5580
acaaagcggg ttctaggaga gagtggagag atggatgctc tacgaataca gatggaagag   5640
cgattcatgg cttccaatcc ttccaaggtc tcctatcagc caatcactac tactttaaaa   5700
cgaaaacaag aggaagtatc tgctgtcatt attcagcgtg cttacagacg ccaccttta   5760 aagcgaactg taaacaagc ttcctttacg tacaataaaa acaaatcaa aggtggggct   5820 aatcttctta taaagaaga catgataatt gacagaataa atgaaaactc tattacagaa   5880
aaaactgatc tgaccatgtc cactgcagct tgtccacctt cctatgaccg ggtgacaaag   5940
ccaattgtgg aaaaacatga gcaagaaggc aaagatgaaa aagccaaagg gaaatga      5997
```

<210> SEQ ID NO 2
<211> LENGTH: 1998
<212> TYPE: PRT
<213> ORGANISM: Homo sapiens

<400> SEQUENCE: 2

```
Met Glu Gln Thr Val Leu Val Pro Pro Gly Pro Asp Ser Phe Asn Phe
  1               5                  10                  15

Phe Thr Arg Glu Ser Leu Ala Ala Ile Glu Arg Arg Ile Ala Glu Glu
             20                  25                  30

Lys Ala Lys Asn Pro Lys Pro Asp Lys Lys Asp Asp Glu Asn Gly
         35                  40                  45

Pro Lys Pro Asn Ser Asp Leu Glu Ala Gly Lys Asn Leu Pro Phe Ile
     50                  55                  60

Tyr Gly Asp Ile Pro Pro Glu Met Val Ser Glu Pro Leu Glu Asp Leu
 65                  70                  75                  80

Asp Pro Tyr Tyr Ile Asn Lys Lys Thr Phe Ile Val Leu Asn Lys Gly
                 85                  90                  95

Lys Ala Ile Phe Arg Phe Ser Ala Thr Ser Ala Leu Tyr Ile Leu Thr
            100                 105                 110

Pro Phe Asn Pro Leu Arg Lys Ile Ala Ile Lys Ile Leu Val His Ser
        115                 120                 125

Leu Phe Ser Met Leu Ile Met Cys Thr Ile Leu Thr Asn Cys Val Phe
    130                 135                 140

Met Thr Met Ser Asn Pro Pro Asp Trp Thr Lys Asn Val Glu Tyr Thr
145                 150                 155                 160

Phe Thr Gly Ile Tyr Thr Phe Glu Ser Leu Ile Lys Ile Ile Ala Arg
                165                 170                 175

Gly Phe Cys Leu Glu Asp Phe Thr Phe Leu Arg Asp Pro Trp Asn Trp
            180                 185                 190

Leu Asp Phe Thr Val Ile Thr Phe Ala Tyr Val Thr Glu Phe Val Asp
        195                 200                 205

Leu Gly Asn Val Ser Ala Leu Arg Thr Phe Arg Val Leu Arg Ala Leu
    210                 215                 220

Lys Thr Ile Ser Val Ile Pro Gly Leu Lys Thr Ile Val Gly Ala Leu
225                 230                 235                 240

Ile Gln Ser Val Lys Lys Leu Ser Asp Val Met Ile Leu Thr Val Phe
                245                 250                 255

Cys Leu Ser Val Phe Ala Leu Ile Gly Leu Gln Leu Phe Met Gly Asn
            260                 265                 270

Leu Arg Asn Lys Cys Ile Gln Trp Pro Pro Thr Asn Ala Ser Leu Glu
```

-continued

```
                275                 280                 285
Glu His Ser Ile Glu Lys Asn Ile Thr Val Asn Tyr Asn Gly Thr Leu
290                 295                 300
Ile Asn Glu Thr Val Phe Glu Phe Asp Trp Lys Ser Tyr Ile Gln Asp
305                 310                 315                 320
Ser Arg Tyr His Tyr Phe Leu Glu Gly Phe Leu Asp Ala Leu Leu Cys
                325                 330                 335
Gly Asn Ser Ser Asp Ala Gly Gln Cys Pro Glu Gly Tyr Met Cys Val
                340                 345                 350
Lys Ala Gly Arg Asn Pro Asn Tyr Gly Tyr Thr Ser Phe Asp Thr Phe
                355                 360                 365
Ser Trp Ala Phe Leu Ser Leu Phe Arg Leu Met Thr Gln Asp Phe Trp
370                 375                 380
Glu Asn Leu Tyr Gln Leu Thr Leu Arg Ala Ala Gly Lys Thr Tyr Met
385                 390                 395                 400
Ile Phe Phe Val Leu Val Ile Phe Leu Gly Ser Phe Tyr Leu Ile Asn
                405                 410                 415
Leu Ile Leu Ala Val Val Ala Met Ala Tyr Glu Glu Gln Asn Gln Ala
                420                 425                 430
Thr Leu Glu Glu Ala Glu Gln Lys Glu Ala Glu Phe Gln Gln Met Ile
                435                 440                 445
Glu Gln Leu Lys Lys Gln Gln Glu Ala Ala Gln Gln Ala Ala Thr Ala
                450                 455                 460
Thr Ala Ser Glu His Ser Arg Glu Pro Ser Ala Ala Gly Arg Leu Ser
465                 470                 475                 480
Asp Ser Ser Ser Glu Ala Ser Lys Leu Ser Ser Lys Ser Ala Lys Glu
                485                 490                 495
Arg Arg Asn Arg Arg Lys Lys Arg Lys Gln Lys Glu Gln Ser Gly Gly
                500                 505                 510
Glu Glu Lys Asp Glu Asp Glu Phe Gln Lys Ser Glu Ser Glu Asp Ser
                515                 520                 525
Ile Arg Arg Lys Gly Phe Arg Phe Ser Ile Glu Gly Asn Arg Leu Thr
530                 535                 540
Tyr Glu Lys Arg Tyr Ser Ser Pro His Gln Ser Leu Leu Ser Ile Arg
545                 550                 555                 560
Gly Ser Leu Phe Ser Pro Arg Arg Asn Ser Arg Thr Ser Leu Phe Ser
                565                 570                 575
Phe Arg Gly Arg Ala Lys Asp Val Gly Ser Glu Asn Asp Phe Ala Asp
                580                 585                 590
Asp Glu His Ser Thr Phe Glu Asp Asn Glu Ser Arg Arg Asp Ser Leu
                595                 600                 605
Phe Val Pro Arg Arg His Gly Glu Arg Arg Asn Ser Asn Leu Ser Gln
                610                 615                 620
Thr Ser Arg Ser Ser Arg Met Leu Ala Val Phe Pro Ala Asn Gly Lys
625                 630                 635                 640
Met His Ser Thr Val Asp Cys Asn Gly Val Val Ser Leu Val Gly Gly
                645                 650                 655
Pro Ser Val Pro Thr Ser Pro Val Gly Gln Leu Leu Pro Glu Gly Thr
                660                 665                 670
Thr Thr Glu Thr Glu Met Arg Lys Arg Arg Ser Ser Ser Phe His Val
                675                 680                 685
Ser Met Asp Phe Leu Glu Asp Pro Ser Gln Arg Gln Arg Ala Met Ser
                690                 695                 700
```

-continued

```
Ile Ala Ser Ile Leu Thr Asn Thr Val Glu Glu Leu Glu Ser Arg
705                 710                 715                 720

Gln Lys Cys Pro Pro Cys Trp Tyr Lys Phe Ser Asn Ile Phe Leu Ile
            725                 730                 735

Trp Asp Cys Ser Pro Tyr Trp Leu Lys Val Lys His Val Val Asn Leu
                740                 745                 750

Val Val Met Asp Pro Phe Val Asp Leu Ala Ile Thr Ile Cys Ile Val
            755                 760                 765

Leu Asn Thr Leu Phe Met Ala Met Glu His Tyr Pro Met Thr Asp His
    770                 775                 780

Phe Asn Asn Val Leu Thr Val Gly Asn Leu Val Phe Thr Gly Ile Phe
785                 790                 795                 800

Thr Ala Glu Met Phe Leu Lys Ile Ile Ala Met Asp Pro Tyr Tyr Tyr
                805                 810                 815

Phe Gln Glu Gly Trp Asn Ile Phe Asp Gly Phe Ile Val Thr Leu Ser
            820                 825                 830

Leu Val Glu Leu Gly Leu Ala Asn Val Glu Gly Leu Ser Val Leu Arg
    835                 840                 845

Ser Phe Arg Leu Leu Arg Val Phe Lys Leu Ala Lys Ser Trp Pro Thr
    850                 855                 860

Leu Asn Met Leu Ile Lys Ile Ile Gly Asn Ser Val Gly Ala Leu Gly
865                 870                 875                 880

Asn Leu Thr Leu Val Leu Ala Ile Ile Val Phe Ile Phe Ala Val Val
                885                 890                 895

Gly Met Gln Leu Phe Gly Lys Ser Tyr Lys Asp Cys Val Cys Lys Ile
            900                 905                 910

Ala Ser Asp Cys Gln Leu Pro Arg Trp His Met Asn Asp Phe Phe His
    915                 920                 925

Ser Phe Leu Ile Val Phe Arg Val Leu Cys Gly Glu Trp Ile Glu Thr
    930                 935                 940

Met Trp Asp Cys Met Glu Val Ala Gly Gln Ala Met Cys Leu Thr Val
945                 950                 955                 960

Phe Met Met Val Met Val Ile Gly Asn Leu Val Val Leu Asn Leu Phe
                965                 970                 975

Leu Ala Leu Leu Leu Ser Ser Phe Ser Ala Asp Asn Leu Ala Ala Thr
            980                 985                 990

Asp Asp Asp Asn Glu Met Asn Asn Leu Gln Ile Ala Val Asp Arg Met
    995                 1000                1005

His Lys Gly Val Ala Tyr Val Lys Arg Lys Ile Tyr Glu Phe Ile Gln
    1010                1015                1020

Gln Ser Phe Ile Arg Lys Gln Lys Ile Leu Asp Glu Ile Lys Pro Leu
1025                1030                1035                1040

Asp Asp Leu Asn Asn Lys Lys Asp Ser Cys Met Ser Asn His Thr Thr
                1045                1050                1055

Glu Ile Gly Lys Asp Leu Asp Tyr Leu Lys Asp Val Asn Gly Thr Thr
            1060                1065                1070

Ser Gly Ile Gly Thr Gly Ser Ser Val Glu Lys Tyr Ile Ile Asp Glu
    1075                1080                1085

Ser Asp Tyr Met Ser Phe Ile Asn Asn Pro Ser Leu Thr Val Thr Val
    1090                1095                1100

Pro Ile Ala Val Gly Glu Ser Asp Phe Glu Asn Leu Asn Thr Glu Asp
1105                1110                1115                1120
```

-continued

```
Phe Ser Ser Glu Ser Asp Leu Glu Glu Ser Lys Glu Lys Leu Asn Glu
            1125                1130                1135

Ser Ser Ser Ser Glu Gly Ser Thr Val Asp Ile Gly Ala Pro Val
        1140                1145                1150

Glu Glu Gln Pro Val Val Glu Pro Glu Thr Leu Glu Pro Glu Ala
        1155                1160                1165

Cys Phe Thr Glu Gly Cys Val Gln Arg Phe Lys Cys Cys Gln Ile Asn
        1170                1175                1180

Val Glu Glu Gly Arg Gly Lys Gln Trp Trp Asn Leu Arg Arg Thr Cys
1185                1190                1195                1200

Phe Arg Ile Val Glu His Asn Trp Phe Glu Thr Phe Ile Val Phe Met
            1205                1210                1215

Ile Leu Leu Ser Ser Gly Ala Leu Ala Phe Glu Asp Ile Tyr Ile Asp
            1220                1225                1230

Gln Arg Lys Thr Ile Lys Thr Met Leu Glu Tyr Ala Asp Lys Val Phe
            1235                1240                1245

Thr Tyr Ile Phe Ile Leu Glu Met Leu Leu Lys Trp Val Ala Tyr Gly
            1250                1255                1260

Tyr Gln Thr Tyr Phe Thr Asn Ala Trp Cys Trp Leu Asp Phe Leu Ile
1265                1270                1275                1280

Val Asp Val Ser Leu Val Ser Leu Thr Ala Asn Ala Leu Gly Tyr Ser
            1285                1290                1295

Glu Leu Gly Ala Ile Lys Ser Leu Arg Thr Leu Arg Ala Leu Arg Pro
            1300                1305                1310

Leu Arg Ala Leu Ser Arg Phe Glu Gly Met Arg Val Val Asn Ala
            1315                1320                1325

Leu Leu Gly Ala Ile Pro Ser Ile Met Asn Val Leu Leu Val Cys Leu
            1330                1335                1340

Ile Phe Trp Leu Ile Phe Ser Ile Met Gly Val Asn Leu Phe Ala Gly
1345                1350                1355                1360

Lys Phe Tyr His Cys Ile Asn Thr Thr Thr Gly Asp Arg Phe Asp Ile
            1365                1370                1375

Glu Asp Val Asn Asn His Thr Asp Cys Leu Lys Leu Ile Glu Arg Asn
            1380                1385                1390

Glu Thr Ala Arg Trp Lys Asn Val Lys Val Asn Phe Asp Asn Val Gly
            1395                1400                1405

Phe Gly Tyr Leu Ser Leu Leu Gln Val Ala Thr Phe Lys Gly Trp Met
            1410                1415                1420

Asp Ile Met Tyr Ala Ala Val Asp Ser Arg Asn Val Glu Leu Gln Pro
1425                1430                1435                1440

Lys Tyr Glu Glu Ser Leu Tyr Met Tyr Leu Tyr Phe Val Ile Phe Ile
            1445                1450                1455

Ile Phe Gly Ser Phe Phe Thr Leu Asn Leu Phe Ile Gly Val Ile Ile
            1460                1465                1470

Asp Asn Phe Asn Gln Gln Lys Lys Lys Phe Gly Gly Gln Asp Ile Phe
            1475                1480                1485

Met Thr Glu Glu Gln Lys Lys Tyr Tyr Asn Ala Met Lys Lys Leu Gly
            1490                1495                1500

Ser Lys Lys Pro Gln Lys Pro Ile Pro Arg Pro Gly Asn Lys Phe Gln
1505                1510                1515                1520

Gly Met Val Phe Asp Phe Val Thr Arg Gln Val Phe Asp Ile Ser Ile
            1525                1530                1535

Met Ile Leu Ile Cys Leu Asn Met Val Thr Met Met Val Glu Thr Asp
```

-continued

```
                 1540                1545                1550
Asp Gln Ser Glu Tyr Val Thr Thr Ile Leu Ser Arg Ile Asn Leu Val
            1555                1560                1565
Phe Ile Val Leu Phe Thr Gly Glu Cys Val Leu Lys Leu Ile Ser Leu
        1570                1575                1580
Arg His Tyr Tyr Phe Thr Ile Gly Trp Asn Ile Phe Asp Phe Val Val
1585                1590                1595                1600
Val Ile Leu Ser Ile Val Gly Met Phe Leu Ala Glu Leu Ile Glu Lys
                1605                1610                1615
Tyr Phe Val Ser Pro Thr Leu Phe Arg Val Ile Arg Leu Ala Arg Ile
            1620                1625                1630
Gly Arg Ile Leu Arg Leu Ile Lys Gly Ala Lys Gly Ile Arg Thr Leu
        1635                1640                1645
Leu Phe Ala Leu Met Met Ser Leu Pro Ala Leu Phe Asn Ile Gly Leu
    1650                1655                1660
Leu Leu Phe Leu Val Met Phe Ile Tyr Ala Ile Phe Gly Met Ser Asn
1665                1670                1675                1680
Phe Ala Tyr Val Lys Arg Glu Val Gly Ile Asp Asp Met Phe Asn Phe
                1685                1690                1695
Glu Thr Phe Gly Asn Ser Met Ile Cys Leu Phe Gln Ile Thr Thr Ser
            1700                1705                1710
Ala Gly Trp Asp Gly Leu Leu Ala Pro Ile Leu Asn Ser Lys Pro Pro
        1715                1720                1725
Asp Cys Asp Pro Asn Lys Val Asn Pro Gly Ser Ser Val Lys Gly Asp
    1730                1735                1740
Cys Gly Asn Pro Ser Val Gly Ile Phe Phe Phe Val Ser Tyr Ile Ile
1745                1750                1755                1760
Ile Ser Phe Leu Val Val Val Asn Met Tyr Ile Ala Val Ile Leu Glu
                1765                1770                1775
Asn Phe Ser Val Ala Thr Glu Glu Ser Ala Glu Pro Leu Ser Glu Asp
            1780                1785                1790
Asp Phe Glu Met Phe Tyr Glu Val Trp Glu Lys Phe Asp Pro Asp Ala
        1795                1800                1805
Thr Gln Phe Met Glu Phe Glu Lys Leu Ser Gln Phe Ala Ala Ala Leu
    1810                1815                1820
Glu Pro Pro Leu Asn Leu Pro Gln Pro Asn Lys Leu Gln Leu Ile Ala
1825                1830                1835                1840
Met Asp Leu Pro Met Val Ser Gly Asp Arg Ile His Cys Leu Asp Ile
                1845                1850                1855
Leu Phe Ala Phe Thr Lys Arg Val Leu Gly Glu Ser Gly Glu Met Asp
            1860                1865                1870
Ala Leu Arg Ile Gln Met Glu Glu Arg Phe Met Ala Ser Asn Pro Ser
        1875                1880                1885
Lys Val Ser Tyr Gln Pro Ile Thr Thr Thr Leu Lys Arg Lys Gln Glu
    1890                1895                1900
Glu Val Ser Ala Val Ile Ile Gln Arg Ala Tyr Arg Arg His Leu Leu
1905                1910                1915                1920
Lys Arg Thr Val Lys Gln Ala Ser Phe Thr Tyr Asn Lys Asn Lys Ile
                1925                1930                1935
Lys Gly Gly Ala Asn Leu Leu Ile Lys Glu Asp Met Ile Ile Asp Arg
            1940                1945                1950
Ile Asn Glu Asn Ser Ile Thr Glu Lys Thr Asp Leu Thr Met Ser Thr
        1955                1960                1965
```

Ala Ala Cys Pro Pro Ser Tyr Asp Arg Val Thr Lys Pro Ile Val Glu
   1970                1975                1980

Lys His Glu Gln Glu Gly Lys Asp Glu Lys Ala Lys Gly Lys
1985                1990                1995

<210> SEQ ID NO 3
<211> LENGTH: 6018
<212> TYPE: DNA
<213> ORGANISM: Homo sapiens

<400> SEQUENCE: 3

| | | | | | |
|---|---|---|---|---|---|
| atggcacagt | cagtgctggt | accgccagga | cctgacagct | tccgcttctt | taccagggaa | 60 |
| tcccttgctg | ctattgaaca | acgcattgca | gaagagaaag | ctaagagacc | caaacaggaa | 120 |
| cgcaaggatg | aggatgatga | aaatggccca | agccaaaca | gtgacttgga | agcaggaaaa | 180 |
| tctcttccat | ttatttatgg | agacattcct | ccagagatgg | tgtcagtgcc | cctggaggat | 240 |
| ctggacccct | actatatcaa | taagaaaacg | tttatagtat | tgaataaagg | gaaagcaatc | 300 |
| tctcgattca | gtgccacccc | tgccctttac | attttaactc | ccttcaaccc | tattagaaaa | 360 |
| ttagctatta | agattttggt | acattcttta | ttcaatatgc | tcattatgtg | cacgattctt | 420 |
| accaactgtg | tatttatgac | catgagtaac | cctccagact | ggacaaagaa | tgtggagtat | 480 |
| acctttacag | gaatttatac | ttttgaatca | cttattaaaa | tacttgcaag | gggcttttgt | 540 |
| ttagaagatt | tcacattttt | acgggatcca | tggaattggt | tggatttcac | agtcattact | 600 |
| tttgcatatg | tgacagagtt | tgtggacctg | gcaatgtct | cagcgttgag | aacattcaga | 660 |
| gttctccgag | cattgaaaac | aatttcagtc | attccaggcc | tgaagaccat | tgtggggcc | 720 |
| ctgatccagt | cagtgaagaa | gctttctgat | gtcatgatct | tgactgtgtt | ctgtctaagc | 780 |
| gtgtttgcgc | taataggatt | gcagttgttc | atgggcaacc | tacgaaataa | atgtttgcaa | 840 |
| tggcctccag | ataattcttc | ctttgaaata | aatatcactt | ccttctttaa | caattcattg | 900 |
| gatgggaatg | gtactacttt | caataggaca | gtgagcatat | taactgggga | tgaatatatt | 960 |
| gaggataaaa | gtcacttta | tttttagag | gggcaaaatg | atgctctgct | tgtgtggcaac | 1020 |
| agctcagatg | caggccagtg | tcctgaagga | tacatctgtg | tgaaggctgg | tagaaacccc | 1080 |
| aactatggct | acacgagctt | tgacaccttt | agttgggcct | ttttgtcctt | atttcgtctc | 1140 |
| atgactcaag | acttctggga | aaaccttat | caactgacac | tacgtgctgc | tgggaaaacg | 1200 |
| tacatgatat | tttttgtgct | ggtcattttc | ttgggctcat | tctatctaat | aaatttgatc | 1260 |
| ttggctgtgg | tggccatggc | ctatgaggaa | cagaatcagg | ccacattgga | agaggctgaa | 1320 |
| cagaaggaag | ctgaatttca | gcagatgctc | gaacagttga | aaagcaaca | agaagaagct | 1380 |
| caggcggcag | ctgcagccgc | atctgctgaa | tcaagagact | tcagtggtgc | tggtgggata | 1440 |
| ggagtttttt | cagagagttc | ttcagtagca | tctaagttga | gctccaaaag | tgaaaaagag | 1500 |
| ctgaaaaaca | gaagaaagaa | aaagaaacag | aagaacagt | ctggagaaga | agagaaaaat | 1560 |
| gacagagtcc | taaatcgga | atctgaagac | agcataagaa | gaaaaggttt | ccgtttttcc | 1620 |
| ttggaaggaa | gtaggctgac | atatgaaaag | agattttctt | ctccacacca | gtccttactg | 1680 |
| agcatccgtg | gctcccttt | ctctccaaga | cgcaacagta | gggcgagcct | tttcagcttc | 1740 |
| agaggtcgag | caaaggacat | tggctctgag | aatgactttg | ctgatgatga | gcacagcacc | 1800 |
| tttgaggaca | atgacagccg | aagagactct | ctgttcgtgc | cgcacagaca | tggagaacgg | 1860 |
| cgccacagca | atgtcagcca | ggccagccgt | gcctccaggg | tgctccccat | cctgcccatg | 1920 |

```
aatgggaaga tgcatagcgc tgtggactgc aatggtgtgg tctccctggt cgggggccct   1980
tctaccctca catctgctgg gcagctccta ccagagggca caactactga aacagaaata   2040
agaaagagac ggtccagttc ttatcatgtt tccatggatt tattggaaga tcctacatca   2100
aggcaaagag caatgagtat agccagtatt ttgaccaaca ccatggaaga acttgaagaa   2160
tccagacaga aatgcccacc atgctggtat aaatttgcta atatgtgttt gatttgggac   2220
tgttgtaaac catggttaaa ggtgaaacac cttgtcaacc tggttgtaat ggacccattt   2280
gttgacctgg ccatcaccat ctgcattgtc ttaaatacac tcttcatggc tatggagcac   2340
tatcccatga cggagcagtt cagcagtgta ctgtctgttg aaacctggt cttcacaggg    2400
atcttcacag cagaaatgtt tctcaagata attgccatgg atccatatta ttactttcaa   2460
gaaggctgga atattttga tggttttatt gtgagcctta gtttaatgga acttggtttg    2520
gcaaatgtgg aaggattgtc agttctccga tcattccggc tgctccgagt tttcaagttg   2580
gcaaaatctt ggccaactct aaatatgcta attaagatca ttggcaattc tgtggggct    2640
ctaggaaacc tcaccttggt attggccatc atcgtcttca tttttgctgt ggtcggcatg   2700
cagctctttg gtaagagcta caaagaatgt gtctgcaaga tttccaatga ttgtgaactc   2760
ccacgctggc acatgcatga ctttttccac tccttcctga tcgtgttccg cgtgctgtgt   2820
ggagagtgga tagagaccat gtgggactgt atggaggtcg ctggccaaac catgtgcctt   2880
actgtcttca tgatggtcat ggtgattgga aatctagtgg ttctgaacct cttcttggcc   2940
ttgcttttga gttccttcag ttctgacaat cttgctgcca ctgatgatga taacgaaatg   3000
aataatctcc agattgctgt gggaaggatg cagaaaggaa tcgattttgt taaaagaaaa   3060
atacgtgaat ttattcagaa agcctttgtt aggaagcaga agctttaga tgaaattaaa    3120
ccgcttgaag atctaaataa taaaaaagac agctgtattt ccaaccatac caccatagaa   3180
ataggcaaag acctcaatta tctcaaagac ggaaatggaa ctactagtgg cataggcagc   3240
agtgtagaaa aatatgtcgt ggatgaaagt gattacatgt catttataaa caaccctagc   3300
ctcactgtga cagtaccaat tgctgttgga aatctgact ttgaaaattt aaatactgaa     3360
gaattcagca gcgagtcaga tatggaggaa agcaaagaga agctaaatgc aactagttca   3420
tctgaaggca gcacggttga tattggagct cccgccgagg gagaacagcc tgaggttgaa   3480
cctgaggaat cccttgaacc tgaagcctgt tttacagaag actgtgtacg gaagttcaag   3540
tgttgtcaga taagcataga agaaggcaaa gggaaactct ggtggaattt gaggaaaaca   3600
tgctataaga tagtggagca caattggttc gaaaccttca ttgtcttcat gattctgctg   3660
agcagtgggg ctctggcctt tgaagatata tacattgagc agcgaaaaac cattaagacc   3720
atgttagaat atgctgacaa ggttttcact tacatattca ttctggaaat gctgctaaag   3780
tgggttgcat atggttttca agtgtatttt accaatgcct ggtgctggct agacttcctg   3840
attgttgatg tctcactggt tagccttaact gcaaatgcct tgggttactc agaacttggt   3900
gccatcaaat ccctcagaac actaagagct ctgaggccac tgagagcttt gtcccggttt   3960
gaaggaatga gggctgttgt aaatgctctt ttaggagcca ttccatctat catgaatgta   4020
cttctggttt gtctgatctt ttggctaata ttcagtatca tgggagtgaa tctctttgct   4080
ggcaagtttt accattgtat taattacacc actggagaga tgtttgatgt aagcgtggtc   4140
aacaactaca gtgagtgcaa agctctcatt gagagcaatc aaactgccag gtggaaaaat   4200
gtgaaagtaa actttgataa cgtaggactt ggatatctgt ctctacttca gtagccacg    4260
tttaagggat ggatggatat tatgtatgca gctgttgatt cacgaaatgt agaattacaa   4320
```

```
cccaagtatg aagacaacct gtacatgtat ctttattttg tcatctttat tatttttggt    4380
tcattcttta ccttgaatct tttcattggt gtcatcatag ataacttcaa ccaacagaaa    4440
aagaagtttg gaggtcaaga cattttatg acagaagaac agaagaaata ctacaatgca     4500
atgaaaaaac tgggttcaaa gaaccacaa aaacccatac ctcgacctgc taacaaattc     4560
caaggaatgg tctttgattt tgtaaccaaa caagtctttg tatcagcat catgatcctc     4620 atctgcctta acatggtcac catgatggtg aaaccgatg accagagtca gaaatgaca     4680 aacattctgt actggattaa tctggtgttt attgttctgt tcactggaga atgtgtgctg    4740
aaactgatct ctcttcgtta ctactatttc actattggat ggaatatttt tgattttgtg    4800
gtggtcattc tctccattgt aggaatgttt ctggctgaac tgatagaaaa gtattttgtg   4860
tcccctaccc tgttccgagt gatccgtctt gccaggattg gccgaatcct acgtctgatc    4920
aaaggagcaa aggggatccg cacgctgctc tttgctttga tgatgtccct tcctgcgttg    4980
tttaacatcg gcctccttct tttcctggtc atgttcatct acgccatctt tgggatgtcc    5040
aattttgcct atgttaagag ggaagttggg atcgatgaca tgttcaactt tgagaccttt    5100
ggcaacagca tgatctgcct gttccaaatt acaacctctg ctggctggga tggattgcta    5160
gcacctattc ttaatagtgg acctccagac tgtgaccctg acaaagatca ccctggaagc    5220
tcagttaaag gagactgtgg gaacccatct gttgggatt tcttttttgt cagttacatc     5280
atcatatcct tcctggttgt gctgaacatg tacatcgcgg tcatcctgga gaacttcagt   5340
gttgctactg aagaaagtgc agagcctctg agtgaggat actttgagat gttctatgag    5400
gtttgggaga gtttgatcc cgatgcgacc cagtttatag agtttgccaa actttctgat    5460
tttgcagatg ccctggatcc tcctcttctc atagcaaaac ccaacaaagt ccagctcatt    5520
gccatggatc tgcccatggt gagtggtgac cggatccact gtcttgacat cttatttgct    5580
tttacaaagc gtgttttggg tgagagtgga gagatggatg cccttcgaat acagatggaa   5640
gagcgattca tggcatcaaa cccctccaaa gtctcttatg agcccattac gaccacgttg    5700
aaacgcaaac aagaggaggt gtctgctatt attatccaga gggcttacag acgctacctc   5760
ttgaagcaaa agttaaaaa ggtatcaagt atatacaaga aagacaaagg caaagaatgt    5820 gatgaacac ccatcaaaga agatactctc attgataaac tgaatgagaa ttcaactcca    5880 gagaaaccg atatgacgcc ttccaccacg tctccaccct cgtatgatag tgtgaccaaa    5940
ccagaaaaag aaaaatttga aaagacaaa tcagaaaagg aagacaaagg gaaagatatc     6000
agggaaagta aaaagtaa                                                   6018
```

<210> SEQ ID NO 4
<211> LENGTH: 2005
<212> TYPE: PRT
<213> ORGANISM: Homo sapiens

<400> SEQUENCE: 4

Met Ala Gln Ser Val Leu Val Pro Pro Gly Pro Asp Ser Phe Arg Phe
 1               5                   10                  15

Phe Thr Arg Glu Ser Leu Ala Ala Ile Glu Gln Arg Ile Ala Glu Glu
                 20                  25                  30

Lys Ala Lys Arg Pro Lys Gln Glu Arg Lys Asp Glu Asp Asp Glu Asn
             35                  40                  45

Gly Pro Lys Pro Asn Ser Asp Leu Glu Ala Gly Lys Ser Leu Pro Phe
         50                  55                  60

```
Ile Tyr Gly Asp Ile Pro Pro Glu Met Val Ser Val Pro Leu Glu Asp
 65                  70                  75                  80

Leu Asp Pro Tyr Tyr Ile Asn Lys Lys Thr Phe Ile Val Leu Asn Lys
                 85                  90                  95

Gly Lys Ala Ile Ser Arg Phe Ser Ala Thr Pro Ala Leu Tyr Ile Leu
            100                 105                 110

Thr Pro Phe Asn Pro Ile Arg Lys Leu Ala Ile Lys Ile Leu Val His
            115                 120                 125

Ser Leu Phe Asn Met Leu Ile Met Cys Thr Ile Leu Thr Asn Cys Val
    130                 135                 140

Phe Met Thr Met Ser Asn Pro Pro Asp Trp Thr Lys Asn Val Glu Tyr
145                 150                 155                 160

Thr Phe Thr Gly Ile Tyr Thr Phe Glu Ser Leu Ile Lys Ile Leu Ala
                165                 170                 175

Arg Gly Phe Cys Leu Glu Asp Phe Thr Phe Leu Arg Asp Pro Trp Asn
            180                 185                 190

Trp Leu Asp Phe Thr Val Ile Thr Phe Ala Tyr Val Thr Glu Phe Val
    195                 200                 205

Asp Leu Gly Asn Val Ser Ala Leu Arg Thr Phe Arg Val Leu Arg Ala
210                 215                 220

Leu Lys Thr Ile Ser Val Ile Pro Gly Leu Lys Thr Ile Val Gly Ala
225                 230                 235                 240

Leu Ile Gln Ser Val Lys Lys Leu Ser Asp Val Met Ile Leu Thr Val
                245                 250                 255

Phe Cys Leu Ser Val Phe Ala Leu Ile Gly Leu Gln Leu Phe Met Gly
            260                 265                 270

Asn Leu Arg Asn Lys Cys Leu Gln Trp Pro Pro Asp Asn Ser Ser Phe
    275                 280                 285

Glu Ile Asn Ile Thr Ser Phe Phe Asn Asn Ser Leu Asp Gly Asn Gly
290                 295                 300

Thr Thr Phe Asn Arg Thr Val Ser Ile Phe Asn Trp Asp Glu Tyr Ile
305                 310                 315                 320

Glu Asp Lys Ser His Phe Tyr Phe Leu Glu Gly Gln Asn Asp Ala Leu
                325                 330                 335

Leu Cys Gly Asn Ser Ser Asp Ala Gly Gln Cys Pro Glu Gly Tyr Ile
            340                 345                 350

Cys Val Lys Ala Gly Arg Asn Pro Asn Tyr Gly Tyr Thr Ser Phe Asp
    355                 360                 365

Thr Phe Ser Trp Ala Phe Leu Ser Leu Phe Arg Leu Met Thr Gln Asp
370                 375                 380

Phe Trp Glu Asn Leu Tyr Gln Leu Thr Leu Arg Ala Ala Gly Lys Thr
385                 390                 395                 400

Tyr Met Ile Phe Phe Val Leu Val Ile Phe Leu Gly Ser Phe Tyr Leu
                405                 410                 415

Ile Asn Leu Ile Leu Ala Val Val Ala Met Ala Tyr Glu Glu Gln Asn
            420                 425                 430

Gln Ala Thr Leu Glu Glu Ala Glu Gln Lys Glu Ala Glu Phe Gln Gln
    435                 440                 445

Met Leu Glu Gln Leu Lys Lys Gln Gln Glu Ala Gln Ala Ala Ala Ala
450                 455                 460

Ala Ala Ala Ser Ala Glu Ser Arg Asp Phe Ser Gly Ala Gly Gly Ile
465                 470                 475                 480

Gly Val Phe Ser Glu Ser Ser Ser Val Ala Ser Lys Leu Ser Ser Lys
```

-continued

```
                485                 490                 495
Ser Glu Lys Glu Leu Lys Asn Arg Arg Lys Lys Lys Gln Lys Glu
                500                 505                 510
Gln Ser Gly Glu Glu Lys Asn Asp Arg Val Leu Lys Ser Glu Ser
                515                 520                 525
Glu Asp Ser Ile Arg Arg Lys Gly Phe Arg Phe Ser Leu Glu Gly Ser
                530                 535                 540
Arg Leu Thr Tyr Glu Lys Arg Phe Ser Pro His Gln Ser Leu Leu
545                 550                 555                 560
Ser Ile Arg Gly Ser Leu Phe Ser Pro Arg Asn Ser Arg Ala Ser
                565                 570                 575
Leu Phe Ser Phe Arg Gly Arg Ala Lys Asp Ile Gly Ser Glu Asn Asp
                580                 585                 590
Phe Ala Asp Asp Glu His Ser Thr Phe Glu Asp Asn Asp Ser Arg Arg
                595                 600                 605
Asp Ser Leu Phe Val Pro His Arg His Gly Glu Arg Arg His Ser Asn
                610                 615                 620
Val Ser Gln Ala Ser Arg Ala Ser Arg Val Leu Pro Ile Leu Pro Met
625                 630                 635                 640
Asn Gly Lys Met His Ser Ala Val Asp Cys Asn Gly Val Val Ser Leu
                645                 650                 655
Val Gly Gly Pro Ser Thr Leu Thr Ser Ala Gly Gln Leu Leu Pro Glu
                660                 665                 670
Gly Thr Thr Thr Glu Thr Glu Ile Arg Lys Arg Arg Ser Ser Ser Tyr
                675                 680                 685
His Val Ser Met Asp Leu Leu Glu Asp Pro Thr Ser Arg Gln Arg Ala
                690                 695                 700
Met Ser Ile Ala Ser Ile Leu Thr Asn Thr Met Glu Glu Leu Glu Glu
705                 710                 715                 720
Ser Arg Gln Lys Cys Pro Pro Cys Trp Tyr Lys Phe Ala Asn Met Cys
                725                 730                 735
Leu Ile Trp Asp Cys Cys Lys Pro Trp Leu Lys Val Lys His Leu Val
                740                 745                 750
Asn Leu Val Val Met Asp Pro Phe Val Asp Leu Ala Ile Thr Ile Cys
                755                 760                 765
Ile Val Leu Asn Thr Leu Phe Met Ala Met Glu His Tyr Pro Met Thr
                770                 775                 780
Glu Gln Phe Ser Ser Val Leu Ser Val Gly Asn Leu Val Phe Thr Gly
785                 790                 795                 800
Ile Phe Thr Ala Glu Met Phe Leu Lys Ile Ile Ala Met Asp Pro Tyr
                805                 810                 815
Tyr Tyr Phe Gln Glu Gly Trp Asn Ile Phe Asp Gly Phe Ile Val Ser
                820                 825                 830
Leu Ser Leu Met Glu Leu Gly Leu Ala Asn Val Glu Gly Leu Ser Val
                835                 840                 845
Leu Arg Ser Phe Arg Leu Leu Arg Val Phe Lys Leu Ala Lys Ser Trp
850                 855                 860
Pro Thr Leu Asn Met Leu Ile Lys Ile Ile Gly Asn Ser Val Gly Ala
865                 870                 875                 880
Leu Gly Asn Leu Thr Leu Val Leu Ala Ile Ile Val Phe Ile Phe Ala
                885                 890                 895
Val Val Gly Met Gln Leu Phe Gly Lys Ser Tyr Lys Glu Cys Val Cys
                900                 905                 910
```

-continued

```
Lys Ile Ser Asn Asp Cys Glu Leu Pro Arg Trp His Met His Asp Phe
        915                 920                 925
Phe His Ser Phe Leu Ile Val Phe Arg Val Leu Cys Gly Glu Trp Ile
        930                 935                 940
Glu Thr Met Trp Asp Cys Met Glu Val Ala Gly Gln Thr Met Cys Leu
945                 950                 955                 960
Thr Val Phe Met Met Val Met Val Ile Gly Asn Leu Val Val Leu Asn
                965                 970                 975
Leu Phe Leu Ala Leu Leu Leu Ser Ser Phe Ser Ser Asp Asn Leu Ala
            980                 985                 990
Ala Thr Asp Asp Asp Asn Glu Met Asn Asn Leu Gln Ile Ala Val Gly
            995                 1000                1005
Arg Met Gln Lys Gly Ile Asp Phe Val Lys Arg Lys Ile Arg Glu Phe
            1010                1015                1020
Ile Gln Lys Ala Phe Val Arg Lys Gln Lys Ala Leu Asp Glu Ile Lys
1025                1030                1035                1040
Pro Leu Glu Asp Leu Asn Asn Lys Lys Asp Ser Cys Ile Ser Asn His
                1045                1050                1055
Thr Thr Ile Glu Ile Gly Lys Asp Leu Asn Tyr Leu Lys Asp Gly Asn
            1060                1065                1070
Gly Thr Thr Ser Gly Ile Gly Ser Ser Val Glu Lys Tyr Val Val Asp
            1075                1080                1085
Glu Ser Asp Tyr Met Ser Phe Ile Asn Asn Pro Ser Leu Thr Val Thr
            1090                1095                1100
Val Pro Ile Ala Val Gly Glu Ser Asp Phe Glu Asn Leu Asn Thr Glu
1105                1110                1115                1120
Glu Phe Ser Ser Glu Ser Asp Met Glu Glu Ser Lys Glu Lys Leu Asn
                1125                1130                1135
Ala Thr Ser Ser Ser Glu Gly Ser Thr Val Asp Ile Gly Ala Pro Ala
            1140                1145                1150
Glu Gly Glu Gln Pro Glu Val Glu Pro Glu Glu Ser Leu Glu Pro Glu
            1155                1160                1165
Ala Cys Phe Thr Glu Asp Cys Val Arg Lys Phe Lys Cys Cys Gln Ile
            1170                1175                1180
Ser Ile Glu Glu Gly Lys Gly Lys Leu Trp Trp Asn Leu Arg Lys Thr
1185                1190                1195                1200
Cys Tyr Lys Ile Val Glu His Asn Trp Phe Glu Thr Phe Ile Val Phe
                1205                1210                1215
Met Ile Leu Leu Ser Ser Gly Ala Leu Ala Phe Glu Asp Ile Tyr Ile
            1220                1225                1230
Glu Gln Arg Lys Thr Ile Lys Thr Met Leu Glu Tyr Ala Asp Lys Val
            1235                1240                1245
Phe Thr Tyr Ile Phe Ile Leu Glu Met Leu Leu Lys Trp Val Ala Tyr
            1250                1255                1260
Gly Phe Gln Val Tyr Phe Thr Asn Ala Trp Cys Trp Leu Asp Phe Leu
1265                1270                1275                1280
Ile Val Asp Val Ser Leu Val Ser Leu Thr Ala Asn Ala Leu Gly Tyr
                1285                1290                1295
Ser Glu Leu Gly Ala Ile Lys Ser Leu Arg Thr Leu Arg Ala Leu Arg
            1300                1305                1310
Pro Leu Arg Ala Leu Ser Arg Phe Glu Gly Met Arg Ala Val Val Asn
            1315                1320                1325
```

-continued

```
Ala Leu Leu Gly Ala Ile Pro Ser Ile Met Asn Val Leu Leu Val Cys
    1330                1335                1340

Leu Ile Phe Trp Leu Ile Phe Ser Ile Met Gly Val Asn Leu Phe Ala
1345                1350                1355                1360

Gly Lys Phe Tyr His Cys Ile Asn Tyr Thr Thr Gly Glu Met Phe Asp
                1365                1370                1375

Val Ser Val Val Asn Asn Tyr Ser Glu Cys Lys Ala Leu Ile Glu Ser
                1380                1385                1390

Asn Gln Thr Ala Arg Trp Lys Asn Val Lys Val Asn Phe Asp Asn Val
                1395                1400                1405

Gly Leu Gly Tyr Leu Ser Leu Leu Gln Val Ala Thr Phe Lys Gly Trp
                1410                1415                1420

Met Asp Ile Met Tyr Ala Ala Val Asp Ser Arg Asn Val Glu Leu Gln
1425                1430                1435                1440

Pro Lys Tyr Glu Asp Asn Leu Tyr Met Tyr Leu Tyr Phe Val Ile Phe
                1445                1450                1455

Ile Ile Phe Gly Ser Phe Phe Thr Leu Asn Leu Phe Ile Gly Val Ile
                1460                1465                1470

Ile Asp Asn Phe Asn Gln Gln Lys Lys Lys Phe Gly Gly Gln Asp Ile
                1475                1480                1485

Phe Met Thr Glu Glu Gln Lys Lys Tyr Tyr Asn Ala Met Lys Lys Leu
                1490                1495                1500

Gly Ser Lys Lys Pro Gln Lys Pro Ile Pro Arg Pro Ala Asn Lys Phe
1505                1510                1515                1520

Gln Gly Met Val Phe Asp Phe Val Thr Lys Gln Val Phe Asp Ile Ser
                1525                1530                1535

Ile Met Ile Leu Ile Cys Leu Asn Met Val Thr Met Met Val Glu Thr
                1540                1545                1550

Asp Asp Gln Ser Gln Glu Met Thr Asn Ile Leu Tyr Trp Ile Asn Leu
                1555                1560                1565

Val Phe Ile Val Leu Phe Thr Gly Glu Cys Val Leu Lys Leu Ile Ser
                1570                1575                1580

Leu Arg Tyr Tyr Tyr Phe Thr Ile Gly Trp Asn Ile Phe Asp Phe Val
1585                1590                1595                1600

Val Val Ile Leu Ser Ile Val Gly Met Phe Leu Ala Glu Leu Ile Glu
                1605                1610                1615

Lys Tyr Phe Val Ser Pro Thr Leu Phe Arg Val Ile Arg Leu Ala Arg
                1620                1625                1630

Ile Gly Arg Ile Leu Arg Leu Ile Lys Gly Ala Lys Gly Ile Arg Thr
                1635                1640                1645

Leu Leu Phe Ala Leu Met Met Ser Leu Pro Ala Leu Phe Asn Ile Gly
                1650                1655                1660

Leu Leu Leu Phe Leu Val Met Phe Ile Tyr Ala Ile Phe Gly Met Ser
1665                1670                1675                1680

Asn Phe Ala Tyr Val Lys Arg Glu Val Gly Ile Asp Asp Met Phe Asn
                1685                1690                1695

Phe Glu Thr Phe Gly Asn Ser Met Ile Cys Leu Phe Gln Ile Thr Thr
                1700                1705                1710

Ser Ala Gly Trp Asp Gly Leu Leu Ala Pro Ile Leu Asn Ser Gly Pro
                1715                1720                1725

Pro Asp Cys Asp Pro Asp Lys Asp His Pro Gly Ser Ser Val Lys Gly
                1730                1735                1740

Asp Cys Gly Asn Pro Ser Val Gly Ile Phe Phe Phe Val Ser Tyr Ile
```

-continued

```
1745                1750                1755                1760
Ile Ile Ser Phe Leu Val Val Leu Asn Met Tyr Ile Ala Val Ile Leu
                1765                1770                1775
Glu Asn Phe Ser Val Ala Thr Glu Glu Ser Ala Glu Pro Leu Ser Glu
            1780                1785                1790
Asp Asp Phe Glu Met Phe Tyr Glu Val Trp Glu Lys Phe Asp Pro Asp
        1795                1800                1805
Ala Thr Gln Phe Ile Glu Phe Ala Lys Leu Ser Asp Phe Ala Asp Ala
    1810                1815                1820
Leu Asp Pro Pro Leu Leu Ile Ala Lys Pro Asn Lys Val Gln Leu Ile
1825                1830                1835                1840
Ala Met Asp Leu Pro Met Val Ser Gly Asp Arg Ile His Cys Leu Asp
                1845                1850                1855
Ile Leu Phe Ala Phe Thr Lys Arg Val Leu Gly Glu Ser Gly Glu Met
            1860                1865                1870
Asp Ala Leu Arg Ile Gln Met Glu Glu Arg Phe Met Ala Ser Asn Pro
        1875                1880                1885
Ser Lys Val Ser Tyr Glu Pro Ile Thr Thr Thr Leu Lys Arg Lys Gln
    1890                1895                1900
Glu Glu Val Ser Ala Ile Ile Ile Gln Arg Ala Tyr Arg Arg Tyr Leu
1905                1910                1915                1920
Leu Lys Gln Lys Val Lys Val Ser Ser Ile Tyr Lys Lys Asp Lys
                1925                1930                1935
Gly Lys Glu Cys Asp Gly Thr Pro Ile Lys Glu Asp Thr Leu Ile Asp
            1940                1945                1950
Lys Leu Asn Glu Asn Ser Thr Pro Glu Lys Thr Asp Met Thr Pro Ser
        1955                1960                1965
Thr Thr Ser Pro Pro Ser Tyr Asp Ser Val Thr Lys Pro Glu Lys Glu
    1970                1975                1980
Lys Phe Glu Lys Asp Lys Ser Glu Lys Glu Asp Lys Gly Lys Asp Ile
1985                1990                1995                2000
Arg Glu Ser Lys Lys
            2005
```

<210> SEQ ID NO 5
<211> LENGTH: 6003
<212> TYPE: DNA
<213> ORGANISM: Homo sapiens

<400> SEQUENCE: 5

```
atggcacagg cactgttggt accccagga  cctgaaagct tccgcctttt tactagagaa    60
tctcttgctg ctatcgaaaa acgtgctgca gaagagaaag ccaagaagcc caaaaaggaa   120
caagataatg atgatgagaa caaaccaaag ccaaatagtg acttggaagc tggaaagaac   180
cttccattta tttatggaga cattcctcca gagatggtgt cagagcccct ggaggacctg   240
gatccctact atatcaataa gaaaactttt atagtaatga ataaaggaaa ggcaattttc   300
cgattcagtg ccacctctgc cttgtatatt ttaactccac taaaccctgt taggaaaatt   360
gctatcaaga ttttggtaca ttctttattc agcatgctta tcatgtgcac tattttgacc   420
aactgtgtat ttatgacctt gagcaaccct cctgactgga caaagaatgt agagtacaca   480
ttcactggaa tctataccct tgagtcactt ataaaaatct ggcaagaggg ttttgctta    540
gaagatttta cgtttcttcg tgatccatgg aactggctgg atttcagtgt cattgtgatg   600
gcatatgtga cagagtttgt ggacctgggc aatgtctcag cgttgagaac attcagagtt    660
```

```
ctccgagcac tgaaaacaat tcagtcatt ccaggtttaa agaccattgt gggggccctg    720
atccagtcgg taaagaagct ttctgatgtg atgatcctga ctgtgttctg tctgagcgtg    780
tttgctctca ttgggctgca gctgttcatg ggcaatctga ggaataaatg tttgcagtgg    840
cccccaagcg attctgcttt tgaaaccaac accacttcct actttaatgg cacaatggat    900
tcaaatggga catttgttaa tgtaacaatg agcacattta ctggaaagga ttacattgga    960
gatgacagtc acttttatgt tttggatggg caaaagacc ctttactctg tggaaatggc    1020
tcagatgcag gccagtgtcc agaaggatac atctgtgtga aggctggtcg aaaccccaac    1080
tatggctaca caagctttga cacctttagc tgggctttcc tgtctctatt tcgactcatg    1140
actcaagact attgggaaaa tcttttaccag ttgacattac gtgctgctgg aaaacatac    1200 atgatatttt ttgtcctggt cattttcttg ggctcatttt atttggtgaa tttgatcctg    1260
gctgtggtgg ccatggccta tgaggagcag aatcaggcca ccttggaaga agcagaacaa    1320
aaagaggccg aatttcagca gatgctcgaa cagcttaaaa agcaacagga gaagctcag    1380 gcagttgcgg cagcatcagc tgcttcaaga gatttcagtg gagtaggtgg gttaggagag    1440
ctgttggaaa gttcttcaga agcatcaaag ttgagttcca aaggtgctaa agaatggagg    1500
aaccggagga agaaaagaag acagagagag caccttgaag gaaacaacaa aggagagaga    1560
gacagctttc ccaaatccga atctgaagac agcgtcaaaa gaagcagctt ccttttctcc    1620
atggatggaa acagactgac cagtgacaaa aaattctgct cccctcatca gtctctcttg    1680
agtatccgtg gctccctgtt ttcccccaaga cgcaatagca aaacaagcat tttcagtttc    1740
agaggtcggg caaaggatgt tggatctgaa aatgactttg ctgatgatga acacagcaca    1800
tttgaagacg gcgaaagcag gagagactca ctgtttgtgc cgcacagaca tggagagcga    1860
cgcaacagta acgttagtca ggccagtatg tcatccagga tggtgccagg gcttccagca    1920
aatgggaaga tgcacagcac tgtggattgc aatggtgtgg tttccttggt gggtggacct    1980
tcagctctaa cgtcacctac tggacaactt cccccagagg gcaccaccac tgaaacggaa    2040
gtcagaaaga gaaggttaag ctcttaccag atttcaatgg agatgctgga ggattcctct    2100
ggaaggcaaa gagccgtgag catagccagc attctgacca acacaatgga agaacttgaa    2160
gaatctagac agaaatgtcc gccatgctgg tatagatttg ccaatgtgtt cttgatctgg    2220
gactgctgtg atgcatggtt aaaagtaaaa catcttgtga atttaattgt tatggatcca    2280
tttgttgatc ttgccatcac tatttgcatt gtcttaaata ccctctttat ggccatggag    2340
cactacccca tgactgagca attcagtagt gtgttgactg taggaaacct ggtctttact    2400
gggattttca cagcagaaat ggttctcaag atcattgcca tggatcctta ttactatttc    2460
caagaaggct ggaatatctt tgatggaatt attgtcagcc tcagtttaat ggagcttggt    2520
ctgtcaaatg tggagggatt gtctgtactg cgatcattca gactgcttag agttttcaag    2580
ttggcaaaat cctggcccac actaaatatg ctaattaaga tcattggcaa ttctgtgggg    2640
gctctaggaa acctcacctt ggtgttggcc atcatcgtct tcattttgc tgtggtcggc    2700 atgcagctct ttggtaagag ctacaaagaa tgtgtctgca agatcaatga tgactgtacg    2760
ctcccacggt ggcacatgaa cgacttcttc cactccttcc tgattgtgtt ccgcgtgctg    2820
tgtggagagt ggatagagac catgtgggac tgtatggagg tcgctggcca aaccatgtgc    2880
cttattgttt tcatgttggt catggtcatt ggaaacctg tggttctgaa cctctttctg    2940
gccttattat tgagttcatt tagctcagac aaccttgctg ctactgatga tgacaatgaa    3000
```

-continued

```
atgaataatc tgcagattgc agtaggaaga atgcaaaagg gaattgatta tgtgaaaaat    3060
aagatgcggg agtgtttcca aaaagccttt tttagaaagc caaaagttat agaaatccat    3120
gaaggcaata agatagacag ctgcatgtcc aataatactg gaattgaaat aagcaaagag    3180
cttaattatc ttagagatgg gaatggaacc accagtggtg taggtactgg aagcagtgtt    3240
gaaaaatacg taatcgatga aaatgattat atgtcattca taaacaaccc cagcctcacc    3300
gtcacagtgc caattgctgt tggagagtct gactttgaaa acttaaatac tgaagagttc    3360
agcagtgagt cagaactaga agaaagcaaa gagaaattaa atgcaaccag ctcatctgaa    3420
ggaagcacag ttgatgttgt tctaccccga gaaggtgaac aagctgaaac tgaacccgaa    3480
gaagacttta aaccggaagc ttgttttact gagggtgta ttaaaaagtt tccattctgt    3540
caagtaagta cagaagaagg caaagggaag atctggtgga atcttcgaaa aacctgctac    3600
agtattgttg agcacaactg gtttgagact ttcattgtgt tcatgatcct tctcagtagt    3660
ggtgcattgg cctttgaaga tatatacatt gaacagcgaa agactatcaa aaccatgcta    3720
gaatatgctg acaaagtctt tacctatata ttcattctgg aaatgcttct caaatgggtt    3780
gcttatggat ttcaaacata tttcactaat gcctggtgct ggctagattt cttgatcgtt    3840
gatgtttctt tggttagcct ggtagccaat gctcttggct actcagaact cggtgccatc    3900
aaatcattac ggacattaag agctttaaga cctctaagag ccttatcccg gtttgaaggc    3960
atgagggtgg ttgtgaatgc tcttgttgga gcaattccct ctatcatgaa tgtgctgttg    4020
gtctgtctca tcttctggtt gatctttagc atcatgggtg tgaatttgtt tgctggcaag    4080
ttctaccact gtgttaacat gacaacgggt aacatgtttg acattagtga tgttaacaat    4140
ttgagtgact gtcaggctct tggcaagcaa gctcggtgga aaaacgtgaa agtaaacttt    4200
gataatgttg gcgctggcta tcttgcactg cttcaagtgg ccacatttaa aggctggatg    4260
gatattatgt atgcagctgt tgattcacga gatgttaaac ttcagcctgt atatgaagaa    4320
aatctgtaca tgtatttata ctttgtcatc tttatcatct ttgggtcatt cttcactctg    4380
aatctattca ttggtgtcat catagataac ttcaaccagc agaaaaagaa gtttggaggt    4440
caagacatct ttatgacaga ggaacagaaa aaatattaca atgcaatgaa gaaacttgga    4500
tccaagaaac ctcagaaacc catacctcgc ccagcaaaca aattccaagg aatggtcttt    4560
gatttttgtaa ccagacaagt ctttgatatc agcatcatga tcctcatctg cctcaacatg    4620
gtcaccatga tggtggaaac ggatgaccag ggcaaataca tgaccctagt tttgtcccgg    4680
atcaacctag tgttcattgt tctgttcact ggagaatttg tgctgaagct cgtttccctc    4740
agacactact acttcactat aggctggaac atctttgact ttgtggtggt gattctctcc    4800
attgtaggta tgtttctggc tgagatgata gaaaagtatt ctgtgtcccc taccttgttc    4860
cgagtgatcc gtcttgccag gattggccga atcctacgtc tgatcaaagg agcaaagggg    4920
atccgcacgc tgctctttgc tttgatgatg tcccttcctg cgttgtttaa catcggcctc    4980
ctgctcttcc tggtcatgtt tatctatgcc atctttggga tgtccaactt tgcctatgtt    5040
aaaaaggaag ctggaattga tgacatgttc aactttgaga cctttggcaa cagcatgatc    5100
tgcttgttcc aaattacaac ctctgctggc tgggatggat tgctagcacc tattcttaat    5160
agtgcaccac ccgactgtga ccctgacaca attcaccctg cagctcagt taagggagac    5220
cgtgggggacc catctgttgg gattttcttt tttgtcagtt acatcatcat atccttcctg    5280
gttgtggtga acatgtacat cgcggtcatc ctggagaact tcagtgttgc tactgaagaa    5340
agtgcagagc ccctgagtga ggatgacttt gagatgttct atgaggtttg ggaaaagttt    5400
```

-continued

```
gatcccgatg cgacccagtt tatagagttc tctaaactct ctgattttgc agctgccctg    5460
gatcctcctc ttctcatagc aaaacccaac aaagtccagc ttattgccat ggatctgccc    5520
atggtcagtg gtgaccggat ccactgtctt gatattttat ttgcctttac aaagcgtgtt    5580
ttgtgtgaga gtggagagat ggatgccctt cgaatacaga tggaagacag gtttatggca    5640
tcaaacccct ccaaagtctc ttatgagcct attacaacca ctttgaaacg taaacaagag    5700
gaggtgtctg ccgctatcat tcagcgtaat ttcagatgtt atcttttaaa gcaaaggtta    5760
aaaaatatat caagtaacta taacaaagag gcaattaaag ggaggattga cttacctata    5820
aaacaagaca tgattattga caaactaaat gggaactcca ctccagaaaa aacagatggg    5880
agttcctcta ccacccctcc tccttcctat gatagtgtaa caaaaccaga caaggaaaag    5940
tttgagaaag acaaaccaga aaagaaagc aaggaaaag aggtcagaga aaatcaaaag    6000
taa                                                                  6003
```

<210> SEQ ID NO 6
<211> LENGTH: 2000
<212> TYPE: PRT
<213> ORGANISM: Homo sapiens

<400> SEQUENCE: 6

```
Met Ala Gln Ala Leu Leu Val Pro Pro Gly Pro Glu Ser Phe Arg Leu
  1               5                  10                  15

Phe Thr Arg Glu Ser Leu Ala Ala Ile Glu Lys Arg Ala Ala Glu Glu
             20                  25                  30

Lys Ala Lys Lys Pro Lys Lys Glu Gln Asp Asn Asp Asp Glu Asn Lys
         35                  40                  45

Pro Lys Pro Asn Ser Asp Leu Glu Ala Gly Lys Asn Leu Pro Phe Ile
     50                  55                  60

Tyr Gly Asp Ile Pro Pro Glu Met Val Ser Glu Pro Leu Glu Asp Leu
 65                  70                  75                  80

Asp Pro Tyr Tyr Ile Asn Lys Lys Thr Phe Ile Val Met Asn Lys Gly
                 85                  90                  95

Lys Ala Ile Phe Arg Phe Ser Ala Thr Ser Ala Leu Tyr Ile Leu Thr
            100                 105                 110

Pro Leu Asn Pro Val Arg Lys Ile Ala Ile Lys Ile Leu Val His Ser
        115                 120                 125

Leu Phe Ser Met Leu Ile Met Cys Thr Ile Leu Thr Asn Cys Val Phe
    130                 135                 140

Met Thr Leu Ser Asn Pro Pro Asp Trp Thr Lys Asn Val Glu Tyr Thr
145                 150                 155                 160

Phe Thr Gly Ile Tyr Thr Phe Glu Ser Leu Ile Lys Ile Leu Ala Arg
                165                 170                 175

Gly Phe Cys Leu Glu Asp Phe Thr Phe Leu Arg Asp Pro Trp Asn Trp
            180                 185                 190

Leu Asp Phe Ser Val Ile Val Met Ala Tyr Val Thr Glu Phe Val Ser
        195                 200                 205

Leu Gly Asn Val Ser Ala Leu Arg Thr Phe Arg Val Leu Arg Ala Leu
    210                 215                 220

Lys Thr Ile Ser Val Ile Pro Gly Leu Lys Thr Ile Val Gly Ala Leu
225                 230                 235                 240

Ile Gln Ser Val Lys Lys Leu Ser Asp Val Met Ile Leu Thr Val Phe
                245                 250                 255
```

```
Cys Leu Ser Val Phe Ala Leu Ile Gly Leu Gln Leu Phe Met Gly Asn
            260                 265                 270

Leu Arg Asn Lys Cys Leu Gln Trp Pro Pro Ser Asp Ser Ala Phe Glu
        275                 280                 285

Thr Asn Thr Thr Ser Tyr Phe Asn Gly Thr Met Asp Ser Asn Gly Thr
    290                 295                 300

Phe Val Asn Val Thr Met Ser Thr Phe Asn Trp Lys Asp Tyr Ile Gly
305                 310                 315                 320

Asp Asp Ser His Phe Tyr Val Leu Asp Gly Gln Lys Asp Pro Leu Leu
                325                 330                 335

Cys Gly Asn Gly Ser Asp Ala Gly Gln Cys Pro Glu Gly Tyr Ile Cys
            340                 345                 350

Val Lys Ala Gly Arg Asn Pro Asn Tyr Gly Tyr Thr Ser Phe Asp Thr
        355                 360                 365

Phe Ser Trp Ala Phe Leu Ser Leu Phe Arg Leu Met Thr Gln Asp Tyr
    370                 375                 380

Trp Glu Asn Leu Tyr Gln Leu Thr Leu Arg Ala Ala Gly Lys Thr Tyr
385                 390                 395                 400

Met Ile Phe Phe Val Leu Val Ile Phe Leu Gly Ser Phe Tyr Leu Val
                405                 410                 415

Asn Leu Ile Leu Ala Val Val Ala Met Ala Tyr Glu Glu Gln Asn Gln
            420                 425                 430

Ala Thr Leu Glu Glu Ala Glu Gln Lys Glu Ala Glu Phe Gln Gln Met
        435                 440                 445

Leu Glu Gln Leu Lys Lys Gln Gln Glu Ala Gln Ala Val Ala Ala
    450                 455                 460

Ala Ser Ala Ala Ser Arg Asp Phe Ser Gly Ile Gly Gly Leu Gly Glu
465                 470                 475                 480

Leu Leu Glu Ser Ser Ser Glu Ala Ser Lys Leu Ser Ser Lys Ser Ala
                485                 490                 495

Lys Glu Trp Arg Asn Arg Arg Lys Lys Arg Arg Gln Arg Glu His Leu
            500                 505                 510

Glu Gly Asn Asn Lys Gly Glu Arg Asp Ser Phe Pro Lys Ser Glu Ser
        515                 520                 525

Glu Asp Ser Val Lys Arg Ser Ser Phe Leu Phe Ser Met Asp Gly Asn
    530                 535                 540

Arg Leu Thr Ser Asp Lys Lys Phe Cys Ser Pro His Gln Ser Leu Leu
545                 550                 555                 560

Ser Ile Arg Gly Ser Leu Phe Ser Pro Arg Arg Asn Ser Lys Thr Ser
                565                 570                 575

Ile Phe Ser Phe Arg Gly Arg Ala Lys Asp Val Gly Ser Glu Asn Asp
            580                 585                 590

Phe Ala Asp Asp Glu His Ser Thr Phe Glu Asp Ser Glu Ser Arg Arg
        595                 600                 605

Asp Ser Leu Phe Val Pro His Arg His Gly Glu Arg Arg Asn Ser Asn
    610                 615                 620

Val Ser Gln Ala Ser Met Ser Ser Arg Met Val Pro Gly Leu Pro Ala
625                 630                 635                 640

Asn Gly Lys Met His Ser Thr Val Asp Cys Asn Gly Val Val Ser Leu
                645                 650                 655

Val Gly Gly Pro Ser Ala Leu Thr Ser Pro Thr Gly Gln Leu Pro Pro
            660                 665                 670

Glu Gly Thr Thr Thr Glu Thr Glu Val Arg Lys Arg Arg Leu Ser Ser
```

-continued

```
              675                 680                 685
Tyr Gln Ile Ser Met Glu Met Leu Glu Asp Ser Ser Gly Arg Gln Arg
    690                 695                 700

Ala Val Ser Ile Ala Ser Ile Leu Thr Asn Thr Met Glu Glu Leu Glu
705                 710                 715                 720

Glu Ser Arg Gln Lys Cys Pro Pro Cys Trp Tyr Arg Phe Ala Asn Val
                725                 730                 735

Phe Leu Ile Trp Asp Cys Cys Asp Ala Trp Leu Lys Val Lys His Leu
                740                 745                 750

Val Asn Leu Ile Val Met Asp Pro Phe Val Asp Leu Ala Ile Thr Ile
                755                 760                 765

Cys Ile Val Leu Asn Thr Leu Phe Met Ala Met Glu His Tyr Pro Met
770                 775                 780

Thr Glu Gln Phe Ser Ser Val Leu Thr Val Gly Asn Leu Val Phe Thr
785                 790                 795                 800

Gly Ile Phe Thr Ala Glu Met Val Leu Lys Ile Ala Met Asp Pro
                805                 810                 815

Tyr Tyr Tyr Phe Gln Glu Gly Trp Asn Ile Phe Asp Gly Ile Ile Val
                820                 825                 830

Ser Leu Ser Leu Met Glu Leu Gly Leu Ser Asn Val Glu Gly Leu Ser
                835                 840                 845

Val Leu Arg Ser Phe Arg Leu Leu Arg Val Phe Lys Leu Ala Lys Ser
                850                 855                 860

Trp Pro Thr Leu Asn Met Leu Ile Lys Ile Ile Gly Asn Ser Val Gly
865                 870                 875                 880

Ala Leu Gly Asn Leu Thr Leu Val Leu Ala Ile Ile Val Phe Ile Phe
                885                 890                 895

Ala Val Val Gly Met Gln Leu Phe Gly Lys Ser Tyr Lys Glu Cys Val
                900                 905                 910

Cys Lys Ile Asn Asp Asp Cys Thr Leu Pro Arg Trp His Met Asn Asp
                915                 920                 925

Phe Phe His Ser Phe Leu Ile Val Phe Arg Val Leu Cys Gly Glu Trp
                930                 935                 940

Ile Glu Thr Met Trp Asp Cys Met Glu Val Ala Gly Gln Thr Met Cys
945                 950                 955                 960

Leu Ile Val Phe Met Leu Val Met Val Ile Gly Asn Leu Val Val Leu
                965                 970                 975

Asn Leu Phe Leu Ala Leu Leu Leu Ser Ser Phe Ser Ser Asp Asn Leu
                980                 985                 990

Ala Ala Thr Asp Asp Asp Asn Glu Met Asn Asn Leu Gln Ile Ala Val
                995                 1000                1005

Gly Arg Met Gln Lys Gly Ile Asp Tyr Val Lys Asn Lys Met Arg Glu
    1010                1015                1020

Cys Phe Gln Lys Ala Phe Phe Arg Lys Pro Lys Val Ile Glu Ile His
1025                1030                1035                1040

Glu Gly Asn Lys Ile Asp Ser Cys Met Ser Asn Asn Thr Gly Ile Glu
                1045                1050                1055

Ile Ser Lys Glu Leu Asn Tyr Leu Arg Asp Gly Asn Gly Thr Thr Ser
                1060                1065                1070

Gly Val Gly Thr Gly Ser Ser Val Glu Lys Tyr Val Ile Asp Glu Asn
            1075                1080                1085

Asp Tyr Met Ser Phe Ile Asn Asn Pro Ser Leu Thr Val Thr Val Pro
    1090                1095                1100
```

```
Ile Ala Val Gly Glu Ser Asp Phe Glu Asn Leu Asn Thr Glu Glu Phe
1105                1110                1115                1120

Ser Ser Glu Ser Glu Leu Glu Ser Lys Glu Lys Leu Asn Ala Thr
            1125                1130                1135

Ser Ser Ser Glu Gly Ser Thr Val Asp Val Leu Pro Arg Glu Gly
                1140                1145                1150

Glu Gln Ala Glu Thr Glu Pro Glu Glu Asp Leu Lys Pro Glu Ala Cys
            1155                1160                1165

Phe Thr Glu Gly Cys Ile Lys Lys Phe Pro Phe Cys Gln Val Ser Thr
            1170                1175                1180

Glu Glu Gly Lys Gly Lys Ile Trp Trp Asn Leu Arg Lys Thr Cys Tyr
1185                1190                1195                1200

Ser Ile Val Glu His Asn Trp Phe Glu Thr Phe Ile Val Phe Met Ile
                1205                1210                1215

Leu Leu Ser Ser Gly Ala Leu Ala Phe Glu Asp Ile Tyr Ile Glu Gln
                1220                1225                1230

Arg Lys Thr Ile Lys Thr Met Leu Glu Tyr Ala Asp Lys Val Phe Thr
            1235                1240                1245

Tyr Ile Phe Ile Leu Glu Met Leu Leu Lys Trp Val Ala Tyr Gly Phe
            1250                1255                1260

Gln Thr Tyr Phe Thr Asn Ala Trp Cys Trp Leu Asp Phe Leu Ile Val
1265                1270                1275                1280

Asp Val Ser Leu Val Ser Leu Val Ala Asn Ala Leu Gly Tyr Ser Glu
                1285                1290                1295

Leu Gly Ala Ile Lys Ser Leu Arg Thr Leu Arg Ala Leu Arg Pro Leu
                1300                1305                1310

Arg Ala Leu Ser Arg Phe Glu Gly Met Arg Val Val Val Asn Ala Leu
            1315                1320                1325

Val Gly Ala Ile Pro Ser Ile Met Asn Val Leu Leu Val Cys Leu Ile
            1330                1335                1340

Phe Trp Leu Ile Phe Ser Ile Met Gly Val Asn Leu Phe Ala Gly Lys
1345                1350                1355                1360

Phe Tyr His Cys Val Asn Met Thr Thr Gly Asn Met Phe Asp Ile Ser
            1365                1370                1375

Asp Val Asn Asn Leu Ser Asp Cys Gln Ala Leu Gly Lys Gln Ala Arg
            1380                1385                1390

Trp Lys Asn Val Lys Val Asn Phe Asp Asn Val Gly Ala Gly Tyr Leu
            1395                1400                1405

Ala Leu Leu Gln Val Ala Thr Phe Lys Gly Trp Met Asp Ile Met Tyr
1410                1415                1420

Ala Ala Val Asp Ser Arg Asp Val Lys Leu Gln Pro Val Tyr Glu Glu
1425                1430                1435                1440

Asn Leu Tyr Met Tyr Leu Tyr Phe Val Ile Phe Ile Ile Phe Gly Ser
            1445                1450                1455

Phe Phe Thr Leu Asn Leu Phe Ile Gly Val Ile Ile Asp Asn Phe Asn
            1460                1465                1470

Gln Gln Lys Lys Lys Phe Gly Gly Gln Asp Ile Phe Met Thr Glu Glu
            1475                1480                1485

Gln Lys Lys Tyr Tyr Asn Ala Met Lys Lys Leu Gly Ser Lys Lys Pro
            1490                1495                1500

Gln Lys Pro Ile Pro Arg Pro Ala Asn Lys Phe Gln Gly Met Val Phe
1505                1510                1515                1520
```

```
Asp Phe Val Thr Arg Gln Val Phe Asp Ile Ser Ile Met Ile Leu Ile
            1525                1530                1535

Cys Leu Asn Met Val Thr Met Met Val Glu Thr Asp Asp Gln Gly Lys
            1540                1545                1550

Tyr Met Thr Leu Val Leu Ser Arg Ile Asn Leu Val Phe Ile Val Leu
            1555                1560                1565

Phe Thr Gly Glu Phe Val Leu Lys Leu Val Ser Leu Arg His Tyr Tyr
            1570                1575                1580

Phe Thr Ile Gly Trp Asn Ile Phe Asp Phe Val Val Ile Leu Ser
1585                1590                1595                1600

Ile Val Gly Met Phe Leu Ala Glu Met Ile Glu Lys Tyr Phe Val Ser
            1605                1610                1615

Pro Thr Leu Phe Arg Val Ile Arg Leu Ala Arg Ile Gly Arg Ile Leu
            1620                1625                1630

Arg Leu Ile Lys Gly Ala Lys Gly Ile Arg Thr Leu Leu Phe Ala Leu
            1635                1640                1645

Met Met Ser Leu Pro Ala Leu Phe Asn Ile Gly Leu Leu Leu Phe Leu
            1650                1655                1660

Val Met Phe Ile Tyr Ala Ile Phe Gly Met Ser Asn Phe Ala Tyr Val
1665                1670                1675                1680

Lys Lys Glu Ala Gly Ile Asp Asp Met Phe Asn Phe Glu Thr Phe Gly
            1685                1690                1695

Asn Ser Met Ile Cys Leu Phe Gln Ile Thr Thr Ser Ala Gly Trp Asp
            1700                1705                1710

Gly Leu Leu Ala Pro Ile Leu Asn Ser Ala Pro Pro Asp Cys Asp Pro
            1715                1720                1725

Asp Thr Ile His Pro Gly Ser Ser Val Lys Gly Asp Cys Gly Asn Pro
            1730                1735                1740

Ser Val Gly Ile Phe Phe Phe Val Ser Tyr Ile Ile Ile Ser Phe Leu
1745                1750                1755                1760

Val Val Val Asn Met Tyr Ile Ala Val Ile Leu Glu Asn Phe Ser Val
            1765                1770                1775

Ala Thr Glu Glu Ser Ala Glu Pro Leu Ser Glu Asp Asp Phe Glu Met
            1780                1785                1790

Phe Tyr Glu Val Trp Glu Lys Phe Asp Pro Asp Ala Thr Gln Phe Ile
            1795                1800                1805

Glu Phe Ser Lys Leu Ser Asp Phe Ala Ala Ala Leu Asp Pro Pro Leu
            1810                1815                1820

Leu Ile Ala Lys Pro Asn Lys Val Gln Leu Ile Ala Met Asp Leu Pro
1825                1830                1835                1840

Met Val Ser Gly Asp Arg Ile His Cys Leu Asp Ile Leu Phe Ala Phe
            1845                1850                1855

Thr Lys Arg Val Leu Gly Glu Ser Gly Glu Met Asp Ala Leu Arg Ile
            1860                1865                1870

Gln Met Glu Asp Arg Phe Met Ala Ser Asn Pro Ser Lys Val Ser Tyr
            1875                1880                1885

Glu Pro Ile Thr Thr Thr Leu Lys Arg Lys Gln Glu Glu Val Ser Ala
            1890                1895                1900

Ala Ile Ile Gln Arg Asn Phe Arg Cys Tyr Leu Leu Lys Gln Arg Leu
1905                1910                1915                1920

Lys Asn Ile Ser Ser Asn Tyr Asn Lys Glu Ala Ile Lys Gly Arg Ile
            1925                1930                1935

Asp Leu Pro Ile Lys Gln Asp Met Ile Ile Asp Lys Leu Asn Gly Asn
```

-continued

```
                1940                1945                1950
Ser Thr Pro Glu Lys Thr Asp Gly Ser Ser Thr Thr Ser Pro Pro
        1955                1960                1965

Ser Tyr Asp Ser Val Thr Lys Pro Asp Lys Glu Lys Phe Glu Lys Asp
        1970                1975                1980

Lys Pro Glu Lys Glu Ser Lys Gly Lys Glu Val Arg Glu Asn Gln Lys
1985                1990                1995                2000

<210> SEQ ID NO 7
<211> LENGTH: 5511
<212> TYPE: DNA
<213> ORGANISM: Homo sapiens

<400> SEQUENCE: 7
atggccagac catctctgtg caccctggct cgtctgggcc ctgagtgctt gcgcccttc       60 acccgggagt cactggcagc catagaacag cgggcggtgg aggaggaggc ccggctgcag     120
cggaataagc agatggagat tgaggagccc gaacggaagc cacgaagtga cttggaggct     180
ggcaagaacc tacccatgat ctacggagac ccccgccgg aggtcatcgg catccccctg      240
gaggacctgg atccctacta cagcaataag aagaccttca tcgtactcaa caagggcaag     300
gccatcttcc gcttctccgc cacacctgct ctctacctgc tgagccccctt cagcgtagtc    360 aggcgcgggg ccatcaaggt gctcatccat gcgctgttca gcatgttcat catgatcacc    420
atcttgacca actgcgtatt catgaccatg agtgacccgc tccctggtc caagaatgtg     480 gagtacacct tcacagggat ctacacctt gagtccctca tcaagatact ggcccgaggc     540
ttctgtgtcg acgacttcac attcctccgg daccctgga actggctgga cttcagtgtc    600
atcatgatgg cgtacctgac agagtttgtg gacttgggca catctcagc cctgaggacc     660 ttccggggtgc tgcgggccct caaaaccatc acggtcatcc cagggctgaa gacgatcgtg    720
gggcccctga tccagtcggt gaagaagctg tcggatgtga tgatcctcac tgtcttctgc    780
ctgagcgtct ttgcgctggt aggactgcag ctcttcatgg gaaacctgag gcagaagtgt    840
gtgcgctggc ccccgccgtt caacgacacc aacaccacgt ggtacagcaa tgacacgtgg    900
tacggcaatg acacatggta tggcaatgag atgtggtacg gcaatgactc atggtatgcc    960
aacgacacgt ggaacagcca tgcaagctgg gccaccaacg tacctttga ttgggacgcc    1020 tacatcagtg atgaagggaa cttctacttc ctggagggct ccaacgatgc cctgctctgt   1080
gggaacagca gtgatgctgg gcactgccct aagggttatg agtgcatcaa gaccggggcgg    1140 aaccccaact atggctacac cagctatgac accttcagct gggccttctt ggctctcttc   1200
cgcctcatga cacaggacta ttgggagaac ctcttccagc tgacccttcg agcagctggc   1260
aagacctaca tgatcttctt cgtggtcatc atcttcctgg gctctttcta cctcatcaat   1320
ctgatcctgg ccgtggtggc catggcatat gccgagcaga atgaggccac cctgccgag    1380 gataaggaga agaggagga gtttcagcag atgcttgaga gttcaaaaaa gcaccaggag    1440
gagctggaga aggccaaggc cgcccaagct ctggaaggtg gggaggcaga tgggaccca    1500 gcccatggca aagactgcaa tggcagcctg gacacatcgc aaggggagaa gggagccccg   1560
aggcagagcg gcagcggaga cagcggcatc tccgacgcca tggaagaact ggaagaggcc   1620
caccaaaagt gcccaccatg gtggtacaag tgcgcccaca agtgctcat atgggactgc    1680 tgcgccccgt ggctgaagtt caagaacatc atccacctga tcgtcatgga cccgttcgtg   1740
gacctgggca tcaccatctg catcgtgctc aacaccctct tcatggccat ggaacattac   1800
```

-continued

```
cccatgacgg agcactttga caacgtgctc actgtgggca acctggtctt cacaggcatc    1860
ttcacagcag agatggttct gaagctgatt gccatggacc cctacgagta tttccagcag    1920
ggttggaata tcttcgacag catcatcgtc accctcagcc tggtagagct aggcctggcc    1980
aacgtacagg gactgtctgt gctacgctcc ttccgtctgc tgcgggtctt caagctggcc    2040
aagtcgtggc caacgctgaa catgctcatc aagatcattg caattcagt gggggcgctg     2100
ggtaacctga cgctggtgct ggctatcatc gtgttcatct tcgccgtggt gggcatgcag    2160
ctgtttggca agagctacaa ggagtgcgtg tgcaagattg ccttggactg caacctgccg    2220
cgctggcaca tgcatgattt cttccactcc ttcctcatcg tcttccgcat cctgtgcggg    2280
gagtggatcg agaccatgtg ggactgcatg gaggtggccg gccaagccat gtgcctcacc    2340
gtcttcctca tggtcatggt catcggcaat cttgtggtcc tgaacctgtt cctggctctg    2400
ctgctgagct ccttcagcgc cgacagtctg gcagcctcgg atgaggatgg cgagatgaac    2460
aacctgcaga ttgccatcgg gcgcatcaag ttgggcatcg gctttgccaa ggccttcctc    2520
ctggggctgc tgcatggcaa gatcctgagc cccaaggaca tcatgctcag cctcggggag    2580
gctgacgggg ccggggaggc tggagaggcg ggggagactg cccccgagga tgagaagaag    2640
gagccgcccg aggaggacct gaagaaggac aatcacatcc tgaaccacat gggcctggct    2700
gacggccccc catccagcct cgagctggac caccttaact tcatcaacaa ccccctacctg   2760
accatacagg tgcccatcgc ctccgaggag tccgacctgg agatgcccac cgaggaggaa    2820
accgacactt tctcagagcc tgaggatagc aagaagccgc cgcagcctct ctatgatggg    2880
aactcgtccg tctgcagcac agctgactac aagcccccccg aggaggaccc tgaggagcag   2940
gcagaggaga accccgaggg ggagcagcct gaggagtgct tcactgaggc ctgcgtgcag    3000
cgctggccct gcctctacgt ggacatctcc cagggccgtg ggaagaagtg gtggactctg    3060
cgcagggcct gcttcaagat tgtcgagcac aactggttcg agaccttcat tgtcttcatg    3120
atcctgctca gcagtggggc tctggccttc gaggacatct acattgagca gcggcgagtc    3180
attcgcacca tcctagaata tgccgacaag gtcttcacct acatcttcat catggagatg    3240
ctgctcaaat gggtggccta cggctttaag gtgtacttca ccaacgcctg tgctggctc    3300
gacttcctca tcgtggatgt ctccatcatc agcttggtgg ccaactgct gggctactcg    3360
gagctgggac ccatcaaatc cctgcggaca ctgcgggccc tgcgtcccct gagggcactg    3420
tcccgattcg agggcatgag ggtggtggtg aacgccctcc taggcgccat cccctccatc    3480
atgaatgtgc tgcttgtctg cctcatcttc tggctgatct tcagcatcat gggtgtcaac    3540
ctgtttgccg gcaagttcta ctactgcatc aacaccacca cctctgagag gttcgacatc    3600
tccgaggtca caacaagtc tgagtgcgag agcctcatga cacaggcca ggtccgctgg    3660
ctcaatgtca aggtcaacta cgacaacgtg ggtctgggct acctctccct cctgcaggtg    3720
gccaccttca ggggttggat ggacatcatg tatgcagccg tggactccg ggagaaggag    3780
gagcagccgc agtacgaggt gaacctctac atgtacctct actttgtcat cttcatcatc    3840
tttggctcct tcttcaccct caacctcttc attggcgtca tcattgacaa cttcaaccag    3900
cagaagaaga agttagggg gaaagacatc tttatgacgg aggaacagaa gaaatactat    3960
aacgccatga agaagcttgg ctccaagaag cctcagaagc aattccccg gccccagaac    4020
aagatccagg gcatggtgta tgacctcgtg acgaagcagg ccttcgacat caccatcatg    4080
atcctcatct gcctcaacat ggtcaccatg atggtggaga cagacgacca gagccagctc    4140
aaggtggaca tcctgtacaa catcaacatg atcttcatca tcatcttcac agggagtgc    4200
```

-continued

```
gtgctcaaga tgctcgccct gcgccagtac tacttcaccg ttggctggaa catctttgac    4260
ttcgtggtcg tcatcctgtc cattgtgggc cttgccctct ctgacctgat ccagaagtac    4320
ttcgtgtcac ccacgctgtt ccgtgtgatc cgcctggcgc ggattgggcg tgtcctgcgg    4380
ctgatccgcg gggccaaggg catccggacg ctgctgttcg ccctcatgat gtcgctgcct    4440
gccctcttca acatcggcct cctcctcttc ctggtcatgt tcatctactc catcttcggc    4500
atgtccaact ttgcctacgt caagaaggag tcgggcatcg atgatatgtt caacttcgag    4560
accttcggca acagcatcat ctgcctgttc gagatcacca cgtcggccgg ctgggacggg    4620
ctcctcaacc ccatcctcaa cagcgggccc ccagactgtg accccaacct ggagaacccg    4680
ggcaccagtg tcaagggtga ctgcggcaac ccctccatcg gcatctgctt cttctgcagc    4740
tatatcatca tctccttcct catcgtggtc aacatgtaca tcgccatcat cctggagaac    4800
ttcaatgtgg ccacagagga gagcagcgag ccccttggtg aagatgactt tgagatgttc    4860
tacgagacat gggagaagtt cgaccccgac gccacccagt tcatcgccta cagccgcctc    4920
tcagacttcg tggacaccct gcaggaaccg ctgaggattg ccaagcccaa caagatcaag    4980
ctcatcacac tggacttgcc catggtgcca ggggacaaga tccactgcct ggacatcctc    5040
tttgccctga ccaaagaggt cctgggtgac tctggggaaa tggacgccct caagcagacc    5100
atggaggaga agttcatggc agccaacccc tccaaggtgt cctacgagcc catcaccacc    5160
accctcaaga ggaagcacga ggaggtgtgc gccatcaaga tccagagggc ctaccgccgg    5220
cacctgctac agcgctccat gaagcaggca tcctacatgt accgccacag ccacgacggc    5280
agcgggatga cgcccctga  aaggaggggg ctgcttgcca acaccatgag caagatgtat    5340
ggccacgaga atgggaacag cagctcgcca agcccggagg agaagggcga ggcaggggac    5400
gccggaccca ctatggggct gatgcccatc agcccctcag acactgcctg gcctcccgcc    5460
cctcccccag ggcagactgt gcgcccaggt gtcaaggagt ctcttgtcta g    5511
```

<210> SEQ ID NO 8
<211> LENGTH: 1836
<212> TYPE: PRT
<213> ORGANISM: Homo sapiens

<400> SEQUENCE: 8

```
Met Ala Arg Pro Ser Leu Cys Thr Leu Ala Arg Leu Gly Pro Glu Cys
 1               5                  10                  15

Leu Arg Pro Phe Thr Arg Glu Ser Leu Ala Ala Ile Glu Gln Arg Ala
            20                  25                  30

Val Glu Glu Ala Arg Leu Gln Arg Asn Lys Gln Met Glu Ile Glu
        35                  40                  45

Glu Pro Glu Arg Lys Pro Arg Ser Asp Leu Glu Ala Gly Lys Asn Leu
    50                  55                  60

Pro Met Ile Tyr Gly Asp Pro Pro Glu Val Ile Gly Ile Pro Leu
65                  70                  75                  80

Glu Asp Leu Asp Pro Tyr Tyr Ser Asn Lys Lys Thr Phe Ile Val Leu
                85                  90                  95

Asn Lys Gly Lys Ala Ile Phe Arg Phe Ser Ala Thr Pro Ala Leu Tyr
            100                 105                 110

Leu Leu Ser Pro Phe Ser Val Val Arg Arg Gly Ala Ile Lys Val Leu
        115                 120                 125

Ile His Ala Leu Phe Ser Met Phe Ile Met Ile Thr Ile Leu Thr Asn
    130                 135                 140
```

```
Cys Val Phe Met Thr Met Ser Asp Pro Pro Trp Ser Lys Asn Val
145                 150                 155                 160

Glu Tyr Thr Phe Thr Gly Ile Tyr Thr Phe Glu Ser Leu Ile Lys Ile
                165                 170                 175

Leu Ala Arg Gly Phe Cys Val Asp Asp Phe Thr Phe Leu Arg Asp Pro
            180                 185                 190

Trp Asn Trp Leu Asp Phe Ser Val Ile Met Met Ala Tyr Leu Thr Glu
        195                 200                 205

Phe Val Asp Leu Gly Asn Ile Ser Ala Leu Arg Thr Phe Arg Val Leu
    210                 215                 220

Arg Ala Leu Lys Thr Ile Thr Val Ile Pro Gly Leu Lys Thr Ile Val
225                 230                 235                 240

Gly Ala Leu Ile Gln Ser Val Lys Lys Leu Ser Asp Val Met Ile Leu
                245                 250                 255

Thr Val Phe Cys Leu Ser Val Phe Ala Leu Val Gly Leu Gln Leu Phe
            260                 265                 270

Met Gly Asn Leu Arg Gln Lys Cys Val Arg Trp Pro Pro Pro Phe Asn
        275                 280                 285

Asp Thr Asn Thr Thr Trp Tyr Ser Asn Asp Thr Trp Tyr Gly Asn Asp
    290                 295                 300

Thr Trp Tyr Gly Asn Glu Met Trp Tyr Gly Asn Asp Ser Trp Tyr Ala
305                 310                 315                 320

Asn Asp Thr Trp Asn Ser His Ala Ser Trp Ala Thr Asn Asp Thr Phe
                325                 330                 335

Asp Trp Asp Ala Tyr Ile Ser Asp Glu Gly Asn Phe Tyr Phe Leu Glu
            340                 345                 350

Gly Ser Asn Asp Ala Leu Leu Cys Gly Asn Ser Ser Asp Ala Gly His
        355                 360                 365

Cys Pro Lys Gly Tyr Glu Cys Ile Lys Thr Gly Arg Asn Pro Asn Tyr
    370                 375                 380

Gly Tyr Thr Ser Tyr Asp Thr Phe Ser Trp Ala Phe Leu Ala Leu Phe
385                 390                 395                 400

Arg Leu Met Thr Gln Asp Tyr Trp Glu Asn Leu Phe Gln Leu Thr Leu
                405                 410                 415

Arg Ala Ala Gly Lys Thr Tyr Met Ile Phe Phe Val Val Ile Ile Phe
            420                 425                 430

Leu Gly Ser Phe Tyr Leu Ile Asn Leu Ile Leu Ala Val Val Ala Met
        435                 440                 445

Ala Tyr Ala Glu Gln Asn Glu Ala Thr Leu Ala Glu Asp Lys Glu Lys
    450                 455                 460

Glu Glu Glu Phe Gln Gln Met Leu Glu Lys Phe Lys Lys His Gln Glu
465                 470                 475                 480

Glu Leu Glu Lys Ala Lys Ala Ala Gln Ala Leu Glu Gly Gly Glu Ala
                485                 490                 495

Asp Gly Asp Pro Ala His Gly Lys Asp Cys Asn Gly Ser Leu Asp Thr
            500                 505                 510

Ser Gln Gly Glu Lys Gly Ala Pro Arg Gln Ser Gly Ser Gly Asp Ser
        515                 520                 525

Gly Ile Ser Asp Ala Met Glu Glu Leu Glu Glu Ala His Gln Lys Cys
    530                 535                 540

Pro Pro Trp Trp Tyr Lys Cys Ala His Lys Val Leu Ile Trp Asp Cys
545                 550                 555                 560
```

-continued

```
Cys Ala Pro Trp Leu Lys Phe Lys Asn Ile Ile His Leu Ile Val Met
                565                 570                 575

Asp Pro Phe Val Asp Leu Gly Ile Thr Ile Cys Ile Val Leu Asn Thr
                580                 585                 590

Leu Phe Met Ala Met Glu His Tyr Pro Met Thr Glu His Phe Asp Asn
                595                 600                 605

Val Leu Thr Val Gly Asn Leu Val Phe Thr Gly Ile Phe Thr Ala Glu
            610                 615                 620

Met Val Leu Lys Leu Ile Ala Met Asp Pro Tyr Glu Tyr Phe Gln Gln
625                 630                 635                 640

Gly Trp Asn Ile Phe Asp Ser Ile Ile Val Thr Leu Ser Leu Val Glu
                645                 650                 655

Leu Gly Leu Ala Asn Val Gln Gly Leu Ser Val Leu Arg Ser Phe Arg
            660                 665                 670

Leu Leu Arg Val Phe Lys Leu Ala Lys Ser Trp Pro Thr Leu Asn Met
            675                 680                 685

Leu Ile Lys Ile Ile Gly Asn Ser Val Gly Ala Leu Gly Asn Leu Thr
            690                 695                 700

Leu Val Leu Ala Ile Ile Val Phe Ile Phe Ala Val Val Gly Met Gln
705                 710                 715                 720

Leu Phe Gly Lys Ser Tyr Lys Glu Cys Val Cys Lys Ile Ala Leu Asp
                725                 730                 735

Cys Asn Leu Pro Arg Trp His Met His Asp Phe Phe His Ser Phe Leu
                740                 745                 750

Ile Val Phe Arg Ile Leu Cys Gly Glu Trp Ile Glu Thr Met Trp Asp
            755                 760                 765

Cys Met Glu Val Ala Gly Gln Ala Met Cys Leu Thr Val Phe Leu Met
770                 775                 780

Val Met Val Ile Gly Asn Leu Val Val Leu Asn Leu Phe Leu Ala Leu
785                 790                 795                 800

Leu Leu Ser Ser Phe Ser Ala Asp Ser Leu Ala Ala Ser Asp Glu Asp
                805                 810                 815

Gly Glu Met Asn Asn Leu Gln Ile Ala Ile Gly Arg Ile Lys Leu Gly
            820                 825                 830

Ile Gly Phe Ala Lys Ala Phe Leu Leu Gly Leu Leu His Gly Lys Ile
            835                 840                 845

Leu Ser Pro Lys Asp Ile Met Leu Ser Leu Gly Glu Ala Asp Gly Ala
850                 855                 860

Gly Glu Ala Gly Glu Ala Gly Glu Thr Ala Pro Glu Asp Glu Lys Lys
865                 870                 875                 880

Glu Pro Pro Glu Glu Asp Leu Lys Lys Asp Asn His Ile Leu Asn His
                885                 890                 895

Met Gly Leu Ala Asp Gly Pro Pro Ser Ser Leu Glu Leu Asp His Leu
            900                 905                 910

Asn Phe Ile Asn Asn Pro Tyr Leu Thr Ile Gln Val Pro Ile Ala Ser
            915                 920                 925

Glu Glu Ser Asp Leu Glu Met Pro Thr Glu Glu Thr Asp Thr Phe
            930                 935                 940

Ser Glu Pro Glu Asp Ser Lys Lys Pro Pro Gln Pro Leu Tyr Asp Gly
945                 950                 955                 960

Asn Ser Ser Val Cys Ser Thr Ala Asp Tyr Lys Pro Pro Glu Glu Asp
                965                 970                 975

Pro Glu Glu Gln Ala Glu Glu Asn Pro Glu Gly Glu Gln Pro Glu Glu
```

-continued

```
                980             985             990
Cys Phe Thr Glu Ala Cys Val Gln Arg Trp Pro Cys Leu Tyr Val Asp
        995            1000            1005

Ile Ser Gln Gly Arg Gly Lys Lys Trp Trp Thr Leu Arg Arg Ala Cys
       1010            1015            1020

Phe Lys Ile Val Glu His Asn Trp Phe Glu Thr Phe Ile Val Phe Met
1025            1030            1035            1040

Ile Leu Leu Ser Ser Gly Ala Leu Ala Phe Glu Asp Ile Tyr Ile Glu
            1045            1050            1055

Gln Arg Arg Val Ile Arg Thr Ile Leu Glu Tyr Ala Asp Lys Val Phe
            1060            1065            1070

Thr Tyr Ile Phe Ile Met Glu Met Leu Leu Lys Trp Val Ala Tyr Gly
            1075            1080            1085

Phe Lys Val Tyr Phe Thr Asn Ala Trp Cys Trp Leu Asp Phe Leu Ile
            1090            1095            1100

Val Asp Val Ser Ile Ile Ser Leu Val Ala Asn Trp Leu Gly Tyr Ser
1105            1110            1115            1120

Glu Leu Gly Pro Ile Lys Ser Leu Arg Thr Leu Arg Ala Leu Arg Pro
            1125            1130            1135

Leu Arg Ala Leu Ser Arg Phe Glu Gly Met Arg Val Val Val Asn Ala
            1140            1145            1150

Leu Leu Gly Ala Ile Pro Ser Ile Met Asn Val Leu Leu Val Cys Leu
            1155            1160            1165

Ile Phe Trp Leu Ile Phe Ser Ile Met Gly Val Asn Leu Phe Ala Gly
            1170            1175            1180

Lys Phe Tyr Tyr Cys Ile Asn Thr Thr Thr Ser Glu Arg Phe Asp Ile
1185            1190            1195            1200

Ser Glu Val Asn Asn Lys Ser Glu Cys Glu Ser Leu Met His Thr Gly
            1205            1210            1215

Gln Val Arg Trp Leu Asn Val Lys Val Asn Tyr Asp Asn Val Gly Leu
            1220            1225            1230

Gly Tyr Leu Ser Leu Leu Gln Val Ala Thr Phe Lys Gly Trp Met Asp
            1235            1240            1245

Ile Met Tyr Ala Ala Val Asp Ser Arg Glu Lys Glu Glu Pro Gln
            1250            1255            1260

Tyr Glu Val Asn Leu Tyr Met Tyr Leu Tyr Phe Val Ile Phe Ile Ile
1265            1270            1275            1280

Phe Gly Ser Phe Phe Thr Leu Asn Leu Phe Ile Gly Val Ile Ile Asp
            1285            1290            1295

Asn Phe Asn Gln Gln Lys Lys Lys Leu Gly Gly Lys Asp Ile Phe Met
            1300            1305            1310

Thr Glu Glu Gln Lys Lys Tyr Tyr Asn Ala Met Lys Lys Leu Gly Ser
            1315            1320            1325

Lys Lys Pro Gln Lys Pro Ile Pro Arg Pro Gln Asn Lys Ile Gln Gly
            1330            1335            1340

Met Val Tyr Asp Leu Val Thr Lys Gln Ala Phe Asp Ile Thr Ile Met
1345            1350            1355            1360

Ile Leu Ile Cys Leu Asn Met Val Thr Met Met Val Glu Thr Asp Asp
            1365            1370            1375

Gln Ser Gln Leu Lys Val Asp Ile Leu Tyr Asn Ile Asn Met Ile Phe
            1380            1385            1390

Ile Ile Ile Phe Thr Gly Glu Cys Val Leu Lys Met Leu Ala Leu Arg
            1395            1400            1405
```

-continued

```
Gln Tyr Tyr Phe Thr Val Gly Trp Asn Ile Phe Asp Phe Val Val Val
    1410                1415                1420

Ile Leu Ser Ile Val Gly Leu Ala Leu Ser Asp Leu Ile Gln Lys Tyr
1425                1430                1435                1440

Phe Val Ser Pro Thr Leu Phe Arg Val Ile Arg Leu Ala Arg Ile Gly
                1445                1450                1455

Arg Val Leu Arg Leu Ile Arg Gly Ala Lys Gly Ile Arg Thr Leu Leu
                1460                1465                1470

Phe Ala Leu Met Met Ser Leu Pro Ala Leu Phe Asn Ile Gly Leu Leu
                1475                1480                1485

Leu Phe Leu Val Met Phe Ile Tyr Ser Ile Phe Gly Met Ser Asn Phe
    1490                1495                1500

Ala Tyr Val Lys Lys Glu Ser Gly Ile Asp Asp Met Phe Asn Phe Glu
1505                1510                1515                1520

Thr Phe Gly Asn Ser Ile Ile Cys Leu Phe Glu Ile Thr Thr Ser Ala
                1525                1530                1535

Gly Trp Asp Gly Leu Leu Asn Pro Ile Leu Asn Ser Gly Pro Pro Asp
                1540                1545                1550

Cys Asp Pro Asn Leu Glu Asn Pro Gly Thr Ser Val Lys Gly Asp Cys
                1555                1560                1565

Gly Asn Pro Ser Ile Gly Ile Cys Phe Phe Cys Ser Tyr Ile Ile Ile
    1570                1575                1580

Ser Phe Leu Ile Val Val Asn Met Tyr Ile Ala Ile Ile Leu Glu Asn
1585                1590                1595                1600

Phe Asn Val Ala Thr Glu Glu Ser Ser Glu Pro Leu Gly Glu Asp Asp
                1605                1610                1615

Phe Glu Met Phe Tyr Glu Thr Trp Glu Lys Phe Asp Pro Asp Ala Thr
                1620                1625                1630

Gln Phe Ile Ala Tyr Ser Arg Leu Ser Asp Phe Val Asp Thr Leu Gln
                1635                1640                1645

Glu Pro Leu Arg Ile Ala Lys Pro Asn Lys Ile Lys Leu Ile Thr Leu
    1650                1655                1660

Asp Leu Pro Met Val Pro Gly Asp Lys Ile His Cys Leu Asp Ile Leu
1665                1670                1675                1680

Phe Ala Leu Thr Lys Glu Val Leu Gly Asp Ser Gly Glu Met Asp Ala
                1685                1690                1695

Leu Lys Gln Thr Met Glu Glu Lys Phe Met Ala Ala Asn Pro Ser Lys
                1700                1705                1710

Val Ser Tyr Glu Pro Ile Thr Thr Thr Leu Lys Arg Lys His Glu Glu
    1715                1720                1725

Val Cys Ala Ile Lys Ile Gln Arg Ala Tyr Arg Arg His Leu Leu Gln
1730                1735                1740

Arg Ser Met Lys Gln Ala Ser Tyr Met Tyr Arg His Ser His Asp Gly
1745                1750                1755                1760

Ser Gly Asp Asp Ala Pro Glu Lys Glu Gly Leu Leu Ala Asn Thr Met
                1765                1770                1775

Ser Lys Met Tyr Gly His Glu Asn Gly Asn Ser Ser Ser Pro Ser Pro
                1780                1785                1790

Glu Glu Lys Gly Glu Ala Gly Asp Ala Gly Pro Thr Met Gly Leu Met
                1795                1800                1805

Pro Ile Ser Pro Ser Asp Thr Ala Trp Pro Pro Ala Pro Pro Pro Gly
    1810                1815                1820
```

```
Gln Thr Val Arg Pro Gly Val Lys Glu Ser Leu Val
1825                1830                1835

<210> SEQ ID NO 9
<211> LENGTH: 6051
<212> TYPE: DNA
<213> ORGANISM: Homo sapiens

<400> SEQUENCE: 9
atggcaaact tcctattacc tcggggcacc agcagcttcc gcaggttcac acgggagtcc      60
ctggcagcca tcgagaagcg catggcggag aagcaagccc gcggctcaac caccttgcag     120
gagagccgag aggggctgcc cgaggaggag ctccccggc cccagctgga cctgcaggcc      180
tccaaaaagc tgccagatct ctatggcaat ccaccccaag agctcatcgg agagcccctg     240
gaggacctgg accccttcta tagcacccaa aagactttca tcgtactgaa taaaggcaag     300
accatcttcc ggttcagtgc caccaacgcc ttgtatgtcc tcagtccctt ccaccccatc     360
cggagagcgg ctgtgaagat tctggttcac tcgctcttca acatgctcat catgtgcacc     420
atcctcacca actgcgtgtt catggcccag acgaccctc cacctggac caagtatgtc      480 gagtacacct tcaccgccat ttacaccttt gagtctctgg tcaagattct ggctcgaggc     540
ttctgcctgc acgcgttcac tttccttcgg gacccatgga actggctgga ctttagtgtg     600
attatcatgg catacacaac tgaatttgtg acctgggca atgtctcagc cttacgcacc     660
ttccgagtcc tccggccct gaaaactata tcagtcattt cagggctgaa gaccatcgtg     720
ggggccctga tccagtctgt gaagaagctg gctgatgtga tggtcctcac agtcttctgc     780
ctcagcgtct ttgccctcat cggcctgcag ctcttcatgg gcaacctaag gcacaagtgc     840
gtgcgcaact tcacagcgct caacggcacc aacggctccg tggaggccga cggcttggtc     900
tgggaatccc tggacctttta cctcagtgat ccagaaaatt acctgctcaa gaacggcacc     960
tctgatgtgt tactgtgtgg gaacagctct gacgctggga catgtccgga gggctaccgg    1020
tgcctaaagg caggcgagaa ccccgaccac ggctacacca gcttcgattc ctttgcctgg    1080 gccttcttg cactcttccg cctgatgacg caggactgct gggagcgcct ctatcagcag    1140
accctcaggt ccgcagggaa gatctacatg atcttcttca tgcttgtcat cttcctgggg    1200
tccttctacc tggtgaacct gatcctggcc gtggtcgcaa tggcctatga ggagcaaaac    1260
caagccacca tcgctgagac cgaggagaag gaaaagcgct tccaggaggc catggaaatg    1320
ctcaagaaag aacacgaggc cctcaccatc agggggtgtgg ataccgtgtc ccgtagctcc    1380
ttggagatgt ccccttttggc cccagtaaac agccatgaga aagaagcaa gaggagaaaa    1440 cggatgtctt caggaactga ggagtgtggg gaggacaggc tccccaagtc tgactcagaa    1500
gatggtccca gagcaatgaa tcatctcagc ctcacccgtg gcctcagcag gacttctatg    1560
aagccacgtt ccagccgcgg gagcattttc acctttcgca ggcgagacct gggttctgaa    1620
gcagattttg cagatgatga aaacagcaca gcgggggaga gcgagagcca ccacacatca    1680
ctgctggtgc cctggcccct cgcgcggacc agtgccagg acagcccag tcccggaacc    1740 tcggctcctg gccacgccct ccatggcaaa agaacagca ctgtggactg caatgggtg    1800 gtctcattac tgggggcagg cgacccgag gccacatccc caggaagcca cctcctccgc    1860
cctgtgatgc tagagcaccc gccagacacg accacgccat cggaggagcc aggcgggccc    1920
cagatgctga cctcccaggc tccgtgtgta gatggcttcg aggagccagg agcacggcag    1980
cgggccctca gcgcagtcag cgtcctcacc agcgcactgg aagagttaga ggagtctcgc    2040
```

```
cacaagtgtc caccatgctg gaaccgtctc gcccagcgct acctgatctg ggagtgctgc    2100
ccgctgtgga tgtccatcaa gcagggagtg aagttggtgg tcatggaccc gtttactgac    2160
ctcaccatca ctatgtgcat cgtactcaac acactcttca tggcgctgga gcactacaac    2220
atgacaagtg aattcgagga gatgctgcag gtcggaaacc tggtcttcac agggattttc    2280
acagcagaga tgaccttcaa gatcattgcc ctcgacccct actactactt ccaacagggc    2340
tggaacatct tcgacagcat catcgtcatc cttagcctca tggagctggg cctgtcccgc    2400
atgagcaact tgtcggtgct gcgctccttc cgcctgctgc gggtcttcaa gctggccaaa    2460
tcatggccca ccctgaacac actcatcaag atcatcggga actcagtggg ggcactgggg    2520
aacctgacac tggtgctagc catcatcgtg ttcatctttg ctgtggtggg catgcagctc    2580
tttggcaaga actactcgga gctgagggac agcgactcag gcctgctgcc tcgctggcac    2640
atgatggact tctttcatgc cttcctcatc atcttccgca tcctctgtgg agagtggatc    2700
gagaccatgt gggactgcat ggaggtgtcg gggcagtcat tatgcctgct ggtcttcttg    2760
cttgttatgg tcattggcaa ccttgtggtc ctgaatctct tcctggcctt gctgctcagc    2820
tccttcagtg cagacaacct cacagcccct gatgaggaca gagagatgaa caacctccag    2880
ctggccctgg cccgcatcca gaggggcctg cgctttgtca gcggaccac ctgggatttc    2940 tgctgtggtc tcctgcggca gcggcctcag aagcccgcag ccttgccgc ccagggccag    3000 ctgcccagct gcattgccac ccctactcc ccgccacccc cagagacgga aaggtgcct    3060 cccacccgca aggaaacacg gtttgaggaa ggcgagcaac caggccaggg cacccccggg    3120
gatccagagc ccgtgtgtgt gcccatcgct gtggccgagt cagacacaga tgaccaagaa    3180
gaagatgagg agaacagcct gggcacggag gaggagtcca gcaagcagca ggaatcccag    3240
cctgtgtccg gtggcccaga ggcccctccg gattccagga cctggagcca ggtgtcagcg    3300
actgcctcct ctgaggccga ggccagtgca tctcaggccg actggcggca gcagtggaaa    3360
gcggaacccc aggcccagg gtgcggtgag accccagagg acagttgctc cgagggcagc    3420
acagcagaca tgaccaacac cgctgagctc ctggagcaga tccctgacct cggccaggat    3480
gtcaaggacc cagaggactg cttcactgaa ggctgtgtcc ggcgctgtcc ctgctgtgcg    3540
gtggacacca cacaggcccc agggaaggtc tggtggcggt tgcgcaagac ctgctaccac    3600
atcgtggagc acagctggtt cgagacattc atcatcttca tgatcctact cagcagtgga    3660
gcgctggcct tcgaggacat ctacctagag gagcggaaga ccatcaaggt tctgcttgag    3720
tatgccgaca agatgttcac atatgtcttc gtgctggaga tgctgctcaa gtgggtggcc    3780
tacggcttca gaagtactt caccaatgcc tggtgctggc tcgacttcct catcgtagac    3840
gtctctctgg tcagcctggt ggccaacacc ctgggctttg ccgagatggg ccccatcaag    3900
tcactgcgga cgctgcgtgc actccgtcct ctgagagctc tgtcacgatt tgagggcatg    3960
agggtggtgg tcaatgccct ggtgggcgcc atccgtcca tcatgaacgt cctcctcgtc    4020
tgcctcatct tctggctcat cttcagcatc atgggcgtga acctctttgc ggggaagttt    4080
gggaggtgca tcaaccagac agagggagac ttgcctttga actacaccat cgtgaacaac    4140
aagagccagt gtgagtcctt gaacttgacc ggagaattgt actggaccaa ggtgaaagtc    4200
aactttgaca cgtggggggc cgggtacctg gcccttctgc aggtggcaac atttaaaggc    4260
tggatggaca ttatgtatgc agctgtggac tccaggggggt atgaagagca gcctcagtgg    4320
gaatacaacc tctacatgta catctatttt gtcattttca tcatctttgg gtctttcttc    4380
accctgaacc tctttattgg tgtcatcatt gacaacttca accaacagaa gaaaaagtta    4440
```

```
gggggccagg acatcttcat gacagaggag cagaagaagt actacaatgc catgaagaag    4500
ctgggctcca agaagcccca agcccatc ccacggcccc tgaacaagta ccagggcttc      4560
atattcgaca ttgtgaccaa gcaggccttt gacgtcacca tcatgtttct gatctgcttg    4620
aatatggtga ccatgatggt ggagacagat gaccaaagtc ctgagaaaat caacatcttg    4680
gccaagatca acctgctctt tgtggccatc ttcacaggcg agtgtattgt caagctggct    4740
gccctgcgcc actactactt caccaacagc tggaatatct tcgacttcgt ggttgtcatc    4800
ctctccatcg tgggcactgt gctctcggac atcatccaga agtacttctt ctccccgacg    4860
ctcttccgag tcatccgcct ggcccgaata ggccgcatcc tcagactgat ccgaggggcc    4920
aaggggatcc gcacgctgct ctttgcccte atgatgtccc tgcctgccct cttcaacatc    4980
gggctgctgc tcttcctcgt catgttcatc tactccatct ttggcatggc caacttcgct    5040
tatgtcaagt gggaggctgg catcgacgac atgttcaact tccagacctt cgccaacagc    5100
atgctgtgcc tcttccagat caccacgtcg gccggctggg atggcctcct cagccccatc    5160
ctcaacactg gccgcccta ctgcgacccc actctgccca acagcaatgg ctctcggggg     5220
gactgcggga gccagccgt gggcatcctc ttcttcacca cctacatcat catctccttc     5280
ctcatcgtgg tcaacatgta cattgccatc atcctggaga acttcagcgt ggccacggag    5340
gagagcaccg agccctgag tgaggacgac ttcgatatgt tctatgagat ctgggagaaa     5400
tttgacccag aggccactca gtttattgag tattcggtcc tgtctgactt tgccgatgcc    5460
ctgtctgagc cactccgtat cgccaagccc aaccagataa gcctcatcaa catggacctg    5520
cccatggtga gtgggaccg catccattgc atggacattc tctttgcctt caccaaaagg    5580
gtcctggggg agtctgggga gatggacgcc ctgaagatcc agatggagga gaagttcatg    5640
gcagccaacc catccaagat ctcctacgag cccatcacca ccacactccg gcgcaagcac    5700
gaagaggtgt cggccatggt tatccagaga gccttccgca ggcacctgct gcaacgctct    5760
ttgaagcatg cctccttcct cttccgtcag caggcgggca gcggcctctc gaagaggat    5820
gcccctgagc gagagggcct catcgcctac gtgatgagtg agaacttctc ccgacccctt    5880
ggcccaccct ccagctcctc catctcctcc acttccttcc caccctccta tgacagtgtc    5940
actagagcca ccagcgataa cctccaggtg cggggtctg actacagcca cagtgaagat    6000
ctcgccgact tcccccttc tccggacagg gaccgtgagt ccatcgtgtg a              6051
```

<210> SEQ ID NO 10
<211> LENGTH: 2016
<212> TYPE: PRT
<213> ORGANISM: Homo sapiens

<400> SEQUENCE: 10

Met Ala Asn Phe Leu Leu Pro Arg Gly Thr Ser Ser Phe Arg Arg Phe
 1               5                   10                  15

Thr Arg Glu Ser Leu Ala Ala Ile Glu Lys Arg Met Ala Glu Lys Gln
            20                  25                  30

Ala Arg Gly Ser Thr Thr Leu Gln Glu Ser Arg Glu Gly Leu Pro Glu
        35                  40                  45

Glu Glu Ala Pro Arg Pro Gln Leu Asp Leu Gln Ala Ser Lys Lys Leu
    50                  55                  60

Pro Asp Leu Tyr Gly Asn Pro Pro Gln Glu Leu Ile Gly Glu Pro Leu
65                  70                  75                  80

Glu Asp Leu Asp Pro Phe Tyr Ser Thr Gln Lys Thr Phe Ile Val Leu

```
                    85                  90                  95
Asn Lys Gly Lys Thr Ile Phe Arg Phe Ser Ala Thr Asn Ala Leu Tyr
                100                 105                 110
Val Leu Ser Pro Phe His Pro Ile Arg Arg Ala Ala Val Lys Ile Leu
                115                 120                 125
Val His Ser Leu Phe Asn Met Leu Ile Met Cys Thr Ile Leu Thr Asn
                130                 135                 140
Cys Val Phe Met Ala Gln His Asp Pro Pro Trp Thr Lys Tyr Val
145                 150                 155                 160
Glu Tyr Thr Phe Thr Ala Ile Tyr Thr Phe Glu Ser Leu Val Lys Ile
                165                 170                 175
Leu Ala Arg Gly Phe Cys Leu His Ala Phe Thr Phe Leu Arg Asp Pro
                180                 185                 190
Trp Asn Trp Leu Asp Phe Ser Val Ile Met Ala Tyr Thr Thr Glu
                195                 200                 205
Phe Val Asp Leu Gly Asn Val Ser Ala Leu Arg Thr Phe Arg Val Leu
                210                 215                 220
Arg Ala Leu Lys Thr Ile Ser Val Ile Ser Gly Leu Lys Thr Ile Val
225                 230                 235                 240
Gly Ala Leu Ile Gln Ser Val Lys Lys Leu Ala Asp Val Met Val Leu
                245                 250                 255
Thr Val Phe Cys Leu Ser Val Phe Ala Leu Ile Gly Leu Gln Leu Phe
                260                 265                 270
Met Gly Asn Leu Arg His Lys Cys Val Arg Asn Phe Thr Ala Leu Asn
                275                 280                 285
Gly Thr Asn Gly Ser Val Glu Ala Asp Gly Leu Val Trp Glu Ser Leu
                290                 295                 300
Asp Leu Tyr Leu Ser Asp Pro Glu Asn Tyr Leu Leu Lys Asn Gly Thr
305                 310                 315                 320
Ser Asp Val Leu Leu Cys Gly Asn Ser Ser Asp Ala Gly Thr Cys Pro
                325                 330                 335
Glu Gly Tyr Arg Cys Leu Lys Ala Gly Glu Asn Pro Asp His Gly Tyr
                340                 345                 350
Thr Ser Phe Asp Ser Phe Ala Trp Ala Phe Leu Ala Leu Phe Arg Leu
                355                 360                 365
Met Thr Gln Asp Cys Trp Glu Arg Leu Tyr Gln Gln Thr Leu Arg Ser
                370                 375                 380
Ala Gly Lys Ile Tyr Met Ile Phe Phe Met Leu Val Ile Phe Leu Gly
385                 390                 395                 400
Ser Phe Tyr Leu Val Asn Leu Ile Leu Ala Val Val Ala Met Ala Tyr
                405                 410                 415
Glu Glu Gln Asn Gln Ala Thr Ile Ala Glu Thr Glu Glu Lys Glu Lys
                420                 425                 430
Arg Phe Gln Glu Ala Met Glu Met Leu Lys Lys Glu His Glu Ala Leu
                435                 440                 445
Thr Ile Arg Gly Val Asp Thr Val Ser Arg Ser Ser Leu Glu Met Ser
                450                 455                 460
Pro Leu Ala Pro Val Asn Ser His Glu Arg Arg Ser Lys Arg Lys
465                 470                 475                 480
Arg Met Ser Ser Gly Thr Glu Glu Cys Gly Glu Asp Arg Leu Pro Lys
                485                 490                 495
Ser Asp Ser Glu Asp Gly Pro Arg Ala Met Asn His Leu Ser Leu Thr
                500                 505                 510
```

-continued

```
Arg Gly Leu Ser Arg Thr Ser Met Lys Pro Arg Ser Ser Arg Gly Ser
            515                 520                 525

Ile Phe Thr Phe Arg Arg Asp Leu Gly Ser Glu Ala Asp Phe Ala
        530                 535                 540

Asp Asp Glu Asn Ser Thr Ala Gly Glu Ser Glu Ser His His Thr Ser
545                 550                 555                 560

Leu Leu Val Pro Trp Pro Leu Arg Arg Thr Ser Ala Gln Gly Gln Pro
                565                 570                 575

Ser Pro Gly Thr Ser Ala Pro Gly His Ala Leu His Gly Lys Lys Asn
            580                 585                 590

Ser Thr Val Asp Cys Asn Gly Val Val Ser Leu Leu Gly Ala Gly Asp
            595                 600                 605

Pro Glu Ala Thr Ser Pro Gly Ser His Leu Leu Arg Pro Val Met Leu
        610                 615                 620

Glu His Pro Pro Asp Thr Thr Thr Pro Ser Glu Glu Pro Gly Gly Pro
625                 630                 635                 640

Gln Met Leu Thr Ser Gln Ala Pro Cys Val Asp Gly Phe Glu Glu Pro
                645                 650                 655

Gly Ala Arg Gln Arg Ala Leu Ser Ala Val Ser Val Leu Thr Ser Ala
            660                 665                 670

Leu Glu Glu Leu Glu Glu Ser Arg His Lys Cys Pro Pro Cys Trp Asn
        675                 680                 685

Arg Leu Ala Gln Arg Tyr Leu Ile Trp Glu Cys Cys Pro Leu Trp Met
        690                 695                 700

Ser Ile Lys Gln Gly Val Lys Leu Val Val Met Asp Pro Phe Thr Asp
705                 710                 715                 720

Leu Thr Ile Thr Met Cys Ile Val Leu Asn Thr Leu Phe Met Ala Leu
                725                 730                 735

Glu His Tyr Asn Met Thr Ser Glu Phe Glu Glu Met Leu Gln Val Gly
            740                 745                 750

Asn Leu Val Phe Thr Gly Ile Phe Thr Ala Glu Met Thr Phe Lys Ile
            755                 760                 765

Ile Ala Leu Asp Pro Tyr Tyr Tyr Phe Gln Gln Gly Trp Asn Ile Phe
        770                 775                 780

Asp Ser Ile Ile Val Ile Leu Ser Leu Met Glu Leu Gly Leu Ser Arg
785                 790                 795                 800

Met Ser Asn Leu Ser Val Leu Arg Ser Phe Arg Leu Leu Arg Val Phe
                805                 810                 815

Lys Leu Ala Lys Ser Trp Pro Thr Leu Asn Thr Leu Ile Lys Ile Ile
            820                 825                 830

Gly Asn Ser Val Gly Ala Leu Gly Asn Leu Thr Leu Val Leu Ala Ile
            835                 840                 845

Ile Val Phe Ile Phe Ala Val Val Gly Met Gln Leu Phe Gly Lys Asn
        850                 855                 860

Tyr Ser Glu Leu Arg Asp Ser Asp Ser Gly Leu Leu Pro Arg Trp His
865                 870                 875                 880

Met Met Asp Phe Phe His Ala Phe Leu Ile Ile Phe Arg Ile Leu Cys
                885                 890                 895

Gly Glu Trp Ile Glu Thr Met Trp Asp Cys Met Glu Val Ser Gly Gln
            900                 905                 910

Ser Leu Cys Leu Leu Val Phe Leu Leu Val Met Val Ile Gly Asn Leu
            915                 920                 925
```

```
Val Val Leu Asn Leu Phe Leu Ala Leu Leu Ser Ser Phe Ser Ala
    930             935             940

Asp Asn Leu Thr Ala Pro Asp Glu Asp Arg Glu Met Asn Asn Leu Gln
945             950              955             960

Leu Ala Leu Ala Arg Ile Gln Arg Gly Leu Arg Phe Val Lys Arg Thr
            965             970             975

Thr Trp Asp Phe Cys Cys Gly Leu Leu Arg Gln Arg Pro Gln Lys Pro
            980             985             990

Ala Ala Leu Ala Ala Gln Gly Gln Leu Pro Ser Cys Ile Ala Thr Pro
        995            1000            1005

Tyr Ser Pro Pro Pro Glu Thr Glu Lys Val Pro Pro Thr Arg Lys
    1010            1015            1020

Glu Thr Arg Phe Glu Glu Gly Glu Gln Pro Gly Gln Gly Thr Pro Gly
1025            1030            1035            1040

Asp Pro Glu Pro Val Cys Val Pro Ile Ala Val Ala Glu Ser Asp Thr
            1045            1050            1055

Asp Asp Gln Glu Glu Asp Glu Glu Asn Ser Leu Gly Thr Glu Glu Glu
            1060            1065            1070

Ser Ser Lys Gln Gln Glu Ser Gln Pro Val Ser Gly Gly Pro Glu Ala
            1075            1080            1085

Pro Pro Asp Ser Arg Thr Trp Ser Gln Val Ser Ala Thr Ala Ser Ser
    1090            1095            1100

Glu Ala Glu Ala Ser Ala Ser Gln Ala Asp Trp Arg Gln Gln Trp Lys
1105            1110            1115            1120

Ala Glu Pro Gln Ala Pro Gly Cys Gly Glu Thr Pro Glu Asp Ser Cys
            1125            1130            1135

Ser Glu Gly Ser Thr Ala Asp Met Thr Asn Thr Ala Glu Leu Leu Glu
            1140            1145            1150

Gln Ile Pro Asp Leu Gly Gln Asp Val Lys Asp Pro Glu Asp Cys Phe
            1155            1160            1165

Thr Glu Gly Cys Val Arg Arg Cys Pro Cys Cys Ala Val Asp Thr Thr
    1170            1175            1180

Gln Ala Pro Gly Lys Val Trp Trp Arg Leu Arg Lys Thr Cys Tyr His
1185            1190            1195            1200

Ile Val Glu His Ser Trp Phe Glu Thr Phe Ile Ile Phe Met Ile Leu
            1205            1210            1215

Leu Ser Ser Gly Ala Leu Ala Phe Glu Asp Ile Tyr Leu Glu Glu Arg
            1220            1225            1230

Lys Thr Ile Lys Val Leu Leu Glu Tyr Ala Asp Lys Met Phe Thr Tyr
            1235            1240            1245

Val Phe Val Leu Glu Met Leu Leu Lys Trp Val Ala Tyr Gly Phe Lys
    1250            1255            1260

Lys Tyr Phe Thr Asn Ala Trp Cys Trp Leu Asp Phe Leu Ile Val Asp
1265            1270            1275            1280

Val Ser Leu Val Ser Leu Val Ala Asn Thr Leu Gly Phe Ala Glu Met
            1285            1290            1295

Gly Pro Ile Lys Ser Leu Arg Thr Leu Arg Ala Leu Arg Pro Leu Arg
            1300            1305            1310

Ala Leu Ser Arg Phe Glu Gly Met Arg Val Val Val Asn Ala Leu Val
    1315            1320            1325

Gly Ala Ile Pro Ser Ile Met Asn Val Leu Leu Val Cys Leu Ile Phe
            1330            1335            1340

Trp Leu Ile Phe Ser Ile Met Gly Val Asn Leu Phe Ala Gly Lys Phe
```

-continued

```
        1345              1350              1355              1360
Gly Arg Cys Ile Asn Gln Thr Glu Gly Asp Leu Pro Leu Asn Tyr Thr
            1365              1370              1375
Ile Val Asn Asn Lys Ser Gln Cys Glu Ser Leu Asn Leu Thr Gly Glu
        1380              1385              1390
Leu Tyr Trp Thr Lys Val Lys Val Asn Phe Asp Asn Val Gly Ala Gly
        1395              1400              1405
Tyr Leu Ala Leu Leu Gln Val Ala Thr Phe Lys Gly Trp Met Asp Ile
        1410              1415              1420
Met Tyr Ala Ala Val Asp Ser Arg Gly Tyr Glu Glu Gln Pro Gln Trp
1425              1430              1435              1440
Glu Tyr Asn Leu Tyr Met Tyr Ile Tyr Phe Val Ile Phe Ile Ile Phe
            1445              1450              1455
Gly Ser Phe Phe Thr Leu Asn Leu Phe Ile Gly Val Ile Ile Asp Asn
        1460              1465              1470
Phe Asn Gln Gln Lys Lys Lys Leu Gly Gly Gln Asp Ile Phe Met Thr
        1475              1480              1485
Glu Glu Gln Lys Lys Tyr Tyr Asn Ala Met Lys Lys Leu Gly Ser Lys
        1490              1495              1500
Lys Pro Gln Lys Pro Ile Pro Arg Pro Leu Asn Lys Tyr Gln Gly Phe
1505              1510              1515              1520
Ile Phe Asp Ile Val Thr Lys Gln Ala Phe Asp Val Thr Ile Met Phe
            1525              1530              1535
Leu Ile Cys Leu Asn Met Val Thr Met Met Val Glu Thr Asp Asp Gln
        1540              1545              1550
Ser Pro Glu Lys Ile Asn Ile Leu Ala Lys Ile Asn Leu Leu Phe Val
        1555              1560              1565
Ala Ile Phe Thr Gly Glu Cys Ile Val Lys Leu Ala Ala Leu Arg His
        1570              1575              1580
Tyr Tyr Phe Thr Asn Ser Trp Asn Ile Phe Asp Phe Val Val Val Ile
1585              1590              1595              1600
Leu Ser Ile Val Gly Thr Val Leu Ser Asp Ile Ile Gln Lys Tyr Phe
            1605              1610              1615
Phe Ser Pro Thr Leu Phe Arg Val Ile Arg Leu Ala Arg Ile Gly Arg
        1620              1625              1630
Ile Leu Arg Leu Ile Arg Gly Ala Lys Gly Ile Arg Thr Leu Leu Phe
        1635              1640              1645
Ala Leu Met Met Ser Leu Pro Ala Leu Phe Asn Ile Gly Leu Leu Leu
        1650              1655              1660
Phe Leu Val Met Phe Ile Tyr Ser Ile Phe Gly Met Ala Asn Phe Ala
1665              1670              1675              1680
Tyr Val Lys Trp Glu Ala Gly Ile Asp Asp Met Phe Asn Phe Gln Thr
            1685              1690              1695
Phe Ala Asn Ser Met Leu Cys Leu Phe Gln Ile Thr Thr Ser Ala Gly
        1700              1705              1710
Trp Asp Gly Leu Leu Ser Pro Ile Leu Asn Thr Gly Pro Pro Tyr Cys
        1715              1720              1725
Asp Pro Thr Leu Pro Asn Ser Asn Gly Ser Arg Gly Asp Cys Gly Ser
        1730              1735              1740
Pro Ala Val Gly Ile Leu Phe Phe Thr Thr Tyr Ile Ile Ile Ser Phe
1745              1750              1755              1760
Leu Ile Val Val Asn Met Tyr Ile Ala Ile Ile Leu Glu Asn Phe Ser
            1765              1770              1775
```

```
Val Ala Thr Glu Glu Ser Thr Glu Pro Leu Ser Glu Asp Asp Phe Asp
            1780                1785                1790

Met Phe Tyr Glu Ile Trp Glu Lys Phe Asp Pro Glu Ala Thr Gln Phe
            1795                1800                1805

Ile Glu Tyr Ser Val Leu Ser Asp Phe Ala Asp Ala Leu Ser Glu Pro
            1810                1815                1820

Leu Arg Ile Ala Lys Pro Asn Gln Ile Ser Leu Ile Asn Met Asp Leu
1825                1830                1835                1840

Pro Met Val Ser Gly Asp Arg Ile His Cys Met Asp Ile Leu Phe Ala
            1845                1850                1855

Phe Thr Lys Arg Val Leu Gly Glu Ser Gly Glu Met Asp Ala Leu Lys
            1860                1865                1870

Ile Gln Met Glu Glu Lys Phe Met Ala Ala Asn Pro Ser Lys Ile Ser
            1875                1880                1885

Tyr Glu Pro Ile Thr Thr Thr Leu Arg Arg Lys His Glu Glu Val Ser
            1890                1895                1900

Ala Met Val Ile Gln Arg Ala Phe Arg Arg His Leu Leu Gln Arg Ser
1905                1910                1915                1920

Leu Lys His Ala Ser Phe Leu Phe Arg Gln Gln Ala Gly Ser Gly Leu
            1925                1930                1935

Ser Glu Glu Asp Ala Pro Glu Arg Glu Gly Leu Ile Ala Tyr Val Met
            1940                1945                1950

Ser Glu Asn Phe Ser Arg Pro Leu Gly Pro Pro Ser Ser Ser Ser Ile
            1955                1960                1965

Ser Ser Thr Ser Phe Pro Pro Ser Tyr Asp Ser Val Thr Arg Ala Thr
            1970                1975                1980

Ser Asp Asn Leu Gln Val Arg Gly Ser Asp Tyr Ser His Ser Glu Asp
1985                1990                1995                2000

Leu Ala Asp Phe Pro Pro Ser Pro Asp Arg Asp Arg Glu Ser Ile Val
            2005                2010                2015

<210> SEQ ID NO 11
<211> LENGTH: 5943
<212> TYPE: DNA
<213> ORGANISM: Homo sapiens

<400> SEQUENCE: 11
atggcagcgc ggctgcttgc accaccaggc cctgatagtt tcaagccttt cacccctgag      60
tcactggcaa acattgagag gcgcattgct gagagcaagc tcaagaaacc accaaaggcc     120
gatggcagtc atcgggagga cgatgaggac agcaagccca agccaaacag cgacctggaa     180
gcagggaaga gtttgccttt catctacggg gacatccccc aaggcctggt tgcagttccc     240
ctggaggact tgacccata ctatttgacg cagaaaacct tgtagtatt aaacagaggg      300 aaaactctct tcagatttag tgccacgcct gccttgtaca ttttaagtcc ttttaacctg     360
ataagaagaa tagctattaa aattttgata cattcagtat ttagcatgat cattatgtgc     420
actattttga ccaactgtgt attcatgact tttagtaacc ctcctgactg gtcgaagaat     480
gtggagtaca cgttcacagg gatttataca tttgaatcac tagtgaaaat cattgcaaga     540
ggtttctgca tagatggctt tacctttta cgggatccat ggaactggtt agatttcagt     600
gtcatcatga tggcgtatat aacagagttt gtaaacctag gcaatgtttc agctctacgc     660
actttcaggg tactgagggc tttgaaaact atttcggtaa tcccaggcct gaagacaatt     720
gtgggtgccc tgattcagtc tgtgaagaaa ctgtcagatg tgatgatcct gacagtgttc     780
```

```
tgcctgagtg ttttgccctt gatcggactg cagctgttca tggggaacct tcgaaacaag    840
tgtgttgtgt ggcccataaa cttcaacgag agctatcttg aaaatggcac caaaggcttt    900
gattgggaag agtatatcaa caataaaaca aatttctaca cagttcctgg catgctggaa    960
cctttactct gtgggaacag ttctgatgct gggcaatgcc cagagggata ccagtgtatg   1020
aaagcaggaa ggaaccccaa ctatggttac acaagttttg acacttttag ctgggccttc   1080
ttggcattat ttcgccttat gacccaggac tattgggaaa acttgtatca attgacttta   1140
cgagcagccg ggaaaacata catgatcttc ttcgtcttgg tcatctttgt gggttctttc   1200
tatctggtga acttgatctt ggctgtggtg gccatggctt atgaagaaca gaatcaggca   1260
acactggagg aggcagaaca aaagaggct gaatttaaag caatgttgga gcaacttaag   1320
aagcaacagg aagaggcaca ggctgctgcg atggccactt cagcaggaac tgtctcagaa   1380
gatgccatag aggaagaagg tgaagaagga gggggctccc ctcggagctc ttctgaaatc   1440
tctaaactca gctcaaagag tgcaaaggaa agacgtaaca ggagaaagaa gaggaagcaa   1500
aaggaactct ctgaaggaga ggagaaaggg gatcccgaga aggtgtttaa gtcagagtca   1560
gaagatggca tgagaaggaa ggcctttcgg ctgccagaca acagaatagg gaggaaattt   1620
tccatcatga atcagtcact gctcagcatc ccaggctcgc ccttcctctc ccgccacaac   1680
agcaagagca gcatcttcag tttcaggga cctgggcggt tccgagaccc gggctccgag   1740
aatgagttcg cggatgacga gcacagcacg gtggaggaga gcgagggccg ccgggactcc   1800
ctcttcatcc ccatccgggc ccgcgagcgc cggagcagct acagcggcta cagcggctac   1860
agccagggca gccgctcctc gcgcatcttc cccagcctgc ggcgcagcgt gaagcgcaac   1920
agcacggtgg actgcaacgg cgtggtgtcc ctcatcggcg gccccggctc ccacatcggc   1980
gggcgtctcc tgccagaggc tacaactgag gtggaaatta agaagaaagg ccctggatct   2040
cttttagttt ccatggacca attagcctcc tacgggcgga aggacagaat caacagtata   2100
atgagtgttg ttacaaatac actagtagaa gaactggaag agtctcagag aaagtgcccg   2160
ccatgctggt ataaatttgc caacactttc ctcatctggg agtgccaccc ctactggata   2220
aaactgaaag agattgtgaa cttgatagtt atggacccctt ttgtggattt agccatcacc   2280
atctgcatcg tcctgaatac actgtttatg gcaatggagc accatcctat gacaccacaa   2340
tttgaacatg tcttggctgt aggaaatctg gttttcactg gaattttcac agcggaaatg   2400
ttcctgaagc tcatagccat ggatccctac tattatttcc aagaaggttg gaacattttt   2460
gacggattta ttgtctcccct cagtttaatg gaactgagtc tagcagacgt ggagggcctt   2520
tcagtgctgc gatcttttccg attgctccga gtcttcaaat tggccaaatc ctggcccacc   2580
ctgaacatgc taatcaagat tattggaaat tcagtgggtg ccctgggcaa cctgacactg   2640
gtgctggcca ttattgtctt catctttgcc gtggtgggga tgcaactctt tggaaaaagc   2700
tacaaagagt gtgtctgcaa gatcaaccag gactgtgaac tccctcgctg gcatatgcat   2760
gactttttcc attccttcct cattgtcttt cgagtgttgt gcggggagtg gattgagacc   2820
atgtgggact gcatggaagt ggcaggccag gccatgtgcc tcattgtctt tatgatggtc   2880
atggtgattg gcaacttggt ggtgctgaac ctgtttctgg ccttgctcct gagctccttc   2940
agtgcagaca acctggctgc cacagatgac gatgggggaaa tgaacaacct ccagatctca   3000
gtgatccgta tcaagaaggg tgtggcctgg accaaactaa aggtgcacgc cttcatgcag   3060
gcccactttta agcagcgtga ggctgatgag gtgaagcctc tggatgagtt gtatgaaaag   3120
```

```
aaggccaact gtatcgccaa tcacaccggt gcagacatcc accggaatgg tgacttccag    3180
aagaatggca atggcacaac cagcggcatt ggcagcagcg tggagaagta catcattgat    3240
gaggaccaca tgtccttcat caacaacccc aacttgactg tacgggtacc cattgctgtg    3300
ggcgagtctg actttgagaa cctcaacaca gaggatgtta gcagcgagtc ggatcctgaa    3360
ggcagcaaag ataaactaga tgacaccagc tcctctgaag gaagcaccat tgatatcaaa    3420
ccagaagtag aagaggtccc tgtggaacag cctgaggaat acttggatcc agatgcctgc    3480
ttcacagaag gttgtgtcca gcggttcaag tgctgccagg tcaacatcga ggaagggcta    3540
ggcaagtctt ggtggatcct gcggaaaacc tgcttcctca tcgtggagca caactggttt    3600
gagaccttca tcatcttcat gattctgctg agcagtggcg ccctggcctt cgaggacatc    3660
tacattgagc agagaaagac catccgcacc atcctggaat atgctgacaa agtcttcacc    3720
tatatcttca tcctggagat gttgctcaag tggacagcct atggcttcgt caagttcttc    3780
accaatgcct ggtgttggct ggacttcctc attgtggctg tctctttagt cagccttata    3840
gctaatgccc tgggctactc ggaactaggt gccataaagt cccttaggac cctaagagct    3900
ttgagaccct aagagccttt atcacgattt gaagggatga gggtggtggt gaatgccttg    3960
gtgggcgcca tccctccat catgaatgtg ctgctggtgt gtctcatctt ctggctgatt    4020
ttcagcatca tgggagttaa cttgtttgcg ggaaagtacc actactgctt taatgagact    4080
tctgaaatcc gatttgaaat tgaagatgtc aacaataaaa ctgaatgtga aaagcttatg    4140
gaggggaaca atacagagat cagatggaag aacgtgaaga tcaactttga caatgttggg    4200
gcaggatacc tggcccttct tcaagtagca accttcaaag gctggatgga catcatgtat    4260
gcagctgtag attcccggaa gcctgatgag cagcctaagt atgaggacaa tatctacatg    4320
tacatctatt ttgtcatctt catcatcttc ggctccttct tcacccctga cctgttcatt    4380
ggtgtcatca ttgataactt caatcaacaa aagaaaaagt tcggaggtca ggacatcttc    4440
atgaccgaag aacagaagaa gtactacaat gccatgaaaa agctgggctc aaagaagcca    4500
cagaaaccca ttccccgccc cttgaacaaa atccaaggaa tcgtctttga ttttgtcact    4560
cagcaagcct ttgacattgt tatcatgatg ctcatctgcc ttaacatggt gacaatgatg    4620
gtggagacag acactcaaag caagcagatg gagaacatcc tctactggat taacctggtg    4680
tttgttatct tcttcacctg tgagtgtgtg ctcaaaatgt ttgcgttgag gcactactac    4740
ttcaccattg gctggaacat cttcgacttc gtggtagtca tcctctccat tgtgggaatg    4800
ttcctggcag atataattga gaaatacttt gtttccccaa ccctattccg agtcatccga    4860
ttggcccgta ttgggcgcat cttgcgtctg atcaaaggcg ccaaagggat tcgtaccctg    4920
ctctttgcct taatgatgtc cttgcctgcc ctgttcaaca tcggccttct gctcttcctg    4980
gtcatgttca tcttctccat tttggggatg tccaattttg catatgtgaa gcacgaggct    5040
ggtatcgatg acatgttcaa ctttgagaca tttgcaaca gcatgatctg cctgtttcaa    5100
atcacaacct cagctggttg ggatggcctg ctgctgccca tcctaaaccg ccccctgac     5160 tgcagcctag ataaggaaca cccagggagt ggctttaagg gagattgtgg aaccccctca    5220
gtgggcatct tcttctttgt aagctacatc atcatctctt tcctaattgt cgtgaacatg    5280
tacattgcca tcatcctgga gaacttcagt gtagccacag aggaaagtgc agaccctctg    5340
agtgaggatg actttgagac cttctatgag atctgggaga agttcgaccc cgatgccacc    5400
cagttcattg agtactgtaa gctggcagac tttgcagatg ccttggagca tcctctccga    5460
gtgcccaagc caaataccat tgagctcatc gctatggatc tgccaatggt gagcgggat     5520
```

-continued

```
cgcatccact gcttggacat ccttttttgcc ttcaccaagc gggtcctggg agatagcggg      5580
gagttggaca tcctgcggca gcagatggaa gagcggttcg tggcatccaa tccttccaaa      5640
gtgtcttacg agccaatcac aaccacactg cgtcgcaagc aggaggaggt atctgcagtg      5700
gtcctgcagc gtgcctaccg ggacatttg gcaaggcggg gcttcatctg caaaaagaca       5760
acttctaata agctggagaa tggaggcaca caccgggaga aaaagagaag caccccatct      5820
acagcctccc tcccgtccta tgacagtgta actaaacctg aaaaggagaa acagcagcgg      5880
gcagaggaag gaagaaggga aagagccaaa agacaaaaag aggtcagaga atccaagtgt      5940
tag                                                                   5943
```

<210> SEQ ID NO 12
<211> LENGTH: 1980
<212> TYPE: PRT
<213> ORGANISM: Homo sapiens

<400> SEQUENCE: 12

```
Met Ala Ala Arg Leu Leu Ala Pro Pro Gly Pro Asp Ser Phe Lys Pro
  1               5                  10                  15

Phe Thr Pro Glu Ser Leu Ala Asn Ile Glu Arg Arg Ile Ala Glu Ser
                 20                  25                  30

Lys Leu Lys Lys Pro Pro Lys Ala Asp Gly Ser His Arg Glu Asp Asp
             35                  40                  45

Glu Asp Ser Lys Pro Lys Pro Asn Ser Asp Leu Glu Ala Gly Lys Ser
 50                  55                  60

Leu Pro Phe Ile Tyr Gly Asp Ile Pro Gln Gly Leu Val Ala Val Pro
 65                  70                  75                  80

Leu Glu Asp Phe Asp Pro Tyr Tyr Leu Thr Gln Lys Thr Phe Val Val
                 85                  90                  95

Leu Asn Arg Gly Lys Thr Leu Phe Arg Phe Ser Ala Thr Pro Ala Leu
            100                 105                 110

Tyr Ile Leu Ser Pro Phe Asn Leu Ile Arg Arg Ile Ala Ile Lys Ile
        115                 120                 125

Leu Ile His Ser Val Phe Ser Met Ile Ile Met Cys Thr Ile Leu Thr
130                 135                 140

Asn Cys Val Phe Met Thr Phe Ser Asn Pro Pro Asp Trp Ser Lys Asn
145                 150                 155                 160

Val Glu Tyr Thr Phe Thr Gly Ile Tyr Thr Phe Glu Ser Leu Val Lys
                165                 170                 175

Ile Ile Ala Arg Gly Phe Cys Ile Asp Gly Phe Thr Phe Leu Arg Asp
            180                 185                 190

Pro Trp Asn Trp Leu Asp Phe Ser Val Ile Met Met Ala Tyr Ile Thr
        195                 200                 205

Glu Phe Val Asn Leu Gly Asn Val Ser Ala Leu Arg Thr Phe Arg Val
    210                 215                 220

Leu Arg Ala Leu Lys Thr Ile Ser Val Ile Pro Gly Leu Lys Thr Ile
225                 230                 235                 240

Val Gly Ala Leu Ile Gln Ser Val Lys Lys Leu Ser Asp Val Met Ile
                245                 250                 255

Leu Thr Val Phe Cys Leu Ser Val Phe Ala Leu Ile Gly Leu Gln Leu
            260                 265                 270

Phe Met Gly Asn Leu Arg Asn Lys Cys Val Val Trp Pro Ile Asn Phe
        275                 280                 285
```

-continued

```
Asn Glu Ser Tyr Leu Glu Asn Gly Thr Lys Gly Phe Asp Trp Glu Glu
    290                 295                 300
Tyr Ile Asn Asn Lys Thr Asn Phe Tyr Thr Val Pro Gly Met Leu Glu
305                 310                 315                 320
Pro Leu Leu Cys Gly Asn Ser Ser Asp Ala Gly Gln Cys Pro Glu Gly
                325                 330                 335
Tyr Gln Cys Met Lys Ala Gly Arg Asn Pro Asn Tyr Gly Tyr Thr Ser
            340                 345                 350
Phe Asp Thr Phe Ser Trp Ala Phe Leu Ala Leu Phe Arg Leu Met Thr
        355                 360                 365
Gln Asp Tyr Trp Glu Asn Leu Tyr Gln Leu Thr Leu Arg Ala Ala Gly
    370                 375                 380
Lys Thr Tyr Met Ile Phe Phe Val Leu Val Ile Phe Val Gly Ser Phe
385                 390                 395                 400
Tyr Leu Val Asn Leu Ile Leu Ala Val Val Ala Met Ala Tyr Glu Glu
                405                 410                 415
Gln Asn Gln Ala Thr Leu Glu Glu Ala Glu Gln Lys Glu Ala Glu Phe
            420                 425                 430
Lys Ala Met Leu Glu Gln Leu Lys Lys Gln Gln Glu Ala Ala Gln Ala
        435                 440                 445
Ala Ala Met Ala Thr Ser Ala Gly Thr Val Ser Glu Asp Ala Ile Glu
    450                 455                 460
Glu Glu Gly Glu Glu Gly Gly Gly Ser Pro Arg Ser Ser Ser Glu Ile
465                 470                 475                 480
Ser Lys Leu Ser Ser Lys Ser Ala Lys Glu Arg Arg Asn Arg Arg Lys
                485                 490                 495
Lys Arg Lys Gln Lys Glu Leu Ser Glu Gly Glu Glu Lys Gly Asp Pro
            500                 505                 510
Glu Lys Val Phe Lys Ser Glu Ser Glu Asp Gly Met Arg Arg Lys Ala
        515                 520                 525
Phe Arg Leu Pro Asp Asn Arg Ile Gly Arg Lys Phe Ser Ile Met Asn
    530                 535                 540
Gln Ser Leu Leu Ser Ile Pro Gly Ser Pro Phe Leu Ser Arg His Asn
545                 550                 555                 560
Ser Lys Ser Ser Ile Phe Ser Phe Arg Gly Pro Gly Arg Phe Arg Asp
                565                 570                 575
Pro Gly Ser Glu Asn Glu Phe Ala Asp Asp Glu His Ser Thr Val Glu
            580                 585                 590
Glu Ser Glu Gly Arg Arg Asp Ser Leu Phe Ile Pro Ile Arg Ala Arg
        595                 600                 605
Glu Arg Arg Ser Ser Tyr Ser Gly Tyr Ser Gly Tyr Ser Gln Gly Ser
    610                 615                 620
Arg Ser Ser Arg Ile Phe Pro Ser Leu Arg Arg Ser Val Lys Arg Asn
625                 630                 635                 640
Ser Thr Val Asp Cys Asn Gly Val Val Ser Leu Ile Gly Gly Pro Gly
                645                 650                 655
Ser His Ile Gly Gly Arg Leu Leu Pro Glu Ala Thr Thr Glu Val Glu
            660                 665                 670
Ile Lys Lys Lys Gly Pro Gly Ser Leu Leu Val Ser Met Asp Gln Leu
        675                 680                 685
Ala Ser Tyr Gly Arg Lys Asp Arg Ile Asn Ser Ile Met Ser Val Val
    690                 695                 700
Thr Asn Thr Leu Val Glu Glu Leu Glu Glu Ser Gln Arg Lys Cys Pro
```

-continued

```
            705                 710                 715                 720
Pro Cys Trp Tyr Lys Phe Ala Asn Thr Phe Leu Ile Trp Glu Cys His
                    725                 730                 735
Pro Tyr Trp Ile Lys Leu Lys Glu Ile Val Asn Leu Ile Val Met Asp
                    740                 745                 750
Pro Phe Val Asp Leu Ala Ile Thr Ile Cys Ile Val Leu Asn Thr Leu
                    755                 760                 765
Phe Met Ala Met Glu His His Pro Met Thr Pro Gln Phe Glu His Val
                    770                 775                 780
Leu Ala Val Gly Asn Leu Val Phe Thr Gly Ile Phe Thr Ala Glu Met
785                 790                 795                 800
Phe Leu Lys Leu Ile Ala Met Asp Pro Tyr Tyr Tyr Phe Gln Glu Gly
                    805                 810                 815
Trp Asn Ile Phe Asp Gly Phe Ile Val Ser Leu Ser Leu Met Glu Leu
                    820                 825                 830
Ser Leu Ala Asp Val Glu Gly Leu Ser Val Leu Arg Ser Phe Arg Leu
                    835                 840                 845
Leu Arg Val Phe Lys Leu Ala Lys Ser Trp Pro Thr Leu Asn Met Leu
                    850                 855                 860
Ile Lys Ile Ile Gly Asn Ser Val Gly Ala Leu Gly Asn Leu Thr Leu
865                 870                 875                 880
Val Leu Ala Ile Ile Val Phe Ile Phe Ala Val Val Gly Met Gln Leu
                    885                 890                 895
Phe Gly Lys Ser Tyr Lys Glu Cys Val Cys Lys Ile Asn Gln Asp Cys
                    900                 905                 910
Glu Leu Pro Arg Trp His Met His Asp Phe Phe His Ser Phe Leu Ile
                    915                 920                 925
Val Phe Arg Val Leu Cys Gly Glu Trp Ile Glu Thr Met Trp Asp Cys
                    930                 935                 940
Met Glu Val Ala Gly Gln Ala Met Cys Leu Ile Val Phe Met Met Val
945                 950                 955                 960
Met Val Ile Gly Asn Leu Val Val Leu Asn Leu Phe Leu Ala Leu Leu
                    965                 970                 975
Leu Ser Ser Phe Ser Ala Asp Asn Leu Ala Ala Thr Asp Asp Asp Gly
                    980                 985                 990
Glu Met Asn Asn Leu Gln Ile Ser Val Ile Arg Ile Lys Lys Gly Val
                    995                 1000                1005
Ala Trp Thr Lys Leu Lys Val His Ala Phe Met Gln Ala His Phe Lys
                    1010                1015                1020
Gln Arg Glu Ala Asp Glu Val Lys Pro Leu Asp Glu Leu Tyr Glu Lys
1025                1030                1035                1040
Lys Ala Asn Cys Ile Ala Asn His Thr Gly Ala Asp Ile His Arg Asn
                    1045                1050                1055
Gly Asp Phe Gln Lys Asn Gly Asn Gly Thr Thr Ser Gly Ile Gly Ser
                    1060                1065                1070
Ser Val Glu Lys Tyr Ile Ile Asp Glu Asp His Met Ser Phe Ile Asn
                    1075                1080                1085
Asn Pro Asn Leu Thr Val Arg Val Pro Ile Ala Val Gly Glu Ser Asp
                    1090                1095                1100
Phe Glu Asn Leu Asn Thr Glu Asp Val Ser Ser Glu Ser Asp Pro Glu
1105                1110                1115                1120
Gly Ser Lys Asp Lys Leu Asp Asp Thr Ser Ser Ser Glu Gly Ser Thr
                    1125                1130                1135
```

-continued

```
Ile Asp Ile Lys Pro Glu Val Glu Val Pro Val Glu Gln Pro Glu
        1140                1145                1150

Glu Tyr Leu Asp Pro Asp Ala Cys Phe Thr Glu Gly Cys Val Gln Arg
        1155                1160                1165

Phe Lys Cys Cys Gln Val Asn Ile Glu Glu Gly Leu Gly Lys Ser Trp
        1170                1175                1180

Trp Ile Leu Arg Lys Thr Cys Phe Leu Ile Val Glu His Asn Trp Phe
1185                1190                1195                1200

Glu Thr Phe Ile Ile Phe Met Ile Leu Ser Ser Gly Ala Leu Ala
        1205                1210                1215

Phe Glu Asp Ile Tyr Ile Glu Gln Arg Lys Thr Ile Arg Thr Ile Leu
        1220                1225                1230

Glu Tyr Ala Asp Lys Val Phe Thr Tyr Ile Phe Ile Leu Glu Met Leu
        1235                1240                1245

Leu Lys Trp Thr Ala Tyr Gly Phe Val Lys Phe Phe Thr Asn Ala Trp
        1250                1255                1260

Cys Trp Leu Asp Phe Leu Ile Val Ala Val Ser Leu Val Ser Leu Ile
1265                1270                1275                1280

Ala Asn Ala Leu Gly Tyr Ser Glu Leu Gly Ala Ile Lys Ser Leu Arg
        1285                1290                1295

Thr Leu Arg Ala Leu Arg Pro Leu Arg Ala Leu Ser Arg Phe Glu Gly
        1300                1305                1310

Met Arg Val Val Val Asn Ala Leu Val Gly Ala Ile Pro Ser Ile Met
        1315                1320                1325

Asn Val Leu Leu Val Cys Leu Ile Phe Trp Leu Ile Phe Ser Ile Met
        1330                1335                1340

Gly Val Asn Leu Phe Ala Gly Lys Tyr His Tyr Cys Phe Asn Glu Thr
1345                1350                1355                1360

Ser Glu Ile Arg Phe Glu Ile Glu Asp Val Asn Asn Lys Thr Glu Cys
        1365                1370                1375

Glu Lys Leu Met Glu Gly Asn Asn Thr Glu Ile Arg Trp Lys Asn Val
        1380                1385                1390

Lys Ile Asn Phe Asp Asn Val Gly Ala Gly Tyr Leu Ala Leu Leu Gln
        1395                1400                1405

Val Ala Thr Phe Lys Gly Trp Met Asp Ile Met Tyr Ala Ala Val Asp
        1410                1415                1420

Ser Arg Lys Pro Asp Glu Gln Pro Lys Tyr Glu Asp Asn Ile Tyr Met
1425                1430                1435                1440

Tyr Ile Tyr Phe Val Ile Phe Ile Ile Phe Gly Ser Phe Phe Thr Leu
        1445                1450                1455

Asn Leu Phe Ile Gly Val Ile Ile Asp Asn Phe Asn Gln Gln Lys Lys
        1460                1465                1470

Lys Phe Gly Gly Gln Asp Ile Phe Met Thr Glu Glu Gln Lys Lys Tyr
        1475                1480                1485

Tyr Asn Ala Met Lys Lys Leu Gly Ser Lys Lys Pro Gln Lys Pro Ile
        1490                1495                1500

Pro Arg Pro Leu Asn Lys Ile Gln Gly Ile Val Phe Asp Phe Val Thr
1505                1510                1515                1520

Gln Gln Ala Phe Asp Ile Val Ile Met Met Leu Ile Cys Leu Asn Met
        1525                1530                1535

Val Thr Met Met Val Glu Thr Asp Thr Gln Ser Lys Gln Met Glu Asn
        1540                1545                1550
```

-continued

```
Ile Leu Tyr Trp Ile Asn Leu Val Phe Val Ile Phe Thr Cys Glu
        1555                1560                1565
Cys Val Leu Lys Met Phe Ala Leu Arg His Tyr Tyr Phe Thr Ile Gly
    1570                1575                1580
Trp Asn Ile Phe Asp Phe Val Val Ile Leu Ser Ile Val Gly Met
1585                1590                1595                1600
Phe Leu Ala Asp Ile Ile Glu Lys Tyr Phe Val Ser Pro Thr Leu Phe
            1605                1610                1615
Arg Val Ile Arg Leu Ala Arg Ile Gly Arg Ile Leu Arg Leu Ile Lys
        1620                1625                1630
Gly Ala Lys Gly Ile Arg Thr Leu Leu Phe Ala Leu Met Met Ser Leu
    1635                1640                1645
Pro Ala Leu Phe Asn Ile Gly Leu Leu Leu Phe Leu Val Met Phe Ile
    1650                1655                1660
Phe Ser Ile Phe Gly Met Ser Asn Phe Ala Tyr Val Lys His Glu Ala
1665                1670                1675                1680
Gly Ile Asp Asp Met Phe Asn Phe Glu Thr Phe Gly Asn Ser Met Ile
            1685                1690                1695
Cys Leu Phe Gln Ile Thr Thr Ser Ala Gly Trp Asp Gly Leu Leu Leu
        1700                1705                1710
Pro Ile Leu Asn Arg Pro Pro Asp Cys Ser Leu Asp Lys Glu His Pro
        1715                1720                1725
Gly Ser Gly Phe Lys Gly Asp Cys Gly Asn Pro Ser Val Gly Ile Phe
    1730                1735                1740
Phe Phe Val Ser Tyr Ile Ile Ile Ser Phe Leu Ile Val Val Asn Met
1745                1750                1755                1760
Tyr Ile Ala Ile Ile Leu Glu Asn Phe Ser Val Ala Thr Glu Glu Ser
            1765                1770                1775
Ala Asp Pro Leu Ser Glu Asp Asp Phe Glu Thr Phe Tyr Glu Ile Trp
            1780                1785                1790
Glu Lys Phe Asp Pro Asp Ala Thr Gln Phe Ile Glu Tyr Cys Lys Leu
        1795                1800                1805
Ala Asp Phe Ala Asp Ala Leu Glu His Pro Leu Arg Val Pro Lys Pro
    1810                1815                1820
Asn Thr Ile Glu Leu Ile Ala Met Asp Leu Pro Met Val Ser Gly Asp
1825                1830                1835                1840
Arg Ile His Cys Leu Asp Ile Leu Phe Ala Phe Thr Lys Arg Val Leu
            1845                1850                1855
Gly Asp Ser Gly Glu Leu Asp Ile Leu Arg Gln Gln Met Glu Glu Arg
        1860                1865                1870
Phe Val Ala Ser Asn Pro Ser Lys Val Ser Tyr Glu Pro Ile Thr Thr
    1875                1880                1885
Thr Leu Arg Arg Lys Gln Glu Glu Val Ser Ala Val Val Leu Gln Arg
    1890                1895                1900
Ala Tyr Arg Gly His Leu Ala Arg Arg Gly Phe Ile Cys Lys Lys Thr
1905                1910                1915                1920
Thr Ser Asn Lys Leu Glu Asn Gly Gly Thr His Arg Glu Lys Lys Glu
            1925                1930                1935
Ser Thr Pro Ser Thr Ala Ser Leu Pro Ser Tyr Asp Ser Val Thr Lys
            1940                1945                1950
Pro Glu Lys Glu Lys Gln Gln Arg Ala Glu Glu Gly Arg Arg Glu Arg
        1955                1960                1965
Ala Lys Arg Gln Lys Glu Val Arg Glu Ser Lys Cys
```

-continued

<210> SEQ ID NO 13
<211> LENGTH: 5934
<212> TYPE: DNA
<213> ORGANISM: Homo sapiens

<400> SEQUENCE: 13

| | | | | | |
|---|---|---|---|---|---|
| atggcaatgt | tgcctccccc | aggacctcag | agctttgtcc | atttcacaaa | acagtctctt | 60 |
| gccctcattg | aacaacgcat | tgctgaaaga | aaatcaaagg | aacccaaaga | agaaaagaaa | 120 |
| gatgatgatg | aagaagcccc | aaagccaagc | agtgacttgg | aagctggcaa | acaactgccc | 180 |
| ttcatctatg | gggacattcc | tcccggcatg | gtgtcagagc | ccctggagga | cttggacccc | 240 |
| tactatgcag | acaaaaagac | tttcatagta | ttgaacaaag | gaaaacaat | cttccgtttc | 300 |
| aatgccacac | ctgctttata | tatgctttct | cctttcagtc | ctctaagaag | aatatctatt | 360 |
| aagattttag | tacactcctt | attcagcatg | ctcatcatgt | gcactattct | gacaaactgc | 420 |
| atatttatga | ccatgaataa | cccgccggac | tggaccaaaa | atgtcgagta | cacttttact | 480 |
| ggaatatata | cttttgaatc | acttgtaaaa | atccttgcaa | gaggcttctg | tgtaggagaa | 540 |
| ttcacttttc | ttcgtgaccc | gtggaactgg | ctggattttg | tcgtcattgt | ttttgcgtat | 600 |
| ttaacagaat | ttgtaaacct | aggcaatgtt | tcagctcttc | gaactttcag | agtattgaga | 660 |
| gctttgaaaa | ctatttctgt | aatcccaggc | ctgaagacaa | ttgtaggggc | tttgatccag | 720 |
| tcagtgaaga | agctttctga | tgtcatgatc | ctgactgtgt | tctgtctgag | tgtgtttgca | 780 |
| ctaattggac | tacagctgtt | catgggaaac | ctgaagcata | aatgttttcg | aaattcactt | 840 |
| gaaaataatg | aaacattaga | aagcataatg | aatacactag | agagtgaaga | agacttaga | 900 |
| aaatattttt | attacttgga | aggatccaaa | gatgctctcc | tttgtggttt | cagcacagat | 960 |
| tcaggtcagt | gtccagaggg | gtacacctgt | gtgaaaattg | gcagaaaccc | tgattatggc | 1020 |
| tacacgagct | ttgacacttt | cagctgggcc | ttcttagcct | tgtttaggct | aatgacccaa | 1080 |
| gattactggg | aaaaccttta | ccaacagacg | ctgcgtgctg | ctggcaaaac | ctacatgatc | 1140 |
| ttctttgtcg | tagtgatttt | cctgggctcc | ttttatctaa | taaacttgat | cctggctgtg | 1200 |
| gttgccatgg | catatgaaga | acagaaccag | gcaaacattg | aagaagctaa | acagaaagaa | 1260 |
| ttagaatttc | aacagatgtt | agaccgtctt | aaaaagagc | aagaagaagc | tgaggcaatt | 1320 |
| gcagcggcag | cggctgaata | tacaagtatt | aggagaagca | gaattatggg | cctctcagag | 1380 |
| agttcttctg | aaacatccaa | actgagctct | aaaagtgcta | agaaagaag | aaacagaaga | 1440 |
| aagaaaaaga | atcaaaagaa | gctctccagt | ggagaggaaa | agggagatgc | tgagaaattg | 1500 |
| tcgaaatcag | aatcagagga | cagcatcaga | agaaaaagtt | tccaccttgg | tgtcgaaggg | 1560 |
| cataggcgag | cacatgaaaa | gaggttgtct | accccccaatc | agtcaccact | cagcattcgt | 1620 |
| ggctcccttg | tttctgcaag | gcgaagcagc | agaacaagtc | ttttttagttt | caaaggcaga | 1680 |
| ggaagagata | taggatctga | gactgaattt | gccgatgatg | agcacagcat | ttttggagac | 1740 |
| aatgagagca | gaaggggctc | actgtttgtg | ccccacagac | cccaggagcg | acgcagcagt | 1800 |
| aacatcagcc | aagccagtag | gtccccacca | atgctgccgg | tgaacgggaa | atgcacagt | 1860 |
| gctgtggact | gcaacggtgt | ggtctccctg | gttgatggac | gctcagccct | catgctcccc | 1920 |
| aatggacagc | ttctgccaga | gggcacgacc | aatcaaatac | acaagaaaag | gcgttgtagt | 1980 |
| tcctatctcc | tttcagagga | tatgctgaat | gatcccaacc | tcagacagag | agcaatgagt | 2040 |
| agagcaagca | tattaacaaa | cactgtggaa | gaacttgaag | agtccagaca | aaaatgtcca | 2100 |

| | |
|---|---|
| ccttggtggt acagatttgc acacaaattc ttgatctgga attgctctcc atattggata | 2160 |
| aaattcaaaa agtgtatcta ttttattgta atggatcctt ttgtagatct tgcaattacc | 2220 |
| atttgcatag ttttaaacac attatttatg gctatggaac accacccaat gactgaggaa | 2280 |
| ttcaaaaatg tacttgctat aggaaatttg gtctttactg gaatctttgc agctgaaatg | 2340 |
| gtattaaaac tgattgccat ggatccatat gagtatttcc aagtaggctg gaatattttt | 2400 |
| gacagcctta ttgtgacttt aagtttagtg gagctctttc tagcagatgt ggaaggattg | 2460 |
| tcagttctgc gatcattcag actgctccga gtcttcaagt tggcaaaatc ctggccaaca | 2520 |
| ttgaacatgc tgattaagat cattggtaac tcagtagggg ctctaggtaa cctcacctta | 2580 |
| gtgttggcca tcatcgtctt cattttgct gtggtcggca tgcagctctt tggtaagagc | 2640 |
| tacaaagaat gtgtctgcaa gatcaatgat gactgtacgc tcccacggtg gcacatgaac | 2700 |
| gacttcttcc actccttcct gattgtgttc cgcgtgctgt gtggagagtg gatagagacc | 2760 |
| atgtgggact gtatggaggt cgctggtcaa gctatgtgcc ttattgttta catgatggtc | 2820 |
| atggtcattg gaaacctggt ggtcctaaac ctatttctgg ccttattatt gagctcattt | 2880 |
| agttcagaca atcttacagc aattgaagaa gaccctgatg caaacaacct ccagattgca | 2940 |
| gtgactagaa ttaaaagggg aataaattat gtgaaacaaa ccttacgtga atttattcta | 3000 |
| aaagcatttt ccaaaaagcc aaagatttcc agggagataa gacaagcaga agatctgaat | 3060 |
| actaagaagg aaaactatat ttctaaccat acacttgctg aaatgagcaa aggtcacaat | 3120 |
| ttcctcaagg aaaaagataa aatcagtggt tttggaagca gcgtggacaa acacttgatg | 3180 |
| gaagacagtg atggtcaatc atttattcac aatcccagcc tcacagtgac agtgccaatt | 3240 |
| gcacctgggg aatccgattt ggaaaatatg aatgctgagg aacttagcag tgattcggat | 3300 |
| agtgaataca gcaaagtgag attaaaccgg tcaagctcct cagagtgcag cacagttgat | 3360 |
| aacccttttgc ctggagaagg agaagaagca gaggctgaac ctatgaattc cgatgagcca | 3420 |
| gaggcctgtt tcacagatgg ttgtgtacgg aggttctcat gctgccaagt taacatagag | 3480 |
| tcagggaaag gaaaaatctg gtggaacatc aggaaaacct gctacaagat tgttgaacac | 3540 |
| agttggtttg aaagcttcat tgtcctcatg atcctgctca gcagtggtgc cctggctttt | 3600 |
| gaagatattt atattgaaag gaaaaagacc attaagatta tcctggagta tgcagacaag | 3660 |
| atcttcactt acatcttcat tctggaaatg cttctaaaat ggatagcata tggttataaa | 3720 |
| acatatttca ccaatgcctg gtgttggctg gatttcctaa ttgttgatgt ttctttggtt | 3780 |
| actttagtgg caaacactct tggctactca gatcttggcc ccattaaatc ccttcggaca | 3840 |
| ctgagagctt taagacctct aagagcctta tctagatttg aaggaatgag ggtcgttgtg | 3900 |
| aatgcactca taggagcaat tccttccatc atgaatgtgc tacttgtgtg tcttatattc | 3960 |
| tggctgatat tcagcatcat gggagtaaat ttgtttgctg gcaagttcta tgagtgtatt | 4020 |
| aacaccacag atgggtcacg gtttcctgca agtcaagttc caaatcgttc gaatgttttt | 4080 |
| gcccttatga atgttagtca aaatgtgcga tggaaaaacc tgaaagtgaa ctttgataat | 4140 |
| gtcggacttg gttacctatc tctgcttcaa gttgcaactt ttaagggatg gacgattatt | 4200 |
| atgtatgcag cagtggattc tgttaatgta gacaagcagc ccaaatatga atatagcctc | 4260 |
| tacatgtata tttattttgt cgtctttatc atctttgggt cattcttcac tttgaacttg | 4320 |
| ttcattggtg tcatcataga taatttcaac caacagaaaa agaagcttgg aggtcaagac | 4380 |
| atctttatga cagaagaaca gaagaaatac tataatgcaa tgaaaagct ggggtccaag | 4440 |

```
aagccacaaa agccaattcc tcgaccaggg aacaaaatcc aaggatgtat atttgaccta    4500
gtgacaaatc aagcctttga tattagtatc atggttctta tctgtctcaa catggtaacc    4560
atgatggtag aaaaggaggg tcaaagtcaa catatgactg aagttttata ttggataaat    4620
gtggttttta taatcctttt cactggagaa tgtgtgctaa aactgatctc cctcagacac    4680
tactacttca ctgtaggatg aatattttt gattttgtgg ttgtgattat ctccattgta    4740
ggtatgtttc tagctgattt gattgaaacg tattttgtgt cccctaccct gttccgagtg    4800
atccgtcttg ccaggattgg ccgaatccta cgtctagtca aaggagcaaa ggggatccgc    4860
acgctgctct ttgctttgat gatgtccctt cctgcgttgt ttaacatcgg cctcctgctc    4920
ttcctggtca tgttcatcta cgccatcttt ggaatgtcca actttgccta tgttaaaaag    4980
gaagatggaa ttaatgacat gttcaatttt gagacctttg caacagtat gatttgcctg    5040 ttccaaatta caacctctgc tggctgggat ggattgctag cacctattct taacagtaag    5100
ccacccgact gtgacccaaa aaagttcat cctggaagtt cagttgaagg agactgtggt    5160
aacccatctg ttggaatatt ctactttgtt agttatatca tcatatcctt cctggttgtg    5220
gtgaacatgt acattgcagt catactggag aattttagtg ttgccactga agaaagtact    5280
gaacctctga gtgaggatga ctttgagatg ttctatgagg tttgggagaa gtttgatccc    5340
gatgcgaccc agtttataga gttctctaaa ctctctgatt ttgcagctgc cctggatcct    5400
cctcttctca tagcaaaacc caacaaagtc cagctcattg ccatggatct gcccatggtt    5460
agtggtgacc ggatccattg tcttgacatc ttatttgctt ttacaaagcg tgttttgggt    5520
gagagtgggg agatggattc tcttcgttca cagatggaag aaaggttcat gtctgcaaat    5580
ccttccaaag tgtcctatga acccatcaca accacactaa acggaaaca agaggatgtg    5640 tctgctactg tcattcagcg tgcttataga cgttaccgct taaggcaaaa tgtcaaaaat    5700
atatcaagta tatacataaa agatggagac agagatgatg atttactcaa taaaaaagat    5760
atggcttttg ataatgttaa tgagaactca agtccagaaa aacagatgc cacttcatcc    5820 accacctctc caccttcata tgatagtgta acaaagccag acaaagagaa atatgaacaa    5880
gacagaacag aaaaggaaga caaagggaaa gacagcaagg aaagcaaaaa atag          5934
```

<210> SEQ ID NO 14
<211> LENGTH: 1977
<212> TYPE: PRT
<213> ORGANISM: Homo sapiens

<400> SEQUENCE: 14

```
Met Ala Met Leu Pro Pro Gly Pro Gln Ser Phe Val His Phe Thr
 1               5                  10                  15

Lys Gln Ser Leu Ala Leu Ile Glu Gln Arg Ile Ala Glu Arg Lys Ser
            20                  25                  30

Lys Glu Pro Lys Glu Glu Lys Lys Asp Asp Asp Glu Glu Ala Pro Lys
        35                  40                  45

Pro Ser Ser Asp Leu Glu Ala Gly Lys Gln Leu Pro Phe Ile Tyr Gly
    50                  55                  60

Asp Ile Pro Pro Gly Met Val Ser Glu Pro Leu Glu Asp Leu Asp Pro
65                  70                  75                  80

Tyr Tyr Ala Asp Lys Lys Thr Phe Ile Val Leu Asn Lys Gly Lys Thr
                85                  90                  95

Ile Phe Arg Phe Asn Ala Thr Pro Ala Leu Tyr Met Leu Ser Pro Phe
            100                 105                 110
```

```
Ser Pro Leu Arg Arg Ile Ser Ile Lys Ile Leu Val His Ser Leu Phe
        115                 120                 125

Ser Met Leu Ile Met Cys Thr Ile Leu Thr Asn Cys Ile Phe Met Thr
    130                 135                 140

Met Asn Asn Pro Pro Asp Trp Thr Lys Asn Val Glu Tyr Thr Phe Thr
145                 150                 155                 160

Gly Ile Tyr Thr Phe Glu Ser Leu Val Lys Ile Leu Ala Arg Gly Phe
                165                 170                 175

Cys Val Gly Glu Phe Thr Phe Leu Arg Asp Pro Trp Asn Trp Leu Asp
            180                 185                 190

Phe Val Val Ile Val Phe Ala Tyr Leu Thr Glu Phe Val Asn Leu Gly
        195                 200                 205

Asn Val Ser Ala Leu Arg Thr Phe Arg Val Leu Arg Ala Leu Lys Thr
210                 215                 220

Ile Ser Val Ile Pro Gly Leu Lys Thr Ile Val Gly Ala Leu Ile Gln
225                 230                 235                 240

Ser Val Lys Lys Leu Ser Asp Val Met Ile Leu Thr Val Phe Cys Leu
                245                 250                 255

Ser Val Phe Ala Leu Ile Gly Leu Gln Leu Phe Met Gly Asn Leu Lys
            260                 265                 270

His Lys Cys Phe Arg Asn Ser Leu Glu Asn Asn Glu Thr Leu Glu Ser
        275                 280                 285

Ile Met Asn Thr Leu Glu Ser Glu Glu Asp Phe Arg Lys Tyr Phe Tyr
    290                 295                 300

Tyr Leu Glu Gly Ser Lys Asp Ala Leu Leu Cys Gly Phe Ser Thr Asp
305                 310                 315                 320

Ser Gly Gln Cys Pro Glu Gly Tyr Thr Cys Val Lys Ile Gly Arg Asn
                325                 330                 335

Pro Asp Tyr Gly Tyr Thr Ser Phe Asp Thr Phe Ser Trp Ala Phe Leu
            340                 345                 350

Ala Leu Phe Arg Leu Met Thr Gln Asp Tyr Trp Glu Asn Leu Tyr Gln
        355                 360                 365

Gln Thr Leu Arg Ala Ala Gly Lys Thr Tyr Met Ile Phe Phe Val Val
    370                 375                 380

Val Ile Phe Leu Gly Ser Phe Tyr Leu Ile Asn Leu Ile Leu Ala Val
385                 390                 395                 400

Val Ala Met Ala Tyr Glu Glu Gln Asn Gln Ala Asn Ile Glu Glu Ala
                405                 410                 415

Lys Gln Lys Glu Leu Glu Phe Gln Gln Met Leu Asp Arg Leu Lys Lys
            420                 425                 430

Glu Gln Glu Glu Ala Glu Ala Ile Ala Ala Ala Ala Glu Tyr Thr
        435                 440                 445

Ser Ile Arg Arg Ser Arg Ile Met Gly Leu Ser Glu Ser Ser Ser Glu
    450                 455                 460

Thr Ser Lys Leu Ser Ser Lys Ser Ala Lys Glu Arg Arg Asn Arg Arg
465                 470                 475                 480

Lys Lys Lys Asn Gln Lys Lys Leu Ser Ser Gly Glu Glu Lys Gly Asp
                485                 490                 495

Ala Glu Lys Leu Ser Lys Ser Glu Ser Glu Asp Ser Ile Arg Arg Lys
            500                 505                 510

Ser Phe His Leu Gly Val Glu Gly His Arg Arg Ala His Glu Lys Arg
        515                 520                 525

Leu Ser Thr Pro Asn Gln Ser Pro Leu Ser Ile Arg Gly Ser Leu Phe
```

```
            530                 535                 540
Ser Ala Arg Arg Ser Ser Arg Thr Ser Leu Phe Ser Phe Lys Gly Arg
545                 550                 555                 560

Gly Arg Asp Ile Gly Ser Glu Thr Glu Phe Ala Asp Asp Glu His Ser
                565                 570                 575

Ile Phe Gly Asp Asn Glu Ser Arg Arg Gly Ser Leu Phe Val Pro His
            580                 585                 590

Arg Pro Gln Glu Arg Ser Ser Asn Ile Ser Gln Ala Ser Arg Ser
        595                 600                 605

Pro Pro Met Leu Pro Val Asn Gly Lys Met His Ser Ala Val Asp Cys
    610                 615                 620

Asn Gly Val Val Ser Leu Val Asp Gly Arg Ser Ala Leu Met Leu Pro
625                 630                 635                 640

Asn Gly Gln Leu Leu Pro Glu Gly Thr Thr Asn Gln Ile His Lys Lys
                645                 650                 655

Arg Arg Cys Ser Ser Tyr Leu Leu Ser Glu Asp Met Leu Asn Asp Pro
            660                 665                 670

Asn Leu Arg Gln Arg Ala Met Ser Arg Ala Ser Ile Leu Thr Asn Thr
        675                 680                 685

Val Glu Glu Leu Glu Glu Ser Arg Gln Lys Cys Pro Pro Trp Trp Tyr
    690                 695                 700

Arg Phe Ala His Lys Phe Leu Ile Trp Asn Cys Ser Pro Tyr Trp Ile
705                 710                 715                 720

Lys Phe Lys Lys Cys Ile Tyr Phe Ile Val Met Asp Pro Phe Val Asp
                725                 730                 735

Leu Ala Ile Thr Ile Cys Ile Val Leu Asn Thr Leu Phe Met Ala Met
            740                 745                 750

Glu His His Pro Met Thr Glu Glu Phe Lys Asn Val Leu Ala Ile Gly
        755                 760                 765

Asn Leu Val Phe Thr Gly Ile Phe Ala Ala Glu Met Val Leu Lys Leu
    770                 775                 780

Ile Ala Met Asp Pro Tyr Glu Tyr Phe Gln Val Gly Trp Asn Ile Phe
785                 790                 795                 800

Asp Ser Leu Ile Val Thr Leu Ser Leu Val Glu Leu Phe Leu Ala Asp
                805                 810                 815

Val Glu Gly Leu Ser Val Leu Arg Ser Phe Arg Leu Leu Arg Val Phe
            820                 825                 830

Lys Leu Ala Lys Ser Trp Pro Thr Leu Asn Met Leu Ile Lys Ile Ile
        835                 840                 845

Gly Asn Ser Val Gly Ala Leu Gly Asn Leu Thr Leu Val Leu Ala Ile
    850                 855                 860

Ile Val Phe Ile Phe Ala Val Val Gly Met Gln Leu Phe Gly Lys Ser
865                 870                 875                 880

Tyr Lys Glu Cys Val Cys Lys Ile Asn Asp Asp Cys Thr Leu Pro Arg
                885                 890                 895

Trp His Met Asn Asp Phe Phe His Ser Phe Leu Ile Val Phe Arg Val
            900                 905                 910

Leu Cys Gly Glu Trp Ile Glu Thr Met Trp Asp Cys Met Glu Val Ala
        915                 920                 925

Gly Gln Ala Met Cys Leu Ile Val Tyr Met Met Val Met Val Ile Gly
    930                 935                 940

Asn Leu Val Val Leu Asn Leu Phe Leu Ala Leu Leu Leu Ser Ser Phe
945                 950                 955                 960
```

```
Ser Ser Asp Asn Leu Thr Ala Ile Glu Glu Asp Pro Asp Ala Asn Asn
            965                 970                 975

Leu Gln Ile Ala Val Thr Arg Ile Lys Lys Gly Ile Asn Tyr Val Lys
            980                 985                 990

Gln Thr Leu Arg Glu Phe Ile Leu Lys Ala Phe Ser Lys Lys Pro Lys
            995                 1000                1005

Ile Ser Arg Glu Ile Arg Gln Ala Glu Asp Leu Asn Thr Lys Lys Glu
        1010                1015                1020

Asn Tyr Ile Ser Asn His Thr Leu Ala Glu Met Ser Lys Gly His Asn
1025                1030                1035                1040

Phe Leu Lys Glu Lys Asp Lys Ile Ser Gly Phe Gly Ser Ser Val Asp
            1045                1050                1055

Lys His Leu Met Glu Asp Ser Asp Gly Gln Ser Phe Ile His Asn Pro
            1060                1065                1070

Ser Leu Thr Val Thr Val Pro Ile Ala Pro Gly Glu Ser Asp Leu Glu
            1075                1080                1085

Asn Met Asn Ala Glu Glu Leu Ser Ser Asp Ser Asp Ser Glu Tyr Ser
            1090                1095                1100

Lys Val Arg Leu Asn Arg Ser Ser Ser Glu Cys Ser Thr Val Asp
1105                1110                1115                1120

Asn Pro Leu Pro Gly Glu Gly Glu Glu Ala Glu Ala Glu Pro Met Asn
            1125                1130                1135

Ser Asp Glu Pro Glu Ala Cys Phe Thr Asp Gly Cys Val Arg Arg Phe
            1140                1145                1150

Ser Cys Cys Gln Val Asn Ile Glu Ser Gly Lys Gly Lys Ile Trp Trp
            1155                1160                1165

Asn Ile Arg Lys Thr Cys Tyr Lys Ile Val Glu His Ser Trp Phe Glu
            1170                1175                1180

Ser Phe Ile Val Leu Met Ile Leu Leu Ser Ser Gly Ala Leu Ala Phe
1185                1190                1195                1200

Glu Asp Ile Tyr Ile Glu Arg Lys Lys Thr Ile Lys Ile Ile Leu Glu
            1205                1210                1215

Tyr Ala Asp Lys Ile Phe Thr Tyr Ile Phe Ile Leu Glu Met Leu Leu
            1220                1225                1230

Lys Trp Ile Ala Tyr Gly Tyr Lys Thr Tyr Phe Thr Asn Ala Trp Cys
            1235                1240                1245

Trp Leu Asp Phe Leu Ile Val Asp Val Ser Leu Val Thr Leu Val Ala
            1250                1255                1260

Asn Thr Leu Gly Tyr Ser Asp Leu Gly Pro Ile Lys Ser Leu Arg Thr
1265                1270                1275                1280

Leu Arg Ala Leu Arg Pro Leu Arg Ala Leu Ser Arg Phe Glu Gly Met
            1285                1290                1295

Arg Val Val Val Asn Ala Leu Ile Gly Ala Ile Pro Ser Ile Met Asn
            1300                1305                1310

Val Leu Leu Val Cys Leu Ile Phe Trp Leu Ile Phe Ser Ile Met Gly
            1315                1320                1325

Val Asn Leu Phe Ala Gly Lys Phe Tyr Glu Cys Ile Asn Thr Thr Asp
            1330                1335                1340

Gly Ser Arg Phe Pro Ala Ser Gln Val Pro Asn Arg Ser Glu Cys Phe
1345                1350                1355                1360

Ala Leu Met Asn Val Ser Gln Asn Val Arg Trp Lys Asn Leu Lys Val
            1365                1370                1375
```

```
Asn Phe Asp Asn Val Gly Leu Gly Tyr Leu Ser Leu Leu Gln Val Ala
            1380                1385                1390

Thr Phe Lys Gly Trp Thr Ile Ile Met Tyr Ala Ala Val Asp Ser Val
        1395                1400                1405

Asn Val Asp Lys Gln Pro Lys Tyr Glu Tyr Ser Leu Tyr Met Tyr Ile
    1410                1415                1420

Tyr Phe Val Val Phe Ile Ile Phe Gly Ser Phe Phe Thr Leu Asn Leu
1425                1430                1435                1440

Phe Ile Gly Val Ile Ile Asp Asn Phe Asn Gln Gln Lys Lys Lys Leu
                1445                1450                1455

Gly Gly Gln Asp Ile Phe Met Thr Glu Gln Lys Lys Tyr Tyr Asn
            1460                1465                1470

Ala Met Lys Lys Leu Gly Ser Lys Lys Pro Gln Lys Pro Ile Pro Arg
    1475                1480                1485

Pro Gly Asn Lys Ile Gln Gly Cys Ile Phe Asp Leu Val Thr Asn Gln
    1490                1495                1500

Ala Phe Asp Ile Ser Ile Met Val Leu Ile Cys Leu Asn Met Val Thr
1505                1510                1515                1520

Met Met Val Glu Lys Glu Gly Gln Ser Gln His Met Thr Glu Val Leu
                1525                1530                1535

Tyr Trp Ile Asn Val Val Phe Ile Ile Leu Phe Thr Gly Glu Cys Val
                1540                1545                1550

Leu Lys Leu Ile Ser Leu Arg His Tyr Tyr Phe Thr Val Gly Trp Asn
                1555                1560                1565

Ile Phe Asp Phe Val Val Val Ile Ser Ile Val Gly Met Phe Leu
    1570                1575                1580

Ala Asp Leu Ile Glu Thr Tyr Phe Val Ser Pro Thr Leu Phe Arg Val
1585                1590                1595                1600

Ile Arg Leu Ala Arg Ile Gly Arg Ile Leu Arg Leu Val Lys Gly Ala
                1605                1610                1615

Lys Gly Ile Arg Thr Leu Leu Phe Ala Leu Met Met Ser Leu Pro Ala
        1620                1625                1630

Leu Phe Asn Ile Gly Leu Leu Leu Phe Leu Val Met Phe Ile Tyr Ala
        1635                1640                1645

Ile Phe Gly Met Ser Asn Phe Ala Tyr Val Lys Lys Glu Asp Gly Ile
    1650                1655                1660

Asn Asp Met Phe Asn Phe Glu Thr Phe Gly Asn Ser Met Ile Cys Leu
1665                1670                1675                1680

Phe Gln Ile Thr Thr Ser Ala Gly Trp Asp Gly Leu Leu Ala Pro Ile
            1685                1690                1695

Leu Asn Ser Lys Pro Pro Asp Cys Asp Pro Lys Lys Val His Pro Gly
        1700                1705                1710

Ser Ser Val Glu Gly Asp Cys Gly Asn Pro Ser Val Gly Ile Phe Tyr
        1715                1720                1725

Phe Val Ser Tyr Ile Ile Ile Ser Phe Leu Val Val Val Asn Met Tyr
    1730                1735                1740

Ile Ala Val Ile Leu Glu Asn Phe Ser Val Ala Thr Glu Glu Ser Thr
1745                1750                1755                1760

Glu Pro Leu Ser Glu Asp Asp Phe Glu Met Phe Tyr Glu Val Trp Glu
            1765                1770                1775

Lys Phe Asp Pro Asp Ala Thr Gln Phe Ile Glu Phe Ser Lys Leu Ser
    1780                1785                1790

Asp Phe Ala Ala Ala Leu Asp Pro Pro Leu Leu Ile Ala Lys Pro Asn
```

-continued

```
                 1795                1800                1805
Lys Val Gln Leu Ile Ala Met Asp Leu Pro Met Val Ser Gly Asp Arg
         1810                1815                1820
Ile His Cys Leu Asp Ile Leu Phe Ala Phe Thr Lys Arg Val Leu Gly
1825                1830                1835                1840
Glu Ser Gly Glu Met Asp Ser Leu Arg Ser Gln Met Glu Glu Arg Phe
             1845                1850                1855
Met Ser Ala Asn Pro Ser Lys Val Ser Tyr Glu Pro Ile Thr Thr Thr
         1860                1865                1870
Leu Lys Arg Lys Gln Glu Asp Val Ser Ala Thr Val Ile Gln Arg Ala
     1875                1880                1885
Tyr Arg Arg Tyr Arg Leu Arg Gln Asn Val Lys Asn Ile Ser Ser Ile
     1890                1895                1900
Tyr Ile Lys Asp Gly Asp Arg Asp Asp Leu Leu Asn Lys Lys Asp
1905                1910                1915                1920
Met Ala Phe Asp Asn Val Asn Glu Asn Ser Ser Pro Glu Lys Thr Asp
             1925                1930                1935
Ala Thr Ser Ser Thr Thr Ser Pro Pro Ser Tyr Asp Ser Val Thr Lys
         1940                1945                1950
Pro Asp Lys Glu Lys Tyr Glu Gln Asp Arg Thr Glu Lys Glu Asp Lys
     1955                1960                1965
Gly Lys Asp Ser Lys Glu Ser Lys Lys
     1970                1975

<210> SEQ ID NO 15
<211> LENGTH: 5874
<212> TYPE: DNA
<213> ORGANISM: Homo sapiens

<400> SEQUENCE: 15
atggaattcc ccattggatc cctcgaaact aacaacttcc gtcgctttac tccggagtca      60
ctggtggaga tagaaagca aattgctgcc aagcagggaa caaagaaagc cagagagaag     120 catgggagc agaaggacca agaagagaag cctcggcccc agctggactt gaaagcctgc     180
aaccagctgc ccaagttcta tggtgagctc ccagcagaac tgatcgggga gcccctggag     240
gatctagatc cgttctacag cacacaccgg acatttatgg tgctgaacaa agggaggacc     300
atttcccggt ttagtgccac tcgggccctg tggctattca gtcctttcaa cctgatcaga     360
agaacggcca tcaaagtgtc tgtccactcg tggttcagtt tatttattac ggtcactatt     420
ttggttaatt gtgtgtgcat gacccgaact gaccttccag agaaaattga atatgtcttc     480
actgtcattt acaccctttga agccttgata aagatactgg caagaggatt ttgtctaaat     540
gagttcacgt acctgagaga tccttggaac tggctggatt ttagcgtcat taccctggca     600
tatgttggca cagcaataga tctccgtggg atctcaggcc tgcggacatt cagagttctt     660
agagcattaa aaacagtttc tgtgatccca ggcctgaagg tcattgtggg ggccctgatt     720
cactcagtga agaaactggc tgatgtgacc atcctcacca tcttctgcct aagtgttttt     780
gccttggtgg ggctgcaact cttcaagggc aacctcaaaa ataaatgtgt caagaatgac     840
atggctgtca atgagacaac caactactca tctcacagaa accagatat ctacataaat     900 aagcgaggca cttctgaccc cttactgtgt ggcaatggat ctgactcagg ccactgccct     960
gatggttata tctgccttaa aacttctgac aacccggatt ttaactacac cagctttgat    1020
tcctttgctt gggctttcct ctcactgttc cgcctcatga cacaggattc ctgggaacgc    1080
```

-continued

| | | | |
|---|---|---|---|
| ctctaccagc agaccctgag gacttctggg aaaatctata tgatctttt tgtgctcgta | 1140 |
| atcttcctgg gatctttcta cctggtcaac ttgatcttgg ctgtagtcac catggcgtat | 1200 |
| gaggagcaga accaggcaac cactgatgaa attgaagcaa aggagaagaa gttccaggag | 1260 |
| gccctcgaga tgctccggaa ggagcaggag gtgctagcag cactagggat tgacacaacc | 1320 |
| tctctccact cccacaatgg atcaccttta acctccaaaa atgccagtga gagaaggcat | 1380 |
| agaataaagc caagagtgtc agagggctcc acagaagaca acaaatcacc ccgctctgat | 1440 |
| ccttacaacc agcgcaggat gtcttttcta ggcctcgcct ctggaaaacg ccgggctagt | 1500 |
| catggcagtg tgttccattt ccggtcccct ggccgagata tctcactccc tgagggagtc | 1560 |
| acagatgatg gagtctttcc tggagaccac gaaagccatc ggggctctct gctgctgggt | 1620 |
| gggggtgctg gccagcaagg ccccctccct agaagccctc ttcctcaacc cagcaaccct | 1680 |
| gactccaggc atggagaaga tgaacaccaa ccgccgccca ctagtgagct tgcccctgga | 1740 |
| gctgtcgatg tctcggcatt cgatgcagga caaaagaaga cttctcttgtc agcagaatac | 1800 |
| ttagatgaac ctttccgggc ccaaagggca atgagtgttg tcagtatcat aacctccgtc | 1860 |
| cttgaggaac tcgaggagtc tgaacagaag tgcccaccct gcttgaccag cttgtctcag | 1920 |
| aagtatctga tctgggattg ctgccccatg tgggtgaagc tcaagacaat tctctttggg | 1980 |
| cttgtgacgg atccctttgc agagctcacc atcaccttgt gcatcgtggt gaacaccatc | 2040 |
| ttcatggcca tggagcacca tggcatgagc cctaccttcg aagccatgct ccagataggc | 2100 |
| aacatcgtct ttaccatatt ttttactgct gaaatggtct tcaaaatcat tgccttcgac | 2160 |
| ccatactatt atttccagaa gaagtggaat atctttgact gcatcatcgt cactgtgagt | 2220 |
| ctgctagagc tgggcgtggc caagaaggga agcctgtctg tgctgcggag cttccgcttg | 2280 |
| ctgcgcgtat tcaagctggc caaatcctgg cccaccttaa acacactcat caagatcatc | 2340 |
| ggaaactcag tgggggcact ggggaacctc accatcatcc tggccatcat tgtcttgtc | 2400 |
| tttgctctgg ttggcaagca gctcctaggg gaaaactacc gtaacaaccg aaaaaatatc | 2460 |
| tccgcgcccc atgaagactg gccccgctgg cacatgcacg acttcttcca ctcttcctc | 2520 |
| attgtcttcc gtatcctctg tggagagtgg attgagaaca tgtgggcctg catggaagtt | 2580 |
| ggccaaaaat ccatatgcct catccttttc ttgacggtga tggtgctagg gaacctggtg | 2640 |
| gtgcttaacc tgttcatcgc cctgctattg aactctttca gtgctgacaa cctcacagcc | 2700 |
| ccggaggacg atgggaggt gaacaacctg caggtggccc tggcacggat ccaggtcttt | 2760 |
| ggccatcgta ccaaacaggc tctttgcagc ttcttcagca ggtcctgccc attcccccag | 2820 |
| cccaaggcag agcctgagct ggtggtgaaa ctcccactct ccagctccaa ggctgagaac | 2880 |
| cacattgctg ccaacactgc caggggagc tctggagggc tccaagctcc cagaggcccc | 2940 |
| agggatgagc acagtgactt catcgctaat ccgactgtgt gggtctctgt gcccattgct | 3000 |
| gagggtgaat ctgatcttga tgacttggag gatgatggtg gggaagatgc tcagagcttc | 3060 |
| cagcaggaag tgatccccaa aggacagcag gagcagctgc agcaagtcga gaggtgtggg | 3120 |
| gaccacctga cacccaggag cccaggcact ggaacatctt ctgaggacct ggctccatcc | 3180 |
| ctgggtgaga cgtggaaaga tgagtctgtt cctcaggccc ctgctgaggg agtggacgac | 3240 |
| acaagctcct ctgagggcag cacggtggac tgcctagatc ctgaggaaat cctgaggaag | 3300 |
| atccctgagc tggcagatga cctggaagaa ccagatgact gcttcacaga aggatgcatt | 3360 |
| cgccactgtc cctgctgcaa actggatacc accaagagtc catgggatgt gggctggcag | 3420 |
| gtgcgcaaga cttgctaccg tatcgtggag cacagctggt ttgagagctt catcatcttc | 3480 |

```
atgatcctgc tcagcagtgg atctctggcc tttgaagact attacctgga ccagaagccc    3540
acggtgaaag ctttgctgga gtacactgac agggtcttca cctttatctt tgtgttcgag    3600
atgctgctta agtgggtggc ctatggcttc aaaaagtact tcaccaatgc ctggtgctgg    3660
ctggacttcc tcattgtgaa tatctcactg ataagtctca cagcgaagat tctggaatat    3720
tctgaagtgg ctcccatcaa agcccttcga acccttcgcg ctctgcggcc actgcgggct    3780 cttctctcgat ttgaaggcat gcgggtggtg gtggatgccc tggtgggcgc catcccatcc    3840
atcatgaatg tcctcctcgt ctgcctcatc ttctggctca tcttcagcat catgggtgtg    3900
aacctcttcg cagggaagtt ttggaggtgc atcaactata ccgatggaga gttttccctt    3960
gtacctttgt cgattgtgaa taacaagtct gactgcaaga ttcaaaactc cactggcagc    4020
ttcttctggg tcaatgtgaa agtcaacttt gataatgttg caatgggtta ccttgcactt    4080
ctgcaggtgg aacctttaa aggctggatg gacattatgt atgcagctgt tgattcccgg    4140
gaggtcaaca tgcaacccaa gtgggaggac aacgtgtaca tgtatttgta ctttgtcatc    4200
ttcatcattt ttggaggctt cttcacactg aatctctttg ttggggtcat aattgacaac    4260
ttcaatcaac agaaaaaaaa gttaggggc caggacatct tcatgacaga ggagcagaag    4320
aaatactaca atgccatgaa gaagttgggc tccaagaagc cccagaagcc catcccacgg    4380
cccctgaaca agttccaggg ttttgtcttt gacatcgtga ccagacaagc ttttgacatc    4440
accatcatgg tcctcatctg cctcaacatg atcaccatga tggtggagac tgatgaccaa    4500
agtgaagaaa agacgaaaat tctgggcaaa atcaaccagt tctttgtggc cgtcttcaca    4560
ggcgaatgtg tcatgaagat gttcgctttg aggcagtact acttcacaaa tggctggaat    4620
gtgtttgact tcattgtggt ggttctctcc attgcgagcc tgattttttc tgcaattctt    4680
aagtcacttc aaagttactt ctccccaacg ctcttcagag tcatccgcct ggcccgaatt    4740
ggccgcatcc tcagactgat ccgagcggcc aaggggatcc gcacactgct ctttgccctc    4800
atgatgtccc tgcctgccct cttcaacatc gggctgttgc tattccttgt catgttcatc    4860
tactccatct tcggtatgtc cagctttccc catgtgaggt gggaggctgg catcgacgac    4920
atgttcaact tccagaccct tgccaacagc atgctgtgcc tcttccagat taccacgtcg    4980
gccggctggg atgccctcct cagccccatc ctcaacacag ggcccccta ctgtgacccc    5040 aatctgccca acagcaatgg caccagaggg gactgtggga gcccagccgt aggcatcatc    5100
ttcttcacca cctacatcat catctccttc ctcatcgtgg tcaacatgta cattgcagtg    5160
attctggaga acttcaatgt ggccacggag agagcactg agcctctgag tgaggacgac    5220
tttgacatgt tctatgagac ctgggagaag tttgacccag aggccactca gtttattacc    5280
ttttctgctc tctcggactt tgcagacact ctctctggtc ccctgagaat cccaaaaccc    5340
aatcgaaata tactgatcca gatggaccctg ccttttggtcc ctggagataa gatccactgc    5400
ttggacatcc ttttttgcttt caccaagaat gtcctaggag aatccgggga gttggattct    5460
ctgaaggcaa atatggagga gaagtttatg gcaactaatc tttcaaaatc atcctatgaa    5520
ccaatagcaa ccactctccg atggaagcaa gaagacattt cagccactgt cattcaaaag    5580
gcctatcgga gctatgtgct gcaccgctcc atggcactct ctaacacccc atgtgtgccc    5640
agagctgagg aggaggctgc atcactccca gatgaaggtt ttgttgcatt cacagcaaat    5700
gaaaattgtg tactcccaga caaatctgaa actgcttctg ccacatcatt cccaccgtcc    5760
tatgagagtg tcactagagg ccttagtgat agagtcaaca tgaggacatc tagctcaata    5820
```

```
caaaatgaag atgaagccac cagtatggag ctgattgccc ctgggcccta gtga        5874
```

<210> SEQ ID NO 16
<211> LENGTH: 1956
<212> TYPE: PRT
<213> ORGANISM: Homo sapiens

<400> SEQUENCE: 16

| Met | Glu | Phe | Pro | Ile | Gly | Ser | Leu | Glu | Thr | Asn | Asn | Phe | Arg | Arg | Phe |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Thr | Pro | Glu | Ser | Leu | Val | Glu | Ile | Glu | Lys | Gln | Ile | Ala | Ala | Lys | Gln |
|     |     |     | 20  |     |     |     |     | 25  |     |     |     |     | 30  |     |     |

| Gly | Thr | Lys | Lys | Ala | Arg | Glu | Lys | His | Arg | Glu | Gln | Lys | Asp | Gln | Glu |
|     |     |     | 35  |     |     |     |     | 40  |     |     |     |     | 45  |     |     |

| Glu | Lys | Pro | Arg | Pro | Gln | Leu | Asp | Leu | Lys | Ala | Cys | Asn | Gln | Leu | Pro |
|     | 50  |     |     |     |     | 55  |     |     |     |     | 60  |     |     |     |     |

| Lys | Phe | Tyr | Gly | Glu | Leu | Pro | Ala | Glu | Leu | Ile | Gly | Glu | Pro | Leu | Glu |
| 65  |     |     |     |     | 70  |     |     |     |     | 75  |     |     |     |     | 80  |

| Asp | Leu | Asp | Pro | Phe | Tyr | Ser | Thr | His | Arg | Thr | Phe | Met | Val | Leu | Asn |
|     |     |     |     | 85  |     |     |     |     | 90  |     |     |     |     | 95  |     |

| Lys | Gly | Arg | Thr | Ile | Ser | Arg | Phe | Ser | Ala | Thr | Arg | Ala | Leu | Trp | Leu |
|     |     |     | 100 |     |     |     |     | 105 |     |     |     |     | 110 |     |     |

| Phe | Ser | Pro | Phe | Asn | Leu | Ile | Arg | Arg | Thr | Ala | Ile | Lys | Val | Ser | Val |
|     |     |     | 115 |     |     |     |     | 120 |     |     |     |     | 125 |     |     |

| His | Ser | Trp | Phe | Ser | Leu | Phe | Ile | Thr | Val | Thr | Ile | Leu | Val | Asn | Cys |
|     |     |     | 130 |     |     |     |     | 135 |     |     |     |     | 140 |     |     |

| Val | Cys | Met | Thr | Arg | Thr | Asp | Leu | Pro | Glu | Lys | Ile | Glu | Tyr | Val | Phe |
| 145 |     |     |     |     | 150 |     |     |     |     | 155 |     |     |     |     | 160 |

| Thr | Val | Ile | Tyr | Thr | Phe | Glu | Ala | Leu | Ile | Lys | Ile | Leu | Ala | Arg | Gly |
|     |     |     |     | 165 |     |     |     |     | 170 |     |     |     |     | 175 |     |

| Phe | Cys | Leu | Asn | Glu | Phe | Thr | Tyr | Leu | Arg | Asp | Pro | Trp | Asn | Trp | Leu |
|     |     |     | 180 |     |     |     |     | 185 |     |     |     |     | 190 |     |     |

| Asp | Phe | Ser | Val | Ile | Thr | Leu | Ala | Tyr | Val | Gly | Thr | Ala | Ile | Asp | Leu |
|     |     |     | 195 |     |     |     |     | 200 |     |     |     |     | 205 |     |     |

| Arg | Gly | Ile | Ser | Gly | Leu | Arg | Thr | Phe | Arg | Val | Leu | Arg | Ala | Leu | Lys |
|     | 210 |     |     |     |     | 215 |     |     |     |     | 220 |     |     |     |     |

| Thr | Val | Ser | Val | Ile | Pro | Gly | Leu | Lys | Val | Ile | Val | Gly | Ala | Leu | Ile |
| 225 |     |     |     |     | 230 |     |     |     |     | 235 |     |     |     |     | 240 |

| His | Ser | Val | Lys | Lys | Leu | Ala | Asp | Val | Thr | Ile | Leu | Thr | Ile | Phe | Cys |
|     |     |     |     | 245 |     |     |     |     | 250 |     |     |     |     | 255 |     |

| Leu | Ser | Val | Phe | Ala | Leu | Val | Gly | Leu | Gln | Leu | Phe | Lys | Gly | Asn | Leu |
|     |     |     | 260 |     |     |     |     | 265 |     |     |     |     | 270 |     |     |

| Lys | Asn | Lys | Cys | Val | Lys | Asn | Asp | Met | Ala | Val | Asn | Glu | Thr | Thr | Asn |
|     |     | 275 |     |     |     |     | 280 |     |     |     |     | 285 |     |     |     |

| Tyr | Ser | Ser | His | Arg | Lys | Pro | Asp | Ile | Tyr | Ile | Asn | Lys | Arg | Gly | Thr |
|     |     | 290 |     |     |     |     | 295 |     |     |     |     | 300 |     |     |     |

| Ser | Asp | Pro | Leu | Leu | Cys | Gly | Asn | Gly | Ser | Asp | Ser | Gly | His | Cys | Pro |
| 305 |     |     |     |     | 310 |     |     |     |     | 315 |     |     |     |     | 320 |

| Asp | Gly | Tyr | Ile | Cys | Leu | Lys | Thr | Ser | Asp | Asn | Pro | Asp | Phe | Asn | Tyr |
|     |     |     |     | 325 |     |     |     |     | 330 |     |     |     |     | 335 |     |

| Thr | Ser | Phe | Asp | Ser | Phe | Ala | Trp | Ala | Phe | Leu | Ser | Leu | Phe | Arg | Leu |
|     |     |     | 340 |     |     |     |     | 345 |     |     |     |     | 350 |     |     |

| Met | Thr | Gln | Asp | Ser | Trp | Glu | Arg | Leu | Tyr | Gln | Gln | Thr | Leu | Arg | Thr |
|     |     |     | 355 |     |     |     |     | 360 |     |     |     |     | 365 |     |     |

```
Ser Gly Lys Ile Tyr Met Ile Phe Phe Val Leu Val Ile Phe Leu Gly
    370                 375                 380

Ser Phe Tyr Leu Val Asn Leu Ile Leu Ala Val Val Thr Met Ala Tyr
385                 390                 395                 400

Glu Glu Gln Asn Gln Ala Thr Thr Asp Glu Ile Glu Ala Lys Glu Lys
                405                 410                 415

Lys Phe Gln Glu Ala Leu Glu Met Leu Arg Lys Glu Gln Glu Val Leu
            420                 425                 430

Ala Ala Leu Gly Ile Asp Thr Thr Ser Leu His Ser His Asn Gly Ser
        435                 440                 445

Pro Leu Thr Ser Lys Asn Ala Ser Glu Arg Arg His Arg Ile Lys Pro
    450                 455                 460

Arg Val Ser Glu Gly Ser Thr Glu Asp Asn Lys Ser Pro Arg Ser Asp
465                 470                 475                 480

Pro Tyr Asn Gln Arg Arg Met Ser Phe Leu Gly Leu Ala Ser Gly Lys
                485                 490                 495

Arg Arg Ala Ser His Gly Ser Val Phe His Phe Arg Ser Pro Gly Arg
            500                 505                 510

Asp Ile Ser Leu Pro Glu Gly Val Thr Asp Asp Gly Val Phe Pro Gly
        515                 520                 525

Asp His Glu Ser His Arg Gly Ser Leu Leu Gly Gly Gly Ala Gly
    530                 535                 540

Gln Gln Gly Pro Leu Pro Arg Ser Pro Leu Pro Gln Pro Ser Asn Pro
545                 550                 555                 560

Asp Ser Arg His Gly Glu Asp Glu His Gln Pro Pro Thr Ser Glu
                565                 570                 575

Leu Ala Pro Gly Ala Val Asp Val Ser Ala Phe Asp Ala Gly Gln Lys
            580                 585                 590

Lys Thr Phe Leu Ser Ala Glu Tyr Leu Asp Glu Pro Phe Arg Ala Gln
        595                 600                 605

Arg Ala Met Ser Val Val Ser Ile Ile Thr Ser Val Leu Glu Glu Leu
    610                 615                 620

Glu Glu Ser Glu Gln Lys Cys Pro Pro Cys Leu Thr Ser Leu Ser Gln
625                 630                 635                 640

Lys Tyr Leu Ile Trp Asp Cys Cys Pro Met Trp Val Lys Leu Lys Thr
                645                 650                 655

Ile Leu Phe Gly Leu Val Thr Asp Pro Phe Ala Glu Leu Thr Ile Thr
            660                 665                 670

Leu Cys Ile Val Val Asn Thr Ile Phe Met Ala Met Glu His His Gly
        675                 680                 685

Met Ser Pro Thr Phe Glu Ala Met Leu Gln Ile Gly Asn Ile Val Phe
    690                 695                 700

Thr Ile Phe Phe Thr Ala Glu Met Val Phe Lys Ile Ile Ala Phe Asp
705                 710                 715                 720

Pro Tyr Tyr Tyr Phe Gln Lys Lys Trp Asn Ile Phe Asp Cys Ile Ile
                725                 730                 735

Val Thr Val Ser Leu Leu Glu Leu Gly Val Ala Lys Lys Gly Ser Leu
            740                 745                 750

Ser Val Leu Arg Ser Phe Arg Leu Leu Arg Val Phe Lys Leu Ala Lys
        755                 760                 765

Ser Trp Pro Thr Leu Asn Thr Leu Ile Lys Ile Ile Gly Asn Ser Val
    770                 775                 780

Gly Ala Leu Gly Asn Leu Thr Ile Ile Leu Ala Ile Ile Val Phe Val
```

```
            785                 790                 795                 800
      Phe Ala Leu Val Gly Lys Gln Leu Leu Gly Glu Asn Tyr Arg Asn Asn
                      805                 810                 815
      Arg Lys Asn Ile Ser Ala Pro His Glu Asp Trp Pro Arg Trp His Met
                      820                 825                 830
      His Asp Phe Phe His Ser Phe Leu Ile Val Phe Arg Ile Leu Cys Gly
                      835                 840                 845
      Glu Trp Ile Glu Asn Met Trp Ala Cys Met Glu Val Gly Gln Lys Ser
                      850                 855                 860
      Ile Cys Leu Ile Leu Phe Leu Thr Val Met Val Leu Gly Asn Leu Val
      865                 870                 875                 880
      Val Leu Asn Leu Phe Ile Ala Leu Leu Leu Asn Ser Phe Ser Ala Asp
                      885                 890                 895
      Asn Leu Thr Ala Pro Glu Asp Asp Gly Glu Val Asn Asn Leu Gln Val
                      900                 905                 910
      Ala Leu Ala Arg Ile Gln Val Phe Gly His Arg Thr Lys Gln Ala Leu
                      915                 920                 925
      Cys Ser Phe Phe Ser Arg Ser Cys Pro Phe Pro Gln Pro Lys Ala Glu
                      930                 935                 940
      Pro Glu Leu Val Val Lys Leu Pro Leu Ser Ser Ser Lys Ala Glu Asn
      945                 950                 955                 960
      His Ile Ala Ala Asn Thr Ala Arg Gly Ser Ser Gly Gly Leu Gln Ala
                      965                 970                 975
      Pro Arg Gly Pro Arg Asp Glu His Ser Asp Phe Ile Ala Asn Pro Thr
                      980                 985                 990
      Val Trp Val Ser Val Pro Ile Ala Glu Gly Glu Ser Asp Leu Asp Asp
                      995                 1000                1005
      Leu Glu Asp Asp Gly Gly Glu Asp Ala Gln Ser Phe Gln Gln Glu Val
                      1010                1015                1020
      Ile Pro Lys Gly Gln Gln Glu Gln Leu Gln Gln Val Glu Arg Cys Gly
      1025                1030                1035                1040
      Asp His Leu Thr Pro Arg Ser Pro Gly Thr Gly Thr Ser Ser Glu Asp
                      1045                1050                1055
      Leu Ala Pro Ser Leu Gly Glu Thr Trp Lys Asp Glu Ser Val Pro Gln
                      1060                1065                1070
      Ala Pro Ala Glu Gly Val Asp Asp Thr Ser Ser Ser Glu Gly Ser Thr
                      1075                1080                1085
      Val Asp Cys Leu Asp Pro Glu Glu Ile Leu Arg Lys Ile Pro Glu Leu
                      1090                1095                1100
      Ala Asp Asp Leu Glu Glu Pro Asp Asp Cys Phe Thr Glu Gly Cys Ile
      1105                1110                1115                1120
      Arg His Cys Pro Cys Cys Lys Leu Asp Thr Thr Lys Ser Pro Trp Asp
                      1125                1130                1135
      Val Gly Trp Gln Val Arg Lys Thr Cys Tyr Arg Ile Val Glu His Ser
                      1140                1145                1150
      Trp Phe Glu Ser Phe Ile Ile Phe Met Ile Leu Leu Ser Ser Gly Ser
                      1155                1160                1165
      Leu Ala Phe Glu Asp Tyr Tyr Leu Asp Gln Lys Pro Thr Val Lys Ala
                      1170                1175                1180
      Leu Leu Glu Tyr Thr Asp Arg Val Phe Thr Phe Ile Phe Val Phe Glu
      1185                1190                1195                1200
      Met Leu Leu Lys Trp Val Ala Tyr Gly Phe Lys Lys Tyr Phe Thr Asn
                      1205                1210                1215
```

```
Ala Trp Cys Trp Leu Asp Phe Leu Ile Val Asn Ile Ser Leu Ile Ser
            1220                1225                1230

Leu Thr Ala Lys Ile Leu Glu Tyr Ser Glu Val Ala Pro Ile Lys Ala
        1235                1240                1245

Leu Arg Thr Leu Arg Ala Leu Arg Pro Leu Arg Ala Leu Ser Arg Phe
    1250                1255                1260

Glu Gly Met Arg Val Val Asp Ala Leu Val Gly Ala Ile Pro Ser
1265                1270                1275                1280

Ile Met Asn Val Leu Leu Val Cys Leu Ile Phe Trp Leu Ile Phe Ser
            1285                1290                1295

Ile Met Gly Val Asn Leu Phe Ala Gly Lys Phe Trp Arg Cys Ile Asn
        1300                1305                1310

Tyr Thr Asp Gly Glu Phe Ser Leu Val Pro Leu Ser Ile Val Asn Asn
    1315                1320                1325

Lys Ser Asp Cys Lys Ile Gln Asn Ser Thr Gly Ser Phe Phe Trp Val
1330                1335                1340

Asn Val Lys Val Asn Phe Asp Asn Val Ala Met Gly Tyr Leu Ala Leu
1345                1350                1355                1360

Leu Gln Val Ala Thr Phe Lys Gly Trp Met Asp Ile Met Tyr Ala Ala
            1365                1370                1375

Val Asp Ser Arg Glu Val Asn Met Gln Pro Lys Trp Glu Asp Asn Val
        1380                1385                1390

Tyr Met Tyr Leu Tyr Phe Val Ile Phe Ile Ile Phe Gly Gly Phe Phe
    1395                1400                1405

Thr Leu Asn Leu Phe Val Gly Val Ile Ile Asp Asn Phe Asn Gln Gln
    1410                1415                1420

Lys Lys Lys Leu Gly Gly Gln Asp Ile Phe Met Thr Glu Glu Gln Lys
1425                1430                1435                1440

Lys Tyr Tyr Asn Ala Met Lys Lys Leu Gly Ser Lys Lys Pro Gln Lys
            1445                1450                1455

Pro Ile Pro Arg Pro Leu Asn Lys Phe Gln Gly Phe Val Phe Asp Ile
        1460                1465                1470

Val Thr Arg Gln Ala Phe Asp Ile Thr Ile Met Val Leu Ile Cys Leu
    1475                1480                1485

Asn Met Ile Thr Met Met Val Glu Thr Asp Asp Gln Ser Glu Glu Lys
        1490                1495                1500

Thr Lys Ile Leu Gly Lys Ile Asn Gln Phe Phe Val Ala Val Phe Thr
1505                1510                1515                1520

Gly Glu Cys Val Met Lys Met Phe Ala Leu Arg Gln Tyr Tyr Phe Thr
            1525                1530                1535

Asn Gly Trp Asn Val Phe Asp Phe Ile Val Val Leu Ser Ile Ala
        1540                1545                1550

Ser Leu Ile Phe Ser Ala Ile Leu Lys Ser Leu Gln Ser Tyr Phe Ser
    1555                1560                1565

Pro Thr Leu Phe Arg Val Ile Arg Leu Ala Arg Ile Gly Arg Ile Leu
    1570                1575                1580

Arg Leu Ile Arg Ala Ala Lys Gly Ile Arg Thr Leu Leu Phe Ala Leu
1585                1590                1595                1600

Met Met Ser Leu Pro Ala Leu Phe Asn Ile Gly Leu Leu Leu Phe Leu
            1605                1610                1615

Val Met Phe Ile Tyr Ser Ile Phe Gly Met Ser Ser Phe Pro His Val
        1620                1625                1630
```

```
Arg Trp Glu Ala Gly Ile Asp Asp Met Phe Asn Phe Gln Thr Phe Ala
        1635                1640                1645

Asn Ser Met Leu Cys Leu Phe Gln Ile Thr Thr Ser Ala Gly Trp Asp
    1650                1655                1660

Gly Leu Leu Ser Pro Ile Leu Asn Thr Gly Pro Pro Tyr Cys Asp Pro
1665                1670                1675                1680

Asn Leu Pro Asn Ser Asn Gly Thr Arg Gly Asp Cys Gly Ser Pro Ala
            1685                1690                1695

Val Gly Ile Ile Phe Phe Thr Thr Tyr Ile Ile Ile Ser Phe Leu Ile
        1700                1705                1710

Val Val Asn Met Tyr Ile Ala Val Ile Leu Glu Asn Phe Asn Val Ala
        1715                1720                1725

Thr Glu Glu Ser Thr Glu Pro Leu Ser Glu Asp Asp Phe Asp Met Phe
    1730                1735                1740

Tyr Glu Thr Trp Glu Lys Phe Asp Pro Glu Ala Thr Gln Phe Ile Thr
1745                1750                1755                1760

Phe Ser Ala Leu Ser Asp Phe Ala Asp Thr Leu Ser Gly Pro Leu Arg
            1765                1770                1775

Ile Pro Lys Pro Asn Arg Asn Ile Leu Ile Gln Met Asp Leu Pro Leu
        1780                1785                1790

Val Pro Gly Asp Lys Ile His Cys Leu Asp Ile Leu Phe Ala Phe Thr
    1795                1800                1805

Lys Asn Val Leu Gly Glu Ser Gly Glu Leu Asp Ser Leu Lys Ala Asn
1810                1815                1820

Met Glu Glu Lys Phe Met Ala Thr Asn Leu Ser Lys Ser Ser Tyr Glu
1825                1830                1835                1840

Pro Ile Ala Thr Thr Leu Arg Trp Lys Gln Glu Asp Ile Ser Ala Thr
            1845                1850                1855

Val Ile Gln Lys Ala Tyr Arg Ser Tyr Val Leu His Arg Ser Met Ala
        1860                1865                1870

Leu Ser Asn Thr Pro Cys Val Pro Arg Ala Glu Glu Glu Ala Ala Ser
        1875                1880                1885

Leu Pro Asp Glu Gly Phe Val Ala Phe Thr Ala Asn Glu Asn Cys Val
    1890                1895                1900

Leu Pro Asp Lys Ser Glu Thr Ala Ser Ala Thr Ser Phe Pro Pro Ser
1905                1910                1915                1920

Tyr Glu Ser Val Thr Arg Gly Leu Ser Asp Arg Val Asn Met Arg Thr
            1925                1930                1935

Ser Ser Ser Ile Gln Asn Glu Asp Glu Ala Thr Ser Met Glu Leu Ile
        1940                1945                1950

Ala Pro Gly Pro
        1955

<210> SEQ ID NO 17
<211> LENGTH: 5376
<212> TYPE: DNA
<213> ORGANISM: Homo sapiens

<400> SEQUENCE: 17
atggatgaca gatgctaccc agtaatcttt ccagatgagc ggaatttccg ccccttcact      60
tccgactctc tggctgcaat tgagaagcgg attgccatcc aaaaggagaa aaagaagtct     120
aaagaccaga caggagaagt accccagcct cggcctcagc ttgacctaaa ggcctccagg     180
aagttgccca agctctatgg cgacattcct cgtgagctca taggaaagcc tctggaagac     240
```

```
ttggacccat tctaccgaaa tcataagaca tttatggtgt taaacagaaa gaggacaatc    300
taccgcttca gtgccaagca tgccttgttc attttggggc ctttcaattc aatcagaagt    360
ttagccatta gagtctcagt ccattcattg ttcagcatgt tcattatcgg caccgttatc    420
atcaactgcg tgttcatggc tacagggcct gctaaaaaca gcaacagtaa caatactgac    480
attgcagagt gtgtcttcac tgggatttat attttttgaag ctttgattaa atatattggca   540 agaggtttca ttctggatga gttttctttc cttcgagatc catggaactg gctggactcc    600
attgtcattg gaatagcgat tgtgtcatat attccaggaa tcaccatcaa actattgccc    660
ctgcgtacct tccgtgtgtt cagagctttg aaagcaattt cagtagtttc acgtctgaag    720
gtcatcgtgg gggccttgct acgctctgtg aagaagctgg tcaacgtgat tatcctcacc    780
ttcttttgcc tcagcatctt tgccctggta ggtcagcagc tcttcatggg aagtctgaac    840
ctgaaatgca tctcgaggga ctgtaaaaat atcagtaacc cggaagctta tgaccattgc    900
tttgaaaaga aagaaaattc acctgaattc aaaatgtgtg gcatctggat gggtaacagt    960
gcctgttcca tacaatatga atgtaagcac accaaaatta atcctgacta taattatacg   1020
aattttgaca actttggctg gtcttttctt gccatgttcc ggctgatgac ccaagattcc   1080
tgggagaagc tttatcaaca gaccctgcgt actactgggc tctactcagt cttcttcttc   1140
attgtggtca ttttcctggg ctccttctac ctgattaact aaccctggcc tgttgttacc   1200
atggcatatg aggagcagaa caagaatgta gctgcagaga tagaggccaa ggaaaagatg   1260
tttcaggaag cccagcagct gttaaaggag gaaaaggagg ctctggttgc catgggaatt   1320
gacagaagtt cacttacttc ccttgaaaca tcatattta ccccaaaaaa gagaaagctc   1380
tttggtaata agaaaaggaa gtccttcttt ttgagagagt ctgggaaaga ccagcctcct   1440
gggtcagatt ctgatgaaga ttgccaaaaa aagccacagc tcctagagca aaccaaacga   1500
ctgtcccaga atcatcact ggaccacttt gatgagcatg gagatcctct ccaaaggcag   1560
agagcactga gtgccgtcag catcctcacc atcaccatga aggaacaaga aaaatcacaa   1620
gagccttgtc tcccttgcgg agaaaacctg gcatccaagt acctcgtgtg gaactgttgc   1680
ccccagtggc tgtgcgttaa gaaggtcctg agaactgtga tgactgaccc gtttactgag   1740
ctggccatca ccatctgcat catcatcaac actgtcttct tggccatgga gcatcacaag   1800
atggaggcca gttttgagaa gatgttgaat atagggaatt tggttttcac tagcattttt   1860
atagcagaaa tgtgcctaaa aatcattgcg ctcgatccct accactactt tcgccgaggc   1920
tggaacattt ttgacagcat tgttgctctt ctgagttttg cagatgtaat gaactgtgta   1980
cttcaaaaga gaagctggcc attcttgcgt tccttcaggg tgctcagggt cttcaagtta   2040
gccaaatcct ggccaacttt gaacacacta attaagataa tcggcaactc tgtcggagcc   2100
cttggaaacc tgactgtggt cctggtcatt gtgatcttta ttttctcagt agttggcatg   2160 cagcttttg gccgtagctt caattcccaa aagagtccaa aactctgtaa cccgacaggc   2220
ccgacagtct catgtttacg gcactggcac atgggggatt tctggcactc cttcctagtg   2280
gtattccgca tcctctgcgg ggaatggatc gaaaatatgt gggaatgtat gcaagaagcg   2340
aatgcatcat catcattgtg tgttattgtc ttcatattga tcacggtgat aggaaaactt   2400
gtggtgctca acctcttcat tgccttactg ctcaattcct ttagcaatga ggaaagaaat   2460
ggaaacttag aaggagaggc caggaaaact aaagtccagt tagcactgga tcgattccgc   2520
cgggcttttt gttttgtgag acacactctt gagcatttct gtcacaagtg gtgcaggaag   2580
caaaacttac cacagcaaaa agaggtggca ggaggctgtg ctgcacaaag caaagacatc   2640
```

```
attcccctgg tcatggagat gaaaagggc tcagagaccc aggaggagct tggtatacta    2700
acctctgtac caaagaccct gggcgtcagg catgattgga cttggttggc accacttgcg    2760
gaggaggaag atgacgttga attttctggt gaagataatg cacagcgcat cacacaacct    2820
gagcctgaac aacaggccta tgagctccat caggagaaca agaagcccac gagccagaga    2880
gttcaaagtg tggaaattga catgttctct gaagatgagc ctcatctgac catacaggat    2940
ccccgaaaga gtctgatgt taccagtata ctatcagaat gtagcaccat tgatcttcag    3000
gatggctttg gatggttacc tgagatggtt cccaaaaagc aaccagagag atgtttgccc    3060
aaaggctttg gttgctgctt ccatgctgt agcgtggaca agagaaagcc tccctgggtc    3120
atttggtgga acctgcggaa aacctgctac caaatagtga aacacagctg gtttgagagc    3180
tttattatct ttgtgattct gctgagcagt ggggcactga tatttgaaga tgttcacctt    3240
gagaaccaac ccaaaatcca agaattacta aattgtactg acattatttt tacacatatt    3300
tttatcctgg agatggtact aaaatgggta gccttcggat ttggaaagta tttcaccagt    3360
gcctggtgct gccttgattt catcattgtg attgtctctg tgaccaccct cattaactta    3420
atggaattga agtccttccg gactctacga gcactgaggc ctcttcgtgc gctgtcccag    3480
tttgaaggaa tgaaggtggt ggtcaatgct ctcataggtg ccatacctgc cattctgaat    3540
gttttgcttg tctgcctcat tttctggctc gtattttgta ttctgggagt atacttcttt    3600
tctggaaaat ttgggaaatg cattaatgga acagactcag ttataaatta taccatcatt    3660
acaaataaaa gtcaatgtga aagtggcaat ttctcttgga tcaaccagaa agtcaacttt    3720
gacaatgtgg gaaatgctta cctcgctctg ctgcaagtgg caacatttaa gggctggatg    3780
gatattatat atgcagctgt tgattccaca gagaaagaac aacagccaga gtttgagagc    3840
aattcactcg gttacatttta cttcgtagtc tttatcatct ttggctcatt cttcactctg    3900
aatctcttca ttggcgttat cattgacaac ttcaaccaac agcagaaaaa gttaggtggc    3960
caagacattt ttatgacaga agaacagaag aaatactata atgcaatgaa aaaattagga    4020
tccaaaaaac ctcaaaaacc cattccacgg cctctgaaca aatgtcaagg tctcgtgttc    4080
gacatagtca aagccagat ctttgacatc atcatcataa gtctcattat cctaaacatg    4140
attagcatga tggctgaatc atacaaccaa cccaaagcca tgaaatccat ccttgaccat    4200
ctcaactggg tctttgtggt catctttacg ttagaatgtc tcatcaaaat ctttgctttg    4260
aggcaatact acttcaccaa tggctggaat ttatttgact gtgtggtcgt gcttctttcc    4320
attgttagta caatgatttc taccttggaa aatcaggagc acattccttt ccctccgacg    4380
ctcttcagaa ttgtccgctt ggctcggatt ggccgaatcc tgaggcttgt ccgggctgca    4440
cgaggaatca ggactctcct ctttgctctg atgatgtcgc ttccttctct gttcaacatt    4500
ggtcttctac tctttctgat tatgtttatc tatgccattc tgggtatgaa ctggtttttcc    4560
aaagtgaatc cagagtctgg aatcgatgac atattcaact tcaagacttt tgccagcagc    4620
atgctctgtc tcttccagat aagcacatca gcaggttggg attccctgct cagccccatg    4680
ctgcgatcaa aagaatcatg taactcttcc tcagaaaact gccacctccc tggcatagcc    4740
acatcctact tgtcagtta cattatcatc tcctttctca ttgttgtcaa catgtacatt    4800
gctgtgattt tagagaactt caatacagcc actgaagaaa gtgaggaccc tttgggtgaa    4860
gatgactttg acatatttta tgaagtgtgg gaaaagtttg acccagaagc aacacaattt    4920
atcaaatatt ctgccctttc tgactttgct gatgccttgc ctgagccttt gcgtgtcgca    4980
```

-continued

```
aagccaaata aatatcaatt tctagtaatg gacttgccca tggtgagtga agatcgcctc        5040
cactgcatgg atattctttt cgccttcacc gctagggtac tcggtggctc tgatggccta        5100
gatagtatga aagcaatgat ggaagagaag ttcatggaag ccaatcctct caagaagttg        5160
tatgaaccca tagtcaccac caccaagaga aggaagagg aaagaggtgc tgctattatt        5220
caaaaggcct ttcgaaagta catgatgaag gtgaccaagg gtgaccaagg tgaccaaaat        5280
gacttggaaa acgggcctca ttcaccactc cagactcttt gcaatggaga cttgtctagc        5340
tttggggtgg ccaagggcaa ggtccactgt gactga                                  5376
```

<210> SEQ ID NO 18
<211> LENGTH: 1791
<212> TYPE: PRT
<213> ORGANISM: Homo sapiens

<400> SEQUENCE: 18

```
Met Asp Asp Arg Cys Tyr Pro Val Ile Phe Pro Asp Glu Arg Asn Phe
  1               5                  10                  15

Arg Pro Phe Thr Ser Asp Ser Leu Ala Ala Ile Glu Lys Arg Ile Ala
             20                  25                  30

Ile Gln Lys Glu Lys Lys Lys Ser Lys Asp Gln Thr Gly Glu Val Pro
         35                  40                  45

Gln Pro Arg Pro Gln Leu Asp Leu Lys Ala Ser Arg Lys Leu Pro Lys
     50                  55                  60

Leu Tyr Gly Asp Ile Pro Arg Glu Leu Ile Gly Lys Pro Leu Glu Asp
 65                  70                  75                  80

Leu Asp Pro Phe Tyr Arg Asn His Lys Thr Phe Met Val Leu Asn Arg
                 85                  90                  95

Lys Arg Thr Ile Tyr Arg Phe Ser Ala Lys His Ala Leu Phe Ile Phe
            100                 105                 110

Gly Pro Phe Asn Ser Ile Arg Ser Leu Ala Ile Arg Val Ser Val His
        115                 120                 125

Ser Leu Phe Ser Met Phe Ile Ile Gly Thr Val Ile Ile Asn Cys Val
    130                 135                 140

Phe Met Ala Thr Gly Pro Ala Lys Asn Ser Asn Ser Asn Asn Thr Asp
145                 150                 155                 160

Ile Ala Glu Cys Val Phe Thr Gly Ile Tyr Ile Phe Glu Ala Leu Ile
                165                 170                 175

Lys Ile Leu Ala Arg Gly Phe Ile Leu Asp Glu Phe Ser Phe Leu Arg
            180                 185                 190

Asp Pro Trp Asn Trp Leu Asp Ser Ile Val Ile Gly Ile Ala Ile Val
        195                 200                 205

Ser Tyr Ile Pro Gly Ile Thr Ile Lys Leu Leu Pro Leu Arg Thr Phe
    210                 215                 220

Arg Val Phe Arg Ala Leu Lys Ala Ile Ser Val Val Ser Arg Leu Lys
225                 230                 235                 240

Val Ile Val Gly Ala Leu Leu Arg Ser Val Lys Lys Leu Val Asn Val
                245                 250                 255

Ile Ile Leu Thr Phe Phe Cys Leu Ser Ile Phe Ala Leu Val Gly Gln
            260                 265                 270

Gln Leu Phe Met Gly Ser Leu Asn Leu Lys Cys Ile Ser Arg Asp Cys
        275                 280                 285

Lys Asn Ile Ser Asn Pro Glu Ala Tyr Asp His Cys Phe Glu Lys Lys
    290                 295                 300
```

-continued

```
Glu Asn Ser Pro Glu Phe Lys Met Cys Gly Ile Trp Met Gly Asn Ser
305                 310                 315                 320

Ala Cys Ser Ile Gln Tyr Glu Cys Lys His Thr Lys Ile Asn Pro Asp
            325                 330                 335

Tyr Asn Tyr Thr Asn Phe Asp Asn Phe Gly Trp Ser Phe Leu Ala Met
        340                 345                 350

Phe Arg Leu Met Thr Gln Asp Ser Trp Glu Lys Leu Tyr Gln Gln Thr
    355                 360                 365

Leu Arg Thr Thr Gly Leu Tyr Ser Val Phe Phe Ile Val Val Ile
370                 375                 380

Phe Leu Gly Ser Phe Tyr Leu Ile Asn Leu Thr Leu Ala Val Val Thr
385                 390                 395                 400

Met Ala Tyr Glu Glu Gln Asn Lys Asn Val Ala Ala Glu Ile Glu Ala
                405                 410                 415

Lys Glu Lys Met Phe Gln Glu Ala Gln Gln Leu Leu Lys Glu Glu Lys
            420                 425                 430

Glu Ala Leu Val Ala Met Gly Ile Asp Arg Ser Ser Leu Thr Ser Leu
        435                 440                 445

Glu Thr Ser Tyr Phe Thr Pro Lys Lys Arg Lys Leu Phe Gly Asn Lys
    450                 455                 460

Lys Arg Lys Ser Phe Phe Leu Arg Glu Ser Gly Lys Asp Gln Pro Pro
465                 470                 475                 480

Gly Ser Asp Ser Asp Glu Asp Cys Gln Lys Pro Gln Leu Leu Glu
                485                 490                 495

Gln Thr Lys Arg Leu Ser Gln Asn Leu Ser Leu Asp His Phe Asp Glu
            500                 505                 510

His Gly Asp Pro Leu Gln Arg Gln Arg Ala Leu Ser Ala Val Ser Ile
        515                 520                 525

Leu Thr Ile Thr Met Lys Glu Gln Glu Lys Ser Gln Glu Pro Cys Leu
    530                 535                 540

Pro Cys Gly Glu Asn Leu Ala Ser Lys Tyr Leu Val Trp Asn Cys Cys
545                 550                 555                 560

Pro Gln Trp Leu Cys Val Lys Lys Val Leu Arg Thr Val Met Thr Asp
                565                 570                 575

Pro Phe Thr Glu Leu Ala Ile Thr Ile Cys Ile Ile Asn Thr Val
            580                 585                 590

Phe Leu Ala Met Glu His His Lys Met Glu Ala Ser Phe Glu Lys Met
        595                 600                 605

Leu Asn Ile Gly Asn Leu Val Phe Thr Ser Ile Phe Ile Ala Glu Met
    610                 615                 620

Cys Leu Lys Ile Ile Ala Leu Asp Pro Tyr His Tyr Phe Arg Arg Gly
625                 630                 635                 640

Trp Asn Ile Phe Asp Ser Ile Val Ala Leu Leu Ser Phe Ala Asp Val
                645                 650                 655

Met Asn Cys Val Leu Gln Lys Arg Ser Trp Pro Phe Leu Arg Ser Phe
            660                 665                 670

Arg Val Leu Arg Val Phe Lys Leu Ala Lys Ser Trp Pro Thr Leu Asn
        675                 680                 685

Thr Leu Ile Lys Ile Ile Gly Asn Ser Val Gly Ala Leu Gly Asn Leu
    690                 695                 700

Thr Val Val Leu Val Ile Val Ile Phe Ile Phe Ser Val Val Gly Met
705                 710                 715                 720

Gln Leu Phe Gly Arg Ser Phe Asn Ser Gln Lys Ser Pro Lys Leu Cys
```

-continued

```
                725                 730                 735
Asn Pro Thr Gly Pro Thr Val Ser Cys Leu Arg His Trp His Met Gly
            740                 745                 750

Asp Phe Trp His Ser Phe Leu Val Val Phe Arg Ile Leu Cys Gly Glu
            755                 760                 765

Trp Ile Glu Asn Met Trp Glu Cys Met Gln Glu Ala Asn Ala Ser Ser
            770                 775                 780

Ser Leu Cys Val Ile Val Phe Ile Leu Ile Thr Val Ile Gly Lys Leu
785                 790                 795                 800

Val Val Leu Asn Leu Phe Ile Ala Leu Leu Asn Ser Phe Ser Asn
                805                 810                 815

Glu Glu Arg Asn Gly Asn Leu Glu Gly Glu Ala Arg Lys Thr Lys Val
                820                 825                 830

Gln Leu Ala Leu Asp Arg Phe Arg Arg Ala Phe Cys Phe Val Arg His
                835                 840                 845

Thr Leu Glu His Phe Cys His Lys Trp Cys Arg Lys Gln Asn Leu Pro
            850                 855                 860

Gln Gln Lys Glu Val Ala Gly Gly Cys Ala Ala Gln Ser Lys Asp Ile
865                 870                 875                 880

Ile Pro Leu Val Met Glu Met Lys Arg Gly Ser Glu Thr Gln Glu Glu
                885                 890                 895

Leu Gly Ile Leu Thr Ser Val Pro Lys Thr Leu Gly Val Arg His Asp
            900                 905                 910

Trp Thr Trp Leu Ala Pro Leu Ala Glu Glu Asp Asp Val Glu Phe
            915                 920                 925

Ser Gly Glu Asp Asn Ala Gln Arg Ile Thr Gln Pro Glu Pro Glu Gln
930                 935                 940

Gln Ala Tyr Glu Leu His Gln Glu Asn Lys Lys Pro Thr Ser Gln Arg
945                 950                 955                 960

Val Gln Ser Val Glu Ile Asp Met Phe Ser Asp Glu Pro His Leu
                965                 970                 975

Thr Ile Gln Asp Pro Arg Lys Lys Ser Asp Val Thr Ser Ile Leu Ser
                980                 985                 990

Glu Cys Ser Thr Ile Asp Leu Gln Asp Gly Phe Gly Trp Leu Pro Glu
            995                 1000                1005

Met Val Pro Lys Lys Gln Pro Glu Arg Cys Leu Pro Lys Gly Phe Gly
    1010                1015                1020

Cys Cys Phe Pro Cys Cys Ser Val Asp Lys Arg Lys Pro Pro Trp Val
1025                1030                1035                1040

Ile Trp Trp Asn Leu Arg Lys Thr Cys Tyr Gln Ile Val Lys His Ser
                1045                1050                1055

Trp Phe Glu Ser Phe Ile Ile Phe Val Ile Leu Leu Ser Ser Gly Ala
            1060                1065                1070

Leu Ile Phe Glu Asp Val His Leu Glu Asn Gln Pro Lys Ile Gln Glu
            1075                1080                1085

Leu Leu Asn Cys Thr Asp Ile Ile Phe Thr His Ile Phe Ile Leu Glu
            1090                1095                1100

Met Val Leu Lys Trp Val Ala Phe Gly Phe Gly Lys Tyr Phe Thr Ser
1105                1110                1115                1120

Ala Trp Cys Cys Leu Asp Phe Ile Ile Val Ile Val Ser Val Thr Thr
                1125                1130                1135

Leu Ile Asn Leu Met Glu Leu Lys Ser Phe Arg Thr Leu Arg Ala Leu
            1140                1145                1150
```

-continued

```
Arg Pro Leu Arg Ala Leu Ser Gln Phe Glu Gly Met Lys Val Val
        1155                1160                1165

Asn Ala Leu Ile Gly Ala Ile Pro Ala Ile Leu Asn Val Leu Leu Val
1170                1175                1180

Cys Leu Ile Phe Trp Leu Val Phe Cys Ile Leu Gly Val Tyr Phe Phe
1185                1190                1195                1200

Ser Gly Lys Phe Gly Lys Cys Ile Asn Gly Thr Asp Ser Val Ile Asn
        1205                1210                1215

Tyr Thr Ile Ile Thr Asn Lys Ser Gln Cys Glu Ser Gly Asn Phe Ser
        1220                1225                1230

Trp Ile Asn Gln Lys Val Asn Phe Asp Asn Val Gly Asn Ala Tyr Leu
        1235                1240                1245

Ala Leu Leu Gln Val Ala Thr Phe Lys Gly Trp Met Asp Ile Ile Tyr
        1250                1255                1260

Ala Ala Val Asp Ser Thr Glu Lys Glu Gln Gln Pro Glu Phe Glu Ser
1265                1270                1275                1280

Asn Ser Leu Gly Tyr Ile Tyr Phe Val Val Phe Ile Ile Phe Gly Ser
        1285                1290                1295

Phe Phe Thr Leu Asn Leu Phe Ile Gly Val Ile Ile Asp Asn Phe Asn
        1300                1305                1310

Gln Gln Gln Lys Lys Leu Gly Gly Gln Asp Ile Phe Met Thr Glu Glu
        1315                1320                1325

Gln Lys Lys Tyr Tyr Asn Ala Met Lys Lys Leu Gly Ser Lys Lys Pro
        1330                1335                1340

Gln Lys Pro Ile Pro Arg Pro Leu Asn Lys Cys Gln Gly Leu Val Phe
1345                1350                1355                1360

Asp Ile Val Thr Ser Gln Ile Phe Asp Ile Ile Ile Ser Leu Ile
        1365                1370                1375

Ile Leu Asn Met Ile Ser Met Met Ala Glu Ser Tyr Asn Gln Pro Lys
        1380                1385                1390

Ala Met Lys Ser Ile Leu Asp His Leu Asn Trp Val Phe Val Val Ile
        1395                1400                1405

Phe Thr Leu Glu Cys Leu Ile Lys Ile Phe Ala Leu Arg Gln Tyr Tyr
        1410                1415                1420

Phe Thr Asn Gly Trp Asn Leu Phe Asp Cys Val Val Val Leu Leu Ser
1425                1430                1435                1440

Ile Val Ser Thr Met Ile Ser Thr Leu Glu Asn Gln Glu His Ile Pro
        1445                1450                1455

Phe Pro Pro Thr Leu Phe Arg Ile Val Arg Leu Ala Arg Ile Gly Arg
        1460                1465                1470

Ile Leu Arg Leu Val Arg Ala Ala Arg Gly Ile Arg Thr Leu Leu Phe
        1475                1480                1485

Ala Leu Met Met Ser Leu Pro Ser Leu Phe Asn Ile Gly Leu Leu Leu
        1490                1495                1500

Phe Leu Ile Met Phe Ile Tyr Ala Ile Leu Gly Met Asn Trp Phe Ser
1505                1510                1515                1520

Lys Val Asn Pro Glu Ser Gly Ile Asp Asp Ile Phe Asn Phe Lys Thr
        1525                1530                1535

Phe Ala Ser Ser Met Leu Cys Leu Phe Gln Ile Ser Thr Ser Ala Gly
        1540                1545                1550

Trp Asp Ser Leu Leu Ser Pro Met Leu Arg Ser Lys Glu Ser Cys Asn
        1555                1560                1565
```

```
Ser Ser Ser Glu Asn Cys His Leu Pro Gly Ile Ala Thr Ser Tyr Phe
    1570                1575                1580

Val Ser Tyr Ile Ile Ile Ser Phe Leu Ile Val Val Asn Met Tyr Ile
1585                1590                1595                1600

Ala Val Ile Leu Glu Asn Phe Asn Thr Ala Thr Glu Glu Ser Glu Asp
                1605                1610                1615

Pro Leu Gly Glu Asp Asp Phe Asp Ile Phe Tyr Glu Val Trp Glu Lys
                1620                1625                1630

Phe Asp Pro Glu Ala Thr Gln Phe Ile Lys Tyr Ser Ala Leu Ser Asp
                1635                1640                1645

Phe Ala Asp Ala Leu Pro Glu Pro Leu Arg Val Ala Lys Pro Asn Lys
            1650                1655                1660

Tyr Gln Phe Leu Val Met Asp Leu Pro Met Val Ser Glu Asp Arg Leu
1665                1670                1675                1680

His Cys Met Asp Ile Leu Phe Ala Phe Thr Ala Arg Val Leu Gly Gly
                1685                1690                1695

Ser Asp Gly Leu Asp Ser Met Lys Ala Met Met Glu Glu Lys Phe Met
                1700                1705                1710

Glu Ala Asn Pro Leu Lys Lys Leu Tyr Glu Pro Ile Val Thr Thr Thr
                1715                1720                1725

Lys Arg Lys Glu Glu Glu Arg Gly Ala Ala Ile Ile Gln Lys Ala Phe
                1730                1735                1740

Arg Lys Tyr Met Met Lys Val Thr Lys Gly Asp Gln Gly Asp Gln Asn
1745                1750                1755                1760

Asp Leu Glu Asn Gly Pro His Ser Pro Leu Gln Thr Leu Cys Asn Gly
                1765                1770                1775

Asp Leu Ser Ser Phe Gly Val Ala Lys Gly Lys Val His Cys Asp
                1780                1785                1790

<210> SEQ ID NO 19
<211> LENGTH: 495
<212> TYPE: PRT
<213> ORGANISM: Homo sapiens

<400> SEQUENCE: 19

Met Thr Val Met Ser Gly Glu Asn Val Asp Glu Ala Ser Ala Ala Pro
1               5                   10                  15

Gly His Pro Gln Asp Gly Ser Tyr Pro Arg Gln Ala Asp His Asp Asp
                20                  25                  30

His Glu Cys Cys Glu Arg Val Val Ile Asn Ile Ser Gly Leu Arg Phe
            35                  40                  45

Glu Thr Gln Leu Lys Thr Leu Ala Gln Phe Pro Asn Thr Leu Leu Gly
        50                  55                  60

Asn Pro Lys Lys Arg Met Arg Tyr Phe Asp Pro Leu Arg Asn Glu Tyr
65                  70                  75                  80

Phe Phe Asp Arg Asn Arg Pro Ser Phe Asp Ala Ile Leu Tyr Tyr Tyr
                85                  90                  95

Gln Ser Gly Gly Arg Leu Arg Arg Pro Val Asn Val Pro Leu Asp Met
                100                 105                 110

Phe Ser Glu Glu Ile Lys Phe Tyr Glu Leu Gly Glu Glu Ala Met Glu
            115                 120                 125

Lys Phe Arg Glu Asp Glu Gly Phe Ile Lys Glu Glu Glu Arg Pro Leu
        130                 135                 140

Pro Glu Lys Glu Tyr Gln Arg Gln Val Trp Leu Leu Phe Glu Tyr Pro
145                 150                 155                 160
```

-continued

Glu Ser Ser Gly Pro Ala Arg Val Ile Ala Ile Val Ser Val Met Val
            165                 170                 175

Ile Leu Ile Ser Ile Val Ile Phe Cys Leu Glu Thr Leu Pro Glu Leu
        180                 185                 190

Lys Asp Asp Lys Asp Phe Thr Gly Thr Val His Arg Ile Asp Asn Thr
    195                 200                 205

Thr Val Ile Tyr Asn Ser Asn Ile Phe Thr Asp Pro Phe Phe Ile Val
210                 215                 220

Glu Thr Leu Cys Ile Ile Trp Phe Ser Phe Glu Leu Val Arg Phe
225                 230                 235                 240

Phe Ala Cys Pro Ser Lys Thr Asp Phe Phe Lys Asn Ile Met Asn Phe
                245                 250                 255

Ile Asp Ile Val Ala Ile Ile Pro Tyr Phe Ile Thr Leu Gly Thr Glu
            260                 265                 270

Ile Ala Glu Gln Glu Gly Asn Gln Lys Gly Glu Gln Ala Thr Ser Leu
        275                 280                 285

Ala Ile Leu Arg Val Ile Arg Leu Val Arg Val Phe Arg Ile Phe Lys
    290                 295                 300

Leu Ser Arg His Ser Lys Gly Leu Gln Ile Leu Gly Gln Thr Leu Lys
305                 310                 315                 320

Ala Ser Met Arg Glu Leu Gly Leu Leu Ile Phe Phe Leu Phe Ile Gly
                325                 330                 335

Val Ile Leu Phe Ser Ser Ala Val Tyr Phe Ala Glu Ala Glu Glu Ala
            340                 345                 350

Glu Ser His Phe Ser Ser Ile Pro Asp Ala Phe Trp Trp Ala Val Val
        355                 360                 365

Ser Met Thr Thr Val Gly Tyr Gly Asp Met Tyr Pro Val Thr Ile Gly
    370                 375                 380

Gly Lys Ile Val Gly Ser Leu Cys Ala Ile Ala Gly Val Leu Thr Ile
385                 390                 395                 400

Ala Leu Pro Val Pro Val Ile Val Ser Asn Phe Asn Tyr Phe Tyr His
                405                 410                 415

Arg Glu Thr Glu Gly Glu Glu Gln Ala Gln Leu Leu His Val Ser Ser
            420                 425                 430

Pro Asn Leu Ala Ser Asp Ser Asp Leu Ser Arg Arg Ser Ser Ser Thr
        435                 440                 445

Met Ser Lys Tyr Glu Tyr Met Glu Ile Glu Glu Asp Met Asn Asn Ser
    450                 455                 460

Ile Ala His Tyr Arg Gln Val Asn Ile Arg Thr Ala Asn Cys Thr Thr
465                 470                 475                 480

Ala Asn Gln Asn Cys Val Asn Lys Ser Lys Leu Leu Thr Asp Val
                485                 490                 495

<210> SEQ ID NO 20
<211> LENGTH: 499
<212> TYPE: PRT
<213> ORGANISM: Homo sapiens

<400> SEQUENCE: 20

Met Thr Val Ala Thr Gly Asp Pro Ala Asp Glu Ala Ala Ala Leu Pro
1               5                   10                  15

Gly His Pro Gln Asp Thr Tyr Asp Pro Glu Ala Asp His Glu Cys Cys
            20                  25                  30

Glu Arg Val Val Ile Asn Ile Ser Gly Leu Arg Phe Glu Thr Gln Leu

-continued

```
                35                  40                  45
Lys Thr Leu Ala Gln Phe Pro Glu Thr Leu Leu Gly Asp Pro Lys Lys
                50                  55                  60
Arg Met Arg Tyr Phe Asp Pro Leu Arg Asn Glu Tyr Phe Phe Asp Arg
 65                  70                  75                  80
Asn Arg Pro Ser Phe Asp Ala Ile Leu Tyr Tyr Tyr Gln Ser Gly Gly
                 85                  90                  95
Arg Leu Arg Arg Pro Val Asn Val Pro Leu Asp Ile Phe Ser Glu Glu
            100                 105                 110
Ile Arg Phe Tyr Glu Leu Gly Glu Ala Met Glu Met Phe Arg Glu
            115                 120                 125
Asp Glu Gly Tyr Ile Lys Glu Glu Arg Pro Leu Pro Glu Asn Glu
        130                 135                 140
Phe Gln Arg Gln Val Trp Leu Leu Phe Glu Tyr Pro Glu Ser Ser Gly
145                 150                 155                 160
Pro Ala Arg Ile Ile Ala Ile Val Ser Val Met Val Ile Leu Ile Ser
                165                 170                 175
Ile Val Ser Phe Cys Leu Glu Thr Leu Pro Ile Phe Arg Asp Glu Asn
            180                 185                 190
Glu Asp Met His Gly Ser Gly Val Thr Phe His Thr Tyr Ser Asn Ser
        195                 200                 205
Thr Ile Gly Tyr Gln Gln Ser Thr Ser Phe Thr Asp Pro Phe Phe Ile
    210                 215                 220
Val Glu Thr Leu Cys Ile Ile Trp Phe Ser Phe Glu Phe Leu Val Arg
225                 230                 235                 240
Phe Phe Ala Cys Pro Ser Lys Ala Gly Phe Phe Thr Asn Ile Met Asn
                245                 250                 255
Ile Ile Asp Ile Val Ala Ile Pro Tyr Phe Ile Thr Leu Gly Thr
            260                 265                 270
Glu Leu Ala Glu Lys Pro Glu Asp Ala Gln Gln Gly Gln Gln Ala Met
        275                 280                 285
Ser Leu Ala Ile Leu Arg Val Ile Arg Leu Val Arg Val Phe Arg Ile
        290                 295                 300
Phe Lys Leu Ser Arg His Ser Lys Gly Leu Gln Ile Leu Gly Gln Thr
305                 310                 315                 320
Leu Lys Ala Ser Met Arg Glu Leu Gly Leu Leu Ile Phe Phe Leu Phe
                325                 330                 335
Ile Gly Val Ile Leu Phe Ser Ser Ala Val Tyr Phe Ala Glu Ala Asp
            340                 345                 350
Glu Arg Glu Ser Gln Phe Pro Ser Ile Pro Asp Ala Phe Trp Trp Ala
        355                 360                 365
Val Val Ser Met Thr Thr Val Gly Tyr Gly Asp Met Val Pro Thr Thr
    370                 375                 380
Ile Gly Gly Lys Ile Val Gly Ser Leu Cys Ala Ile Ala Gly Val Leu
385                 390                 395                 400
Thr Ile Ala Leu Pro Val Pro Val Ile Val Ser Asn Phe Asn Tyr Phe
                405                 410                 415
Tyr His Arg Glu Thr Glu Gly Glu Glu Gln Ala Gln Tyr Leu Gln Val
            420                 425                 430
Thr Ser Cys Pro Lys Ile Pro Ser Ser Pro Asp Leu Lys Lys Ser Arg
        435                 440                 445
Ser Ala Ser Thr Ile Ser Lys Ser Asp Tyr Met Glu Ile Gln Glu Gly
    450                 455                 460
```

Val Asn Asn Ser Asn Glu Asp Phe Arg Glu Glu Asn Leu Lys Thr Ala
465                 470                 475                 480

Asn Cys Thr Leu Ala Asn Thr Asn Tyr Val Asn Ile Thr Lys Met Leu
            485                 490                 495

Thr Asp Val

<210> SEQ ID NO 21
<211> LENGTH: 523
<212> TYPE: PRT
<213> ORGANISM: Homo sapiens

<400> SEQUENCE: 21

Met Thr Val Val Pro Gly Asp His Leu Leu Glu Pro Glu Val Ala Asp
1               5                   10                  15

Gly Gly Gly Ala Pro Pro Gln Gly Gly Cys Gly Gly Gly Gly Cys Asp
            20                  25                  30

Arg Tyr Glu Pro Leu Pro Pro Ser Leu Pro Ala Ala Gly Glu Gln Asp
        35                  40                  45

Cys Cys Gly Glu Arg Val Val Ile Asn Ile Ser Gly Leu Arg Phe Glu
50                  55                  60

Thr Gln Leu Lys Thr Leu Cys Gln Phe Pro Glu Thr Leu Leu Gly Asp
65                  70                  75                  80

Pro Lys Arg Arg Met Arg Tyr Phe Asp Pro Leu Arg Asn Glu Tyr Phe
                85                  90                  95

Phe Asp Arg Asn Arg Pro Ser Phe Asp Ala Ile Leu Tyr Tyr Tyr Gln
            100                 105                 110

Ser Gly Gly Arg Ile Arg Arg Pro Val Asn Val Pro Ile Asp Ile Phe
        115                 120                 125

Ser Glu Glu Ile Arg Phe Tyr Gln Leu Gly Glu Glu Ala Met Glu Lys
130                 135                 140

Phe Arg Glu Asp Glu Gly Phe Leu Arg Glu Glu Glu Arg Pro Leu Pro
145                 150                 155                 160

Arg Arg Asp Phe Gln Arg Gln Val Trp Leu Leu Phe Glu Tyr Pro Glu
                165                 170                 175

Ser Ser Gly Pro Ala Arg Gly Ile Ala Ile Val Ser Val Leu Val Ile
            180                 185                 190

Leu Ile Ser Ile Val Ile Phe Cys Leu Glu Thr Leu Pro Glu Phe Arg
        195                 200                 205

Asp Glu Lys Asp Tyr Pro Ala Ser Thr Ser Gln Asp Ser Phe Glu Ala
210                 215                 220

Ala Gly Asn Ser Thr Ser Gly Ser Arg Ala Gly Ala Ser Ser Phe Ser
225                 230                 235                 240

Asp Pro Phe Phe Val Val Glu Thr Leu Cys Ile Ile Trp Phe Ser Phe
                245                 250                 255

Glu Leu Leu Val Arg Phe Phe Ala Cys Pro Ser Lys Ala Thr Phe Ser
            260                 265                 270

Arg Asn Ile Met Asn Leu Ile Asp Ile Val Ala Ile Ile Pro Tyr Phe
        275                 280                 285

Ile Thr Leu Gly Thr Glu Leu Ala Glu Arg Gln Gly Asn Gly Gln Gln
290                 295                 300

Ala Met Ser Leu Ala Ile Leu Arg Val Ile Arg Leu Val Arg Val Phe
305                 310                 315                 320

Arg Ile Phe Lys Leu Ser Arg His Ser Lys Gly Leu Gln Ile Leu Gly
                325                 330                 335

-continued

```
Gln Thr Leu Lys Ala Ser Met Arg Glu Leu Gly Leu Ile Phe Phe
            340                 345                 350

Leu Phe Ile Gly Val Ile Leu Phe Ser Ser Ala Val Tyr Phe Ala Glu
            355                 360                 365

Ala Asp Asp Pro Thr Ser Gly Phe Ser Ser Ile Pro Asp Ala Phe Trp
            370                 375                 380

Trp Ala Val Val Thr Met Thr Thr Val Gly Tyr Gly Asp Met His Pro
385                 390                 395                 400

Val Thr Ile Gly Gly Lys Ile Val Gly Ser Leu Cys Ala Ile Ala Gly
                405                 410                 415

Val Leu Thr Ile Ala Leu Pro Val Pro Val Ile Val Ser Asn Phe Asn
            420                 425                 430

Tyr Phe Tyr His Arg Glu Thr Glu Gly Glu Glu Gln Ser Gln Tyr Met
            435                 440                 445

His Val Gly Ser Cys Gln His Leu Ser Ser Ser Ala Glu Glu Leu Arg
            450                 455                 460

Lys Ala Arg Ser Asn Ser Thr Leu Ser Lys Ser Glu Tyr Met Val Ile
465                 470                 475                 480

Glu Glu Gly Gly Met Asn His Ser Ala Phe Pro Gln Thr Pro Phe Lys
                485                 490                 495

Thr Gly Asn Ser Thr Ala Thr Cys Thr Thr Asn Asn Asn Pro Asn Ser
            500                 505                 510

Cys Val Asn Ile Lys Lys Ile Phe Thr Asp Val
            515                 520
```

<210> SEQ ID NO 22
<211> LENGTH: 653
<212> TYPE: PRT
<213> ORGANISM: Homo sapiens

<400> SEQUENCE: 22

```
Met Glu Val Ala Met Val Ser Ala Glu Ser Ser Gly Cys Asn Ser His
1               5                   10                  15

Met Pro Tyr Gly Tyr Ala Ala Gln Ala Arg Ala Arg Glu Arg Glu Arg
                20                  25                  30

Leu Ala His Ser Arg Ala Ala Ala Ala Ala Val Ala Ala Ala Thr
            35                  40                  45

Ala Ala Val Glu Gly Ser Gly Gly Ser Gly Gly Ser His His His
        50                  55                  60

His Gln Ser Arg Gly Ala Cys Thr Ser His Asp Pro Gln Ser Ser Arg
65                  70                  75                  80

Gly Ser Arg Arg Arg Arg Gln Arg Ser Glu Lys Lys Lys Ala His
                85                  90                  95

Tyr Arg Gln Ser Ser Phe Pro His Cys Ser Asp Leu Met Pro Ser Gly
                100                 105                 110

Ser Glu Glu Lys Ile Leu Arg Glu Leu Ser Glu Glu Glu Glu Asp Glu
            115                 120                 125

Glu Glu Glu Glu Glu Glu Glu Gly Arg Phe Tyr Tyr Ser Glu
            130                 135                 140

Asp Asp His Gly Asp Glu Cys Ser Tyr Thr Asp Leu Leu Pro Gln Asp
145                 150                 155                 160

Glu Gly Gly Gly Gly Tyr Ser Ser Val Arg Tyr Ser Asp Cys Cys Glu
                165                 170                 175

Arg Val Val Ile Asn Val Ser Gly Leu Arg Phe Glu Thr Gln Met Lys
```

-continued

```
                180                 185                 190
Thr Leu Ala Gln Phe Pro Glu Thr Leu Gly Asp Pro Glu Lys Arg
            195                 200                 205
Thr Gln Tyr Phe Asp Pro Leu Arg Asn Glu Tyr Phe Phe Asp Arg Asn
        210                 215                 220
Arg Pro Ser Phe Asp Ala Ile Leu Tyr Tyr Tyr Gln Ser Gly Gly Arg
225                 230                 235                 240
Leu Lys Arg Pro Val Asn Val Pro Phe Asp Ile Phe Thr Glu Glu Val
                245                 250                 255
Lys Phe Tyr Gln Leu Gly Glu Glu Ala Leu Leu Lys Phe Arg Glu Asp
            260                 265                 270
Glu Gly Phe Val Arg Glu Glu Asp Arg Ala Leu Pro Glu Asn Glu
        275                 280                 285
Phe Lys Lys Gln Ile Trp Leu Leu Phe Glu Tyr Pro Glu Ser Ser Ser
        290                 295                 300
Pro Ala Arg Gly Ile Ala Ile Val Ser Val Leu Val Ile Leu Ile Ser
305                 310                 315                 320
Ile Val Ile Phe Cys Leu Glu Thr Leu Pro Glu Phe Arg Asp Asp Arg
                325                 330                 335
Asp Leu Val Met Ala Leu Ser Ala Gly Gly His Gly Gly Leu Leu Asn
            340                 345                 350
Asp Thr Ser Ala Pro His Leu Glu Asn Ser Gly His Thr Ile Phe Asn
        355                 360                 365
Asp Pro Phe Phe Ile Val Glu Thr Val Cys Ile Val Trp Phe Ser Phe
    370                 375                 380
Glu Phe Val Val Arg Cys Phe Ala Cys Pro Ser Gln Ala Leu Phe Phe
385                 390                 395                 400
Lys Asn Ile Met Asn Ile Ile Asp Ile Val Ser Ile Leu Pro Tyr Phe
                405                 410                 415
Ile Thr Leu Gly Thr Asp Leu Ala Gln Gln Gly Gly Asn Gly
            420                 425                 430
Gln Gln Gln Gln Ala Met Ser Phe Ala Ile Leu Arg Ile Ile Arg Leu
        435                 440                 445
Val Arg Val Phe Arg Ile Phe Lys Leu Ser Arg His Ser Lys Gly Leu
    450                 455                 460
Gln Ile Leu Gly His Thr Leu Arg Ala Ser Met Arg Glu Leu Gly Leu
465                 470                 475                 480
Leu Ile Phe Phe Leu Phe Ile Gly Val Ile Leu Phe Ser Ser Ala Val
                485                 490                 495
Tyr Phe Ala Glu Ala Asp Glu Pro Thr Thr His Phe Gln Ser Ile Pro
            500                 505                 510
Asp Ala Phe Trp Trp Ala Val Val Thr Met Thr Thr Val Gly Tyr Gly
        515                 520                 525
Asp Met Lys Pro Ile Thr Val Gly Gly Lys Ile Val Gly Ser Leu Cys
    530                 535                 540
Ala Ile Ala Gly Val Leu Thr Ile Ala Leu Pro Val Pro Val Ile Val
545                 550                 555                 560
Ser Asn Phe Asn Tyr Phe Tyr His Arg Glu Thr Glu Asn Glu Glu Gln
                565                 570                 575
Thr Gln Leu Thr Gln Asn Ala Val Ser Cys Pro Tyr Leu Pro Ser Asn
            580                 585                 590
Leu Leu Lys Lys Phe Arg Ser Ser Thr Ser Ser Ser Leu Gly Asp Lys
        595                 600                 605
```

Ser Glu Tyr Leu Glu Met Glu Glu Gly Val Lys Glu Ser Leu Cys Ala
610                 615                 620

Lys Glu Glu Lys Cys Gln Gly Lys Gly Asp Asp Ser Glu Thr Asp Lys
625                 630                 635                 640

Asn Asn Cys Ser Asn Ala Lys Ala Val Glu Thr Asp Val
                645                 650

<210> SEQ ID NO 23
<211> LENGTH: 613
<212> TYPE: PRT
<213> ORGANISM: Homo sapiens

<400> SEQUENCE: 23

Met Glu Ile Ala Leu Val Pro Leu Glu Asn Gly Gly Ala Met Thr Val
1               5                   10                  15

Arg Gly Gly Asp Glu Ala Arg Ala Gly Cys Gly Gln Ala Thr Gly Gly
                20                  25                  30

Glu Leu Gln Cys Pro Pro Thr Ala Gly Leu Ser Asp Gly Pro Lys Glu
            35                  40                  45

Pro Ala Pro Lys Gly Arg Gly Ala Gln Arg Asp Ala Asp Ser Gly Val
    50                  55                  60

Arg Pro Leu Pro Pro Leu Pro Asp Pro Gly Val Arg Pro Leu Pro Pro
65                  70                  75                  80

Leu Pro Glu Glu Leu Pro Arg Pro Arg Arg Pro Pro Glu Asp Glu
                85                  90                  95

Glu Glu Glu Gly Asp Pro Gly Leu Gly Thr Val Glu Asp Gln Ala Leu
            100                 105                 110

Gly Thr Ala Ser Leu His His Gln Arg Val His Ile Asn Ile Ser Gly
        115                 120                 125

Leu Arg Phe Glu Thr Gln Leu Gly Thr Leu Ala Gln Phe Pro Asn Thr
130                 135                 140

Leu Leu Gly Asp Pro Ala Lys Arg Leu Arg Tyr Phe Asp Pro Leu Arg
145                 150                 155                 160

Asn Glu Tyr Phe Phe Asp Arg Asn Arg Pro Ser Phe Asp Gly Ile Leu
                165                 170                 175

Tyr Tyr Tyr Gln Ser Gly Gly Arg Leu Arg Arg Pro Val Asn Val Ser
            180                 185                 190

Leu Asp Val Phe Ala Asp Glu Ile Arg Phe Tyr Gln Leu Gly Asp Glu
        195                 200                 205

Ala Met Glu Arg Phe Arg Glu Asp Glu Gly Phe Ile Lys Glu Glu Glu
    210                 215                 220

Lys Pro Leu Pro Arg Asn Glu Phe Gln Arg Gln Val Trp Leu Ile Phe
225                 230                 235                 240

Glu Tyr Pro Glu Ser Ser Gly Ser Ala Arg Ala Ile Ala Ile Val Ser
                245                 250                 255

Val Leu Val Ile Leu Ile Ser Ile Ile Thr Phe Cys Leu Glu Thr Leu
            260                 265                 270

Pro Glu Phe Arg Asp Glu Arg Glu Leu Leu Arg His Pro Pro Ala Pro
        275                 280                 285

His Gln Pro Pro Ala Pro Ala Pro Gly Ala Asn Gly Ser Gly Val Met
    290                 295                 300

Ala Pro Pro Ser Gly Pro Thr Val Ala Pro Leu Leu Pro Arg Thr Leu
305                 310                 315                 320

Ala Asp Pro Phe Phe Ile Val Glu Thr Thr Cys Val Ile Trp Phe Thr

```
                    325                 330                 335
Phe Glu Leu Leu Val Arg Phe Phe Ala Cys Pro Ser Lys Ala Gly Phe
            340                 345                 350

Ser Arg Asn Ile Met Asn Ile Ile Asp Val Val Ala Ile Phe Pro Tyr
            355                 360                 365

Phe Ile Thr Leu Gly Thr Glu Leu Ala Glu Gln Gln Pro Gly Gly Gly
            370                 375                 380

Gly Gly Gly Gln Asn Gly Gln Gln Ala Met Ser Leu Ala Ile Leu Arg
385                 390                 395                 400

Val Ile Arg Leu Val Arg Val Phe Arg Ile Phe Lys Leu Ser Arg His
            405                 410                 415

Ser Lys Gly Leu Gln Ile Leu Gly Lys Thr Leu Gln Ala Ser Met Arg
            420                 425                 430

Glu Leu Gly Leu Leu Ile Phe Phe Leu Phe Ile Gly Val Ile Leu Phe
            435                 440                 445

Ser Ser Ala Val Tyr Phe Ala Glu Ala Asp Asn Gln Gly Thr His Phe
            450                 455                 460

Ser Ser Ile Pro Asp Ala Phe Trp Trp Ala Val Val Thr Met Thr Thr
465                 470                 475                 480

Val Gly Tyr Gly Asp Met Arg Pro Ile Thr Val Gly Gly Lys Ile Val
            485                 490                 495

Gly Ser Leu Cys Ala Ile Ala Gly Val Leu Thr Ile Ala Leu Pro Val
            500                 505                 510

Pro Val Ile Val Ser Asn Phe Asn Tyr Phe Tyr His Arg Glu Thr Asp
            515                 520                 525

His Glu Glu Pro Ala Val Leu Lys Glu Glu Gln Gly Thr Gln Ser Gln
            530                 535                 540

Gly Pro Gly Leu Asp Arg Gly Val Gln Arg Lys Val Ser Gly Ser Arg
545                 550                 555                 560

Gly Ser Phe Cys Lys Ala Gly Gly Thr Leu Glu Asn Ala Asp Ser Ala
            565                 570                 575

Arg Arg Gly Ser Cys Pro Leu Glu Lys Cys Asn Val Lys Ala Lys Ser
            580                 585                 590

Asn Val Asp Leu Arg Arg Ser Leu Tyr Ala Leu Cys Leu Asp Thr Ser
            595                 600                 605

Arg Glu Thr Asp Leu
            610

<210> SEQ ID NO 24
<211> LENGTH: 858
<212> TYPE: PRT
<213> ORGANISM: Homo sapiens

<400> SEQUENCE: 24

Met Pro Ala Gly Met Thr Lys His Gly Ser Arg Ser Thr Ser Ser Leu
1               5                   10                  15

Pro Pro Glu Pro Met Glu Ile Val Arg Ser Lys Ala Cys Ser Arg Arg
            20                  25                  30

Val Arg Leu Asn Val Gly Gly Leu Ala His Glu Val Leu Trp Arg Thr
            35                  40                  45

Leu Asp Arg Leu Pro Arg Thr Arg Leu Gly Lys Leu Arg Asp Cys Asn
            50                  55                  60

Thr His Asp Ser Leu Leu Glu Val Cys Asp Asp Tyr Ser Leu Asp Asp
65                  70                  75                  80
```

-continued

```
Asn Glu Tyr Phe Phe Asp Arg His Pro Gly Ala Phe Thr Ser Ile Leu
                85                  90                  95

Asn Phe Tyr Arg Thr Gly Arg Leu His Met Met Glu Met Cys Ala
            100                 105                 110

Leu Ser Phe Ser Gln Glu Leu Asp Tyr Trp Gly Ile Asp Glu Ile Tyr
            115                 120                 125

Leu Glu Ser Cys Cys Gln Ala Arg Tyr His Gln Lys Lys Glu Gln Met
        130                 135                 140

Asn Glu Glu Leu Lys Arg Glu Ala Glu Thr Leu Arg Glu Arg Glu Gly
145                 150                 155                 160

Glu Glu Phe Asp Asn Thr Cys Cys Ala Glu Lys Arg Lys Lys Leu Trp
                165                 170                 175

Asp Leu Leu Glu Lys Pro Asn Ser Ser Val Ala Lys Ile Leu Ala
            180                 185                 190

Ile Ile Ser Ile Met Phe Ile Val Leu Ser Thr Ile Ala Leu Ser Leu
        195                 200                 205

Asn Thr Leu Pro Glu Leu Gln Ser Leu Asp Glu Phe Gly Gln Ser Thr
210                 215                 220

Asp Asn Pro Gln Leu Ala His Val Glu Ala Val Cys Ile Ala Trp Phe
225                 230                 235                 240

Thr Met Glu Tyr Leu Leu Arg Phe Leu Ser Ser Pro Lys Lys Trp Lys
                245                 250                 255

Phe Phe Lys Gly Pro Leu Asn Ala Ile Asp Leu Leu Ala Ile Leu Pro
            260                 265                 270

Tyr Tyr Val Thr Ile Phe Leu Thr Glu Ser Asn Lys Ser Val Leu Gln
        275                 280                 285

Phe Gln Asn Val Arg Arg Val Val Gln Ile Phe Arg Ile Met Arg Ile
    290                 295                 300

Leu Arg Ile Leu Lys Leu Ala Arg His Ser Thr Gly Leu Gln Ser Leu
305                 310                 315                 320

Gly Phe Thr Leu Arg Arg Ser Tyr Asn Glu Leu Gly Leu Leu Ile Leu
                325                 330                 335

Phe Leu Ala Met Gly Ile Met Ile Phe Ser Ser Leu Val Phe Phe Ala
            340                 345                 350

Glu Lys Asp Glu Asp Asp Thr Lys Phe Lys Ser Ile Pro Ala Ser Phe
        355                 360                 365

Trp Trp Ala Thr Ile Thr Met Thr Thr Val Gly Tyr Gly Asp Ile Tyr
370                 375                 380

Pro Lys Thr Leu Leu Gly Lys Ile Val Gly Gly Leu Cys Cys Ile Ala
385                 390                 395                 400

Gly Val Leu Val Ile Ala Leu Pro Ile Pro Ile Ile Val Asn Asn Phe
                405                 410                 415

Ser Glu Phe Tyr Lys Glu Gln Lys Arg Gln Glu Lys Ala Ile Lys Arg
            420                 425                 430

Arg Glu Ala Leu Glu Arg Ala Lys Arg Asn Gly Ser Ile Val Ser Met
        435                 440                 445

Asn Met Lys Asp Ala Phe Ala Arg Ser Ile Glu Met Met Asp Ile Val
    450                 455                 460

Val Glu Lys Asn Gly Glu Asn Met Gly Lys Lys Asp Lys Val Gln Asp
465                 470                 475                 480

Asn His Leu Ser Pro Asn Lys Trp Lys Trp Thr Lys Arg Thr Leu Ser
                485                 490                 495

Glu Thr Ser Ser Ser Lys Ser Phe Glu Thr Lys Glu Gln Gly Ser Pro
```

```
                500             505             510
Glu Lys Ala Arg Ser Ser Ser Pro Gln His Leu Asn Val Gln Gln
        515                 520                 525
Leu Glu Asp Met Tyr Asn Lys Met Ala Lys Thr Gln Ser Gln Pro Ile
    530                 535                 540
Leu Asn Thr Lys Glu Ser Ala Ala Gln Ser Lys Pro Lys Glu Glu Leu
545                 550                 555                 560
Glu Met Glu Ser Ile Pro Ser Pro Val Ala Pro Leu Pro Thr Arg Thr
                565                 570                 575
Glu Gly Val Ile Asp Met Arg Ser Met Ser Ser Ile Asp Ser Phe Ile
            580                 585                 590
Ser Cys Ala Thr Asp Phe Pro Glu Ala Thr Arg Phe Ser His Ser Pro
                595                 600                 605
Leu Thr Ser Leu Pro Ser Lys Thr Gly Gly Ser Thr Ala Pro Glu Val
    610                 615                 620
Gly Trp Arg Gly Ala Leu Gly Ala Ser Gly Gly Arg Phe Val Glu Ala
625                 630                 635                 640
Asn Pro Ser Pro Asp Ala Ser Gln His Ser Ser Phe Phe Ile Glu Ser
                645                 650                 655
Pro Lys Ser Ser Met Lys Thr Asn Asn Pro Leu Lys Leu Arg Ala Leu
            660                 665                 670
Lys Val Asn Phe Met Glu Gly Asp Pro Ser Pro Leu Leu Pro Val Leu
        675                 680                 685
Gly Met Tyr His Asp Pro Leu Arg Asn Arg Gly Ser Ala Ala Ala Ala
    690                 695                 700
Val Ala Gly Leu Glu Cys Ala Thr Leu Leu Asp Lys Ala Val Leu Ser
705                 710                 715                 720
Pro Glu Ser Ser Ile Tyr Thr Thr Ala Ser Ala Lys Thr Pro Pro Arg
                725                 730                 735
Ser Pro Glu Lys His Thr Ala Ile Ala Phe Asn Phe Glu Ala Gly Val
            740                 745                 750
His Gln Tyr Ile Asp Ala Asp Thr Asp Asp Glu Gly Gln Leu Leu Tyr
        755                 760                 765
Ser Val Asp Ser Ser Pro Pro Lys Ser Leu Pro Gly Ser Thr Ser Pro
    770                 775                 780
Lys Phe Ser Thr Gly Thr Arg Ser Glu Lys Asn His Phe Glu Ser Ser
785                 790                 795                 800
Pro Leu Pro Thr Ser Pro Lys Phe Leu Arg Gln Asn Cys Ile Tyr Ser
                805                 810                 815
Thr Glu Ala Leu Thr Gly Lys Gly Pro Ser Gly Gln Glu Lys Cys Lys
            820                 825                 830
Leu Glu Asn His Ile Ser Pro Asp Val Arg Val Leu Pro Gly Gly Gly
        835                 840                 845
Ala His Gly Ser Thr Arg Asp Gln Ser Ile
    850                 855

<210> SEQ ID NO 25
<211> LENGTH: 911
<212> TYPE: PRT
<213> ORGANISM: Homo sapiens

<400> SEQUENCE: 25

Met Ala Glu Lys Ala Pro Pro Gly Leu Asn Arg Lys Thr Ser Arg Ser
1               5                   10                  15
```

-continued

```
Thr Leu Ser Leu Pro Pro Glu Pro Val Asp Ile Ile Arg Ser Lys Thr
         20                  25                  30
Cys Ser Arg Arg Val Lys Ile Asn Val Gly Gly Leu Asn His Glu Val
         35                  40                  45
Leu Trp Arg Thr Leu Asp Arg Leu Pro Arg Thr Arg Leu Gly Lys Leu
 50                  55                  60
Arg Asp Cys Asn Thr His Glu Ser Leu Leu Glu Val Cys Asp Asp Tyr
 65                  70                  75                  80
Asn Leu Asn Glu Asn Glu Tyr Phe Phe Asp Arg His Pro Gly Ala Phe
                 85                  90                  95
Thr Ser Ile Leu Asn Phe Tyr Arg Thr Gly Lys Leu His Met Met Glu
             100                 105                 110
Glu Met Cys Ala Leu Ser Phe Gly Gln Glu Leu Asp Tyr Trp Gly Ile
         115                 120                 125
Asp Glu Ile Tyr Leu Glu Ser Cys Cys Gln Ala Arg Tyr His Gln Lys
     130                 135                 140
Lys Glu Gln Met Asn Glu Glu Leu Arg Arg Glu Ala Glu Thr Met Arg
145                 150                 155                 160
Glu Arg Glu Gly Glu Glu Phe Asp Asn Thr Cys Cys Pro Asp Lys Arg
                165                 170                 175
Lys Lys Leu Trp Asp Leu Leu Glu Lys Pro Asn Ser Ser Val Ala Ala
            180                 185                 190
Lys Ile Leu Ala Ile Val Ser Ile Leu Phe Ile Val Leu Ser Thr Ile
        195                 200                 205
Ala Leu Ser Leu Asn Thr Leu Pro Glu Leu Gln Glu Thr Asp Glu Phe
    210                 215                 220
Gly Gln Leu Asn Asp Asn Arg Gln Leu Ala His Val Glu Ala Val Cys
225                 230                 235                 240
Ile Ala Trp Phe Thr Met Glu Tyr Leu Leu Arg Phe Leu Ser Ser Pro
                245                 250                 255
Asn Lys Trp Lys Phe Phe Lys Gly Pro Leu Asn Val Ile Asp Leu Leu
            260                 265                 270
Ala Ile Leu Pro Tyr Tyr Val Thr Ile Phe Leu Thr Glu Ser Asn Lys
        275                 280                 285
Ser Val Leu Gln Phe Gln Asn Val Arg Arg Val Val Gln Ile Phe Arg
    290                 295                 300
Ile Met Arg Ile Leu Arg Ile Leu Lys Leu Ala Arg His Ser Thr Gly
305                 310                 315                 320
Leu Gln Ser Leu Gly Phe Thr Leu Arg Arg Ser Tyr Asn Glu Leu Gly
                325                 330                 335
Leu Leu Ile Leu Phe Leu Ala Met Gly Ile Met Ile Phe Ser Ser Leu
            340                 345                 350
Val Phe Phe Ala Glu Lys Asp Glu Asp Ala Thr Lys Phe Thr Ser Ile
        355                 360                 365
Pro Ala Ser Phe Trp Trp Ala Thr Ile Thr Met Thr Thr Val Gly Tyr
    370                 375                 380
Gly Asp Ile Tyr Pro Lys Thr Leu Leu Gly Lys Ile Val Gly Gly Leu
385                 390                 395                 400
Cys Cys Ile Ala Gly Val Leu Val Ile Ala Leu Pro Ile Pro Ile Ile
                405                 410                 415
Val Asn Asn Phe Ser Glu Phe Tyr Lys Glu Gln Lys Arg Gln Glu Lys
            420                 425                 430
Ala Ile Lys Arg Arg Glu Ala Leu Glu Arg Ala Lys Arg Asn Gly Ser
```

-continued

```
                435                 440                 445
Ile Val Ser Met Asn Leu Lys Asp Ala Phe Ala Arg Ser Met Glu Leu
450                 455                 460
Ile Asp Val Ala Val Glu Lys Ala Gly Glu Ser Ala Asn Thr Lys Asp
465                 470                 475                 480
Ser Ala Asp Asp Asn His Leu Ser Pro Ser Arg Trp Lys Trp Ala Arg
                485                 490                 495
Lys Ala Leu Ser Glu Thr Ser Ser Asn Lys Ser Phe Glu Asn Lys Tyr
                500                 505                 510
Gln Glu Val Ser Gln Lys Asp Ser His Glu Gln Leu Asn Asn Thr Ser
                515                 520                 525
Ser Ser Ser Pro Gln His Leu Ser Ala Gln Lys Leu Glu Met Leu Tyr
530                 535                 540
Asn Glu Ile Thr Lys Thr Gln Pro His Ser His Pro Asn Pro Asp Cys
545                 550                 555                 560
Gln Glu Lys Pro Glu Arg Pro Ser Ala Tyr Glu Glu Ile Glu Met
                565                 570                 575
Glu Glu Val Val Cys Pro Gln Glu Gln Leu Ala Val Ala Gln Thr Glu
                580                 585                 590
Val Ile Val Asp Met Lys Ser Thr Ser Ser Ile Asp Ser Phe Thr Ser
                595                 600                 605
Cys Ala Thr Asp Phe Thr Glu Thr Glu Arg Ser Pro Leu Pro Pro Pro
610                 615                 620
Ser Ala Ser His Leu Gln Met Lys Phe Pro Thr Asp Leu Pro Gly Thr
625                 630                 635                 640
Glu Glu His Gln Arg Ala Arg Gly Pro Pro Phe Leu Thr Leu Ser Arg
                645                 650                 655
Glu Lys Gly Pro Ala Ala Arg Asp Gly Thr Leu Glu Tyr Ala Pro Val
                660                 665                 670
Asp Ile Thr Val Asn Leu Asp Ala Ser Gly Ser Gln Cys Gly Leu His
                675                 680                 685
Ser Pro Leu Gln Ser Asp Asn Ala Thr Asp Ser Pro Lys Ser Ser Leu
                690                 695                 700
Lys Gly Ser Asn Pro Leu Lys Ser Arg Ser Leu Lys Val Asn Phe Lys
705                 710                 715                 720
Glu Asn Arg Gly Ser Ala Pro Gln Thr Pro Ser Thr Ala Arg Pro
                725                 730                 735
Leu Pro Val Thr Thr Ala Asp Phe Ser Leu Thr Thr Pro Gln His Ile
                740                 745                 750
Ser Thr Ile Leu Leu Glu Glu Thr Pro Ser Gln Gly Asp Arg Pro Leu
                755                 760                 765
Leu Gly Thr Glu Val Ser Ala Pro Cys Gln Gly Pro Ser Lys Gly Leu
                770                 775                 780
Ser Pro Arg Phe Pro Lys Gln Lys Leu Phe Pro Phe Ser Ser Arg Glu
785                 790                 795                 800
Arg Arg Ser Phe Thr Glu Ile Asp Thr Gly Asp Asp Glu Asp Phe Leu
                805                 810                 815
Glu Leu Pro Gly Ala Arg Glu Glu Lys Gln Val Asp Ser Ser Pro Asn
                820                 825                 830
Cys Phe Ala Asp Lys Pro Ser Asp Gly Arg Asp Pro Leu Arg Glu Glu
                835                 840                 845
Gly Ser Val Gly Ser Ser Pro Gln Asp Thr Gly His Asn Cys Arg
850                 855                 860
```

Gln Asp Ile Tyr His Ala Val Ser Glu Val Lys Lys Asp Ser Ser Gln
865                 870                 875                 880

Glu Gly Cys Lys Met Glu Asn His Leu Phe Ala Pro Glu Ile His Ser
            885                 890                 895

Asn Pro Gly Asp Thr Gly Tyr Cys Pro Thr Arg Glu Thr Ser Met
        900                 905                 910

<210> SEQ ID NO 26
<211> LENGTH: 511
<212> TYPE: PRT
<213> ORGANISM: Homo sapiens

<400> SEQUENCE: 26

Met Gly Gln Gly Asp Glu Ser Glu Arg Ile Val Ile Asn Val Gly Gly
1               5                   10                  15

Thr Arg His Gln Thr His Arg Ser Thr Leu Arg Thr Leu Pro Gly Thr
            20                  25                  30

Arg Leu Ala Trp Leu Ala Glu Pro Asp Ala His Ser His Phe Asp Tyr
        35                  40                  45

Asp Pro Arg Ala Asp Glu Phe Phe Phe Asp Arg His Pro Gly Val Phe
    50                  55                  60

Ala His Ile Leu Asn Tyr Tyr Arg Thr Gly Lys Leu His Cys Pro Ala
65                  70                  75                  80

Asp Val Cys Gly Pro Leu Tyr Glu Glu Leu Ala Phe Trp Gly Ile
                85                  90                  95

Asp Glu Thr Asp Val Glu Pro Cys Cys Trp Met Thr Tyr Arg Gln His
            100                 105                 110

Arg Asp Ala Glu Glu Ala Leu Asp Ser Phe Gly Gly Ala Pro Leu Asp
        115                 120                 125

Asn Ser Ala Asp Asp Ala Asp Ala Asp Gly Pro Gly Asp Ser Gly Asp
    130                 135                 140

Gly Glu Asp Glu Leu Glu Met Thr Lys Arg Leu Ala Leu Ser Asp Ser
145                 150                 155                 160

Pro Asp Gly Arg Pro Gly Gly Phe Trp Arg Arg Trp Gln Pro Arg Ile
                165                 170                 175

Trp Ala Leu Phe Glu Asp Pro Tyr Ser Ser Arg Tyr Ala Arg Tyr Val
            180                 185                 190

Ala Phe Ala Ser Leu Phe Phe Ile Leu Val Ser Ile Thr Thr Phe Cys
        195                 200                 205

Leu Glu Thr His Glu Arg Phe Asn Pro Ile Val Asn Lys Thr Glu Ile
    210                 215                 220

Glu Asn Val Arg Asn Gly Thr Gln Val Arg Tyr Tyr Arg Glu Ala Glu
225                 230                 235                 240

Thr Glu Ala Phe Leu Thr Tyr Ile Glu Gly Val Cys Val Val Trp Phe
                245                 250                 255

Thr Phe Glu Phe Leu Met Arg Val Ile Phe Cys Pro Asn Lys Val Glu
            260                 265                 270

Phe Ile Lys Asn Ser Leu Asn Ile Asp Phe Val Ala Ile Leu Pro
        275                 280                 285

Phe Tyr Leu Glu Val Gly Leu Ser Gly Leu Ser Ser Lys Ala Ala Lys
    290                 295                 300

Asp Val Leu Gly Phe Leu Arg Val Val Arg Phe Val Arg Ile Leu Arg
305                 310                 315                 320

Ile Phe Lys Leu Thr Arg His Phe Val Gly Leu Arg Val Leu Gly His

```
                325                 330                 335
Thr Leu Arg Ala Ser Thr Asn Glu Phe Leu Leu Ile Ile Phe Leu
            340                 345                 350

Ala Leu Gly Val Leu Ile Phe Ala Thr Met Ile Tyr Tyr Ala Glu Arg
            355                 360                 365

Ile Gly Ala Gln Pro Asn Asp Pro Ser Ala Ser Glu His Thr His Phe
        370                 375                 380

Lys Asn Ile Pro Ile Gly Phe Trp Trp Ala Val Val Thr Met Thr Thr
385                 390                 395                 400

Leu Gly Tyr Gly Asp Met Tyr Pro Gln Thr Trp Ser Gly Met Leu Val
                405                 410                 415

Gly Ala Leu Cys Ala Leu Ala Gly Val Leu Thr Ile Ala Met Pro Val
            420                 425                 430

Pro Val Ile Val Asn Asn Phe Gly Met Tyr Tyr Ser Leu Ala Met Ala
            435                 440                 445

Lys Gln Lys Leu Pro Lys Lys Lys Lys His Ile Pro Arg Pro Pro
450                 455                 460

Gln Leu Gly Ser Pro Asn Tyr Cys Lys Ser Val Val Asn Ser Pro His
465                 470                 475                 480

His Ser Thr Gln Ser Asp Thr Cys Pro Leu Ala Gln Glu Glu Ile Leu
                485                 490                 495

Glu Ile Asn Arg Ala Gly Arg Lys Pro Leu Arg Gly Met Ser Ile
                500                 505                 510

<210> SEQ ID NO 27
<211> LENGTH: 613
<212> TYPE: PRT
<213> ORGANISM: Homo sapiens

<400> SEQUENCE: 27

Met Gly Lys Ile Glu Asn Asn Glu Arg Val Ile Leu Asn Val Gly Gly
1               5                   10                  15

Thr Arg His Glu Thr Tyr Arg Ser Thr Leu Lys Thr Leu Pro Gly Thr
                20                  25                  30

Arg Leu Ala Leu Leu Ala Ser Ser Glu Pro Pro Gly Asp Cys Leu Thr
            35                  40                  45

Thr Ala Gly Asp Lys Leu Gln Pro Ser Pro Pro Leu Ser Pro Pro
        50                  55                  60

Pro Arg Ala Pro Pro Leu Ser Pro Gly Pro Gly Gly Cys Phe Glu Gly
65                  70                  75                  80

Gly Ala Gly Asn Cys Ser Ser Arg Gly Arg Ala Ser Asp His Pro
                85                  90                  95

Gly Gly Gly Arg Glu Phe Phe Asp Arg His Pro Gly Val Phe Ala
                100                 105                 110

Tyr Val Leu Asn Tyr Tyr Arg Thr Gly Lys Leu His Cys Pro Ala Asp
            115                 120                 125

Val Cys Gly Pro Leu Phe Glu Glu Glu Leu Ala Phe Trp Gly Ile Asp
        130                 135                 140

Glu Thr Asp Val Glu Pro Cys Cys Trp Met Thr Tyr Arg Gln His Arg
145                 150                 155                 160

Asp Ala Glu Glu Ala Leu Asp Ile Phe Glu Thr Pro Asp Leu Ile Gly
                165                 170                 175

Gly Asp Pro Gly Asp Asp Glu Asp Leu Ala Ala Lys Arg Leu Gly Ile
                180                 185                 190
```

```
Glu Asp Ala Ala Gly Leu Gly Gly Pro Asp Gly Lys Ser Gly Arg Trp
        195                 200                 205

Arg Arg Leu Gln Pro Arg Met Trp Ala Leu Phe Glu Asp Pro Tyr Ser
    210                 215                 220

Ser Arg Ala Ala Arg Phe Ile Ala Phe Ala Ser Leu Phe Phe Ile Leu
225                 230                 235                 240

Val Ser Ile Thr Thr Phe Cys Leu Glu Thr His Glu Ala Phe Asn Ile
                245                 250                 255

Val Lys Asn Lys Thr Glu Pro Val Ile Asn Gly Thr Ser Val Val Leu
            260                 265                 270

Gln Tyr Glu Ile Glu Thr Asp Pro Ala Leu Thr Tyr Val Glu Gly Val
        275                 280                 285

Cys Val Val Trp Phe Thr Phe Glu Phe Leu Val Arg Ile Val Phe Ser
    290                 295                 300

Pro Asn Lys Leu Glu Phe Ile Lys Asn Leu Leu Asn Ile Ile Asp Phe
305                 310                 315                 320

Val Ala Ile Leu Pro Phe Tyr Leu Glu Val Gly Leu Ser Gly Leu Ser
                325                 330                 335

Ser Lys Ala Ala Lys Asp Val Leu Gly Phe Leu Arg Val Val Arg Phe
            340                 345                 350

Val Arg Ile Leu Arg Ile Phe Lys Leu Thr Arg His Phe Val Gly Leu
        355                 360                 365

Arg Val Leu Gly His Thr Leu Arg Ala Ser Thr Asn Glu Phe Leu Leu
    370                 375                 380

Leu Ile Ile Phe Leu Ala Leu Gly Val Leu Ile Phe Ala Thr Met Ile
385                 390                 395                 400

Tyr Tyr Ala Glu Arg Val Gly Ala Gln Pro Asn Asp Pro Ser Ala Ser
                405                 410                 415

Glu His Thr Gln Phe Lys Asn Ile Pro Ile Gly Phe Trp Trp Ala Val
            420                 425                 430

Val Thr Met Thr Thr Leu Gly Tyr Gly Asp Met Tyr Pro Gln Thr Trp
        435                 440                 445

Ser Gly Met Leu Val Gly Ala Leu Cys Ala Leu Ala Gly Val Leu Thr
    450                 455                 460

Ile Ala Met Pro Val Pro Val Ile Val Asn Asn Phe Gly Met Tyr Tyr
465                 470                 475                 480

Ser Leu Ala Met Ala Lys Gln Lys Leu Pro Arg Lys Arg Lys Lys His
                485                 490                 495

Ile Pro Pro Ala Pro Gln Ala Ser Ser Pro Thr Phe Cys Lys Thr Glu
            500                 505                 510

Leu Asn Met Ala Cys Asn Ser Thr Gln Ser Asp Thr Cys Leu Gly Lys
        515                 520                 525

Asp Asn Arg Leu Leu Glu His Asn Arg Ser Val Leu Ser Gly Asp Asp
    530                 535                 540

Ser Thr Gly Ser Glu Pro Pro Leu Ser Pro Glu Arg Leu Pro Ile
545                 550                 555                 560

Arg Arg Ser Ser Thr Arg Asp Lys Asn Arg Arg Gly Glu Thr Cys Phe
                565                 570                 575

Leu Leu Thr Thr Gly Asp Tyr Thr Cys Ala Ser Asp Gly Gly Ile Arg
            580                 585                 590

Lys Asp Asn Cys Lys Glu Val Val Ile Thr Gly Tyr Thr Gln Ala Glu
        595                 600                 605

Ala Arg Ser Leu Thr
```

-continued

<210> SEQ ID NO 28
<211> LENGTH: 638
<212> TYPE: PRT
<213> ORGANISM: Homo sapiens

<400> SEQUENCE: 28

```
Met Gly Lys Ile Glu Asn Asn Glu Arg Val Ile Leu Asn Val Gly Gly
  1               5                  10                  15

Thr Arg His Glu Thr Tyr Arg Ser Thr Leu Lys Thr Leu Pro Gly Thr
             20                  25                  30

Arg Leu Ala Leu Leu Ala Ser Ser Glu Pro Pro Gly Asp Cys Leu Thr
         35                  40                  45

Thr Ala Gly Asp Lys Leu Gln Pro Ser Pro Pro Leu Ser Pro Pro
     50                  55                  60

Pro Arg Ala Pro Pro Leu Ser Pro Gly Pro Gly Cys Phe Glu Gly
 65                  70                  75                  80

Gly Ala Gly Asn Cys Ser Ser Arg Gly Gly Arg Ala Ser Asp His Pro
                 85                  90                  95

Gly Gly Gly Arg Glu Phe Phe Phe Asp Arg His Pro Gly Val Phe Ala
            100                 105                 110

Tyr Val Leu Asn Tyr Tyr Arg Thr Gly Lys Leu His Cys Pro Ala Asp
            115                 120                 125

Val Cys Gly Pro Leu Phe Glu Glu Glu Leu Ala Phe Trp Gly Ile Asp
        130                 135                 140

Glu Thr Asp Val Glu Pro Cys Cys Trp Met Thr Tyr Arg Gln His Arg
145                 150                 155                 160

Asp Ala Glu Glu Ala Leu Asp Ile Phe Glu Thr Pro Asp Leu Ile Gly
                165                 170                 175

Gly Asp Pro Gly Asp Asp Glu Asp Leu Ala Ala Lys Arg Leu Gly Ile
            180                 185                 190

Glu Asp Ala Ala Gly Leu Gly Gly Pro Asp Gly Lys Ser Gly Arg Trp
        195                 200                 205

Arg Arg Leu Gln Pro Arg Met Trp Ala Leu Phe Glu Asp Pro Tyr Ser
    210                 215                 220

Ser Arg Ala Ala Arg Phe Ile Ala Phe Ala Ser Leu Phe Phe Ile Leu
225                 230                 235                 240

Val Ser Ile Thr Thr Phe Cys Leu Glu Thr His Glu Ala Phe Asn Ile
                245                 250                 255

Val Lys Asn Lys Thr Glu Pro Val Ile Asn Gly Thr Ser Val Val Leu
            260                 265                 270

Gln Tyr Glu Ile Glu Thr Asp Pro Ala Leu Thr Tyr Val Glu Gly Val
        275                 280                 285

Cys Val Val Trp Phe Thr Phe Glu Phe Leu Val Arg Ile Val Phe Ser
    290                 295                 300

Pro Asn Lys Leu Glu Phe Ile Lys Asn Leu Leu Asn Ile Ile Asp Phe
305                 310                 315                 320

Val Ala Ile Leu Pro Phe Tyr Leu Glu Val Gly Leu Ser Gly Leu Ser
                325                 330                 335

Ser Lys Ala Ala Lys Asp Val Leu Gly Phe Leu Arg Val Val Arg Phe
            340                 345                 350

Val Arg Ile Leu Arg Ile Phe Lys Leu Thr Arg His Phe Val Gly Leu
        355                 360                 365
```

```
Arg Val Leu Gly His Thr Leu Arg Ala Ser Thr Asn Glu Phe Leu Leu
    370                 375                 380

Leu Ile Ile Phe Leu Ala Leu Gly Val Leu Ile Phe Ala Thr Met Ile
385                 390                 395                 400

Tyr Tyr Ala Glu Arg Val Gly Ala Gln Pro Asn Asp Pro Ser Ala Ser
                405                 410                 415

Glu His Thr Gln Phe Lys Asn Ile Pro Ile Gly Phe Trp Trp Ala Val
                420                 425                 430

Val Thr Met Thr Thr Leu Gly Tyr Gly Asp Met Tyr Pro Gln Thr Trp
                435                 440                 445

Ser Gly Met Leu Val Gly Ala Leu Cys Ala Leu Ala Gly Val Leu Thr
    450                 455                 460

Ile Ala Met Pro Val Pro Val Ile Val Asn Asn Phe Gly Met Tyr Tyr
465                 470                 475                 480

Ser Leu Ala Met Ala Lys Gln Lys Leu Pro Arg Lys Arg Lys Lys His
                485                 490                 495

Ile Pro Pro Ala Pro Gln Ala Ser Ser Pro Thr Phe Cys Lys Thr Glu
                500                 505                 510

Leu Asn Met Ala Cys Asn Ser Thr Gln Ser Asp Thr Cys Leu Gly Lys
    515                 520                 525

Asp Asn Arg Leu Leu Glu His Asn Arg Ser Val Leu Ser Gly Asp Asp
530                 535                 540

Ser Thr Gly Ser Glu Pro Pro Leu Ser Pro Glu Arg Leu Pro Ile
545                 550                 555                 560

Arg Arg Ser Ser Thr Arg Asp Lys Asn Arg Arg Gly Glu Thr Cys Phe
                565                 570                 575

Leu Leu Thr Thr Gly Asp Tyr Thr Cys Ala Ser Asp Gly Gly Ile Arg
                580                 585                 590

Lys Gly Tyr Glu Lys Ser Arg Ser Leu Asn Asn Ile Ala Gly Leu Ala
                595                 600                 605

Gly Asn Ala Leu Arg Leu Ser Pro Val Thr Ser Pro Tyr Asn Ser Pro
    610                 615                 620

Cys Pro Leu Arg Arg Ser Arg Ser Pro Ile Pro Ser Ile Leu
625                 630                 635

<210> SEQ ID NO 29
<211> LENGTH: 558
<212> TYPE: PRT
<213> ORGANISM: Homo sapiens

<400> SEQUENCE: 29

Met Gly Lys Ile Glu Asn Asn Glu Arg Val Ile Leu Asn Val Gly Gly
1               5                   10                  15

Thr Arg His Glu Thr Tyr Arg Ser Thr Leu Lys Thr Leu Pro Gly Thr
                20                  25                  30

Arg Leu Ala Leu Leu Ala Ser Ser Glu Pro Pro Gly Asp Cys Leu Thr
            35                  40                  45

Thr Ala Gly Asp Lys Leu Gln Pro Ser Pro Pro Leu Ser Pro Pro
    50                  55                  60

Pro Arg Ala Pro Pro Leu Ser Pro Gly Pro Gly Cys Phe Glu Gly
65                  70                  75                  80

Gly Ala Gly Asn Cys Ser Ser Arg Gly Arg Ala Ser Asp His Pro
                85                  90                  95

Gly Gly Gly Arg Glu Phe Phe Phe Asp Arg His Pro Gly Val Phe Ala
                100                 105                 110
```

-continued

```
Tyr Val Leu Asn Tyr Tyr Arg Thr Gly Lys Leu His Cys Pro Ala Asp
        115                 120                 125

Val Cys Gly Pro Leu Phe Glu Glu Leu Ala Phe Trp Gly Ile Asp
    130                 135                 140

Glu Thr Asp Val Glu Pro Cys Cys Trp Met Thr Tyr Arg Gln His Arg
145                 150                 155                 160

Asp Ala Glu Glu Ala Leu Asp Ile Phe Glu Thr Pro Asp Leu Ile Gly
                165                 170                 175

Gly Asp Pro Gly Asp Asp Glu Asp Leu Ala Ala Lys Arg Leu Gly Ile
            180                 185                 190

Glu Asp Ala Ala Gly Leu Gly Gly Pro Asp Gly Lys Ser Gly Arg Trp
        195                 200                 205

Arg Arg Leu Gln Pro Arg Met Trp Ala Leu Phe Glu Asp Pro Tyr Ser
    210                 215                 220

Ser Arg Ala Ala Arg Phe Ile Ala Phe Ala Ser Leu Phe Phe Ile Leu
225                 230                 235                 240

Val Ser Ile Thr Thr Phe Cys Leu Glu Thr His Glu Ala Phe Asn Ile
                245                 250                 255

Val Lys Asn Lys Thr Glu Pro Val Ile Asn Gly Thr Ser Val Val Leu
            260                 265                 270

Gln Tyr Glu Ile Glu Thr Asp Pro Ala Leu Thr Tyr Val Glu Gly Val
        275                 280                 285

Cys Val Val Trp Phe Thr Phe Glu Phe Leu Val Arg Ile Val Phe Ser
    290                 295                 300

Pro Asn Lys Leu Glu Phe Ile Lys Asn Leu Leu Asn Ile Ile Asp Phe
305                 310                 315                 320

Val Ala Ile Leu Pro Phe Tyr Leu Glu Val Gly Leu Ser Gly Leu Ser
                325                 330                 335

Ser Lys Ala Ala Lys Asp Val Leu Gly Phe Leu Arg Val Val Arg Phe
            340                 345                 350

Val Arg Ile Leu Arg Ile Phe Lys Leu Thr Arg His Phe Val Gly Leu
        355                 360                 365

Arg Val Leu Gly His Thr Leu Arg Ala Ser Thr Asn Glu Phe Leu Leu
    370                 375                 380

Leu Ile Ile Phe Leu Ala Leu Gly Val Leu Ile Phe Ala Thr Met Ile
385                 390                 395                 400

Tyr Tyr Ala Glu Arg Val Gly Ala Gln Pro Asn Asp Pro Ser Ala Ser
                405                 410                 415

Glu His Thr Gln Phe Lys Asn Ile Pro Ile Gly Phe Trp Trp Ala Val
            420                 425                 430

Val Thr Met Thr Thr Leu Gly Tyr Gly Asp Met Tyr Pro Gln Thr Trp
        435                 440                 445

Ser Gly Met Leu Val Gly Ala Leu Cys Ala Leu Ala Gly Val Leu Thr
    450                 455                 460

Ile Ala Met Pro Val Pro Val Ile Val Asn Asn Phe Gly Met Tyr Tyr
465                 470                 475                 480

Ser Leu Ala Met Ala Lys Gln Lys Leu Pro Arg Lys Arg Lys Lys His
                485                 490                 495

Ile Pro Pro Ala Pro Gln Ala Ser Ser Pro Thr Phe Cys Lys Thr Glu
            500                 505                 510

Leu Asn Met Ala Cys Asn Ser Thr Gln Ser Asp Thr Cys Leu Gly Lys
        515                 520                 525
```

-continued

```
Asp Asn Arg Leu Leu Glu His Asn Arg Ser Asp Asn Cys Lys Glu Val
    530                 535                 540

Val Ile Thr Gly Tyr Thr Gln Ala Glu Ala Arg Ser Leu Thr
545                 550                 555

<210> SEQ ID NO 30
<211> LENGTH: 757
<212> TYPE: PRT
<213> ORGANISM: Homo sapiens

<400> SEQUENCE: 30

Met Leu Ser Ser Val Cys Val Ser Ser Phe Arg Gly Arg Gln Gly Ala
  1               5                  10                  15

Ser Lys Gln Gln Pro Ala Pro Pro Gln Pro Pro Glu Ser Pro Pro
             20                  25                  30

Pro Pro Pro Leu Pro Pro Gln Gln Gln Gln Pro Ala Gln Pro Gly Pro
             35                  40                  45

Ala Ala Ser Pro Ala Gly Pro Pro Ala Pro Arg Gly Pro Gly Asp Arg
 50                  55                  60

Arg Ala Glu Pro Cys Pro Gly Leu Pro Ala Ala Met Gly Arg His
 65                  70                  75                  80

Gly Gly Gly Gly Gly Asp Ser Gly Lys Ile Val Ile Asn Val Gly Gly
                 85                  90                  95

Val Arg His Glu Thr Tyr Arg Ser Thr Leu Arg Thr Leu Pro Gly Thr
                100                 105                 110

Arg Leu Ala Gly Leu Thr Glu Pro Glu Ala Ala Ala Arg Phe Asp Tyr
            115                 120                 125

Asp Pro Gly Ala Asp Glu Phe Phe Phe Asp Arg His Pro Gly Val Phe
130                 135                 140

Ala Tyr Val Leu Asn Tyr Tyr Arg Thr Gly Lys Leu His Cys Pro Ala
145                 150                 155                 160

Asp Val Cys Gly Pro Leu Phe Glu Glu Glu Leu Gly Phe Trp Gly Ile
                165                 170                 175

Asp Glu Thr Asp Val Glu Ala Cys Cys Trp Met Thr Tyr Arg Gln His
                180                 185                 190

Arg Asp Ala Glu Glu Ala Leu Asp Ser Phe Glu Ala Pro Asp Pro Ala
            195                 200                 205

Gly Ala Ala Asn Ala Ala Asn Ala Ala Gly Ala His Asp Gly Gly Leu
210                 215                 220

Asp Asp Glu Ala Gly Ala Gly Gly Gly Leu Asp Gly Ala Gly Gly
225                 230                 235                 240

Glu Leu Lys Arg Leu Cys Phe Gln Asp Ala Gly Gly Ala Gly Gly
                245                 250                 255

Pro Pro Gly Gly Ala Gly Gly Ala Gly Gly Thr Trp Trp Arg Arg Trp
            260                 265                 270

Gln Pro Arg Val Trp Ala Leu Phe Glu Asp Pro Tyr Ser Ser Arg Ala
        275                 280                 285

Ala Arg Tyr Val Ala Phe Ala Ser Leu Phe Phe Ile Leu Ile Ser Ile
    290                 295                 300

Thr Thr Phe Cys Leu Glu Thr His Glu Gly Phe Ile His Ile Ser Asn
305                 310                 315                 320

Lys Thr Val Thr Gln Ala Ser Pro Ile Pro Gly Ala Pro Pro Glu Asn
                325                 330                 335

Ile Thr Asn Val Glu Val Glu Thr Glu Pro Phe Leu Thr Tyr Val Glu
            340                 345                 350
```

```
Gly Val Cys Val Val Trp Phe Thr Phe Glu Phe Leu Met Arg Ile Thr
        355                 360                 365

Phe Cys Pro Asp Lys Val Glu Phe Leu Lys Ser Ser Leu Asn Ile Ile
        370                 375                 380

Asp Cys Val Ala Ile Leu Pro Phe Tyr Leu Glu Val Gly Leu Ser Gly
385                 390                 395                 400

Leu Ser Ser Lys Ala Ala Lys Asp Val Leu Gly Phe Leu Arg Val Val
                405                 410                 415

Arg Phe Val Arg Ile Leu Arg Ile Phe Lys Leu Thr Arg His Phe Val
                420                 425                 430

Gly Leu Arg Val Leu Gly His Thr Leu Arg Ala Ser Thr Asn Glu Phe
                435                 440                 445

Leu Leu Leu Ile Ile Phe Leu Ala Leu Gly Val Leu Ile Phe Ala Thr
        450                 455                 460

Met Ile Tyr Tyr Ala Glu Arg Ile Gly Ala Asp Pro Asp Asp Ile Leu
465                 470                 475                 480

Gly Ser Asn His Thr Tyr Phe Lys Asn Ile Pro Ile Gly Phe Trp Trp
                485                 490                 495

Ala Val Val Thr Met Thr Thr Leu Gly Tyr Gly Asp Met Tyr Pro Lys
                500                 505                 510

Thr Trp Ser Gly Met Leu Val Gly Ala Leu Cys Ala Leu Ala Gly Val
        515                 520                 525

Leu Thr Ile Ala Met Pro Val Pro Val Ile Val Asn Asn Phe Gly Met
        530                 535                 540

Tyr Tyr Ser Leu Ala Met Ala Lys Gln Lys Leu Pro Lys Lys Lys Asn
545                 550                 555                 560

Lys His Ile Pro Arg Pro Pro Gln Pro Gly Ser Pro Asn Tyr Cys Lys
                565                 570                 575

Pro Asp Pro Pro Pro Pro Pro Pro His Pro His His Gly Ser Gly
                580                 585                 590

Gly Ile Ser Pro Pro Pro Ile Thr Pro Pro Ser Met Gly Val Thr
                595                 600                 605

Val Ala Gly Ala Tyr Pro Ala Gly Pro His Thr His Pro Gly Leu Leu
        610                 615                 620

Arg Gly Gly Ala Gly Leu Gly Ile Met Gly Leu Pro Pro Leu Pro
625                 630                 635                 640

Ala Pro Gly Glu Pro Cys Pro Leu Ala Gln Glu Glu Val Ile Glu Ile
                645                 650                 655

Asn Arg Ala Asp Pro Arg Pro Asn Gly Asp Pro Ala Ala Ala Leu
                660                 665                 670

Ala His Glu Asp Cys Pro Ala Ile Asp Gln Pro Ala Met Ser Pro Glu
        675                 680                 685

Asp Lys Ser Pro Ile Thr Pro Gly Ser Arg Gly Arg Tyr Ser Arg Asp
                690                 695                 700

Arg Ala Cys Phe Leu Leu Thr Asp Tyr Ala Pro Ser Pro Asp Gly Ser
705                 710                 715                 720

Ile Arg Lys Ala Thr Gly Ala Pro Pro Leu Pro Pro Gln Asp Trp Arg
                725                 730                 735

Lys Pro Gly Pro Pro Ser Phe Leu Pro Asp Leu Asn Ala Asn Ala Ala
                740                 745                 750

Ala Trp Ile Ser Pro
        755
```

```
<210> SEQ ID NO 31
<211> LENGTH: 635
<212> TYPE: PRT
<213> ORGANISM: Homo sapiens

<400> SEQUENCE: 31

Met Ile Ser Ser Val Cys Val Ser Ser Tyr Arg Gly Arg Lys Ser Gly
 1               5                  10                  15

Asn Lys Pro Pro Ser Lys Thr Cys Leu Lys Glu Met Ala Lys Gly
                20                  25                  30

Glu Ala Ser Glu Lys Ile Ile Ile Asn Val Gly Gly Thr Arg His Glu
         35                  40                  45

Thr Tyr Arg Ser Thr Leu Arg Thr Leu Pro Gly Thr Arg Leu Ala Trp
     50                  55                  60

Leu Ala Asp Pro Asp Gly Gly Arg Pro Glu Thr Asp Gly Gly Gly
 65                  70                  75                  80

Val Gly Ser Ser Gly Ser Gly Gly Gly Cys Glu Phe Phe Phe
                 85                  90                  95

Asp Arg His Pro Gly Val Phe Ala Tyr Val Leu Asn Tyr Tyr Arg Thr
                100                 105                 110

Gly Lys Leu His Cys Pro Ala Asp Val Cys Gly Pro Leu Phe Glu Glu
            115                 120                 125

Glu Leu Thr Phe Trp Gly Ile Asp Glu Thr Asp Val Glu Pro Cys Cys
        130                 135                 140

Trp Met Thr Tyr Arg Gln His Arg Asp Ala Glu Glu Ala Leu Asp Ile
145                 150                 155                 160

Phe Glu Ser Pro Asp Gly Gly Ser Gly Ala Gly Pro Ser Asp Glu
                165                 170                 175

Ala Gly Asp Asp Glu Arg Glu Leu Ala Leu Gln Arg Leu Gly Pro His
                180                 185                 190

Glu Gly Gly Ala Gly His Gly Ala Gly Ser Gly Gly Cys Arg Gly Trp
            195                 200                 205

Gln Pro Arg Met Trp Ala Leu Phe Glu Asp Pro Tyr Ser Ser Arg Ala
        210                 215                 220

Ala Arg Val Val Ala Phe Ala Ser Leu Phe Phe Ile Leu Val Ser Ile
225                 230                 235                 240

Thr Thr Phe Cys Leu Glu Thr His Glu Ala Phe Asn Ile Asp Arg Asn
                245                 250                 255

Val Thr Glu Ile Leu Arg Val Gly Asn Ile Thr Ser Val His Phe Arg
                260                 265                 270

Arg Glu Val Glu Thr Glu Pro Ile Leu Thr Tyr Ile Glu Gly Val Cys
            275                 280                 285

Val Leu Trp Phe Thr Leu Glu Phe Leu Val Arg Ile Val Cys Cys Pro
        290                 295                 300

Asp Thr Leu Asp Phe Val Lys Asn Leu Leu Asn Ile Ile Asp Phe Val
305                 310                 315                 320

Ala Ile Leu Pro Phe Tyr Leu Glu Val Gly Leu Ser Gly Leu Ser Ser
                325                 330                 335

Lys Ala Ala Arg Asp Val Leu Gly Phe Leu Arg Val Val Arg Phe Val
                340                 345                 350

Arg Ile Leu Arg Ile Phe Lys Leu Thr Arg His Phe Val Gly Leu Arg
            355                 360                 365

Val Leu Gly His Thr Leu Arg Ala Ser Thr Asn Glu Phe Leu Leu Leu
        370                 375                 380
```

Ile Ile Phe Leu Ala Leu Gly Val Leu Ile Phe Ala Thr Met Ile Tyr
385                 390                 395                 400

Tyr Ala Glu Arg Ile Ala Arg Pro Ser Asp Pro Arg Gly Asn Asp
            405                 410                 415

His Thr Asp Phe Lys Asn Ile Pro Ile Gly Phe Trp Trp Ala Val Val
            420                 425                 430

Thr Met Thr Thr Leu Gly Tyr Gly Asp Met Tyr Pro Lys Thr Trp Ser
            435                 440                 445

Gly Met Leu Val Gly Ala Leu Cys Ala Leu Ala Gly Val Leu Thr Ile
    450                 455                 460

Ala Met Pro Val Pro Val Ile Val Asn Asn Phe Gly Met Tyr Tyr Ser
465                 470                 475                 480

Leu Ala Met Ala Lys Gln Lys Leu Pro Lys Lys Arg Lys Lys His Val
                485                 490                 495

Pro Arg Pro Ala Gln Leu Glu Ser Pro Met Tyr Cys Lys Ser Glu Glu
                500                 505                 510

Thr Ser Pro Arg Asp Ser Thr Cys Ser Asp Thr Ser Pro Pro Ala Arg
            515                 520                 525

Glu Glu Gly Met Ile Glu Arg Lys Arg Ala Asp Ser Lys Gln Asn Gly
530                 535                 540

Asp Ala Asn Ala Val Leu Ser Asp Glu Glu Gly Ala Gly Leu Thr Gln
545                 550                 555                 560

Pro Leu Ala Ser Ser Pro Thr Pro Glu Glu Arg Arg Ala Leu Arg Arg
                565                 570                 575

Ser Thr Thr Arg Asp Arg Asn Lys Lys Ala Ala Ala Cys Phe Leu Leu
            580                 585                 590

Ser Thr Gly Asp Tyr Ala Cys Ala Asp Gly Ser Val Arg Lys Gly Thr
            595                 600                 605

Phe Val Leu Arg Asp Leu Pro Leu Gln His Ser Pro Glu Ala Ala Cys
            610                 615                 620

Pro Pro Thr Ala Gly Thr Leu Phe Leu Pro His
625                 630                 635

<210> SEQ ID NO 32
<211> LENGTH: 582
<212> TYPE: PRT
<213> ORGANISM: Homo sapiens

<400> SEQUENCE: 32

Met Ile Ser Ser Val Cys Val Ser Ser Tyr Arg Gly Arg Lys Ser Gly
1               5                   10                  15

Asn Lys Pro Pro Ser Lys Thr Cys Leu Lys Glu Glu Met Ala Lys Gly
            20                  25                  30

Glu Ala Ser Glu Lys Ile Ile Ile Asn Val Gly Gly Thr Arg His Glu
        35                  40                  45

Thr Tyr Arg Ser Thr Leu Arg Thr Leu Pro Gly Thr Arg Leu Ala Trp
    50                  55                  60

Leu Ala Asp Pro Asp Gly Gly Arg Pro Glu Thr Asp Gly Gly Gly
65                  70                  75                  80

Val Gly Ser Ser Gly Ser Ser Gly Gly Gly Cys Glu Phe Phe
                85                  90                  95

Asp Arg His Pro Gly Val Phe Ala Tyr Val Leu Asn Tyr Tyr Arg Thr
            100                 105                 110

Gly Lys Leu His Cys Pro Ala Asp Val Cys Gly Pro Leu Phe Glu Glu

-continued

```
                115                 120                 125
Glu Leu Thr Phe Trp Gly Ile Asp Glu Thr Asp Val Glu Pro Cys Cys
    130                 135                 140

Trp Met Thr Tyr Arg Gln His Arg Asp Ala Glu Glu Ala Leu Asp Ile
145                 150                 155                 160

Phe Glu Ser Pro Asp Gly Gly Ser Gly Ala Gly Pro Ser Asp Glu
                165                 170                 175

Ala Gly Asp Asp Glu Arg Glu Leu Ala Leu Gln Arg Leu Gly Pro His
            180                 185                 190

Glu Gly Gly Ala Gly His Gly Ala Gly Ser Gly Gly Cys Arg Gly Trp
        195                 200                 205

Gln Pro Arg Met Trp Ala Leu Phe Glu Asp Pro Tyr Ser Ser Arg Ala
    210                 215                 220

Ala Arg Val Val Ala Phe Ala Ser Leu Phe Phe Ile Leu Val Ser Ile
225                 230                 235                 240

Thr Thr Phe Cys Leu Glu Thr His Glu Ala Phe Asn Ile Asp Arg Asn
                245                 250                 255

Val Thr Glu Ile Leu Arg Val Gly Asn Ile Thr Ser Val His Phe Arg
            260                 265                 270

Arg Glu Val Glu Thr Glu Pro Ile Leu Thr Tyr Ile Glu Gly Val Cys
        275                 280                 285

Val Leu Trp Phe Thr Leu Glu Phe Leu Val Arg Ile Val Cys Cys Pro
    290                 295                 300

Asp Thr Leu Asp Phe Val Lys Asn Leu Leu Asn Ile Ile Asp Phe Val
305                 310                 315                 320

Ala Ile Leu Pro Phe Tyr Leu Glu Val Gly Leu Ser Gly Leu Ser Ser
                325                 330                 335

Lys Ala Ala Arg Asp Val Leu Gly Phe Leu Arg Val Val Arg Phe Val
            340                 345                 350

Arg Ile Leu Arg Ile Phe Lys Leu Thr Arg His Phe Val Gly Leu Arg
        355                 360                 365

Val Leu Gly His Thr Leu Arg Ala Ser Thr Asn Glu Phe Leu Leu Leu
    370                 375                 380

Ile Ile Phe Leu Ala Leu Gly Val Leu Ile Phe Ala Thr Met Ile Tyr
385                 390                 395                 400

Tyr Ala Glu Arg Ile Gly Ala Arg Pro Ser Asp Pro Arg Gly Asn Asp
                405                 410                 415

His Thr Asp Phe Lys Asn Ile Pro Ile Gly Phe Trp Trp Ala Val Val
            420                 425                 430

Thr Met Thr Thr Leu Gly Tyr Gly Asp Met Tyr Pro Lys Thr Trp Ser
        435                 440                 445

Gly Met Leu Val Gly Ala Leu Cys Ala Leu Ala Gly Val Leu Thr Ile
    450                 455                 460

Ala Met Pro Val Pro Val Ile Val Asn Asn Phe Gly Met Tyr Tyr Ser
465                 470                 475                 480

Leu Ala Met Ala Lys Gln Lys Leu Pro Lys Arg Lys Lys His Val
                485                 490                 495

Pro Arg Pro Ala Gln Leu Glu Ser Pro Met Tyr Cys Lys Ser Glu Glu
            500                 505                 510

Thr Ser Pro Arg Asp Ser Thr Cys Ser Asp Thr Ser Pro Pro Ala Arg
        515                 520                 525

Glu Glu Gly Met Ile Glu Arg Lys Arg Ala Gly Glu Ile Arg Gly Trp
    530                 535                 540
```

Glu Gly Lys Ser Leu Phe Pro Gln Trp Pro Arg Glu Phe Pro Asn Gly
545                 550                 555                 560

Pro Gln Thr Leu Gly Phe Gly Met Cys Phe Val Trp Gly Phe Pro Lys
                565                 570                 575

His Lys Asp Val Pro Leu
            580

<210> SEQ ID NO 33
<211> LENGTH: 647
<212> TYPE: PRT
<213> ORGANISM: Homo sapiens

<400> SEQUENCE: 33

Met Ala Gly Leu Ala Thr Trp Leu Pro Phe Ala Arg Ala Ala Ala
1               5                   10                  15

Val Gly Trp Leu Pro Leu Ala Gln Gln Pro Leu Pro Pro Ala Pro Gly
            20                  25                  30

Val Lys Ala Ser Arg Gly Asp Glu Val Leu Val Val Asn Val Ser Gly
        35                  40                  45

Arg Arg Phe Glu Thr Trp Lys Asn Thr Leu Asp Arg Tyr Pro Asp Thr
    50                  55                  60

Leu Leu Gly Ser Ser Glu Lys Glu Phe Phe Tyr Asp Ala Asp Ser Gly
65                  70                  75                  80

Glu Tyr Phe Phe Asp Arg Asp Pro Asp Met Phe Arg His Val Leu Asn
                85                  90                  95

Phe Tyr Arg Thr Gly Arg Leu His Cys Pro Arg Gln Glu Cys Ile Gln
            100                 105                 110

Ala Phe Asp Glu Glu Leu Ala Phe Tyr Gly Leu Val Pro Glu Leu Val
        115                 120                 125

Gly Asp Cys Cys Leu Glu Glu Tyr Arg Asp Arg Lys Lys Glu Asn Ala
    130                 135                 140

Glu Arg Leu Ala Glu Asp Glu Glu Ala Glu Gln Ala Gly Asp Gly Pro
145                 150                 155                 160

Ala Leu Pro Ala Gly Ser Ser Leu Arg Gln Arg Leu Trp Arg Ala Phe
                165                 170                 175

Glu Asn Pro His Thr Ser Thr Ala Ala Leu Val Phe Tyr Tyr Val Thr
            180                 185                 190

Gly Phe Phe Ile Ala Val Ser Val Ile Ala Asn Val Val Glu Thr Ile
        195                 200                 205

Pro Cys Arg Gly Ser Ala Arg Arg Ser Ser Arg Glu Gln Pro Cys Gly
    210                 215                 220

Glu Arg Phe Pro Gln Ala Phe Phe Cys Met Asp Thr Ala Cys Val Leu
225                 230                 235                 240

Ile Phe Thr Gly Glu Tyr Leu Leu Arg Leu Phe Ala Ala Pro Ser Arg
                245                 250                 255

Cys Arg Phe Leu Arg Ser Val Met Ser Leu Ile Asp Val Val Ala Ile
            260                 265                 270

Leu Pro Tyr Tyr Ile Gly Leu Leu Val Pro Lys Asn Asp Asp Val Ser
        275                 280                 285

Gly Ala Phe Val Thr Leu Arg Val Phe Arg Val Phe Arg Ile Phe Lys
    290                 295                 300

Phe Ser Arg His Ser Gln Gly Leu Arg Ile Leu Gly Tyr Thr Leu Lys
305                 310                 315                 320

Ser Cys Ala Ser Glu Leu Gly Phe Leu Leu Phe Ser Leu Thr Met Ala

```
                325                 330                 335
Ile Ile Ile Phe Ala Thr Val Met Phe Tyr Ala Glu Lys Gly Thr Asn
            340                 345                 350

Lys Thr Asn Phe Thr Ser Ile Pro Ala Ala Phe Trp Tyr Thr Ile Val
        355                 360                 365

Thr Met Thr Thr Leu Gly Tyr Gly Asp Met Val Pro Ser Thr Ile Ala
    370                 375                 380

Gly Lys Ile Phe Gly Ser Ile Cys Ser Leu Ser Gly Val Leu Val Ile
385                 390                 395                 400

Ala Leu Pro Val Pro Val Ile Val Ser Asn Phe Ser Arg Ile Tyr His
            405                 410                 415

Gln Asn Gln Arg Ala Asp Lys Arg Ala Gln Gln Lys Val Arg Leu
        420                 425                 430

Ala Arg Ile Arg Leu Ala Lys Ser Gly Thr Thr Asn Ala Phe Leu Gln
    435                 440                 445

Tyr Lys Gln Asn Gly Gly Leu Glu Asp Ser Gly Ser Gly Glu Glu Gln
450                 455                 460

Ala Leu Cys Val Arg Asn Arg Ser Ala Phe Glu Gln Gln His His His
465                 470                 475                 480

Leu Leu His Cys Leu Glu Lys Thr Thr Cys His Glu Phe Thr Asp Glu
            485                 490                 495

Leu Thr Phe Ser Glu Ala Leu Gly Ala Val Ser Pro Gly Gly Arg Thr
        500                 505                 510

Ser Arg Ser Thr Ser Val Ser Ser Gln Pro Val Gly Pro Gly Ser Leu
    515                 520                 525

Leu Ser Ser Cys Cys Pro Arg Arg Ala Lys Arg Arg Ala Ile Arg Leu
530                 535                 540

Ala Asn Ser Thr Ala Ser Val Ser Arg Gly Ser Met Gln Glu Leu Asp
545                 550                 555                 560

Met Leu Ala Gly Leu Arg Arg Ser His Ala Pro Gln Ser Arg Ser Ser
            565                 570                 575

Leu Asn Ala Lys Pro His Asp Ser Leu Asp Leu Asn Cys Asp Ser Arg
        580                 585                 590

Asp Phe Val Ala Ala Ile Ile Ser Ile Pro Thr Pro Pro Ala Asn Thr
    595                 600                 605

Pro Asp Glu Ser Gln Pro Ser Ser Pro Gly Gly Gly Arg Ala Gly
610                 615                 620

Ser Thr Leu Arg Asn Ser Ser Leu Gly Thr Pro Cys Leu Phe Pro Glu
625                 630                 635                 640

Thr Val Lys Ile Ser Ser Leu
            645

<210> SEQ ID NO 34
<211> LENGTH: 630
<212> TYPE: PRT
<213> ORGANISM: Homo sapiens

<400> SEQUENCE: 34

Met Ala Ala Gly Val Ala Ala Trp Leu Pro Phe Ala Arg Ala Ala Ala
1               5                   10                  15

Ile Gly Trp Met Pro Val Ala Ser Gly Pro Met Pro Ala Pro Pro Arg
            20                  25                  30

Gln Glu Arg Lys Arg Thr Gln Asp Ala Leu Ile Val Leu Asn Val Ser
        35                  40                  45
```

-continued

```
Gly Thr Arg Phe Gln Thr Trp Gln Asp Thr Leu Glu Arg Tyr Pro Asp
        50                  55                  60

Thr Leu Leu Gly Ser Ser Glu Arg Asp Phe Phe Tyr His Pro Glu Thr
 65                  70                  75                  80

Gln Gln Tyr Phe Phe Asp Arg Asp Pro Asp Ile Phe Arg His Ile Leu
                     85                  90                  95

Asn Phe Tyr Arg Thr Gly Lys Leu His Tyr Pro Arg His Glu Cys Ile
                100                 105                 110

Ser Ala Tyr Asp Glu Glu Leu Ala Phe Phe Gly Leu Ile Pro Glu Ile
                115                 120                 125

Ile Gly Asp Cys Cys Tyr Glu Glu Tyr Lys Asp Arg Arg Arg Glu Asn
        130                 135                 140

Ala Glu Arg Leu Gln Asp Asp Ala Asp Thr Asp Thr Ala Gly Glu Ser
145                 150                 155                 160

Ala Leu Pro Thr Met Thr Ala Arg Gln Arg Val Trp Arg Ala Phe Glu
                165                 170                 175

Asn Pro His Thr Ser Thr Met Ala Leu Val Phe Tyr Tyr Val Thr Gly
                180                 185                 190

Phe Phe Ile Ala Val Ser Val Ile Ala Asn Val Val Glu Thr Val Pro
                195                 200                 205

Cys Gly Ser Ser Pro Gly His Ile Lys Glu Leu Pro Cys Gly Glu Arg
        210                 215                 220

Tyr Ala Val Ala Phe Phe Cys Leu Asp Thr Ala Cys Val Met Ile Phe
225                 230                 235                 240

Thr Val Glu Tyr Leu Leu Arg Leu Ala Ala Ala Pro Ser Arg Tyr Arg
                245                 250                 255

Phe Val Arg Ser Val Met Ser Ile Ile Asp Val Val Ala Ile Leu Pro
                260                 265                 270

Tyr Tyr Ile Gly Leu Val Met Thr Asp Asn Glu Asp Val Ser Gly Ala
                275                 280                 285

Phe Val Thr Leu Arg Val Phe Arg Val Phe Arg Ile Phe Lys Phe Ser
                290                 295                 300

Arg His Ser Gln Gly Leu Arg Ile Leu Gly Tyr Thr Leu Lys Ser Cys
305                 310                 315                 320

Ala Ser Glu Leu Gly Phe Leu Leu Phe Ser Leu Thr Met Ala Ile Ile
                325                 330                 335

Ile Phe Ala Thr Val Met Phe Tyr Ala Glu Lys Gly Ser Ser Ala Ser
                340                 345                 350

Lys Phe Thr Ser Ile Pro Ala Ala Phe Trp Tyr Thr Ile Val Thr Met
                355                 360                 365

Thr Thr Leu Gly Tyr Gly Asp Met Val Pro Lys Thr Ile Ala Gly Lys
                370                 375                 380

Ile Phe Gly Ser Ile Cys Ser Leu Ser Gly Val Leu Val Ile Ala Leu
385                 390                 395                 400

Pro Val Pro Val Ile Val Ser Asn Phe Ser Arg Ile Tyr His Gln Asn
                405                 410                 415

Gln Arg Ala Asp Lys Arg Arg Ala Gln Lys Lys Ala Arg Leu Ala Arg
                420                 425                 430

Ile Arg Ala Ala Lys Ser Gly Ser Ala Asn Ala Tyr Met Gln Ser Lys
                435                 440                 445

Arg Asn Gly Leu Leu Ser Asn Gln Leu Gln Ser Ser Glu Asp Glu Gln
            450                 455                 460

Ala Phe Val Ser Lys Ser Gly Ser Ser Phe Glu Thr Gln His His His
```

-continued

```
              465                 470                 475                 480
Leu Leu His Cys Leu Glu Lys Thr Thr Asn His Glu Phe Val Asp Glu
                    485                 490                 495

Gln Val Phe Glu Glu Ser Cys Met Glu Val Ala Thr Val Asn Arg Pro
                500                 505                 510

Ser Ser His Ser Pro Ser Leu Ser Ser Gln Gln Gly Val Thr Ser Thr
                515                 520                 525

Cys Cys Ser Arg Arg His Lys Lys Thr Phe Arg Ile Pro Asn Ala Asn
            530                 535                 540

Val Ser Gly Ser His Gln Gly Ser Ile Gln Glu Leu Ser Thr Ile Gln
545                 550                 555                 560

Ile Arg Cys Val Glu Arg Thr Pro Leu Ser Asn Ser Arg Ser Ser Leu
                565                 570                 575

Asn Ala Lys Met Glu Glu Cys Val Lys Leu Asn Cys Glu Gln Pro Tyr
                580                 585                 590

Val Thr Thr Ala Ile Ile Ser Ile Pro Thr Pro Pro Val Thr Thr Pro
                595                 600                 605

Glu Gly Asp Asp Arg Pro Glu Ser Pro Glu Tyr Ser Gly Gly Asn Ile
            610                 615                 620

Val Arg Val Ser Ala Leu
625                 630

<210> SEQ ID NO 35
<211> LENGTH: 655
<212> TYPE: PRT
<213> ORGANISM: Homo sapiens

<400> SEQUENCE: 35

Met Ala Ala Gly Val Ala Ala Trp Leu Pro Phe Ala Arg Ala Ala Ala
1               5                   10                  15

Ile Gly Trp Met Pro Val Ala Asn Cys Pro Met Pro Leu Ala Pro Ala
                20                  25                  30

Asp Lys Asn Lys Arg Gln Asp Glu Leu Ile Val Leu Asn Val Ser Gly
            35                  40                  45

Arg Arg Phe Gln Thr Trp Arg Thr Thr Leu Glu Arg Tyr Pro Asp Thr
50                  55                  60

Leu Leu Gly Ser Thr Glu Lys Glu Phe Phe Asn Glu Asp Thr Lys
65                  70                  75                  80

Glu Tyr Phe Phe Asp Arg Asp Pro Glu Val Phe Arg Cys Val Leu Asn
                85                  90                  95

Phe Tyr Arg Thr Gly Lys Leu His Tyr Pro Arg Tyr Glu Cys Ile Ser
                100                 105                 110

Ala Tyr Asp Asp Glu Leu Ala Phe Tyr Gly Ile Leu Pro Glu Ile Ile
            115                 120                 125

Gly Asp Cys Cys Tyr Glu Glu Tyr Lys Asp Arg Lys Arg Glu Asn Ala
            130                 135                 140

Glu Arg Leu Met Asp Asp Asn Asp Ser Glu Asn Asn Gln Glu Ser Met
145                 150                 155                 160

Pro Ser Leu Ser Phe Arg Gln Thr Met Trp Arg Ala Phe Glu Asn Pro
                165                 170                 175

His Thr Ser Thr Leu Ala Leu Val Phe Tyr Tyr Val Thr Gly Phe Phe
            180                 185                 190

Ile Ala Val Ser Val Ile Thr Asn Val Val Glu Thr Val Pro Cys Gly
            195                 200                 205
```

-continued

```
Thr Val Pro Gly Ser Lys Glu Leu Pro Cys Gly Arg Tyr Ser Val
    210                 215                 220

Ala Phe Phe Cys Leu Asp Thr Ala Cys Val Met Ile Phe Thr Val Glu
225                 230                 235                 240

Tyr Leu Leu Arg Leu Phe Ala Ala Pro Ser Arg Tyr Arg Phe Ile Arg
                245                 250                 255

Ser Val Met Ser Ile Ile Asp Val Val Ala Ile Met Pro Tyr Tyr Ile
                260                 265                 270

Gly Leu Val Met Thr Asn Asn Glu Asp Val Ser Gly Ala Phe Val Thr
                275                 280                 285

Leu Arg Val Phe Arg Val Phe Arg Ile Phe Lys Phe Ser Arg His Ser
    290                 295                 300

Gln Gly Leu Arg Ile Leu Gly Tyr Thr Leu Lys Ser Cys Ala Ser Glu
305                 310                 315                 320

Leu Gly Phe Leu Leu Phe Ser Leu Thr Met Ala Ile Ile Ile Phe Ala
                325                 330                 335

Thr Val Met Phe Tyr Ala Glu Lys Gly Ser Ser Ala Ser Lys Phe Thr
                340                 345                 350

Ser Ile Pro Ala Ser Phe Trp Tyr Thr Ile Val Thr Met Thr Thr Leu
    355                 360                 365

Gly Tyr Gly Asp Met Val Pro Lys Thr Ile Ala Gly Lys Ile Phe Gly
370                 375                 380

Ser Ile Cys Ser Leu Ser Gly Val Leu Val Ile Ala Leu Pro Val Pro
385                 390                 395                 400

Val Ile Val Ser Asn Phe Ser Arg Ile Tyr His Gln Asn Gln Arg Ala
                405                 410                 415

Asp Lys Arg Arg Ala Gln Lys Lys Ala Arg Leu Ala Arg Ile Arg Val
                420                 425                 430

Ala Lys Thr Gly Ser Ser Asn Ala Tyr Leu His Ser Lys Arg Asn Gly
                435                 440                 445

Leu Leu Asn Glu Ala Leu Glu Leu Thr Gly Thr Pro Glu Glu Glu His
    450                 455                 460

Met Gly Lys Thr Thr Ser Leu Ile Glu Ser Gln His His His Leu Leu
465                 470                 475                 480

His Cys Leu Glu Lys Thr Thr Gly Leu Ser Tyr Leu Val Asp Asp Pro
                485                 490                 495

Leu Leu Ser Val Arg Thr Ser Thr Ile Lys Asn His Glu Phe Ile Asp
                500                 505                 510

Glu Gln Met Phe Glu Gln Asn Cys Met Glu Ser Ser Met Gln Asn Tyr
    515                 520                 525

Pro Ser Thr Arg Ser Pro Ser Leu Ser Ser His Pro Gly Leu Thr Thr
    530                 535                 540

Thr Cys Cys Ser Arg Arg Ser Lys Lys Thr Thr His Leu Pro Asn Ser
545                 550                 555                 560

Asn Leu Pro Ala Thr Arg Leu Arg Ser Met Gln Glu Leu Ser Thr Ile
                565                 570                 575

His Ile Gln Gly Ser Glu Gln Pro Ser Leu Thr Thr Ser Arg Ser Ser
                580                 585                 590

Leu Asn Leu Lys Ala Asp Asp Gly Leu Arg Pro Asn Cys Lys Thr Ser
    595                 600                 605

Gln Ile Thr Thr Ala Ile Ile Ser Ile Pro Thr Pro Pro Ala Leu Thr
    610                 615                 620

Pro Glu Gly Glu Ser Arg Pro Pro Pro Ala Ser Pro Gly Pro Asn Thr
```

Asn Ile Pro Ser Ile Ala Ser Asn Val Val Lys Val Ser Ala Leu
              645                 650                 655

<210> SEQ ID NO 36
<211> LENGTH: 636
<212> TYPE: PRT
<213> ORGANISM: Homo sapiens

<400> SEQUENCE: 36

Met Ala Ala Gly Val Ala Ala Trp Leu Pro Phe Ala Arg Ala Ala Ala
 1               5                  10                  15

Ile Gly Trp Met Pro Val Ala Asn Cys Pro Met Pro Leu Ala Pro Ala
            20                  25                  30

Asp Lys Asn Lys Arg Gln Asp Glu Leu Ile Val Leu Asn Val Ser Gly
        35                  40                  45

Arg Arg Phe Gln Thr Trp Arg Thr Thr Leu Glu Arg Tyr Pro Asp Thr
    50                  55                  60

Leu Leu Gly Ser Thr Glu Lys Glu Phe Phe Phe Asn Glu Asp Thr Lys
65                  70                  75                  80

Glu Tyr Phe Phe Asp Arg Asp Pro Glu Val Phe Arg Cys Val Leu Asn
                85                  90                  95

Phe Tyr Arg Thr Gly Lys Leu His Tyr Pro Arg Tyr Glu Cys Ile Ser
            100                 105                 110

Ala Tyr Asp Asp Glu Leu Ala Phe Tyr Gly Ile Leu Pro Glu Ile Ile
        115                 120                 125

Gly Asp Cys Cys Tyr Glu Glu Tyr Lys Asp Arg Lys Arg Glu Asn Ala
    130                 135                 140

Glu Arg Leu Met Asp Asp Asn Asp Ser Glu Asn Asn Gln Glu Ser Met
145                 150                 155                 160

Pro Ser Leu Ser Phe Arg Gln Thr Met Trp Arg Ala Phe Glu Asn Pro
                165                 170                 175

His Thr Ser Thr Leu Ala Leu Val Phe Tyr Tyr Val Thr Gly Phe Phe
            180                 185                 190

Ile Ala Val Ser Val Ile Thr Asn Val Val Glu Thr Val Pro Cys Gly
        195                 200                 205

Thr Val Pro Gly Ser Lys Glu Leu Pro Cys Gly Glu Arg Tyr Ser Val
    210                 215                 220

Ala Phe Phe Cys Leu Asp Thr Ala Cys Val Met Ile Phe Thr Val Glu
225                 230                 235                 240

Tyr Leu Leu Arg Leu Phe Ala Ala Pro Ser Arg Tyr Arg Phe Ile Arg
                245                 250                 255

Ser Val Met Ser Ile Ile Asp Val Val Ala Ile Met Pro Tyr Tyr Ile
            260                 265                 270

Gly Leu Val Met Thr Asn Asn Glu Asp Val Ser Gly Ala Phe Val Thr
        275                 280                 285

Leu Arg Val Phe Arg Val Phe Arg Ile Phe Lys Phe Ser Arg His Ser
    290                 295                 300

Gln Gly Leu Arg Ile Leu Gly Tyr Thr Leu Lys Ser Cys Ala Ser Glu
305                 310                 315                 320

Leu Gly Phe Leu Leu Phe Ser Leu Thr Met Ala Ile Ile Ile Phe Ala
                325                 330                 335

Thr Val Met Phe Tyr Ala Glu Lys Gly Ser Ser Ala Ser Lys Phe Thr
            340                 345                 350

```
Ser Ile Pro Ala Ser Phe Trp Tyr Thr Ile Val Thr Met Thr Thr Leu
        355                 360                 365
Gly Tyr Gly Asp Met Val Pro Lys Thr Ile Ala Gly Lys Ile Phe Gly
    370                 375                 380
Ser Ile Cys Ser Leu Ser Gly Val Leu Val Ile Ala Leu Pro Val Pro
385                 390                 395                 400
Val Ile Val Ser Asn Phe Ser Arg Ile Tyr His Gln Asn Gln Arg Ala
                405                 410                 415
Asp Lys Arg Arg Ala Gln Lys Lys Ala Arg Leu Ala Arg Ile Arg Val
            420                 425                 430
Ala Lys Thr Gly Ser Ser Asn Ala Tyr Leu His Ser Lys Arg Asn Gly
        435                 440                 445
Leu Leu Asn Glu Ala Leu Glu Leu Thr Gly Thr Pro Glu Glu Glu His
    450                 455                 460
Met Gly Lys Thr Thr Ser Leu Ile Glu Ser Gln His His Leu Leu
465                 470                 475                 480
His Cys Leu Glu Lys Thr Thr Asn His Glu Phe Ile Asp Glu Gln Met
                485                 490                 495
Phe Glu Gln Asn Cys Met Glu Ser Met Gln Asn Tyr Pro Ser Thr
            500                 505                 510
Arg Ser Pro Ser Leu Ser Ser His Pro Gly Leu Thr Thr Thr Cys Cys
    515                 520                 525
Ser Arg Arg Ser Lys Lys Thr Thr His Leu Pro Asn Ser Asn Leu Pro
530                 535                 540
Ala Thr Arg Leu Arg Ser Met Gln Glu Leu Ser Thr Ile His Ile Gln
545                 550                 555                 560
Gly Ser Glu Gln Pro Ser Leu Thr Thr Ser Arg Ser Ser Leu Asn Leu
                565                 570                 575
Lys Ala Asp Asp Gly Leu Arg Pro Asn Cys Lys Thr Ser Gln Ile Thr
            580                 585                 590
Thr Ala Ile Ile Ser Ile Pro Thr Pro Pro Ala Leu Thr Pro Glu Gly
        595                 600                 605
Glu Ser Arg Pro Pro Ala Ser Pro Gly Pro Asn Thr Asn Ile Pro
    610                 615                 620
Ser Ile Ala Ser Asn Val Val Lys Val Ser Ala Leu
625                 630                 635

<210> SEQ ID NO 37
<211> LENGTH: 1023
<212> TYPE: PRT
<213> ORGANISM: Homo sapiens

<400> SEQUENCE: 37

Met Gly Lys Gly Val Gly Arg Asp Lys Tyr Glu Pro Ala Ala Val Ser
 1               5                  10                  15
Glu Gln Gly Asp Lys Lys Gly Lys Gly Lys Lys Asp Arg Asp Met
            20                  25                  30
Asp Glu Leu Lys Lys Glu Val Ser Met Asp Asp His Lys Leu Ser Leu
        35                  40                  45
Asp Glu Leu His Arg Lys Tyr Gly Thr Asp Leu Ser Arg Gly Leu Thr
    50                  55                  60
Ser Ala Arg Ala Ala Glu Ile Leu Ala Arg Asp Gly Pro Asn Ala Leu
65                  70                  75                  80
Thr Pro Pro Pro Thr Thr Pro Glu Trp Ile Lys Phe Cys Arg Gln Leu
                85                  90                  95
```

-continued

```
Phe Gly Gly Phe Ser Met Leu Leu Trp Ile Gly Ala Ile Leu Cys Phe
            100                 105                 110
Leu Ala Tyr Ser Ile Gln Ala Ala Thr Glu Glu Pro Gln Asn Asp
        115                 120                 125
Asn Leu Tyr Leu Gly Val Val Leu Ser Ala Val Ile Ile Thr Gly
    130                 135                 140
Cys Phe Ser Tyr Tyr Gln Glu Ala Lys Ser Ser Lys Ile Met Glu Ser
145                 150                 155                 160
Phe Lys Asn Met Val Pro Gln Gln Ala Leu Val Ile Arg Asn Gly Glu
                165                 170                 175
Lys Met Ser Ile Asn Ala Glu Glu Val Val Val Gly Asp Leu Val Glu
                180                 185                 190
Val Lys Gly Gly Asp Arg Ile Pro Ala Asp Leu Arg Ile Ile Ser Ala
            195                 200                 205
Asn Gly Cys Lys Val Asp Asn Ser Ser Leu Thr Gly Glu Ser Glu Pro
        210                 215                 220
Gln Thr Arg Ser Pro Asp Phe Thr Asn Glu Asn Pro Leu Glu Thr Arg
225                 230                 235                 240
Asn Ile Ala Phe Phe Ser Thr Asn Cys Val Glu Gly Thr Ala Arg Gly
                245                 250                 255
Ile Val Val Tyr Thr Gly Asp Arg Thr Val Met Gly Arg Ile Ala Thr
            260                 265                 270
Leu Ala Ser Gly Leu Glu Gly Gly Gln Thr Pro Ile Ala Ala Glu Ile
        275                 280                 285
Glu His Phe Ile His Ile Ile Thr Gly Val Ala Val Phe Leu Gly Val
    290                 295                 300
Ser Phe Phe Ile Leu Ser Leu Ile Leu Glu Tyr Thr Trp Leu Glu Ala
305                 310                 315                 320
Val Ile Phe Leu Ile Gly Ile Ile Val Ala Asn Val Pro Glu Gly Leu
                325                 330                 335
Leu Ala Thr Val Thr Val Cys Leu Thr Leu Thr Ala Lys Arg Met Ala
            340                 345                 350
Arg Lys Asn Cys Leu Val Lys Asn Leu Glu Ala Val Glu Thr Leu Gly
        355                 360                 365
Ser Thr Ser Thr Ile Cys Ser Asp Lys Thr Gly Thr Leu Thr Gln Asn
    370                 375                 380
Arg Met Thr Val Ala His Met Trp Phe Asp Asn Gln Ile His Glu Ala
385                 390                 395                 400
Asp Thr Thr Glu Asn Gln Ser Gly Val Ser Phe Asp Lys Thr Ser Ala
                405                 410                 415
Thr Trp Leu Ala Leu Ser Arg Ile Ala Gly Leu Cys Asn Arg Ala Val
            420                 425                 430
Phe Gln Ala Asn Gln Glu Asn Leu Pro Ile Leu Lys Arg Ala Val Ala
        435                 440                 445
Gly Asp Ala Ser Glu Ser Ala Leu Leu Lys Cys Ile Glu Leu Cys Cys
    450                 455                 460
Gly Ser Val Lys Glu Met Arg Glu Arg Tyr Ala Lys Ile Val Glu Ile
465                 470                 475                 480
Pro Phe Asn Ser Thr Asn Lys Tyr Gln Leu Ser Ile His Lys Asn Pro
                485                 490                 495
Asn Thr Ser Glu Pro Gln His Leu Leu Val Met Lys Gly Ala Pro Glu
            500                 505                 510
```

```
Arg Ile Leu Asp Arg Cys Ser Ser Ile Leu Leu His Gly Lys Glu Gln
            515                 520                 525

Pro Leu Asp Glu Glu Leu Lys Asp Ala Phe Gln Asn Ala Tyr Leu Glu
        530                 535                 540

Leu Gly Gly Leu Gly Glu Arg Val Leu Gly Phe Cys His Leu Phe Leu
545                 550                 555                 560

Pro Asp Glu Gln Phe Pro Glu Gly Phe Gln Phe Asp Thr Asp Val
                565                 570                 575

Asn Phe Pro Ile Asp Asn Leu Cys Phe Val Gly Leu Ile Ser Met Ile
            580                 585                 590

Asp Pro Pro Arg Ala Ala Val Pro Asp Ala Val Gly Lys Cys Arg Ser
            595                 600                 605

Ala Gly Ile Lys Val Ile Met Val Thr Gly Asp His Pro Ile Thr Ala
        610                 615                 620

Lys Ala Ile Ala Lys Gly Val Gly Ile Ile Ser Glu Gly Asn Glu Thr
625                 630                 635                 640

Val Glu Asp Ile Ala Ala Arg Leu Asn Ile Pro Val Ser Gln Val Asn
                645                 650                 655

Pro Arg Asp Ala Lys Ala Cys Val Val His Gly Ser Asp Leu Lys Asp
            660                 665                 670

Met Thr Ser Glu Gln Leu Asp Asp Ile Leu Lys Tyr His Thr Glu Ile
        675                 680                 685

Val Phe Ala Arg Thr Ser Pro Gln Gln Lys Leu Ile Ile Val Glu Gly
        690                 695                 700

Cys Gln Arg Gln Gly Ala Ile Val Ala Val Thr Gly Asp Gly Val Asn
705                 710                 715                 720

Asp Ser Pro Ala Leu Lys Lys Ala Asp Ile Gly Val Ala Met Gly Ile
                725                 730                 735

Ala Gly Ser Asp Val Ser Lys Gln Ala Ala Asp Met Ile Leu Leu Asp
            740                 745                 750

Asp Asn Phe Ala Ser Ile Val Thr Gly Val Glu Glu Gly Arg Leu Ile
        755                 760                 765

Phe Asp Asn Leu Lys Lys Ser Ile Ala Tyr Thr Leu Thr Ser Asn Ile
770                 775                 780

Pro Glu Ile Thr Pro Phe Leu Ile Phe Ile Ile Ala Asn Ile Pro Leu
785                 790                 795                 800

Pro Leu Gly Thr Val Thr Ile Leu Cys Ile Asp Leu Gly Thr Asp Met
                805                 810                 815

Val Pro Ala Ile Ser Leu Ala Tyr Glu Gln Ala Glu Ser Asp Ile Met
            820                 825                 830

Lys Arg Gln Pro Arg Asn Pro Lys Thr Asp Lys Leu Val Asn Glu Arg
        835                 840                 845

Leu Ile Ser Met Ala Tyr Gly Gln Ile Gly Met Ile Gln Ala Leu Gly
850                 855                 860

Gly Phe Phe Thr Tyr Phe Val Ile Leu Ala Glu Asn Gly Phe Leu Pro
865                 870                 875                 880

Ile His Leu Leu Gly Leu Arg Val Asp Trp Asp Asp Arg Trp Ile Asn
                885                 890                 895

Asp Val Glu Asp Ser Tyr Gly Gln Gln Trp Thr Tyr Glu Gln Arg Lys
            900                 905                 910

Ile Val Glu Phe Thr Cys His Thr Ala Phe Phe Val Ser Ile Val Val
        915                 920                 925

Val Gln Trp Ala Asp Leu Val Ile Cys Lys Thr Arg Arg Asn Ser Val
```

-continued

```
             930                 935                 940
Phe Gln Gln Gly Met Lys Asn Lys Ile Leu Ile Phe Gly Leu Phe Glu
945                 950                 955                 960

Glu Thr Ala Leu Ala Ala Phe Leu Ser Tyr Cys Pro Gly Met Gly Val
                965                 970                 975

Ala Leu Arg Met Tyr Pro Leu Lys Pro Thr Trp Trp Phe Cys Ala Phe
                980                 985                 990

Pro Tyr Ser Leu Leu Ile Phe Val Tyr Asp Glu Val Arg Lys Leu Ile
                995                1000                1005

Ile Arg Arg Pro Gly Gly Trp Val Glu Lys Glu Thr Tyr Tyr
   1010                1015                1020

<210> SEQ ID NO 38
<211> LENGTH: 681
<212> TYPE: PRT
<213> ORGANISM: Homo sapiens

<400> SEQUENCE: 38

Met Gly Lys Gly Val Gly Arg Asp Lys Tyr Glu Pro Ala Ala Val Ser
1               5                  10                  15

Glu Gln Gly Asp Lys Lys Gly Lys Lys Gly Lys Lys Asp Arg Asp Met
                20                  25                  30

Asp Glu Leu Lys Lys Glu Val Ser Met Asp Asp His Lys Leu Ser Leu
            35                  40                  45

Asp Glu Leu His Arg Lys Tyr Gly Thr Asp Leu Ser Arg Gly Leu Thr
        50                  55                  60

Ser Ala Arg Ala Ala Glu Ile Leu Ala Arg Asp Gly Pro Asn Ala Leu
65                  70                  75                  80

Thr Pro Pro Pro Thr Thr Pro Glu Trp Ile Lys Phe Cys Arg Gln Leu
                85                  90                  95

Phe Gly Gly Phe Ser Met Leu Leu Trp Ile Gly Ala Ile Leu Cys Phe
                100                 105                 110

Leu Ala Tyr Ser Ile Gln Ala Ala Thr Glu Glu Pro Gln Asn Asp
            115                 120                 125

Asn Leu Tyr Leu Gly Val Val Leu Ser Ala Val Val Ile Ile Thr Gly
        130                 135                 140

Cys Phe Ser Tyr Tyr Gln Glu Ala Lys Ser Ser Lys Ile Met Glu Ser
145                 150                 155                 160

Phe Lys Asn Met Val Pro Gln Gln Ala Leu Val Ile Arg Asn Gly Glu
                165                 170                 175

Lys Met Ser Ile Asn Ala Glu Glu Val Val Val Gly Asp Leu Val Glu
                180                 185                 190

Val Lys Gly Gly Asp Arg Ile Pro Ala Asp Leu Arg Ile Ile Ser Ala
            195                 200                 205

Asn Gly Cys Lys Val Asp Asn Ser Ser Leu Thr Gly Glu Ser Glu Pro
        210                 215                 220

Gln Thr Arg Ser Pro Asp Phe Thr Asn Glu Asn Pro Leu Glu Thr Arg
225                 230                 235                 240

Asn Ile Ala Phe Phe Ser Thr Asn Cys Val Glu Gly Thr Ala Arg Gly
                245                 250                 255

Ile Val Val Tyr Thr Gly Asp Arg Thr Val Met Gly Arg Ile Ala Thr
                260                 265                 270

Leu Ala Ser Gly Leu Glu Gly Gly Gln Thr Pro Ile Ala Ala Glu Ile
            275                 280                 285
```

-continued

```
Glu His Phe Ile His Ile Ile Thr Gly Val Ala Val Phe Leu Gly Val
    290                 295                 300

Ser Phe Phe Ile Leu Ser Leu Ile Leu Glu Tyr Thr Trp Leu Glu Ala
305                 310                 315                 320

Val Ile Phe Leu Ile Gly Ile Ile Val Ala Asn Val Pro Glu Gly Leu
                325                 330                 335

Leu Ala Thr Val Thr Val Cys Leu Thr Leu Thr Ala Lys Arg Met Ala
            340                 345                 350

Arg Lys Asn Cys Leu Val Lys Asn Leu Glu Ala Val Glu Thr Leu Gly
        355                 360                 365

Ser Thr Ser Thr Ile Cys Ser Asp Lys Thr Gly Thr Leu Thr Gln Asn
    370                 375                 380

Arg Met Thr Val Ala His Met Trp Phe Asp Asn Gln Ile His Glu Ala
385                 390                 395                 400

Asp Thr Thr Glu Asn Gln Ser Gly Val Ser Phe Asp Lys Thr Ser Ala
                405                 410                 415

Thr Trp Leu Ala Leu Ser Arg Ile Ala Gly Leu Cys Asn Arg Ala Val
            420                 425                 430

Phe Gln Ala Asn Gln Glu Asn Leu Pro Ile Leu Lys Arg Ala Val Ala
        435                 440                 445

Gly Asp Ala Ser Glu Ser Ala Leu Leu Lys Cys Ile Glu Leu Cys Cys
    450                 455                 460

Gly Ser Val Lys Glu Met Arg Glu Arg Tyr Ala Lys Ile Val Glu Ile
465                 470                 475                 480

Pro Phe Asn Ser Thr Asn Lys Tyr Gln Leu Ser Ile His Lys Asn Pro
                485                 490                 495

Asn Thr Ser Glu Pro Gln His Leu Leu Val Met Lys Gly Ala Pro Glu
            500                 505                 510

Arg Ile Leu Asp Arg Cys Ser Ser Ile Leu Leu His Gly Lys Glu Gln
        515                 520                 525

Pro Leu Asp Glu Glu Leu Lys Asp Ala Phe Gln Asn Ala Tyr Leu Glu
    530                 535                 540

Leu Gly Gly Leu Gly Glu Arg Val Leu Gly Phe Cys His Leu Phe Leu
545                 550                 555                 560

Pro Asp Glu Gln Phe Pro Glu Gly Phe Gln Phe Asp Thr Asp Asp Val
                565                 570                 575

Asn Phe Pro Ile Asp Asn Leu Cys Phe Val Gly Leu Ile Ser Met Ile
            580                 585                 590

Asp Pro Pro Arg Ala Ala Val Pro Asp Ala Val Gly Lys Cys Arg Ser
        595                 600                 605

Ala Gly Ile Lys Val Ile Met Val Thr Gly Asp His Pro Ile Thr Ala
    610                 615                 620

Lys Ala Ile Ala Lys Gly Val Gly Ile Ile Ser Glu Gly Asn Gly Pro
625                 630                 635                 640

Met Ser Arg Gly Lys Ser Trp Ser Pro Ala Thr Gln Pro Ser Ser
                645                 650                 655

Ser Val Ser Trp Trp Cys Ser Gly Pro Thr Trp Ser Ser Val Arg Pro
            660                 665                 670

Gly Gly Ile Arg Ser Ser Arg Gly
        675                 680

<210> SEQ ID NO 39
<211> LENGTH: 1020
<212> TYPE: PRT
```

<213> ORGANISM: Homo sapiens

<400> SEQUENCE: 39

```
Met Gly Arg Gly Ala Gly Arg Glu Tyr Ser Pro Ala Ala Thr Thr Ala
  1               5                  10                  15
Glu Asn Gly Gly Gly Lys Lys Gln Lys Glu Lys Glu Leu Asp Glu
                 20                  25                  30
Leu Lys Lys Glu Val Ala Met Asp Asp His Lys Leu Ser Leu Asp Glu
             35                  40                  45
Leu Gly Arg Lys Tyr Gln Val Asp Leu Ser Lys Gly Leu Thr Asn Gln
         50                  55                  60
Arg Ala Gln Asp Val Leu Ala Arg Asp Gly Pro Asn Ala Leu Thr Pro
 65                  70                  75                  80
Pro Pro Thr Thr Pro Glu Trp Val Lys Phe Cys Arg Gln Leu Phe Gly
                 85                  90                  95
Gly Phe Ser Ile Leu Leu Trp Ile Gly Ala Ile Leu Cys Phe Leu Ala
                100                 105                 110
Tyr Gly Ile Gln Ala Ala Met Glu Asp Glu Pro Ser Asn Asp Asn Leu
            115                 120                 125
Tyr Leu Gly Val Val Leu Ala Ala Val Val Ile Val Thr Gly Cys Phe
        130                 135                 140
Ser Tyr Tyr Gln Glu Ala Lys Ser Ser Lys Ile Met Asp Ser Phe Lys
145                 150                 155                 160
Asn Met Val Pro Gln Gln Ala Leu Val Ile Arg Glu Gly Glu Lys Met
                165                 170                 175
Gln Ile Asn Ala Glu Glu Val Val Val Gly Asp Leu Val Glu Val Lys
            180                 185                 190
Gly Gly Asp Arg Val Pro Ala Asp Leu Arg Ile Ile Ser His Gly
        195                 200                 205
Cys Lys Val Asp Asn Ser Ser Leu Thr Gly Glu Ser Glu Pro Gln Thr
210                 215                 220
Arg Ser Pro Glu Phe Thr His Glu Asn Pro Leu Glu Thr Arg Asn Ile
225                 230                 235                 240
Cys Phe Phe Ser Thr Asn Cys Val Glu Gly Thr Ala Arg Gly Ile Val
                245                 250                 255
Ile Ala Thr Gly Asp Arg Thr Val Met Gly Arg Ile Ala Thr Leu Ala
            260                 265                 270
Ser Gly Leu Glu Val Gly Arg Thr Pro Ile Ala Met Glu Ile Glu His
        275                 280                 285
Phe Ile Gln Leu Ile Thr Gly Val Ala Val Phe Leu Gly Val Ser Phe
290                 295                 300
Phe Val Leu Ser Leu Ile Leu Gly Tyr Ser Trp Leu Glu Ala Val Ile
305                 310                 315                 320
Phe Leu Ile Gly Ile Ile Val Ala Asn Val Pro Glu Gly Leu Leu Ala
                325                 330                 335
Thr Val Thr Val Cys Leu Thr Leu Thr Ala Lys Arg Met Ala Arg Lys
            340                 345                 350
Asn Cys Leu Val Lys Asn Leu Glu Ala Val Glu Thr Leu Gly Ser Thr
        355                 360                 365
Ser Thr Ile Cys Ser Asp Lys Thr Gly Thr Leu Thr Gln Asn Arg Met
    370                 375                 380
Thr Val Ala His Met Trp Phe Asp Asn Gln Ile His Glu Ala Asp Thr
385                 390                 395                 400
```

-continued

```
Thr Glu Asp Gln Ser Gly Ala Thr Phe Asp Lys Arg Ser Pro Thr Trp
            405                 410                 415
Thr Ala Leu Ser Arg Ile Ala Gly Leu Cys Asn Arg Ala Val Phe Lys
        420                 425                 430
Ala Gly Gln Glu Asn Ile Ser Val Ser Lys Arg Asp Thr Ala Gly Asp
    435                 440                 445
Ala Ser Glu Ser Ala Leu Leu Lys Cys Ile Glu Leu Ser Cys Gly Ser
450                 455                 460
Val Arg Lys Met Arg Asp Arg Asn Pro Lys Val Ala Glu Ile Pro Phe
465                 470                 475                 480
Asn Ser Thr Asn Lys Tyr Gln Leu Ser Ile His Glu Arg Glu Asp Ser
                485                 490                 495
Pro Gln Ser His Val Leu Val Met Lys Gly Ala Pro Glu Arg Ile Leu
            500                 505                 510
Asp Arg Cys Ser Thr Ile Leu Val Gln Gly Lys Glu Ile Pro Leu Asp
        515                 520                 525
Lys Glu Met Gln Asp Ala Phe Gln Asn Ala Tyr Met Glu Leu Gly Gly
    530                 535                 540
Leu Gly Glu Arg Val Leu Gly Phe Cys Gln Leu Asn Leu Pro Ser Gly
545                 550                 555                 560
Lys Phe Pro Arg Gly Phe Lys Phe Asp Thr Asp Glu Leu Asn Phe Pro
                565                 570                 575
Thr Glu Lys Leu Cys Phe Val Gly Leu Met Ser Met Ile Asp Pro Pro
            580                 585                 590
Arg Ala Ala Val Pro Asp Ala Val Gly Lys Cys Arg Ser Ala Gly Ile
        595                 600                 605
Lys Val Ile Met Val Thr Gly Asp His Pro Ile Thr Ala Lys Ala Ile
    610                 615                 620
Ala Lys Gly Val Gly Ile Ile Ser Glu Gly Asn Glu Thr Val Glu Asp
625                 630                 635                 640
Ile Ala Ala Arg Leu Asn Ile Pro Met Ser Gln Val Asn Pro Arg Glu
                645                 650                 655
Ala Lys Ala Cys Val Val His Gly Ser Asp Leu Lys Asp Met Thr Ser
            660                 665                 670
Glu Gln Leu Asp Glu Ile Leu Lys Asn His Thr Glu Ile Val Phe Ala
        675                 680                 685
Arg Thr Ser Pro Gln Gln Lys Leu Ile Ile Val Glu Gly Cys Gln Arg
    690                 695                 700
Gln Gly Ala Ile Val Ala Val Thr Gly Asp Gly Val Asn Asp Ser Pro
705                 710                 715                 720
Ala Leu Lys Lys Ala Asp Ile Gly Ile Ala Met Gly Ile Ser Gly Ser
                725                 730                 735
Asp Val Ser Lys Gln Ala Ala Asp Met Ile Leu Leu Asp Asp Asn Phe
            740                 745                 750
Ala Ser Ile Val Thr Gly Val Glu Glu Gly Arg Leu Ile Phe Asp Asn
        755                 760                 765
Leu Lys Lys Ser Ile Ala Tyr Thr Leu Thr Ser Asn Ile Pro Glu Ile
    770                 775                 780
Thr Pro Phe Leu Leu Phe Ile Ile Ala Asn Ile Pro Leu Pro Leu Gly
785                 790                 795                 800
Thr Val Thr Ile Leu Cys Ile Asp Leu Gly Thr Asp Met Val Pro Ala
                805                 810                 815
Ile Ser Leu Ala Tyr Glu Ala Ala Glu Ser Asp Ile Met Lys Arg Gln
```

-continued

```
                820                 825                 830
Pro Arg Asn Ser Gln Thr Asp Lys Leu Val Asn Glu Arg Leu Ile Ser
        835                 840                 845
Met Ala Tyr Gly Gln Ile Gly Met Ile Gln Ala Leu Gly Gly Phe Phe
850                 855                 860
Thr Tyr Phe Val Ile Leu Ala Glu Asn Gly Phe Leu Pro Ser Arg Leu
865                 870                 875                 880
Leu Gly Ile Arg Leu Asp Trp Asp Arg Thr Met Asn Asp Leu Glu
            885                 890                 895
Asp Ser Tyr Gly Gln Glu Trp Thr Tyr Glu Gln Arg Lys Val Val Glu
            900                 905                 910
Phe Thr Cys His Thr Ala Phe Phe Ala Ser Ile Val Val Gln Trp
            915                 920                 925
Ala Asp Leu Ile Ile Cys Lys Thr Arg Arg Asn Ser Val Phe Gln Gln
        930                 935                 940
Gly Met Lys Asn Lys Ile Leu Ile Phe Gly Leu Glu Glu Thr Ala
945                 950                 955                 960
Leu Ala Ala Phe Leu Ser Tyr Cys Pro Gly Met Gly Val Ala Leu Arg
                965                 970                 975
Met Tyr Pro Leu Lys Val Thr Trp Trp Phe Cys Ala Phe Pro Tyr Ser
            980                 985                 990
Leu Leu Ile Phe Ile Tyr Asp Glu Val Arg Lys Leu Ile Leu Arg Arg
        995                 1000                1005
Tyr Pro Gly Gly Trp Val Glu Lys Glu Thr Tyr Tyr
    1010                1015                1020

<210> SEQ ID NO 40
<211> LENGTH: 1013
<212> TYPE: PRT
<213> ORGANISM: Homo sapiens

<400> SEQUENCE: 40

Met Gly Asp Lys Lys Asp Asp Lys Asp Ser Pro Lys Lys Asn Lys Gly
1               5                   10                  15
Lys Glu Arg Arg Asp Leu Asp Asp Leu Lys Lys Glu Val Ala Met Thr
            20                  25                  30
Glu His Lys Met Ser Val Glu Glu Val Cys Arg Lys Tyr Asn Thr Asp
        35                  40                  45
Cys Val Gln Gly Leu Thr His Ser Lys Ala Gln Glu Ile Leu Ala Arg
    50                  55                  60
Asp Gly Pro Asn Ala Leu Thr Pro Pro Thr Thr Pro Glu Trp Val
65                  70                  75                  80
Lys Phe Cys Arg Gln Leu Phe Gly Gly Phe Ser Ile Leu Leu Trp Ile
                85                  90                  95
Gly Ala Ile Leu Cys Phe Leu Ala Tyr Gly Ile Gln Ala Gly Thr Glu
            100                 105                 110
Asp Asp Pro Ser Gly Asp Asn Leu Tyr Leu Gly Ile Val Leu Ala Ala
        115                 120                 125
Val Val Ile Ile Thr Gly Cys Phe Ser Tyr Tyr Gln Glu Ala Lys Ser
    130                 135                 140
Ser Lys Ile Met Glu Ser Phe Lys Asn Met Val Pro Gln Gln Ala Leu
145                 150                 155                 160
Val Ile Arg Glu Gly Glu Lys Met Gln Val Asn Ala Glu Glu Val Val
                165                 170                 175
```

```
Val Gly Asp Leu Val Glu Ile Lys Gly Gly Asp Arg Val Pro Ala Asp
            180                 185                 190

Leu Arg Ile Ile Ser Ala His Gly Cys Lys Val Asp Asn Ser Ser Leu
            195                 200                 205

Thr Gly Glu Ser Glu Pro Gln Thr Arg Ser Pro Asp Cys Thr His Asp
            210                 215                 220

Asn Pro Leu Glu Thr Arg Asn Ile Thr Phe Phe Ser Thr Asn Cys Val
225                 230                 235                 240

Glu Gly Thr Ala Arg Gly Val Val Ala Thr Gly Asp Arg Thr Val
                245                 250                 255

Met Gly Arg Ile Ala Thr Leu Ala Ser Gly Leu Glu Val Gly Lys Thr
            260                 265                 270

Pro Ile Ala Ile Glu Ile Glu His Phe Ile Gln Leu Ile Thr Gly Val
            275                 280                 285

Ala Val Phe Leu Gly Val Ser Phe Phe Ile Leu Ser Leu Ile Leu Gly
            290                 295                 300

Tyr Thr Trp Leu Glu Ala Val Ile Phe Leu Ile Gly Ile Ile Val Ala
305                 310                 315                 320

Asn Val Pro Glu Gly Leu Leu Ala Thr Val Thr Val Cys Leu Thr Val
                325                 330                 335

Thr Ala Lys Arg Met Ala Arg Lys Asn Cys Leu Val Lys Asn Leu Glu
            340                 345                 350

Ala Val Glu Thr Leu Gly Ser Thr Ser Thr Ile Cys Ser Asp Lys Thr
            355                 360                 365

Gly Thr Leu Thr Gln Asn Arg Met Thr Val Ala His Met Trp Phe Asp
            370                 375                 380

Asn Gln Ile His Glu Ala Asp Thr Thr Glu Asp Gln Ser Gly Thr Ser
385                 390                 395                 400

Phe Asp Lys Ser Ser His Thr Trp Val Ala Leu Ser His Ile Ala Gly
                405                 410                 415

Leu Cys Asn Arg Ala Val Phe Lys Gly Gly Gln Asp Asn Ile Pro Val
            420                 425                 430

Leu Lys Arg Asp Val Ala Gly Asp Ala Ser Glu Ser Ala Leu Leu Lys
            435                 440                 445

Cys Ile Glu Leu Ser Ser Gly Ser Val Lys Leu Met Arg Glu Arg Asn
450                 455                 460

Lys Lys Val Ala Glu Ile Pro Phe Asn Ser Thr Asn Lys Tyr Gln Leu
465                 470                 475                 480

Ser Ile His Glu Thr Glu Asp Pro Asn Asp Asn Arg Tyr Leu Leu Val
                485                 490                 495

Met Lys Gly Ala Pro Glu Arg Ile Leu Asp Arg Cys Ser Thr Ile Leu
            500                 505                 510

Leu Gln Gly Lys Glu Gln Pro Leu Asp Glu Glu Met Lys Glu Ala Phe
            515                 520                 525

Gln Asn Ala Tyr Leu Glu Leu Gly Gly Leu Gly Glu Arg Val Leu Gly
            530                 535                 540

Phe Cys His Tyr Tyr Leu Pro Glu Glu Gln Phe Pro Lys Gly Phe Ala
545                 550                 555                 560

Phe Asp Cys Asp Asp Val Asn Phe Thr Thr Asp Asn Leu Cys Phe Val
                565                 570                 575

Gly Leu Met Ser Met Ile Asp Pro Pro Arg Ala Ala Val Pro Asp Ala
            580                 585                 590

Val Gly Lys Cys Arg Ser Ala Gly Ile Lys Val Ile Met Val Thr Gly
```

-continued

```
            595                 600                 605
Asp His Pro Ile Thr Ala Lys Ala Ile Ala Lys Gly Val Gly Ile Ile
    610                 615                 620

Ser Glu Gly Asn Glu Thr Val Glu Asp Ile Ala Ala Arg Leu Asn Ile
625                 630                 635                 640

Pro Val Ser Gln Val Asn Pro Arg Asp Ala Lys Ala Cys Val Ile His
                645                 650                 655

Gly Thr Asp Leu Lys Asp Phe Thr Ser Glu Gln Ile Asp Glu Ile Leu
            660                 665                 670

Gln Asn His Thr Glu Ile Val Phe Ala Arg Thr Ser Pro Gln Gln Lys
        675                 680                 685

Leu Ile Ile Val Glu Gly Cys Gln Arg Gln Gly Ala Ile Val Ala Val
    690                 695                 700

Thr Gly Asp Gly Val Asn Asp Ser Pro Ala Leu Lys Lys Ala Asp Ile
705                 710                 715                 720

Gly Val Ala Met Gly Ile Ala Gly Ser Asp Val Ser Lys Gln Ala Ala
                725                 730                 735

Asp Met Ile Leu Leu Asp Asp Asn Phe Ala Ser Ile Val Thr Gly Val
            740                 745                 750

Glu Glu Gly Arg Leu Ile Phe Asp Asn Leu Lys Lys Ser Ile Ala Tyr
        755                 760                 765

Thr Leu Thr Ser Asn Ile Pro Glu Ile Thr Pro Phe Leu Leu Phe Ile
    770                 775                 780

Met Ala Asn Ile Pro Leu Pro Leu Gly Thr Ile Thr Ile Leu Cys Ile
785                 790                 795                 800

Asp Leu Gly Thr Asp Met Val Pro Ala Ile Ser Leu Ala Tyr Glu Ala
                805                 810                 815

Ala Glu Ser Asp Ile Met Lys Arg Gln Pro Arg Asn Pro Arg Thr Asp
            820                 825                 830

Lys Leu Val Asn Glu Arg Leu Ile Ser Met Ala Tyr Gly Gln Ile Gly
        835                 840                 845

Met Ile Gln Ala Leu Gly Gly Phe Phe Ser Tyr Phe Val Ile Leu Ala
850                 855                 860

Glu Asn Gly Phe Leu Pro Gly Asn Leu Val Gly Ile Arg Leu Asn Trp
865                 870                 875                 880

Asp Asp Arg Thr Val Asn Asp Leu Glu Asp Ser Tyr Gly Gln Gln Trp
                885                 890                 895

Thr Tyr Glu Gln Arg Lys Val Val Glu Phe Thr Cys His Thr Ala Phe
            900                 905                 910

Phe Val Ser Ile Val Val Gln Trp Ala Asp Leu Ile Ile Cys Lys
        915                 920                 925

Thr Arg Arg Asn Ser Val Phe Gln Gln Gly Met Lys Asn Lys Ile Leu
    930                 935                 940

Ile Phe Gly Leu Phe Glu Glu Thr Ala Leu Ala Ala Phe Leu Ser Tyr
945                 950                 955                 960

Cys Pro Gly Met Asp Val Ala Leu Arg Met Tyr Pro Leu Lys Pro Ser
                965                 970                 975

Trp Trp Phe Cys Ala Phe Pro Tyr Ser Phe Leu Ile Phe Val Tyr Asp
            980                 985                 990

Glu Ile Arg Lys Leu Ile Leu Arg Arg Asn Pro Gly Gly Trp Val Glu
        995                 1000                1005

Lys Glu Thr Tyr Tyr
    1010
```

<210> SEQ ID NO 41
<211> LENGTH: 1029
<212> TYPE: PRT
<213> ORGANISM: Homo sapiens

<400> SEQUENCE: 41

```
Met Gly Leu Trp Gly Lys Lys Gly Thr Val Ala Pro His Asp Gln Ser
 1               5                  10                  15

Pro Arg Arg Pro Lys Lys Gly Leu Ile Lys Lys Met Val Lys
             20                  25                  30

Arg Glu Lys Gln Lys Arg Asn Met Glu Glu Leu Lys Lys Glu Val Val
         35                  40                  45

Met Asp Asp His Lys Leu Thr Leu Glu Glu Leu Ser Thr Lys Tyr Ser
 50                  55                  60

Val Asp Leu Thr Lys Gly His Ser His Gln Arg Ala Lys Glu Ile Leu
 65                  70                  75                  80

Thr Arg Asp Gly Pro Asn Thr Val Thr Pro Pro Thr Thr Pro Glu
                 85                  90                  95

Trp Val Lys Phe Cys Lys Gln Leu Phe Gly Gly Phe Ser Leu Leu Leu
                100                 105                 110

Trp Thr Gly Ala Ile Leu Cys Phe Val Ala Tyr Ser Ile Gln Ile Tyr
                115                 120                 125

Phe Asn Glu Glu Pro Thr Lys Asp Asn Leu Tyr Leu Ser Ile Val Leu
                130                 135                 140

Ser Val Val Val Ile Val Thr Gly Cys Phe Ser Tyr Tyr Gln Glu Ala
145                 150                 155                 160

Lys Ser Ser Lys Ile Met Glu Ser Phe Lys Asn Met Val Pro Gln Gln
                165                 170                 175

Ala Leu Val Ile Arg Gly Gly Glu Lys Met Gln Ile Asn Val Gln Glu
                180                 185                 190

Val Val Leu Gly Asp Leu Val Glu Ile Lys Gly Gly Asp Arg Val Pro
                195                 200                 205

Ala Asp Leu Arg Leu Ile Ser Ala Gln Gly Cys Lys Val Asp Asn Ser
                210                 215                 220

Ser Leu Thr Gly Glu Ser Glu Pro Gln Ser Arg Ser Pro Asp Phe Thr
225                 230                 235                 240

His Glu Asn Pro Leu Glu Thr Arg Asn Ile Cys Phe Phe Ser Thr Asn
                245                 250                 255

Cys Val Glu Gly Thr Ala Arg Gly Ile Val Ile Ala Thr Gly Asp Ser
                260                 265                 270

Thr Val Met Gly Arg Ile Ala Ser Leu Thr Ser Gly Leu Ala Val Gly
                275                 280                 285

Gln Thr Pro Ile Ala Ala Glu Ile Glu His Phe Ile His Leu Ile Thr
                290                 295                 300

Val Val Ala Val Phe Leu Gly Val Thr Phe Phe Ala Leu Ser Leu Leu
305                 310                 315                 320

Leu Gly Tyr Gly Trp Leu Glu Ala Ile Ile Phe Leu Ile Gly Ile Ile
                325                 330                 335

Val Ala Asn Val Pro Glu Gly Leu Leu Ala Thr Val Thr Val Cys Leu
                340                 345                 350

Thr Leu Thr Ala Lys Arg Met Ala Arg Lys Asn Cys Leu Val Lys Asn
                355                 360                 365

Leu Glu Ala Val Glu Thr Leu Gly Ser Thr Ser Thr Ile Cys Ser Asp
```

-continued

```
              370                 375                 380
Lys Thr Gly Thr Leu Thr Gln Asn Arg Met Thr Val Ala His Met Trp
385                 390                 395                 400

Phe Asp Met Thr Val Tyr Glu Ala Asp Thr Thr Glu Glu Gln Thr Gly
                405                 410                 415

Lys Thr Phe Thr Lys Ser Ser Asp Thr Trp Phe Met Leu Ala Arg Ile
                420                 425                 430

Ala Gly Leu Cys Asn Arg Ala Asp Phe Lys Ala Asn Gln Glu Ile Leu
                435                 440                 445

Pro Ile Ala Lys Arg Ala Thr Thr Gly Asp Ala Ser Glu Ser Ala Leu
450                 455                 460

Leu Lys Phe Ile Glu Gln Ser Tyr Ser Ser Val Ala Glu Met Arg Glu
465                 470                 475                 480

Lys Asn Pro Lys Val Ala Glu Ile Pro Phe Asn Ser Thr Asn Lys Tyr
                485                 490                 495

Gln Met Ser Ile His Leu Arg Glu Asp Ser Ser Gln Thr His Val Leu
                500                 505                 510

Met Met Lys Gly Ala Pro Glu Arg Ile Leu Glu Phe Cys Ser Thr Phe
                515                 520                 525

Leu Leu Asn Gly Gln Glu Tyr Ser Met Asn Asp Glu Met Lys Glu Ala
530                 535                 540

Phe Gln Asn Ala Tyr Leu Glu Leu Gly Gly Leu Gly Glu Arg Val Leu
545                 550                 555                 560

Gly Phe Cys Phe Leu Asn Leu Pro Ser Ser Phe Ser Lys Gly Phe Pro
                565                 570                 575

Phe Asn Thr Asp Glu Ile Asn Phe Pro Met Asp Asn Leu Cys Phe Val
                580                 585                 590

Gly Leu Ile Ser Met Ile Asp Pro Pro Arg Ala Ala Val Pro Asp Ala
                595                 600                 605

Val Ser Lys Cys Arg Ser Ala Gly Ile Lys Val Ile Met Val Thr Gly
                610                 615                 620

Asp His Pro Ile Thr Ala Lys Ala Ile Ala Lys Gly Val Gly Ile Ile
625                 630                 635                 640

Ser Glu Gly Thr Glu Thr Ala Glu Glu Val Ala Ala Arg Leu Lys Ile
                645                 650                 655

Pro Ile Ser Lys Val Asp Ala Ser Ala Ala Lys Ala Ile Val Val His
                660                 665                 670

Gly Ala Glu Leu Lys Asp Ile Gln Ser Lys Gln Leu Asp Gln Ile Leu
                675                 680                 685

Gln Asn His Pro Glu Ile Val Phe Ala Arg Thr Ser Pro Gln Gln Lys
                690                 695                 700

Leu Ile Ile Val Glu Gly Cys Gln Arg Leu Gly Ala Val Val Ala Val
705                 710                 715                 720

Thr Gly Asp Gly Val Asn Asp Ser Pro Ala Leu Lys Lys Ala Asp Ile
                725                 730                 735

Gly Ile Ala Met Gly Ile Ser Gly Ser Asp Val Ser Lys Gln Ala Ala
                740                 745                 750

Asp Met Ile Leu Leu Asp Asp Asn Phe Ala Ser Ile Val Thr Gly Val
                755                 760                 765

Glu Glu Gly Arg Leu Ile Phe Asp Asn Leu Lys Lys Ser Ile Met Tyr
                770                 775                 780

Thr Leu Thr Ser Asn Ile Pro Glu Ile Thr Pro Phe Leu Met Phe Ile
785                 790                 795                 800
```

-continued

```
Ile Leu Gly Ile Pro Leu Pro Leu Gly Thr Ile Thr Ile Leu Cys Ile
            805             810                 815

Asp Leu Gly Thr Asp Met Val Pro Ala Ile Ser Leu Ala Tyr Glu Ser
            820             825                 830

Ala Glu Ser Asp Ile Met Lys Arg Leu Pro Arg Asn Pro Lys Thr Asp
            835             840             845

Asn Leu Val Asn His Arg Leu Ile Gly Met Ala Tyr Gly Gln Ile Gly
    850             855             860

Met Ile Gln Ala Leu Ala Gly Phe Phe Thr Tyr Phe Val Ile Leu Ala
865             870             875                 880

Glu Asn Gly Phe Arg Pro Val Asp Leu Leu Gly Ile Arg Leu His Trp
                885             890             895

Glu Asp Lys Tyr Leu Asn Asp Leu Glu Asp Ser Tyr Gly Gln Gln Trp
            900             905             910

Thr Tyr Glu Gln Arg Lys Val Val Glu Phe Thr Cys Gln Thr Ala Phe
            915             920             925

Phe Val Thr Ile Val Val Val Gln Trp Ala Asp Leu Ile Ile Ser Lys
    930             935             940

Thr Arg Arg Asn Ser Leu Phe Gln Gln Gly Met Arg Asn Lys Val Leu
945             950             955             960

Ile Phe Gly Ile Leu Glu Glu Thr Leu Leu Ala Ala Phe Leu Ser Tyr
            965             970             975

Thr Pro Gly Met Asp Val Ala Leu Arg Met Tyr Pro Leu Lys Ile Thr
            980             985             990

Trp Trp Leu Cys Ala Ile Pro Tyr Ser Ile Leu Ile Phe Val Tyr Asp
        995             1000            1005

Glu Ile Arg Lys Leu Leu Ile Arg Gln His Pro Asp Gly Trp Val Glu
    1010            1015            1020

Arg Glu Thr Tyr Tyr
1025
```